US011553879B2

(12) United States Patent
Bremer

(10) Patent No.: US 11,553,879 B2
(45) Date of Patent: Jan. 17, 2023

(54) SYSTEMS AND METHODS FOR CONTINUOUS HEALTH MONITORING USING AN OPTO-ENZYMATIC ANALYTE SENSOR

(71) Applicant: Metronom Health, Inc., Laguna Hills, CA (US)

(72) Inventor: Troy M. Bremer, Irvine, CA (US)

(73) Assignee: Metronom Health, Inc., Laguna Hills, CA (US)

( * ) Notice: Subject to any disclaimer, the term of this patent is extended or adjusted under 35 U.S.C. 154(b) by 339 days.

(21) Appl. No.: 15/754,271

(22) PCT Filed: Sep. 1, 2016

(86) PCT No.: PCT/US2016/049989
§ 371 (c)(1),
(2) Date: Feb. 21, 2018

(87) PCT Pub. No.: WO2017/040849
PCT Pub. Date: Mar. 9, 2017

(65) Prior Publication Data
US 2019/0021672 A1    Jan. 24, 2019

Related U.S. Application Data

(60) Provisional application No. 62/213,570, filed on Sep. 2, 2015.

(51) Int. Cl.
*A61B 5/00* (2006.01)
*A61B 5/1459* (2006.01)
(Continued)

(52) U.S. Cl.
CPC .......... *A61B 5/6833* (2013.01); *A61B 5/1459* (2013.01); *A61B 5/14532* (2013.01);
(Continued)

(58) Field of Classification Search
None
See application file for complete search history.

(56) References Cited

U.S. PATENT DOCUMENTS 3,878,080 A    4/1975   Luck
4,336,248 A    6/1982   Bonhard et al.
(Continued)

FOREIGN PATENT DOCUMENTS

WO    WO 03/059286    7/2003
WO    WO 03/077941    9/2003
(Continued)

OTHER PUBLICATIONS

Yu, J., et al. 2003 Analytica Chimica Acta 486: 209-216.
(Continued)

*Primary Examiner* — Michael R Bloch
(74) *Attorney, Agent, or Firm* — Knobbe, Martens, Olson & Bear, LLP

(57) ABSTRACT

Certain embodiments described herein pertain to optical sensors, systems and methods for continuous glucose monitoring. In some embodiments, methods of preparing a layered optical sensor are disclosed. The optical sensor can be formed by laminating a plurality of sheets together to form a final sensor. In some embodiments, the sensor tip comprises a oxygen conduit, an enzymatic layer, and an sensing layer. In some embodiments, the sensor includes a plurality of waveguides configured to direct light to and from a target material, such as an oxygen sensing polymer. Systems are also disclosed for an adhesive system for attaching an optical sensor-transmitter system. Methods and systems are also disclosed for a sensor inserter system. The inserter can include a lancet tip that includes a convex feature attached to a first surface of the lancet tip.

23 Claims, 85 Drawing Sheets

(51) Int. Cl.
  *A61B 5/1486* (2006.01)
  *A61B 5/145* (2006.01)
  *C09J 7/29* (2018.01)
(52) U.S. Cl.
  CPC .......... *A61B 5/14865* (2013.01); *C09J 7/29* (2018.01); *A61B 2560/0223* (2013.01); *A61B 2560/063* (2013.01); *A61B 2562/0238* (2013.01); *C09J 2301/18* (2020.08); *C09J 2301/312* (2020.08)

(56) References Cited

U.S. PATENT DOCUMENTS

| | | | |
|---|---|---|---|
| 4,343,715 A | 8/1982 | Bonaventura et al. | |
| 4,484,987 A | 11/1984 | Gough | |
| 4,680,268 A | 7/1987 | Clark, Jr. | |
| 4,986,271 A | 1/1991 | Wilkins et al. | |
| 5,091,991 A | 2/1992 | Briggs et al. | |
| 5,391,250 A | 2/1995 | Cheney et al. | |
| 5,443,080 A | 8/1995 | D'Angelo et al. | |
| 5,494,562 A | 2/1996 | Maley et al. | |
| 5,628,310 A * | 5/1997 | Rao | A61B 5/0017 600/317 |
| 5,733,563 A | 3/1998 | Fortier | |
| 5,756,209 A | 5/1998 | Hale | |
| 5,804,048 A | 9/1998 | Wong et al. | |
| 5,964,993 A | 10/1999 | Blubaugh, Jr. et al. | |
| 6,001,067 A | 12/1999 | Shults et al. | |
| 6,074,607 A | 6/2000 | Slovacek et al. | |
| 6,121,508 A | 9/2000 | Bischof et al. | |
| 6,172,261 B1 | 1/2001 | Vermeulin et al. | |
| 6,249,638 B1 | 6/2001 | Hale | |
| 6,325,978 B1 | 12/2001 | Labuda et al. | |
| 6,340,588 B1 | 1/2002 | Nova et al. | |
| 6,343,225 B1 | 1/2002 | Clark, Jr. | |
| 6,387,379 B1 | 5/2002 | Goldberg et al. | |
| 6,679,841 B2 | 1/2004 | Bojan et al. | |
| 6,721,587 B2 | 4/2004 | Gough | |
| 6,741,877 B1 | 5/2004 | Shults et al. | |
| 6,771,860 B2 | 8/2004 | Trezza et al. | |
| 6,773,703 B1 | 8/2004 | Ettner | |
| 6,818,018 B1 | 11/2004 | Sawhney | |
| 6,893,552 B1 | 5/2005 | Wang et al. | |
| 6,960,031 B2 | 11/2005 | McFarland et al. | |
| 7,054,514 B2 * | 5/2006 | Uchiyama | A61B 5/14525 385/12 |
| 7,146,203 B2 | 12/2006 | Botvinick et al. | |
| 7,160,923 B1 | 1/2007 | Vermeulin et al. | |
| 7,248,912 B2 | 7/2007 | Gough | |
| 7,336,984 B2 | 2/2008 | Gough | |
| 7,405,055 B2 | 6/2008 | Dunn et al. | |
| 7,413,781 B2 | 8/2008 | Hubbell et al. | |
| 7,625,862 B2 | 12/2009 | Winslow et al. | |
| 7,721,412 B2 | 5/2010 | Say et al. | |
| 7,725,149 B2 | 5/2010 | Peyser et al. | |
| 7,783,399 B1 | 8/2010 | Young et al. | |
| 7,813,780 B2 | 10/2010 | Shah et al. | |
| 7,860,354 B2 | 12/2010 | Uematsu et al. | |
| 7,873,399 B2 | 1/2011 | Berner et al. | |
| 7,935,499 B2 | 5/2011 | Dunn et al. | |
| 7,989,414 B2 | 8/2011 | Winslow et al. | |
| 8,377,868 B2 | 2/2013 | Winslow et al. | |
| 8,543,182 B2 | 9/2013 | Botvinick et al. | |
| 9,034,893 B2 | 5/2015 | Shafer et al. | |
| 9,060,742 B2 | 6/2015 | Brister et al. | |
| 9,357,952 B2 | 6/2016 | Botvinick et al. | |
| 10,695,000 B2 | 6/2020 | Bremer | |
| 11,160,474 B2 | 11/2021 | Botvinivk et al. | |
| 2002/0151772 A1* | 10/2002 | Polak | A61B 5/14532 600/310 |
| 2002/0161286 A1* | 10/2002 | Gerber | A61B 5/14532 600/310 |
| 2003/0032874 A1 | 2/2003 | Rhodes et al. | |
| 2003/0050542 A1* | 3/2003 | Reihl | A61B 5/1459 600/316 |
| 2003/0180365 A1 | 9/2003 | Barnikol | |
| 2003/0180942 A1 | 9/2003 | Van Der Merwe et al. | |
| 2004/0180391 A1 | 9/2004 | Gratzl et al. | |
| 2005/0059871 A1* | 3/2005 | Gough | A61B 5/14865 600/347 |
| 2005/0098431 A1 | 5/2005 | Hodges | |
| 2005/0148003 A1* | 7/2005 | Keith | G01N 21/6428 435/6.11 |
| 2006/0224108 A1 | 10/2006 | Brauker et al. | |
| 2006/0247423 A1 | 11/2006 | Su et al. | |
| 2006/0251694 A1 | 11/2006 | Nielsen et al. | |
| 2007/0270674 A1* | 11/2007 | Kane | A61B 5/14546 600/315 |
| 2007/0276088 A1 | 11/2007 | Maynard et al. | |
| 2008/0186483 A1* | 8/2008 | Kiesel | G01N 21/31 356/246 |
| 2009/0149857 A1 | 6/2009 | Culbert et al. | |
| 2009/0156917 A1* | 6/2009 | Martini | A61B 5/14532 600/341 |
| 2009/0311235 A1 | 12/2009 | Elenko et al. | |
| 2011/0043727 A1 | 2/2011 | Bösl et al. | |
| 2011/0184265 A1 | 7/2011 | Hayter | |
| 2011/0250445 A1 | 10/2011 | Alderson et al. | |
| 2012/0059232 A1* | 3/2012 | Gross | A61B 5/14532 600/316 |
| 2012/0078204 A1 | 3/2012 | Jackson et al. | |
| 2012/0197206 A1 | 8/2012 | Glenn | |
| 2012/0226118 A1 | 9/2012 | Delbeke et al. | |
| 2012/0226122 A1 | 9/2012 | Meuniot et al. | |
| 2013/0060107 A1 | 3/2013 | Crane et al. | |
| 2013/0150970 A1 | 6/2013 | Thaiyananthan | |
| 2013/0172699 A1 | 7/2013 | Rebec | |
| 2013/0211213 A1* | 8/2013 | DeHennis | A61B 5/0031 600/316 |
| 2013/0331667 A1* | 12/2013 | Colvin, Jr. | A61B 5/1459 600/316 |
| 2013/0338342 A1 | 12/2013 | Komatsu et al. | |
| 2013/0338569 A1 | 12/2013 | Tsai et al. | |
| 2014/0011760 A1 | 1/2014 | Xu et al. | |
| 2014/0018644 A1* | 1/2014 | Colvin, Jr. | A61B 5/14556 600/316 |
| 2014/0060145 A1* | 3/2014 | Hoss | G01N 33/48792 73/1.03 |
| 2014/0171759 A1* | 6/2014 | White | A61B 5/4875 600/306 |
| 2014/0200431 A1 | 7/2014 | Jamieson et al. | |
| 2014/0275869 A1* | 9/2014 | Kintz | A61B 5/1459 600/310 |
| 2014/0286875 A1 | 9/2014 | Gamsey et al. | |
| 2014/0364707 A1 | 12/2014 | Kintz et al. | |
| 2016/0270703 A1 | 9/2016 | Botvinick et al. | |
| 2016/0278646 A1* | 9/2016 | Hu | A61B 5/7475 |
| 2017/0238856 A1* | 8/2017 | Botvinick | A61B 5/4845 |
| 2019/0083037 A1 | 3/2019 | Bremer | |
| 2020/0352511 A1 | 11/2020 | Bremer | |
| 2022/0079474 A1 | 3/2022 | Botvinick et al. | |

FOREIGN PATENT DOCUMENTS

| | | |
|---|---|---|
| WO | WO 2005/062765 | 7/2005 |
| WO | WO 2010022391 | 2/2010 |
| WO | WO 2010/151592 | 12/2010 |
| WO | WO 2012/148832 | 11/2012 |
| WO | WO 2013/028784 | 2/2013 |
| WO | WO 2013/090882 | 6/2013 |
| WO | WO 2014/006215 | 1/2014 |
| WO | WO 2015/076991 | 5/2015 |
| WO | WO 2017/040849 | 3/2017 |

OTHER PUBLICATIONS

Alvord, Larry. "Oxygen Permeability of a New Type of High Dk Soft Contact Lens Material". Optometry and Vision Science, vol. 75, No. 1, pp. 30-36. Jan. 1998.

European Search Report dated Mar. 25, 2019 for Application No. 16843019.7, filed Mar. 8, 2018.

(56) References Cited

OTHER PUBLICATIONS

International Search Report and Written Opinion dated Jan. 24, 2017 for PCT Application No. PCT/US2016/049989, filed Sep. 1, 2016.
Office Action dated Feb. 20, 2020 of related application EP 16 187 592.7.
Office Action dated Apr. 29, 2011, of related application EP 04814404. 2-1526.
Office Action dated Sep. 8, 2020 of related application 201680060436. 7. (Pursuant to 37 CFR 1.56(c) and 37 CFR 1.98, this is a foreign office action rejecting potentially-similar claims for lack of unity based on a combination of the D1-D3 references cited in the ISR).
Amao et al. 2001. Platinum tetrakis(pentafluorophenyl) porphyrin immobilized in polytrifluoroethylmethacrylate film as a photostable optical oxygen detection material, Journal of Fluorine Chemistry 107(1):101-106.

\* cited by examiner

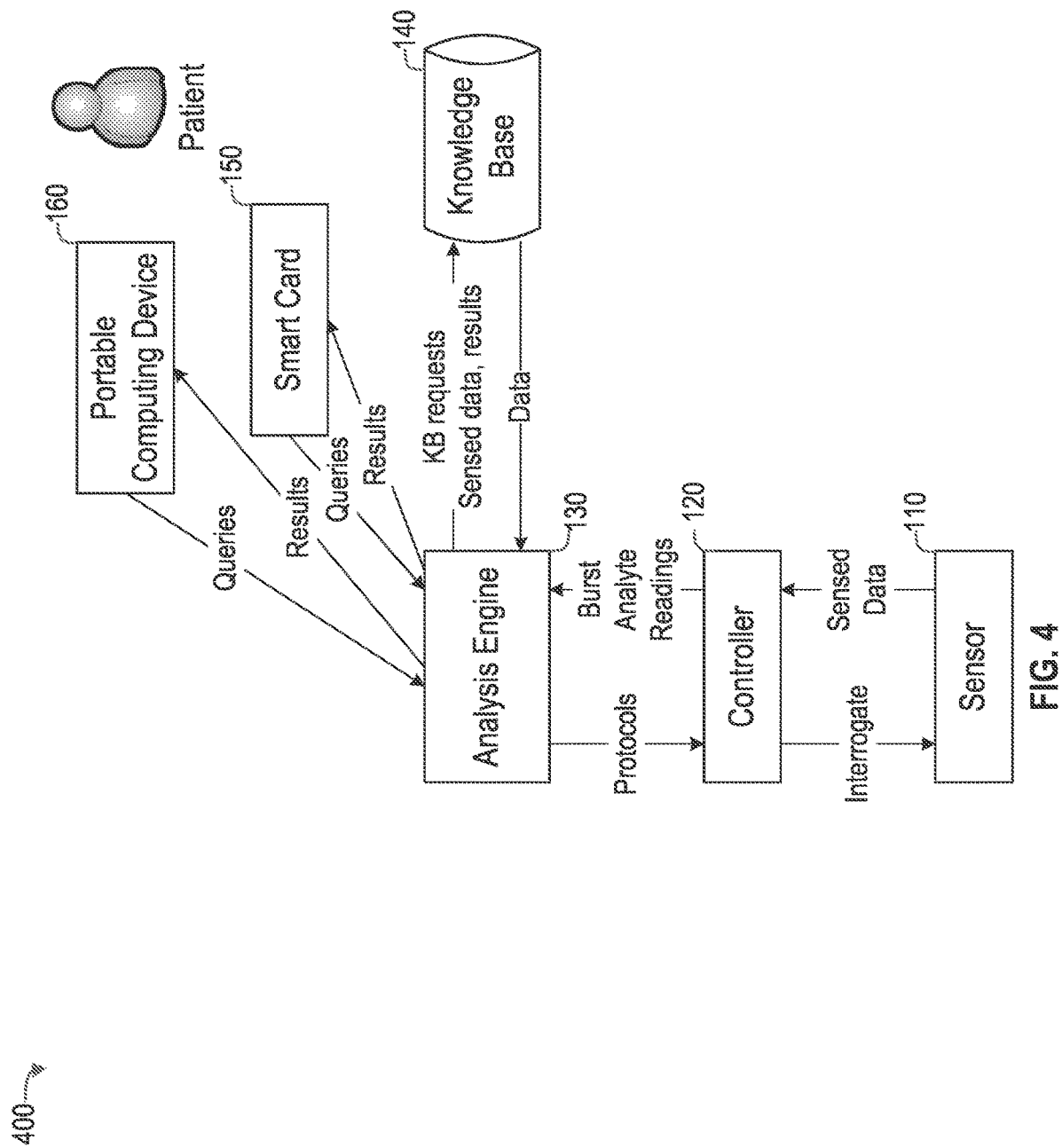

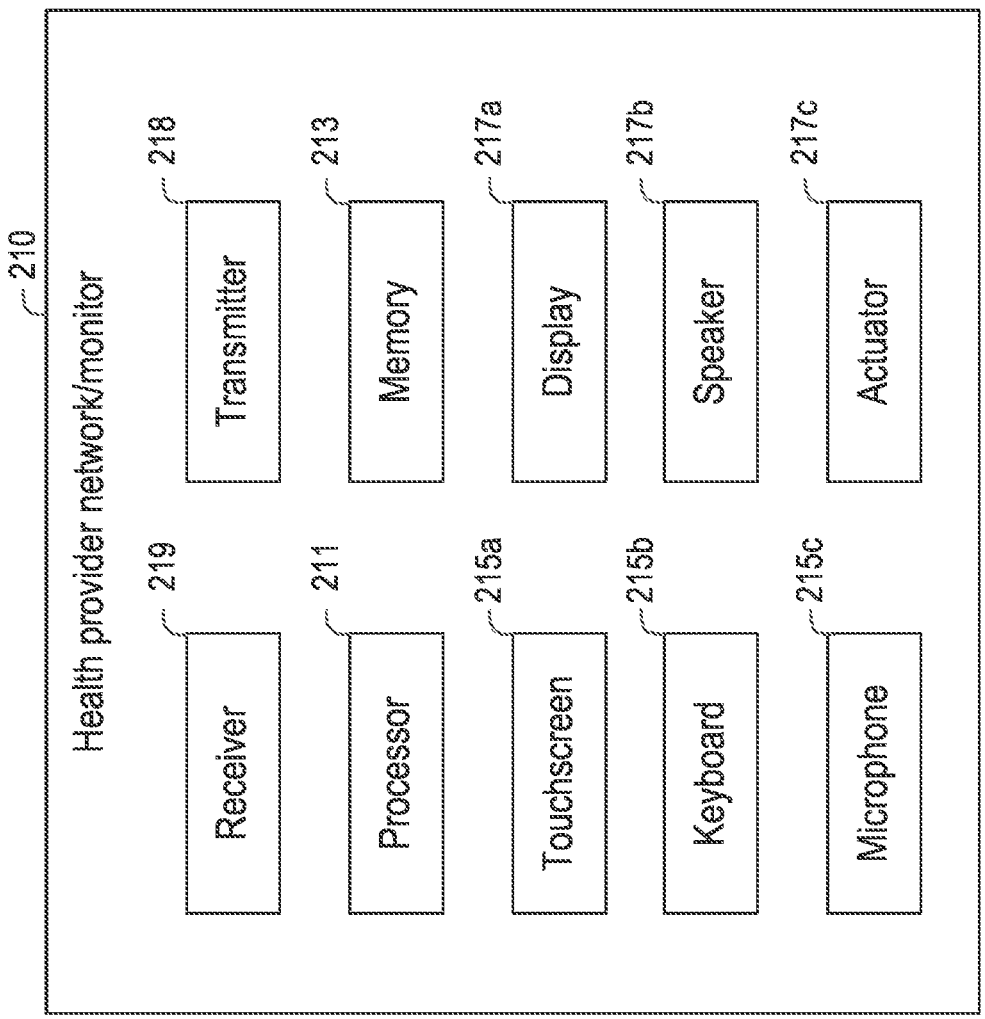
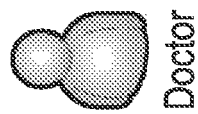
FIG. 11

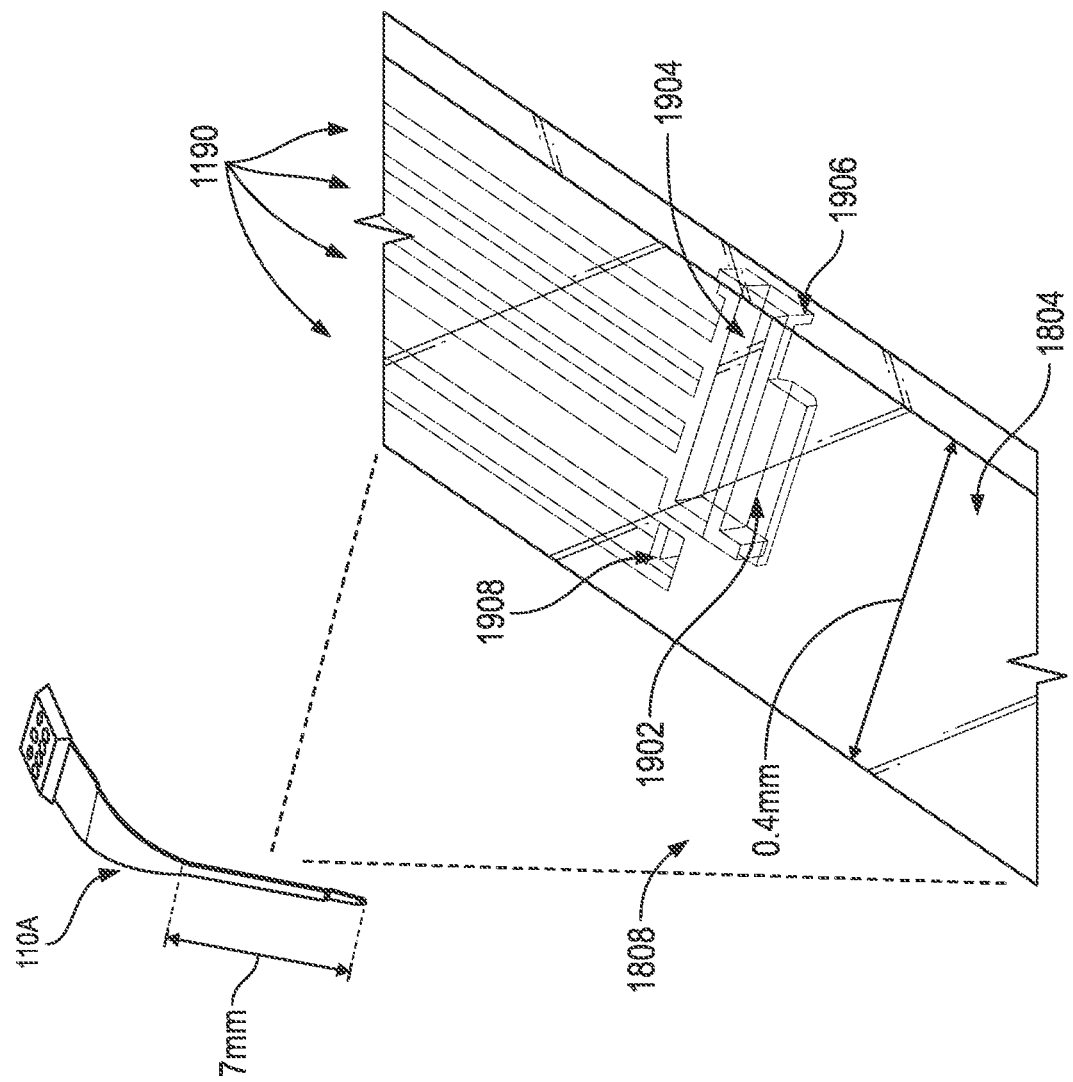

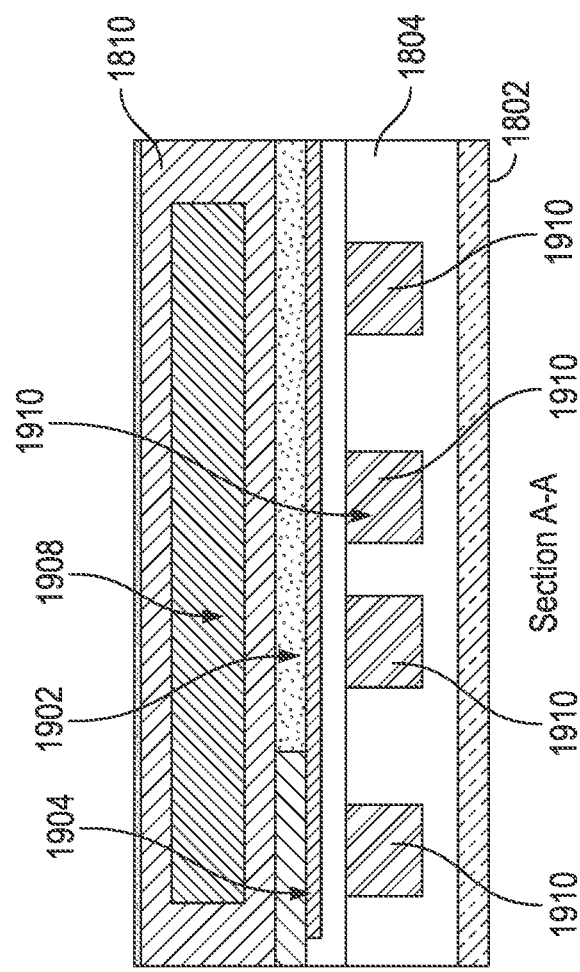
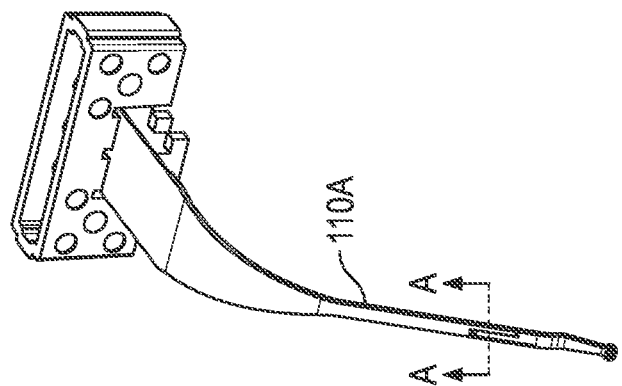
FIG. 20B

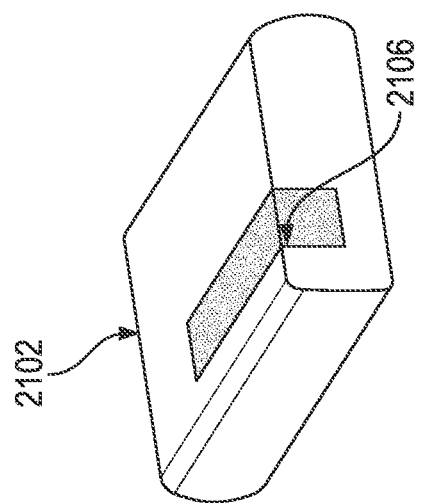
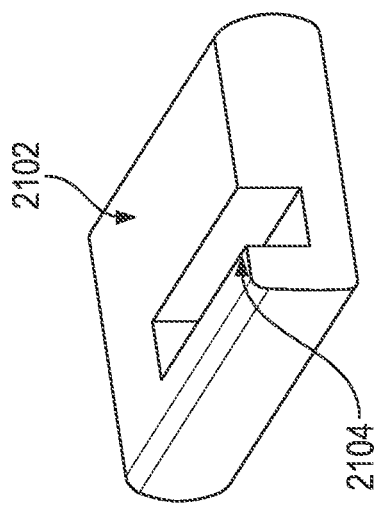
FIG. 21

| | N | MARD | 15/15 | 20/20 | 30/30 |
|---|---|---|---|---|---|
| Overall | 1641 | 9 | 83 | 94 | 98 |
| REF BG<80 mg/dl | 159 | 12.6* | 86 | 94 | 99 |
| REF BG 80-180 mg/dl | 430 | 10.2 | 74 | 90 | 97 |
| REF BG>180 mg/dl | 1052 | 7.9 | 86 | 95 | 99 |
| \|BG rate\| <=1 | 1043 | 8.6 | 86 | 95 | 99 |
| 1<\|BG rate\| <=2 | 411 | 9 | 80 | 93 | 99 |
| \|BG Rate\|>2 | 187 | 11.1 | 71 | 88 | 96 |

* MAD (REF BG<80) = 7.7 mg/dL

FIG. 27

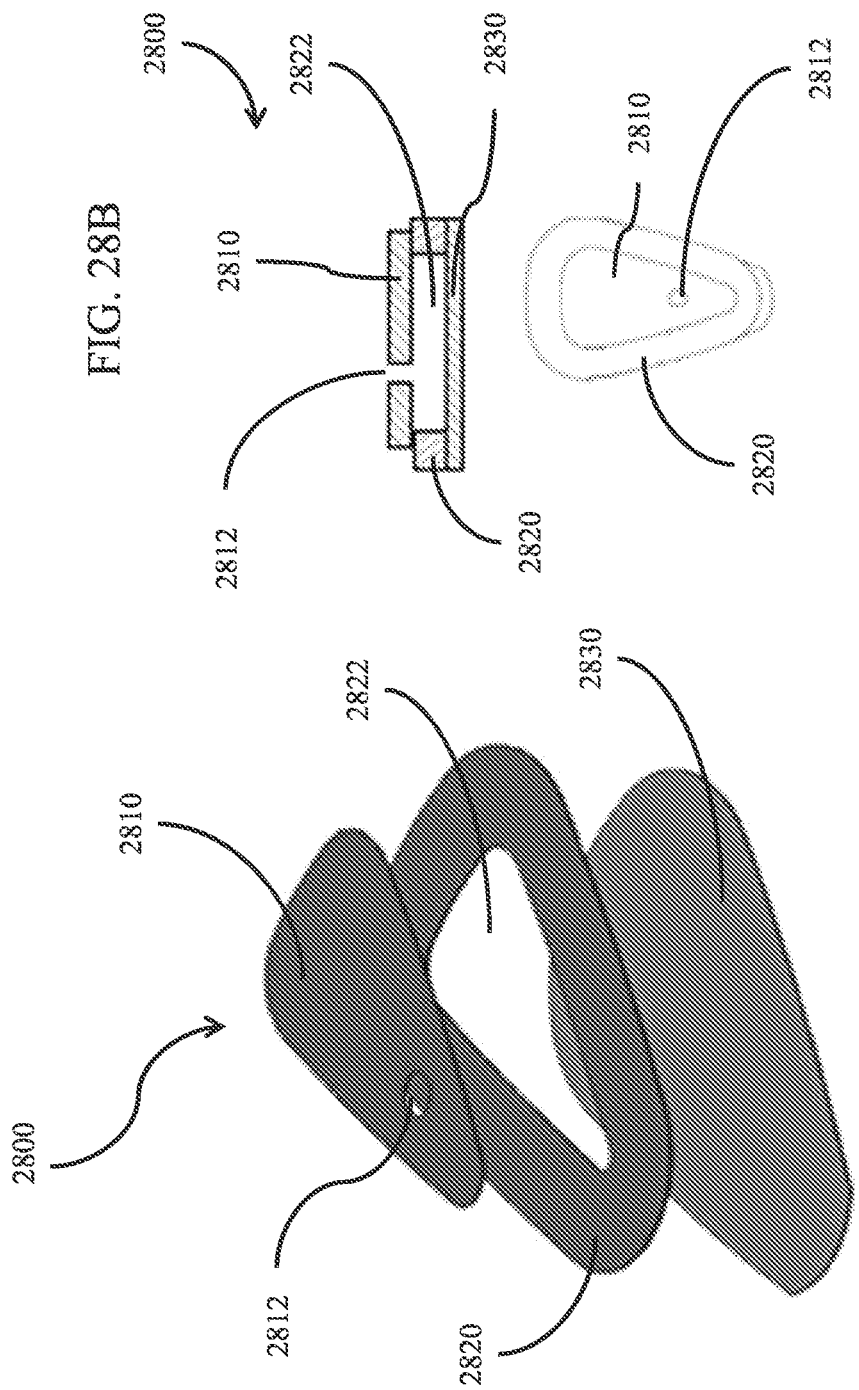

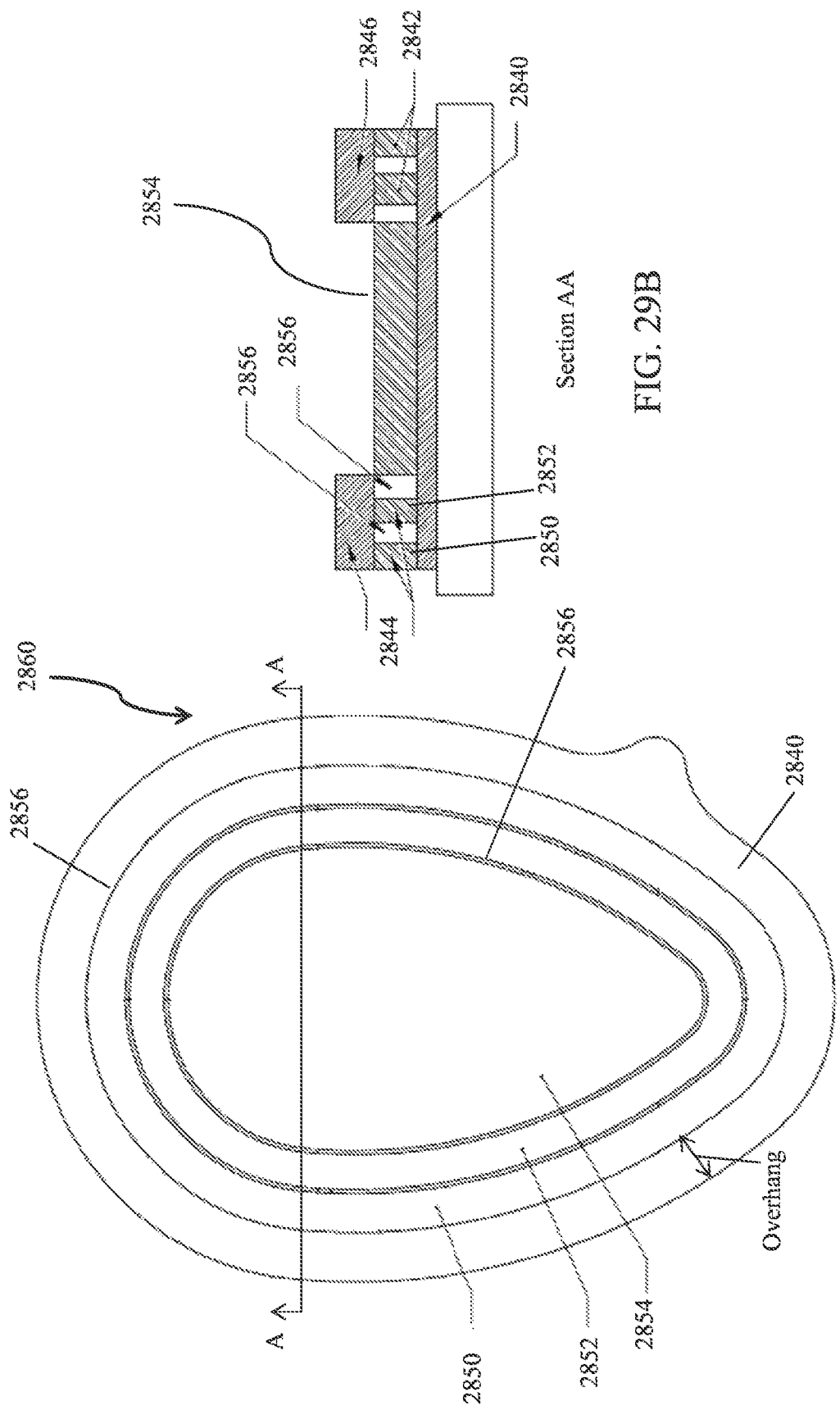

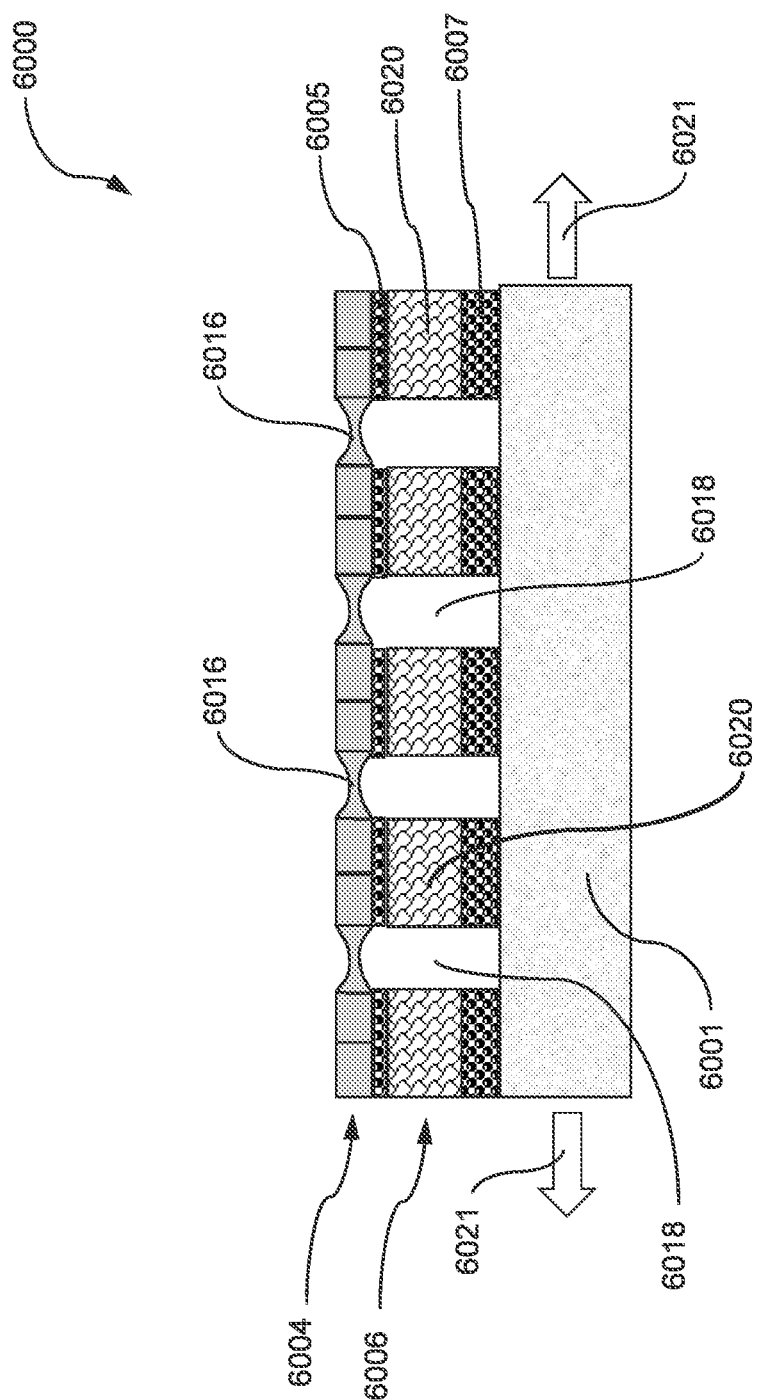

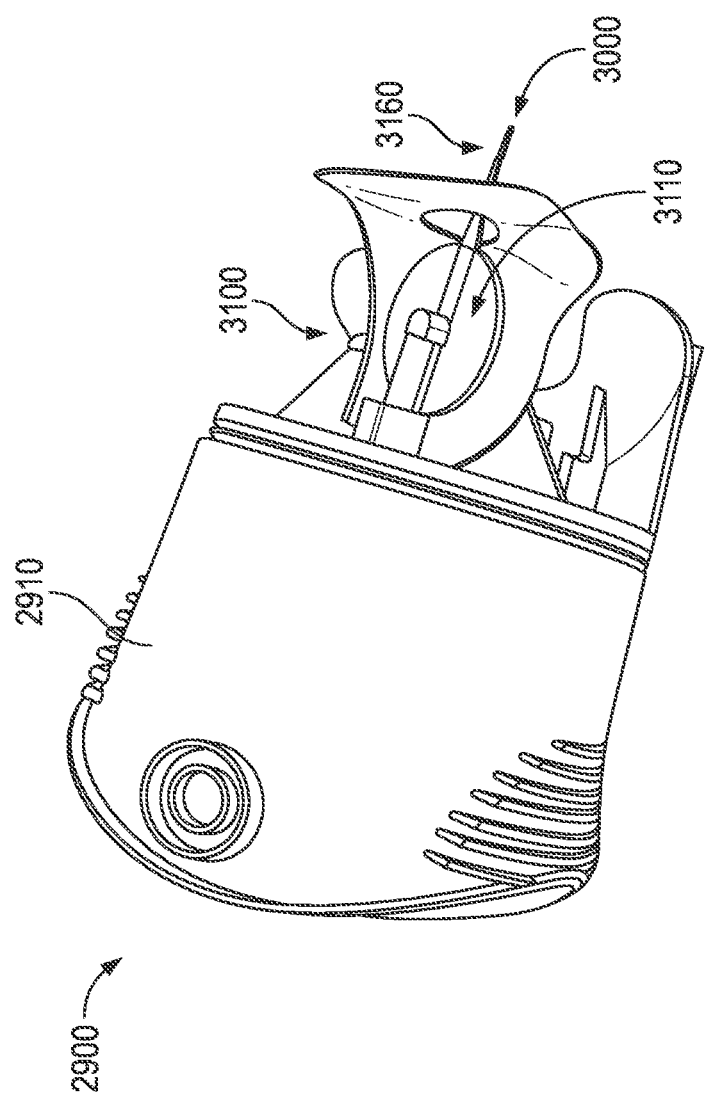

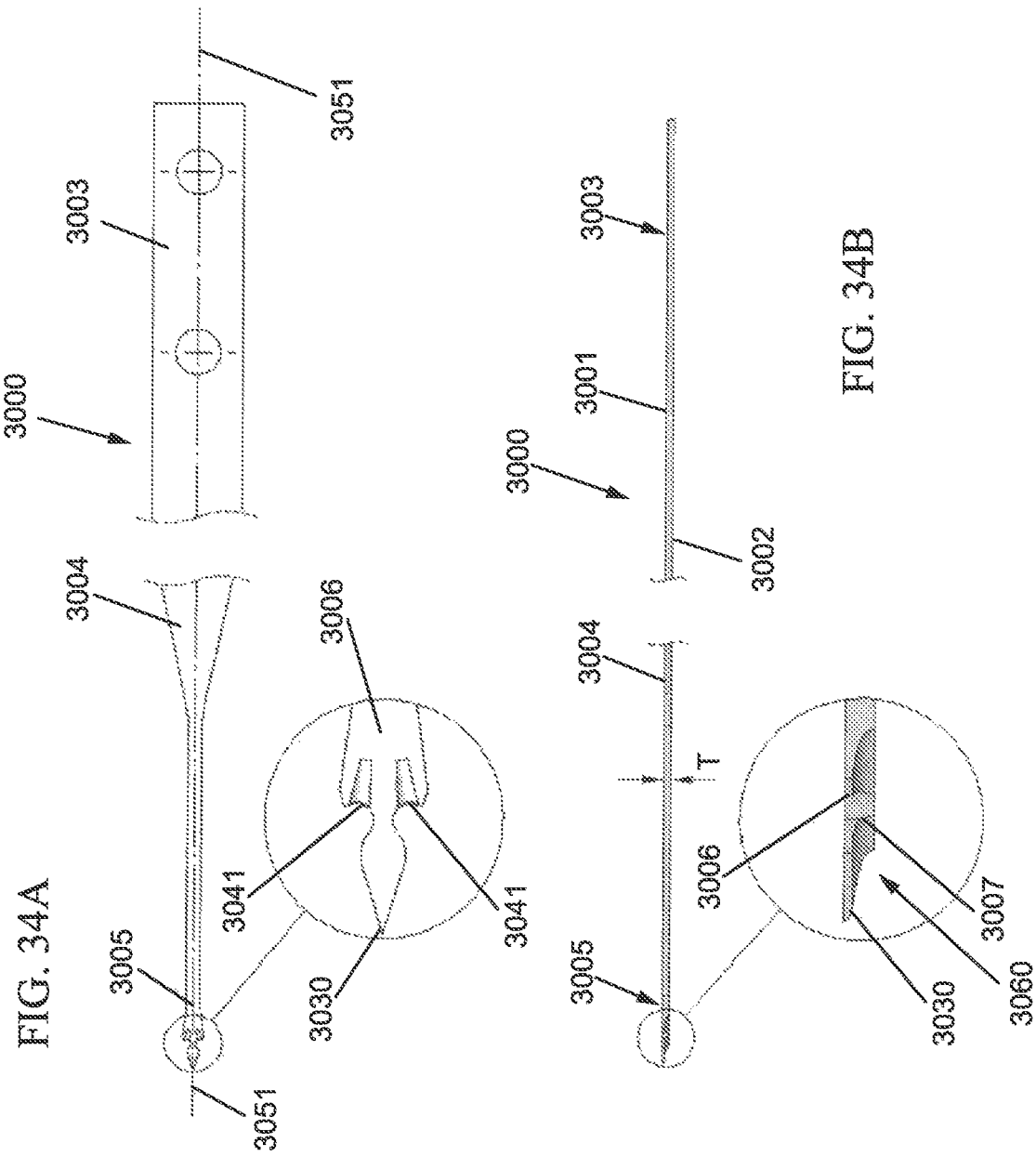

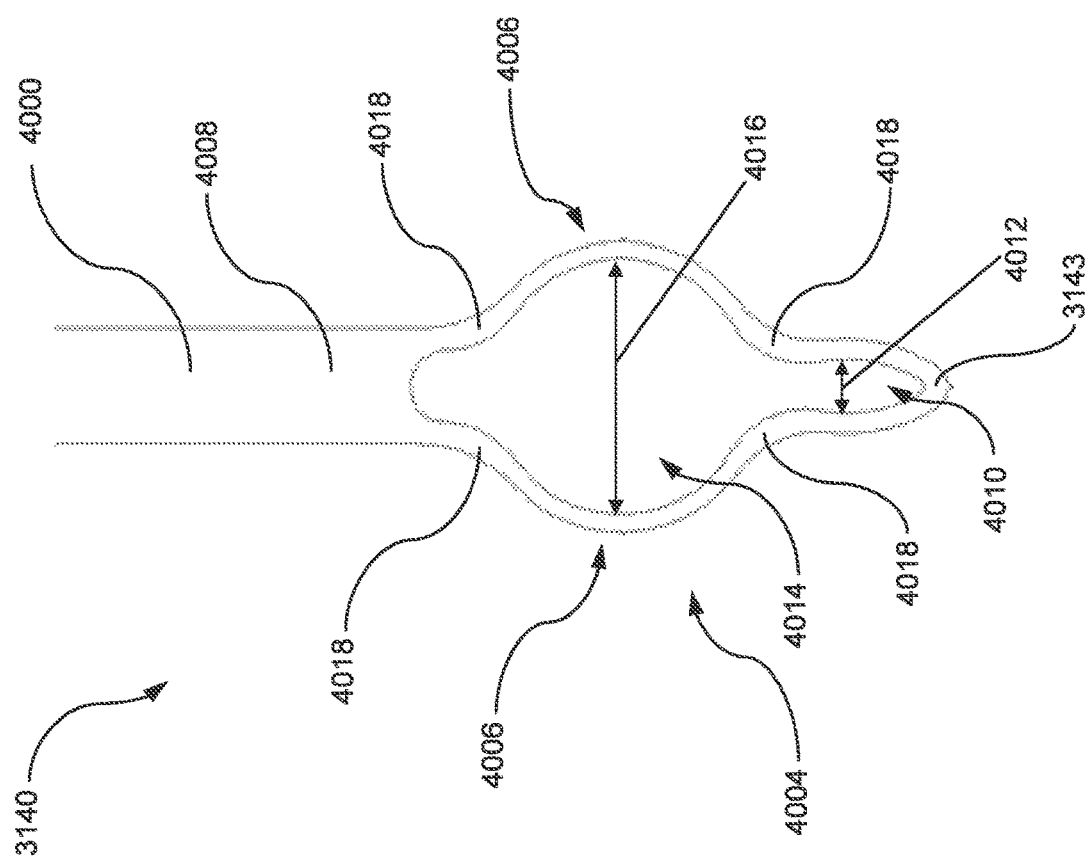

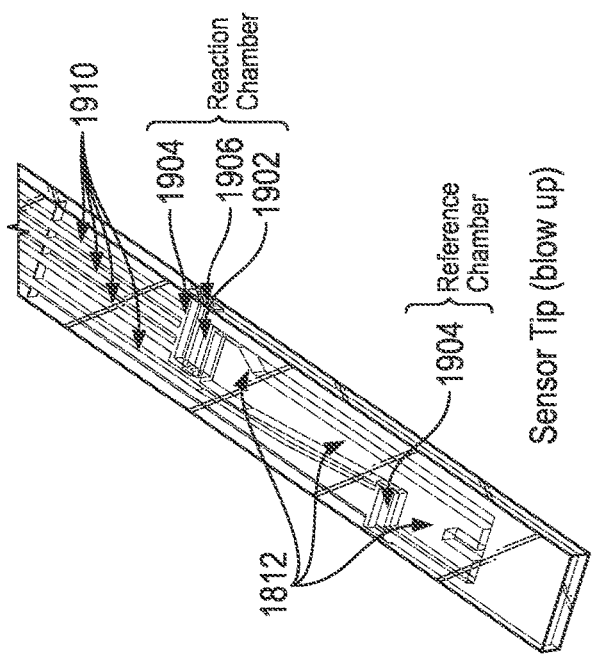
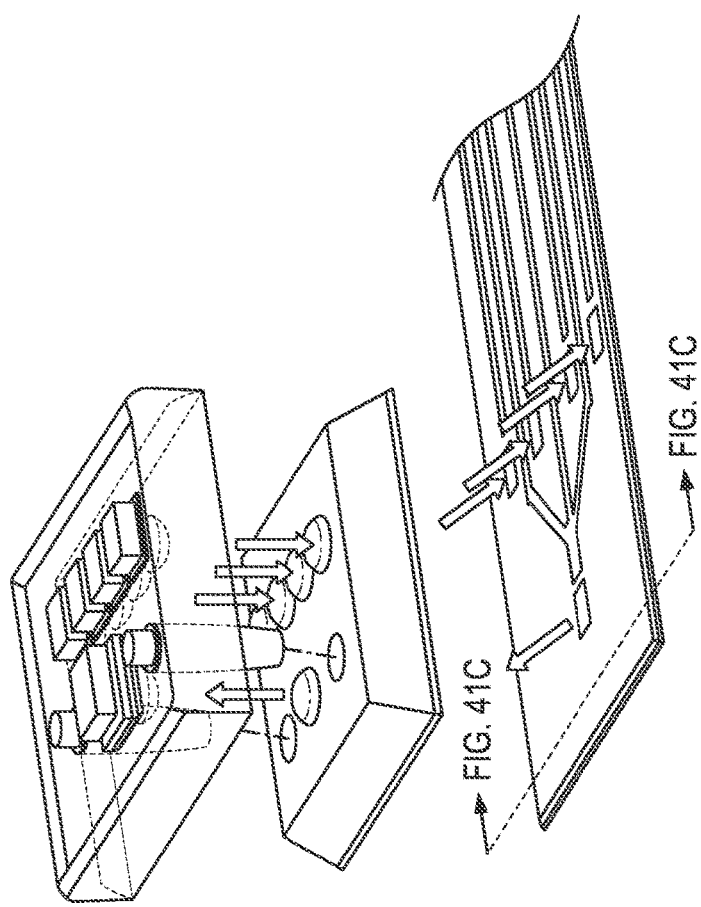
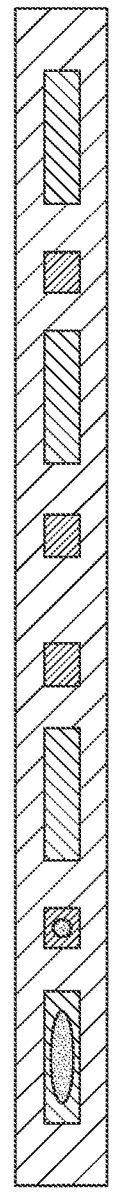
*FIG. 41A*
*FIG. 41B*
*FIG. 41C*

SYSTEMS AND METHODS FOR CONTINUOUS HEALTH MONITORING USING AN OPTO-ENZYMATIC ANALYTE SENSOR

RELATED APPLICATIONS

This application claims the benefit of U.S. Provisional Application No. 62/213,570, filed Sep. 2, 2015, the entire contents of which are incorporated herein by reference in their entirety for all purposes.

BACKGROUND

Field

The disclosed and described technology relates generally to: (1) continuous health monitoring, and more specifically to methods and systems for continuous health monitoring using an analyte sensor, an analysis engine, and a knowledge base; (2) opto-enzymatic analyte sensors, such as, for example, layered glucose sensors; (3) systems and methods for adhering a medical device to the skin of a patient (4) devices and methods for transdermally inserting a sensor for a continuous glucose monitoring system; (5) optical communication between an opto-enzymatic sensor implanted in a patient and a controller adhered to a patient's skin; and (6) optical enzymatic analyte sensors, such as, for example, glucose sensors, using waveguides with separate emission and excitation paths to a target material.

Description of the Related Technology

Diabetes is a disease of insufficient blood glucose regulation. In non-diabetic people, the body's beta cells monitor glucose and deliver just the right amount of insulin on, for example, a minute-by-minute basis for tissues in the body to uptake the right amount of glucose, keeping blood glucose at healthy levels. In diabetic patients, this regulation primarily fails due to: 1) insufficient insulin production and secretion, and/or 2) a lack of normal sensitivity to insulin by the tissues of the body. Glucose sensors can be used to monitor glucose levels in diabetic patients allowing proper dosing of diabetic treatments, including, for example, insulin.

More generally, analyte tracking and monitoring enable improved monitoring, diagnosis, and treatment of diseases, including diabetes. Existing methods to measure, monitor, and track analyte levels, may include sampling a bodily fluid, preparing the sample for measurement, and estimating the analyte level in the sample. For example, a diabetic may prick a finger to obtain a blood sample to measure glucose in a glucose monitoring unit. Such existing methods may be painful, unpleasant or inconvenient for the patient, resulting in lower compliance with physician orders to, for example, take glucose readings at certain times each day or based on patient activity. Moreover, effective monitoring, diagnosis, and treatment may benefit from fusing multiple sensor readings that measure different aspects of a patient's state. Readings from one or more analyte sensors, as well as other bio sensor systems and/or activity sensors may be combined with past readings to determine results that characterize a patient's state, and may be used to monitor, diagnose, and treat a patient. For example, an alarm may be triggered if a patient's glucose level exceeds a threshold.

Accordingly, there is a need for analyte sensors (1) that do not require unpleasant blood draws or sample preparation if measurements are to be taken multiple times each day, (2) to be sufficiently selective, sensitive, and to provide repeatable and reproducible measurements, and (3) that are stable with low drift. There is also a need for controllers that may interrogate sensors based on protocols that define sampling timing, duration, and frequency.

Moreover, there is a need for analysis engines or tools (1) to analyze raw sensor readings and determine various results including, for example, sensor readings including analyte levels, trends, and alarms, (2) to incorporate past readings and patient history from a knowledge base, (3) to incorporate patient activity data, so that sensor readings may be correlated with and analyzed based on activities, enabling, for example, alarm conditions that vary with patient activity levels, and (4) to incorporate and fuse data from other bio sensors, which measure other aspects of a patient's condition.

Additionally, there is a need for analysis engines to (1) receive and accept orders and instructions from a physician, via a network, so that the orders and instructions may be converted to protocols that set sensor operating parameters and reading requirements (for example, a protocol to a controller that increases frequency or reduces the duration of a reading), (2) accept queries from physicians over a network, or from patients over a portable computing device (for example, a smart phone), for results of data that has been taken, or to modify a protocol, and (3) transmit results to a physician, as well as to a patient or caretaker.

Analyte sensors, such as glucose sensors, can produce a digital electronic signal that depends on the concentration of a specific chemical or set of chemicals (analyte) in bodily fluid or tissue. The sensor usually includes two main components, (1) a chemical or biological part that reacts or complexes with the analyte in question to form new chemical or biological products or changes in energy that can be detected by means of the second component and (2) a transducer. The first component (chemical or biological) can be said to act as a receptor/indicator for the analyte. For the second component, a variety of transduction methods can be used including, for example, electrochemical (such as potentiometric, amperometric, conductimetric, impedimetric), optical, calorimetric, and acoustic. After transduction, the signal is usually converted to an electronic digital signal that corresponds to a concentration of a particular analyte. Example analytes that can be measured using the embodiments of the inventions disclosed and described herein include, and are not limited to, glucose, galactose, fructose, lactose, peroxide, cholesterol, amino acids, alcohol, lactic acid, and mixtures of the foregoing.

The disclosed technology integrates an innovative analyte sensor, controlled by a controller, with an analysis engine that incorporates historical data and protocols from a knowledge base, bio sensor data from a biological sensor system, and activity data from an activity sensor system/database to generate results for measuring, monitoring and diagnosing a patient. The disclosed technology details embodiments of a laminate optical analyte sensor, methods for manufacturing it, systems and methods for inserting it, and systems and methods for adhering a medical device on the skin of a patient, such as a controller in communications with the sensor.

SUMMARY

Methods and apparatuses or devices being disclosed herein each have several aspects, no single one of which is solely responsible for its desirable attributes. Without limiting the scope of this disclosure, for example, as expressed by the claims which follow, its more prominent features will now be discussed briefly. After considering this discussion, and particularly after reading the section entitled "Detailed Description," one will understand how the features being disclosed and described provide advantages that include monitoring, diagnosing, and treating a patient using results obtained from an analyte sensor.

Certain embodiments described herein pertain to continuous glucose monitors, components thereof, and methods of making the same. In some embodiments, methods of preparing a component layers for a sensor tip for a glucose monitoring device are described. In some embodiments, the methods pertain to fabricating a sensor tip that is small enough to be inserted subcutaneously into a patient. In some embodiments, the sensor tip comprises an oxygen conduit, an enzymatic layer, and a sensing layer.

Systems and methods for continuous health monitoring are disclosed. One aspect is a system including a sensor implanted in a patient. The sensor transduces an interstitial analyte concentration to a measure, and communicates the measure when interrogated with visible light. The system includes a controller affixed to a patient's skin. The controller interrogates the sensor with visible light, receives the measure, determines when to interrogate the sensor, stores measures of the analyte concentration, and transmits the measures in bursts. The system includes a knowledge base that stores the measures. The system includes an analysis engine that transmits interrogation protocols, receives the plurality measures, determines a result based on the measures, and transmits the result. The system includes a display device selected from a smart card, a portable computing device or both, that may display results, display system component status, and/or accept queries from a patient or provider.

Embodiments of a layered optical sensor are disclosed. The optical sensor can be formed by laminating a plurality of sheets together to form a final sensor. Further, bossing and embossing and capillary filling can be used to form sensor components within the optical sensor. Also disclosed herein are embodiments of a method of mass manufacturing optical sensors.

Systems are disclosed for an adhesive system for attaching an optical sensor-transmitter system. In one example, the adhesive system is for adhering a medical device to the skin of a patient. The adhesive system can include an outside layer, wherein the outside layer is elastic and re-sealable to the skin of the patient. The outside layer can be configured to form a ring. The adhesive system can include an inside layer, wherein the inside layer is composed of a material with a high moisture vapor transmission rate. The inside layer can be joined with the outside layer such that a small gap is formed between the inside layer and the outside layer.

Methods and systems are disclosed for an inserter system for a minimally invasive tissue implant. As will be readily apparent to those skilled in the art, the methods and inserted systems disclosed herein are equally applicable for use with, for example, biosensors, micro catheters and drug eluting implants. In some embodiments, the inserter system is for use with as continuous glucose monitoring system. In one example, the system for sensor implantation can include an inserter and a sensor. The inserter can include a lancet tip that includes a convex feature attached to a first surface of the lancet tip. The inserter can also include an inset on either side of the lancet tip. The sensor can include a distal end that is configured to form a loop. The loop is configured to pass around the insets of the lancet tip, with a portion of the loop positioned adjacent the convex feature.

One aspect discloses a continuous health monitoring system. The system may include a sensor, configured to be implanted in a patient, the sensor configured to transduce a concentration of an analyte to a measure of the analyte concentration, the sensor further configured to communicate the measure of the analyte concentration when the sensor is interrogated with visible light. The system may include a controller, configured to be affixed to skin of the patient, the controller in optical communication with the sensor, the controller further configured to interrogate the sensor with visible light, the controller further configured to receive the measure of the analyte concentration, the controller further configured to determine a frequency, a timing, and/or a duration of interrogating the sensor in response to a protocol, the controller configured to store a plurality of measures of the analyte concentration, the controller configured to transmit the plurality of measures of the analyte concentration. The system may include a knowledge base configured to store the plurality of measures of the analyte concentration. The system may include an analysis engine in communication with the controller and the knowledge base, the analysis engine configured to transmit the protocol to the controller, the analysis engine configured to receive the plurality of measures of the analyte concentration, the analysis engine further configured to determine a result in response to the plurality of measures of the analyte concentration, the analysis engine further configured to transmit the result. The system may include a display device selected from a smart card, a portable computing device or both. The smart card may be in communication with the analysis engine. The smart card may be configured to display the result. The smart card may be configured to display a status of the sensor, the controller, and/or the analysis engine. The portable computing device may be configured to display the result, and optionally a status of the sensor, the controller, and/or the analysis engine. The portable computing device may be configured to accept a query.

In an embodiment, the analyte is glucose. In an embodiment, the knowledge base includes a memory unit, the memory unit configured to store a patient identifying information, patient history information, patient condition information, sensed data readings, results, trends, patterns, normal levels, ranges, alert conditions, alerts, mapping of an order to a protocol, mapping of a query to a protocol, sensor calibration data, and/or analysis support data.

In an embodiment, the result is a glucose level, a glycemic history, a glycemic dynamics envelope, insulin levels, and/or normative glycemic profiles with insulin overlay.

In an embodiment, the system includes an activity sensor system comprised to estimate an activity of the patient, wherein the activity comprises at least one of sleeping, walking, strenuous exercise, and eating.

In an embodiment, the system includes a bio sensor system comprised to measure a biological factor of the patient, the biological factor at least one of another analyte concentration, a pulse rate, a systolic pressure, a diastolic pressure, and/or a temperature.

In an embodiment, the analysis engine is in communication with the activity sensor system, wherein the analysis engine is in communication with the bio sensor system, and wherein the analysis system is configured to determine a result in response to the activity, the analyte concentration, the estimated activity, the biological factor, and/or data from the knowledge base.

In an embodiment, the system includes an interface to a network, the analysis engine in communication with the network, the analysis engine configured to transmit a result via the interface to a health care provider network/monitor, the analysis engine configured to receive an order via the interface from the health care provider network/monitor, wherein the knowledge base is configured to map the order to the protocol.

In an embodiment, the portable communication device runs a software application (app) that when executed is configured to display the result determined by the analysis engine, the result comprising a level, a pattern and/or a trend in response to the analyte concentration. The application is configured to display a status of the sensor, the controller, the knowledge base, and/or the analysis engine. The application is configured to display an alert, wherein display includes at least one of a visual display, an audio display, and a tactile display. The application is configured to accept a query, the query comprising at least one of displaying sensed data, displaying the result, displaying the alert, displaying data from the knowledge base, requesting an analysis, and/or requesting a protocol to sense the analyte concentration.

Another aspect is a method for continuous health monitoring. The method includes transducing, by a sensor implanted in a patient, a concentration of an analyte to a measure of the analyte concentration. The method includes interrogating, by a controller affixed to skin of the patient, the sensor with visible light. The method includes communicating, by the sensor, the measure of the analyte concentration in response to the interrogating with visible light. The method includes receiving, by the controller, the measure of the analyte concentration. The method includes determining, by the controller, a frequency, a timing, and/or a duration of interrogating the sensor in response to a protocol. The method includes storing, by the controller, a plurality of measures of the analyte concentration. The method includes transmitting, by the controller, the plurality of measures of the analyte concentration. The method includes storing, by a knowledge base, the plurality of measures of the analyte concentration. The method includes transmitting, by an analysis engine, the protocol to the controller. The method includes receiving, by the analysis engine, the plurality of measures of the analyte concentration. The method includes determining, by the analysis engine, a result in response to the plurality of measures of the analyte concentration.

In an embodiment the method may include transmitting, by the analysis engine, the result, to a smart card or a portable computer device. In an embodiment the method may include displaying, by the smart card, the result, and/or a status of the sensor, the controller, and/or the analysis engine. In an embodiment the method may include displaying, by the portable computer device, the result. In an embodiment, the method may include accepting, by the portable computer device, a query.

In an embodiment, the method may include estimating, by an activity sensor system, an activity of the patient, wherein the activity comprises at least one of sleeping, walking, strenuous exercise, and eating.

In an embodiment, the method may include measuring, by a bio sensor system, a biological factor of the patient, the biological factor at least one of another analyte concentration, a pulse rate, a systolic pressure, a diastolic pressure, and/or a temperature.

In an embodiment, the method may include determining a second result in response to the activity, the analyte concentration, the estimated activity, the biological factor, and/or data from the knowledge base.

In an embodiment, the method may include transmitting the result and/or the second result via an interface to a health care provider network/monitor. In an embodiment, the method may include receiving an order from the health care provider network/monitor. In an embodiment, the method may include mapping the order to the protocol.

In an embodiment, the method may include displaying, by the portable communication device, the result comprising a level, a pattern and/or a trend in response to the analyte concentration. In an embodiment, the method may include displaying, by the portable communication device, a status of the sensor, the controller, the knowledge base, and/or the analysis engine. In an embodiment, the method may include displaying, by the portable communication device, an alert, wherein displaying includes at least one of a visual display, an audio display, and a tactile display. In an embodiment, the method may include accepting, by the portable communication device, a query, the query comprising at least one of displaying sensed data, displaying the result, displaying the alert, displaying data from the knowledge base, requesting an analysis, and/or requesting a protocol to sense the analyte concentration.

Another aspect is a non-transitory computer-readable medium storing instructions for continuous health monitoring, the instructions when executed that, when executed, perform a method. The method includes transducing, by a sensor implanted in a patient, a concentration of an analyte to a measure of the analyte concentration. The method includes interrogating, by a controller affixed to skin of the patient, the sensor with visible light. The method includes communicating, by the sensor, the measure of the analyte concentration in response to the interrogating with visible light. The method includes receiving, by the controller, the measure of the analyte concentration. The method includes determining, by the controller, a frequency, a timing, and/or a duration of interrogating the sensor in response to a protocol. The method includes storing, by the controller, a plurality of measures of the analyte concentration. The method includes transmitting, by the controller, the plurality of measures of the analyte concentration. The method includes storing, by a knowledge base, the plurality of measures of the analyte concentration. The method includes transmitting, by an analysis engine, the protocol to the controller. The method includes receiving, by the analysis engine, the plurality of measures of the analyte concentration. The method includes determining, by the analysis engine, a result in response to the plurality of measures of the analyte concentration. The method may include transmitting, by the analysis engine, the result, to a smart card or a portable computer device. The method may include displaying, by the smart card, the result, and/or a status of the sensor, the controller, and/or the analysis engine. The method may include displaying, by the portable computer device, the result. The method may include accepting, by the portable computer device, a query.

Another aspect is a controller for continuous health monitoring. The controller includes a laser source configured to emit a plurality of optical interrogation signals via an optical pathway to a sensor implanted percutaneously in a patient. As used herein, a "laser source" can be a laser or LED. The controller includes a detector configured to measure a plurality of luminescent emissions from the sensor, the luminescent emissions indicative of an interstitial analyte concentration of the patient. The controller includes a processor circuit in communication with the laser source and the detector, the processor circuit configured to determine a measure of analyte concentration based on the detected luminescent emissions. The controller includes a memory circuit in communication with the processor circuit configured to store the determined measure of analyte concentration. The controller includes a transmitter in communication with the processor circuit configured to transmit the measure of analyte concentration.

In an embodiment, the processor circuit is further configured to determine a frequency, a timing, and/or a duration for emitting the plurality of optical interrogation signals.

In an embodiment, the controller includes a receiver in communication with the processor circuit. The receiver may be configured to receive a protocol for determining the frequency, the timing, and/or the duration for emitting the plurality of optical interrogation signals. In an embodiment, the memory circuit is configured to store a plurality of determined measures of analyte concentrations determined during a time interval. In an embodiment, the transmitter is further configured to transmit the plurality of determined measures of analyte concentrations determined during the time interval in a burst transmission.

In an embodiment, the controller includes a temperature sensor configured to measure a temperature. In an embodiment, the processor is configured to determine if the temperature is within an operating limit for the sensor.

In an embodiment, the controller includes a battery configured to supply power to the processor circuit and the laser source.

In an embodiment, the controller includes an assembly configured to house the processor circuit, the memory circuit, the polymer housing, the temperature sensor, the receiver, the transmitter, and the battery. In an embodiment, the assembly is configured to flexibly conform to the patient. In an embodiment, the assembly is configured to be affixed to the patient. In an embodiment, the assembly is configured to be interconnected to the sensor via a connector and a sensor subassembly.

Another aspect is a method for continuous health monitoring. The method includes emitting, by a laser source, a plurality of optical interrogation signals via an optical pathway to a sensor implanted percutaneously in a patient. The method includes measuring, by a detector, a plurality of luminescent emissions from the sensor, the luminescent emissions indicative of an interstitial analyte concentration of the patient. The method includes determining, by a processor circuit, a measure of analyte concentration based on the detected luminescent emissions. The method includes storing, by a memory circuit, the determined measure of analyte concentration. The method includes transmitting, by a transmitter, the measure of analyte concentration.

In an embodiment, the method further includes determining, by the processor, a frequency, a timing, and/or a duration for emitting the plurality of optical interrogation signals.

In an embodiment, the method further includes receiving, by a receiver, a protocol for determining the frequency, the timing, and/or the duration for emitting the plurality of optical interrogation signals. In an embodiment, the method further includes storing, by the memory circuit, a plurality of determined measures of analyte concentrations determined during a time interval. In an embodiment, the method further includes transmitting, by the transmitter, the plurality of determined measures of analyte concentrations determined during the time interval in a burst transmission. In an embodiment, the method further includes measuring, by a temperature sensor, a temperature. In an embodiment, the method further includes determining if the temperature is within an operating limit for the sensor.

Another aspect is a non-transitory computer-readable medium storing instructions for continuous health monitoring, the instructions when executed that, when executed, perform a method. The method includes emitting, by a laser source, a plurality of optical interrogation signals via an optical pathway to a sensor implanted percutaneously in a patient. The method includes measuring, by a detector, a plurality of luminescent emissions from the sensor, the luminescent emissions indicative of an interstitial analyte concentration of the patient. The method includes determining, by a processor circuit, a measure of analyte concentration based on the detected luminescent emissions. The method includes storing, by a memory circuit, the determined measure of analyte concentration. The method includes transmitting, by a transmitter, the measure of analyte concentration.

The disclosed technology includes a laminate optical sensor, comprising a first (bottom) layer configured to provide support for the sensor, a second (middle) layer at least partially overlying the first layer, the second layer comprising a reaction region comprising an analyte inlet and a reaction chemistry immobilized therein, wherein the reaction chemistry is configured to react with the analyte in the presence of oxygen to generate product, wherein the concentration of product is related to the concentration of analyte entering the inlet, a sensing region in contact with the reaction region along an interface therebetween, wherein the interface is permeable to the product, the sensing region comprising a reporter compound configured to bind product, absorb light at a first wavelength, and emit light at a second wavelength, wherein the intensity and/or lifetime of light emitted is related to the amount of product bound, a reference region comprising the same reporter compound, but wherein the reference region is separated from the reaction region, and at least one waveguide in optical communication with each of the sensing region and the reference region, the waveguides being configured to deliver light at the first wavelength to the reporter compound and convey emission light from the reporter compound to a detector, and a third (top) layer at least partially overlying the second layer, the third layer comprising an oxygen conduit comprising a reversible oxygen binding protein stably incorporated therein, wherein the oxygen conduit is configured to deliver oxygen from outside the sensor to the reaction region and the reference region.

In some embodiments, the analyte can be glucose. In some embodiments, the sensor can comprise a plurality of second (middle) layers.

Some embodiments are directed to an active hydrogel compositions that can be used in the optical sensors disclosed herein. In some embodiments, the hydrogel composition is prepared as follows. A nanogel is dispersed in a liquid medium where the nanogel comprises a nanostructure that is covalently linked to a macromer and conjugated to a polymer network. A crosslinker is added to the nanogel dispersed in the liquid medium. Finally, crosslinking is performed to form the active hydrogel composition.

Additional embodiments are directed to a method of making nanogel particles. The method includes functionalizing a nanostructure with a nucleophilic species and then coupling the nanostructure with a hydrophilic polymer linked to a polymerizable unit via the nucleophilic species. Next, a macromere is covalently linked to the nanostructure and then the polymerizable-macromer linked-nanostructure is mixed with a crosslinking agent to form a nanostructure-crosslinking solution. The nanostructure-crosslinking solution is then cross-linked to form the nanogel particles.

Embodiments are also directed to a nanogel particle comprising covalently bonded albumin-hemoglobin(Hb)-PEG-acryl crosslinked with TEGDA, where Hb:albumin is present in a molar ratio range of about 20 to 1:1, PEG-acryl:albumin is present in a molar ratio range of about 40 to 4:1, and TEGDA:PEG is present in a molar ratio range of about 3 to 0.1:1.

In some embodiments, a nanogel particle comprising covalently bonded albumin-glucose oxidase (GOx)-catalase (CAT)-PEG-acryl crosslinked with HEMA, PEGMA and TEGDA is disclosed. In these embodiments, GOx:albumin is present in a molar ratio range of about 10 to 0.5:1, CAT:albumin is present in a molar ratio range of about 2 to 0.02:1, PEG-Acryl:Albumin is present in a molar ratio range of about 30 to 2:1, HEMA:Albumin is present in a molar ratio range of about 400 to 40:1, PEGMA:HEMA is present in a molar ratio range of about 10 to 2:1, and (HEMA+PEGMA):TEGDA is present in a molar ratio range of about 200 to 20:1.

Also disclosed herein are embodiments of a method of manufacturing an analyte sensor, comprising providing a base layer, bonding a middle layer to the base layer, the middle layer comprising an optical circuit void and a plurality of waveguides in optical communication with the optical circuit void, covering at least a portion of the optical circuit void of the middle layer with an embossing material, filling by capillary action the optical circuit void with a sensing polymer comprising an optical reporter, removing the embossing material thereby leaving a void in the sensing polymer, filling by capillary action the void in the sensing polymer with an enzymatic hydrogel, thereby forming the optical circuit, bonding a top layer to the middle layer, the top layer comprising an oxygen conduit void at least partially overlying the optical circuit, and filling the oxygen conduit void with a hydrogel matrix configured to transport oxygen.

Disclosed is an adhesive system for adhering a medical device to the skin of a patient. In some examples, the adhesive system can include an outside layer and an inside layer. In some embodiments, the outside layer is elastic and re-sealable to the skin of the patient. In other embodiments, the outside layer is configured to form a ring. In some embodiments, the inside layer is composed of a material with a high moisture vapor transmission rate. In other embodiments, the inside layer can be joined with the outside layer such that a small gap is formed between the inside layer and the outside layer.

Additional embodiments of the adhesive system are directed to multilayer adhesive systems. In some embodiments, the multilayer adhesive system comprises a first layer that includes a first layer adhesive for attaching to skin. The first layer: (i) has a first area defined by a first perimeter, (ii) has a first layer effective elastic modulus that is maintained for a first strain, and (iii) comprises a material having a first layer intrinsic elastic modulus that is higher than the first layer effective elastic modulus. The adhesive system also includes a second layer that is attached to the first layer. The second layer: (i) has a second area defined by a second perimeter, where portions of the second area extend beyond the first perimeter, (ii) provides mechanical reinforcement to the first layer, (iii) has a second layer effective elastic modulus that is maintained for a second strain, and (iv) comprises a material having a second layer intrinsic elastic modulus that is higher than the second layer effective elastic modulus. In some embodiments, the multilayer adhesive system has an effective system elastic modulus that is maintained for a third strain.

Multilayer adhesive system embodiments disclosed herein can comprise a first layer that includes a first layer adhesive for attaching to skin, where the first layer: (i) has a first area defined by a first perimeter and (ii) comprises a material having a first layer intrinsic elastic modulus. The system also includes a second layer attached to the first layer, where the second layer: (i) has a second area defined by a second perimeter, wherein portions of the second area extend beyond the first perimeter, (ii) provides mechanical reinforcement to the first layer, (iii) has a second layer effective elastic modulus that is maintained for a second strain, and (iv) comprises a material having an second layer intrinsic elastic modulus that is higher than the second layer effective elastic modulus. In some embodiments, the multilayer adhesive system has an effective system elastic modulus that is maintained for a third strain.

Certain embodiments are directed to adhesive systems that include a first layer that comprises a first material that has a first intrinsic elastic modulus, a plurality of first layer perforations that form a plurality of discontinuous portions in the first layer, a first area defined by a first perimeter, an adhesive for attaching to skin, and a first effective elastic modulus that is lower than the first intrinsic elastic modulus. The adhesive system also includes a second layer that comprises a second material that has a second intrinsic elastic modulus, a plurality of second layer perforations, a second area defined by a second perimeter, an adhesive for attaching to the first layer, and a second effective elastic modulus that is lower than the second intrinsic elastic modulus.

The adhesive systems disclosed herein also include embodiments directed composite adhesive system that comprise a first layer for attaching to skin, where the first layer has (i) a first area defined by a first perimeter and (ii) a first layer inherent elastic modulus that is maintained for a first strain. The system also includes a second layer that is attached to the first layer, where the second layer (i) has a second area substantially equal to the first area and a second perimeter substantially equal to the first perimeter, (ii) provides mechanical reinforcement to the first layer, (iii) has a second layer effective elastic modulus that is maintained for a second strain, and (iv) comprises a material having a second layer intrinsic elastic modulus that is higher than the second layer effective elastic modulus. Lastly, the system includes a third layer that is attached to the second layer with a third layer adhesive. The third layer: (i) has a third area defined by a third perimeter, (ii) provides mechanical reinforcement to the second layer, (iii) has a third layer effective elastic modulus that is maintained for a third strain, and (iv) comprises a material having a third layer intrinsic elastic modulus that is higher than the third layer effective elastic modulus. In some embodiments, the composite adhesive system has an adhesive system effective elastic modulus that is maintained for a fourth strain.

Additional embodiments of a three-layer adhesive system include a first layer that has a first layer adhesive for attaching to skin, where the first layer: (i) has a first area defined by a first perimeter, (ii) has a first layer effective elastic modulus that is maintained for a first strain, and (iii) comprises a material having a first layer intrinsic elastic modulus that is higher than the first layer effective elastic modulus. The second layer, which is attached to the first layer, (i) has a second area substantially equal to the first area and a second perimeter substantially equal to the first perimeter, (ii) provides mechanical reinforcement to the first layer, (iii) has a second layer effective elastic modulus that is maintained for a second strain, and (iv) comprises a material having a second layer intrinsic elastic modulus that is higher than the second layer effective elastic modulus. The third layer is attached to the second layer with a third layer adhesive. The third layer: (i) has a third area defined by a third perimeter, (ii) provides mechanical reinforcement to the second layer, (iii) has a third layer effective elastic modulus that is maintained for a third strain, and (iv) comprises a material having a third layer intrinsic elastic modulus that is higher than the third layer effective elastic modulus. In some embodiments, the multilayer adhesive system has an adhesive system effective elastic modulus that is maintained for a fourth strain.

Embodiments are also directed to a method of wearing an adhesive system where the method comprises the steps of providing an adhesive system that includes a first layer made a first material with a first intrinsic elastic modulus and having, a plurality of first layer perforations that form a plurality of discontinuous portions in the first layer, a first area defined by a first perimeter, an adhesive for attaching to skin, and a first effective elastic modulus that is lower than the first intrinsic elastic modulus. The system also includes a second layer made of a second material having a second intrinsic elastic modulus and having a plurality of second layer perforations, a second area defined by a second perimeter, an adhesive for attaching to the first layer, and a second effective elastic modulus that is lower than the second intrinsic elastic modulus. The method includes applying the adhesive system to skin, applying a tensile force to the adhesive system to achieve a strain of up to 0.4, causing at least one discontinuous portion in the first layer to separate from an adjacent discontinuous portion in the first layer, forming concentrated areas of stress between adjacent second layer perforations, causing the second layer to plastically deform under the applied tensile force, and removing the tensile force.

Disclosed are sensor inserter systems and methods for transdermally inserting a sensor for a continuous glucose monitoring system.

In some embodiments, the system for sensor implantation can include an inserter. In some embodiments, the inserter can include a lancet tip. In some embodiments, the lancet tip can include a convex feature that is attached to a first surface of the lancet tip. In some embodiments, the lancet tip can include an inset on either side of the lancet tip. In some embodiments, the system for sensor implantation can include a sensor. In some embodiments, the sensor can include a distal end configured to form a loop. In some embodiments, the loop is configured to pass around the insets of the lancet tip, with a portion of the loop positioned adjacent the convex feature.

In some embodiments, the method for sensor implantation in a patient can include providing a sensor configured to attach to an inserter wherein the sensor includes a distal end configured to form a loop and the inserter includes a lancet tip that includes a convex feature that is attached to a first surface of the lancet tip. In some embodiments, the method can include positioning the loop of the sensor such that the loop passes around both insets on either side of the lancet tip and a portion of the loop is adjacent the convex feature. In some embodiments, the method can include inserting the lancet tip into the tissue of the patient such that a portion of the sensor is inserted transdermally. In some embodiments, the method can include inserting the lancet tip into the tissue of the patient such that the sensor is fully implanted below the epidermis. In some embodiments, the method can include withdrawing the lancet tip from the tissue. In some embodiments, the method can include disengaging the loop from the lancet tip such that a portion of the sensor remains in the tissue.

Embodiments are also directed to an insertion structure for piercing skin tissue. The insertion structure comprises a substantially planar, non-rigid elongate member having a first surface and a second surface. The elongate member includes a proximal portion for attaching to an insertion device, an intermediate portion and a distal portion for piercing the skin tissue. The distal portion comprises a distal portion first surface, a distal portion second surface opposite the first surface, a tip, at least one cutting surface, a plurality of insets extending from the distal portion first surface to the distal portion second surface for receiving at least a portion of a sensing element to be inserted into the skin and a retaining structure on the distal portion second surface. The retaining structure is configured to (i) retain the sensing element on the distal portion prior to and during insertion of the distal portion into the skin and (ii) release the sensing element from the distal portion upon removal of the distal portion from the skin thereby implanting the insertion element within the skin.

Additional embodiments are directed to an insertion member for piercing skin tissue. The insertion member comprises a flexible elongate member that includes a first side, a second side opposite the first side, a proximal portion for connecting to an insertion device, an intermediate portion and a distal tip portion. The distal tip portion comprises a positive convex cutting surface, a plurality of recessed portions extending from the first side to the second side for receiving at least a portion of an insertion element to be inserted into the skin and an engagement structure on the second side, the engagement structure having a substantially forward facing front surface that retains the insertion element on the distal portion during insertion of the distal portion into the skin and releases the insertion element from the distal portion upon removal of the distal portion from the skin thereby implanting the insertion element within the skin.

Certain embodiments are directed to a sensing element insertion member. The sensing element insertion member comprises a sensing element having a sensor looped distal portion formed by a sensor transmission element to be implanted in skin. The sensor looped distal portion includes a loop tip portion that has a first opening with a first width defined by the sensor transmission element, a loop central portion having second opening with a second width defined by the sensor transmission element, where the second width is greater than the first width, a sensor looped transition portion extending between the loop tip portion and the loop central portion, and an elongate sensing portion proximal to the loop central portion. The sensing element further includes a substantially planar, non-rigid elongate member that comprises a first side, a second side opposite the first side, a proximal elongate member portion for attaching to an insertion device, an intermediate elongate member portion, and a distal elongate member portion for piercing the skin tissue. The distal elongate member portion comprises a distal tip, at least one cutting surface, and an engagement structure on the second side, where the engagement structure is configured to (i) retain the sensor looped distal portion on the distal elongate member portion during insertion of the distal elongate member portion into the skin and (ii) release the sensor looped distal portion from the distal elongate member portion upon removal of the distal elongate member portion from the skin thereby leaving the sensor looped distal portion in the skin.

Further embodiments are directed to an insertion element for delivering and anchoring a percutaneous portion of a device in tissue. The insertion element comprises an elongate member having a proximal end for connecting to the device and a distal end. The insertion element also comprises a looped distal portion adjacent the distal end of the proximal portion, the looped distal portion having a flexible element that (i) forms a loop tip portion that has a first opening with a first width defined by the flexible element, (ii) forms a loop central portion having second opening with a second width defined by the flexible element, where the second width is greater than the first width and (iii) includes a plurality of transition regions between (a) the distal end of the elongate member and the loop central portion and (b) the loop central portion and the loop tip portion. The transition regions are thicker than other regions of the flexible element.

A layered optical sensor is disclosed in accordance with another embodiment. The layered optical sensor comprises: a sensing layer including at least one waveguide having an exposed waveguide core; an oxygen sensing polymer region at least partially extending into the sensing layer and in direct communication with the exposed waveguide core, the oxygen sensing polymer region comprising an oxygen sensing polymer that contacts the exposed waveguide core; an enzymatic reaction layer disposed on top of the sensing layer; and an enzymatic hydrogel reaction region formed in the enzymatic reaction layer, the enzymatic hydrogel reaction region at least partially defined by the enzymatic reaction layer and the oxygen sensing polymer, the enzymatic hydrogel reaction region comprising an enzymatic hydrogel, wherein at least a first surface of the oxygen sensing polymer that partially defines the enzymatic hydrogel reaction region includes a surface modification that ensures that the oxygen sensing polymer and the enzymatic hydrogel are in physical contact with each other.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following FIGS. may not be drawn to scale.

FIG. 4 is a functional block diagram illustrating an example of a continuous health monitoring system, including a sensor, a controller, an analysis engine, a knowledge base, a smart card, and/or a portable computing device, according to an embodiment of the present invention.

FIG. 11 is a functional block diagram of a health provider network/monitor, according to an embodiment of the present invention.

FIG. 19 illustrates a close up view of a middle layer of a layered optical sensor, according to an embodiment of the present invention.

FIG. 20B illustrates a cross-section of a layered optical sensor, according to an embodiment of the present invention.

FIG. 21 illustrates a pre and post filled embossing of a layered optical sensor, according to an embodiment of the present invention.

FIG. 27 shows a table of a lag-adjusted retrospectively calibrated sensor 20/20 performance graph with outliers removed.

FIG. 28A-C is an exploded, side, and top view of the adhesive system for attaching an opto-enzymatic device to the surface of skin, according to an embodiment of the present invention.

FIG. 29A is a top view of an adhesive system for attaching an opto-enzymatic device to the surface of skin, according to an embodiment of the present invention.

FIG. 29B is a cross-sectional view taken along line A-A in FIG. 29A. FIG.

FIG. 29V is an illustration of the adhesive system depicted in FIG. 29U on skin when the skin is in a stretched state.

FIGS. 33B-C are perspective and frontal views of the inserter system with the cap removed, according to an embodiment of the present invention.

FIG. 34A is a top view of a lancet, according to an embodiment of the present invention.

FIG. 34B is a side view of the lancet depicted in FIG. 34A, according to an embodiment of the present invention.

FIG. 36F is a top view of a looped sensor lancet interface, according to an embodiment of the present invention.

FIG. 41A illustrates an expanded view of a sensor tip for a glucose monitoring device, according to an embodiment of the present invention.

FIG. 41B illustrates a view of the sensor tip with a detection device, according to an embodiment of the present invention.

FIG. 41C illustrates a cross-sectional view of the sensor tip, according to an embodiment of the present invention.

DETAILED DESCRIPTION

The disclosed and described technology relates to continuous analyte monitoring systems that may include an opto-enzymatic sensor, a controller, an analysis engine, a knowledge base, a smart card, and a portable computing device. Example analytes that can be measured using the embodiments of the invention disclosed and described herein include, and are not limited to, glucose, galactose, fructose, lactose, peroxide, cholesterol, amino acids, alcohol, lactic acid, and mixtures of the foregoing. Although much of the disclosure contained herein is directed to a glucose monitoring system that may include an opto-enzymatic sensor, a controller, an analysis engine, a knowledge base, a smart card, and a portable computing device, the embodiments of the present invention can be used to monitor many different analytes, including and not limited to, the ones listed in this paragraph.

In some embodiments, the system communicates with and incorporates data from activity sensor systems and bio sensor systems. In some embodiments, the system communicates over the cloud or internet with health care providers including doctors and nurses via a health provider network and may also communicate with a patient's caregiver. The disclosed technology provides interconnected care that supports the patient directly, and provides their immediate caregivers, as well as their physician and health provider network, with timely information to support the patient and health care provider goal of sustained glycemic control.

Continuous Health Monitoring System

Figure 1A:
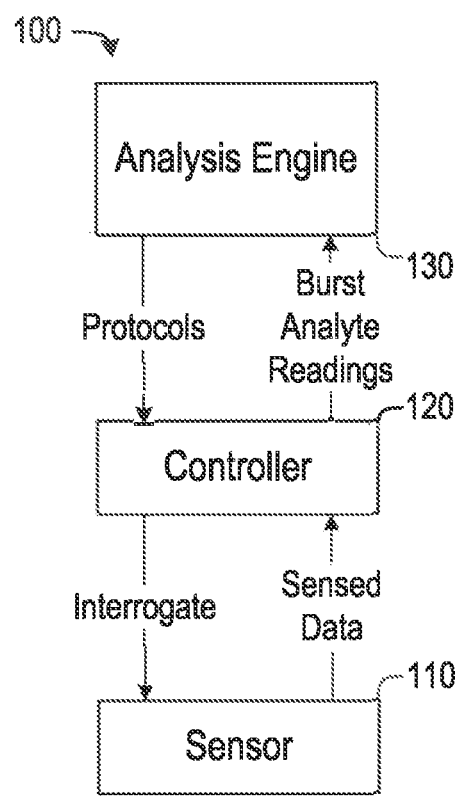
FIG. 1A is a block diagram illustrating an example of a continuous health monitoring system, including a sensor, a controller, and an analysis engine, according to an embodiment of the present invention.

FIG. 1A is a block diagram illustrating an embodiment of a continuous health monitoring system 100, including a sensor 110, a controller 120, and an analysis engine 130. At least a portion of the sensor 110 is implanted in a patient. A controller 120 on the skin of the patient is optically connected to the sensor 110. The controller 120 is in electronic communication with an analysis engine 130, via a wireless or wired connection. The analysis engine 130 may be packaged separately from the controller 120. The analysis engine 130 transmits protocols to the controller 120, which optically interrogates the sensor 110 that senses real-time biological conditions in a patient. In response to the interrogation, sensor 110 optically transmits sensed data to the controller 120. The controller 120 collects one or more analyte readings included in the sensed data, and transmits the collected analyte readings to the analysis engine 130. The readings may be transmitted from the controller to the analysis engine 130 in a burst. For example, the analysis engine 130 may transmit a protocol to controller 120 requesting sensor readings every 30 seconds, and/or bursts of readings every 5 minutes. The controller 120 may interrogate the sensor 110 every 30 seconds, and record the sensed data. Every 5 minutes, corresponding to every 10 sensed readings, the controller 120 may transmit the 10 sensed readings to the analysis engine 130.

In an embodiment, the sensor 110 is an opto-enzymatic (optical-enzymatic) sensor that provides interstitial fluid measurements of an analyte when optically interrogated with visible light. The sensor 110 may be implanted subcutaneously so that the sensor is in contact with interstitial bodily fluid containing analytes. The sensor transduces a concentration of an analyte to determine a measure of the analyte concentration. The sensor 110 communicates the measure of the analyte concentration to the controller 120 over a communication channel between the controller 120 on the skin of the patient and the subcutaneous sensor 110 when the sensor is interrogated with visible light. In an embodiment, the communication channel between the control 120 and the sensor 110 is an optical channel. In an embodiment, the analyte concentration is indicative of a blood sugar condition, such as a blood glucose level.

The controller 120 interrogates the sensor 110 with visible light from a compact laser source 124 or other light source and measures the glucose dependent luminescent emissions from the percutaneous sensing element (sensor) 110. The on-body controller 120 may interrogate the sensor frequently (for example, each minute) and then transmit sensor measurements in bursts (for example, every five minutes). Controller 120 converts the received raw optical signals into glucose measurements and transmits the measurements via a protocol to an external receiver using a wireless communication protocol. In an embodiment, the wireless communication protocol is a Bluetooth, low energy protocol.

Figure 1C:
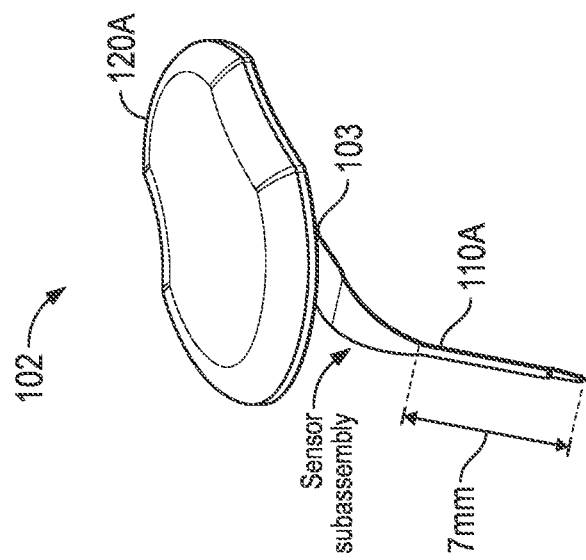
FIG. 1C is an illustration of the sensor of FIG. 1A and the controller of FIG. 1A connected to each to each other, according to an embodiment of the present invention.
Figure 1B:
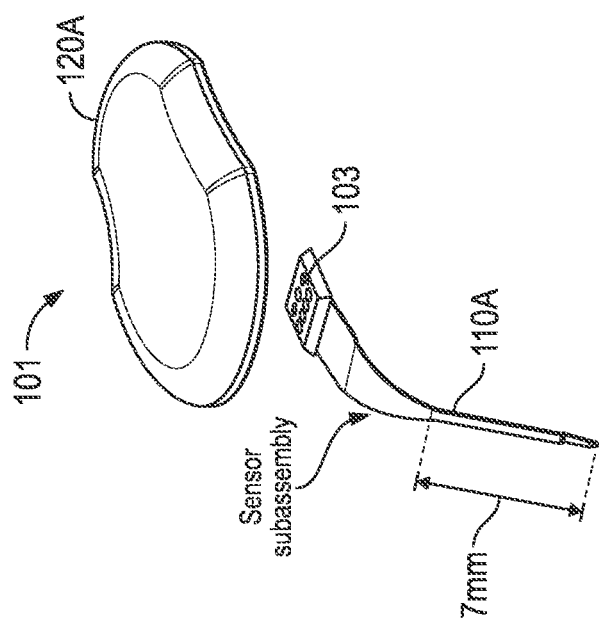
FIG. 1B is an illustration of the sensor of FIG. 1A and the controller of FIG. 1A before they are connected to each to each other, according to an embodiment of the present invention.

The sensor measurements may be analyzed by analysis engine 130 and then displayed or transmitted for display. Analysis engine 130 may be housed in a dedicated computing device, in an insulin pump, or an artificial pancreas device equipped with a Bluetooth receiver and a processor for interpreting the sensor data and converting it into calibrated glucose measurements. By housing the analysis engine 130 in, for example, an insulin pump or artificial pancreas, the disclosed technology enables a closed loop solution for the patient for sensing interstitial glucose levels, and modifying outputs from the insulin pump or artificial pancreas to the patient based at least in part on the sensed glucose levels. Analysis engine 130 transmits protocols to the controller that defines the duration, frequency and timing of sensor interrogation. The analysis engine 130 receives bursts of analyte (for example, glucose) readings from which it determines results, including individual or time series of analyte levels, trends, patterns, graphs, and alerts. The analysis engine 130 may include a processor or processing circuit. The analysis engine 130 may communicate with the controller via a wired or wireless connection FIG. 1B is an illustration 101 of the sensor of FIG. 1A and the controller 120 of FIG. 1A before they are connected to each other. Sensor 110 of FIG. 1A is housed in sensor assembly 110A, which also houses transducer 111 and at least one waveguide 119 (see FIG. 2B) in a sensor subassembly with a connector 103 for connecting to controller 120, which is housed in controller assembly 120A. As used herein, a "waveguide" is an optical path for light based on internal reflection due to a higher index of refraction in the light path than the volume surrounding the light path. A waveguide, or light pipe, is preferably made of polymers. The controller 120 is affixed to the patient's skin and is in optical communication with the sensor 110. The controller (on-body transmitter) may be enclosed in assembly 120A, an ergonomically shaped, low profile, waterproof assembly designed to allow unobtrusive body wear. The on-body transmitter in assembly 120A may be cleanable.

After at least the distal portion of the implantable percutaneous sensor 110 is implanted, the on-body controller 120 is attached to the sensor assembly 110A. FIG. 1C is a corresponding illustration 102 of the sensor of FIG. 1B, and the controller of FIG. 1B connected to each to each other. The controller 120 is not visible because the controller housing is not transparent. The controller assembly 120A is affixed to the patient's skin using, for example, an adhesive system disclosed and described in more detail herein, and the sensor 110 is implanted percutaneously in the patient. The sensor 110 and controller 120 communicate optically through the connector 103.

Figure 2A:
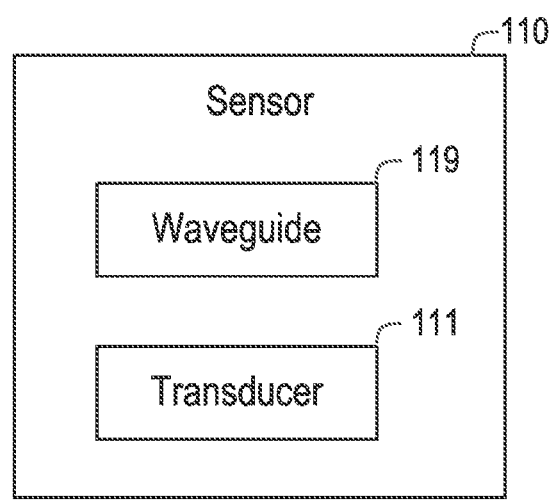
FIG. 2A is a functional block diagram of the sensor in FIG. 1, according to an embodiment of the present invention.

FIG. 2A is a functional block diagram of the sensor 110 in FIG. 1A. Sensor 110 includes a transducer 111 that transduces an interstitial analyte level, such as, for example, a blood glucose level in the bodily fluid/tissue into which the sensor 110 is implanted. A waveguide 119 receives optical interrogation signals, and transmits analyte readings. In an embodiment, the optically received signals and optically transmitted signals may be received and transmitted via an optical pathway through a connector and via optical fiber and/or a waveguide from and to controller 120. Transducer 111 determines interstitial measurements of glucose when the sensing element is optically interrogated with visible light. The sensor provides a measurement of the interstitial glucose based on the difference between an interstitial reference oxygen measurement and measurements of the oxygen remaining after a two stage enzymatic reaction of glucose and oxygen as described in more detail below.

Figure 2B:
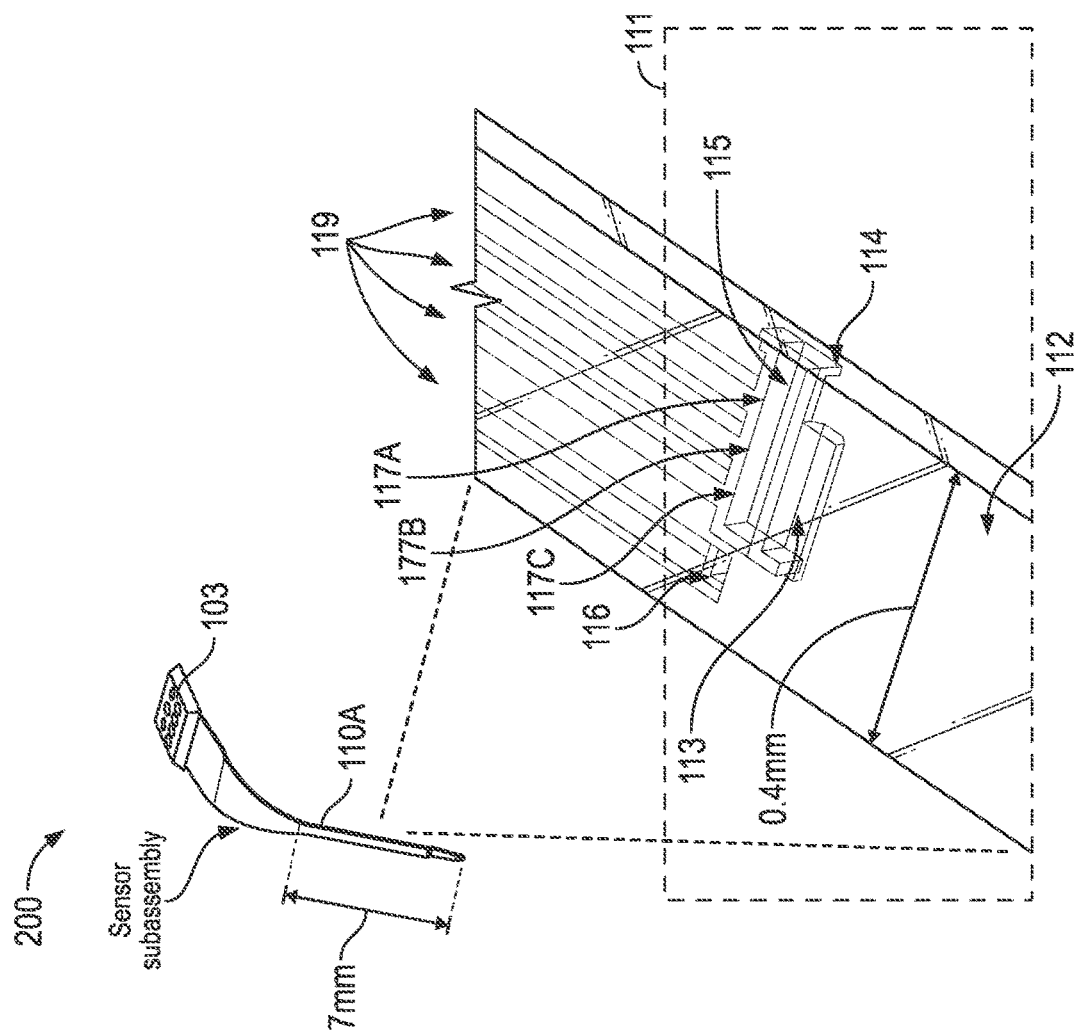
FIG. 2B is an illustration of the sensor of FIG. 2A, according to an embodiment of the present invention.

FIG. 2B is an illustration 200 of an exemplary sensor 110 of FIG. 2A. Illustration 200 depicts a sensor subassembly 110A. As described in more detail below, the sensor assembly 110A may include three layers, including middle layer 112, which houses transducer 111 and waveguide 119. The middle layer 112 may be approximately 7 mm long and 0.4 mm wide. An enzymatic hydrogel channel 113 includes hydrogel that reacts with interstitial glucose that enters in glucose inlet 114 on one side of the middle layer 112, along the width dimension. An oxygen sensing polymer 115 forms a band or channel along the width dimension of the middle layer 112 starting in proximity to the glucose inlet 114 but not necessarily extending across the entire width of middle layer 112. The oxygen sensing polymer band/channel 115 forms a continuous band/channel, but may be considered to be divided into distinct regions, for example, the first region 117A closest to the glucose inlet 114, the second region 117B next closest to the first region 114, and the third region 116 farthest from the glucose inlet. Glucose interacts with the oxygen sensing polymer in the presence of the hydrogel in the enzymatic hydrogel channel 113, and diffuses along the continuous oxygen sensing polymer band 115 starting at the glucose inlet 114 in the first region 117A, then onto the second region 117B, and finally onto the third region 117C, at increasing distances from the glucose inlet 114. When the sensor 110 is interrogated with visible light, the waveguides 119 transmit sensor readings for regions 117A-C and for the oxygen reference 116, which are used to estimate analyte (glucose) concentration. The sensor 110 readings provide oxygen levels, which are an indication of oxygen consumption levels in the oxygen sensing polymer 115 in regions 117A-C. In an embodiment, the oxygen sensing polymer 115 is divided into two regions, three regions (as in the embodiment in FIG. 2B), four regions, 5 regions, or more regions. Dividing the oxygen sensing polymer band 115 into regions corresponds to sampling the oxygen sensing polymer band 115 at different distances from the glucose inlet 114. This sampling makes it possible to estimate a profile along the oxygen sensing polymer band 115. Each "sensor reading" includes a vector of readings—one for each region 117A-C, and an oxygen reference reading 116.

Figure 2C:
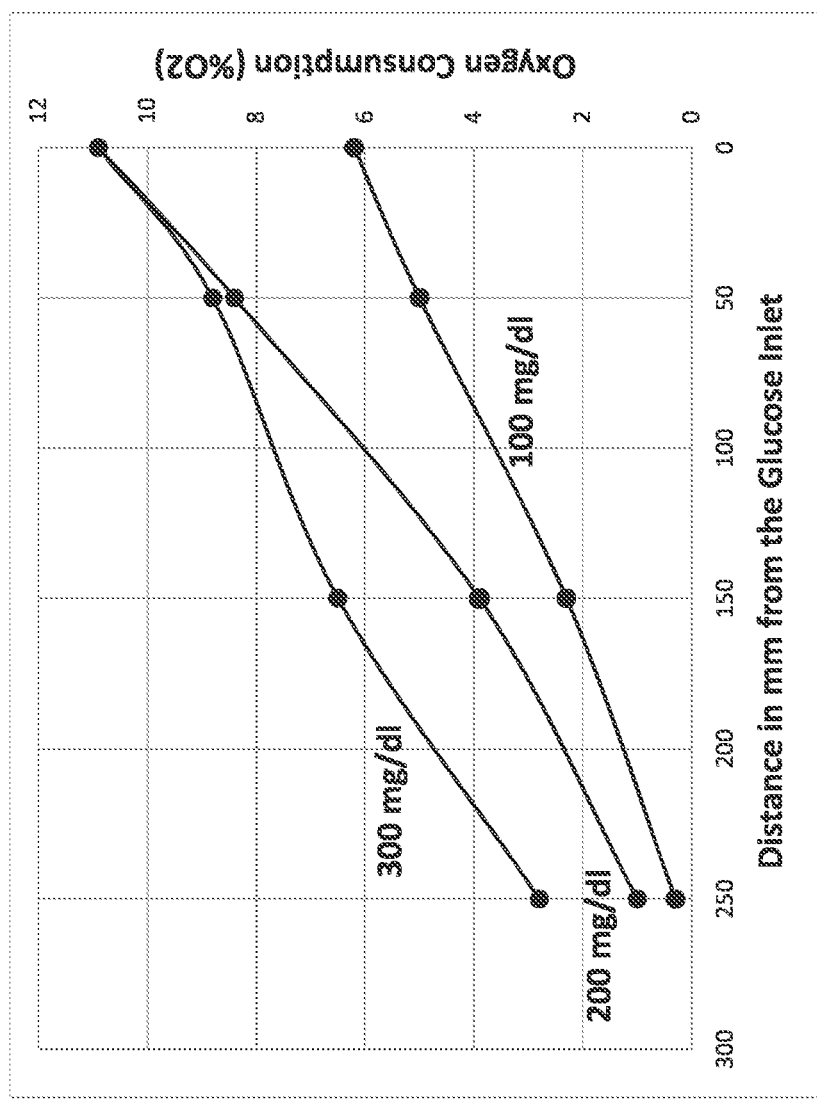
FIG. 2C is a graph of oxygen consumption as a function of distance from the glucose inlet, according to an embodiment of the present invention.

FIG. 2C is a series of curves of oxygen consumption vs. distance (in mm) from the glucose inlet 114, for steady state glucose concentrations of 100 mg/dL, 200 mg/dL, and 300 mg/dL. Close to the glucose inlet 114, there is good discrimination between glucose concentrations 100 mg/dL and 200 mg/dL, but poor discrimination between glucose concentrations 200 mg/dL and 300 mg/dL. In contrast, at distances farther from the glucose inlet 114, there is poor discrimination between glucose concentrations 100 mg/dL and 200 mg/dL, but good discrimination between glucose concentrations 200 mg/dL and 300 mg/dL. Therefore, in this embodiment, there is good sensitivity for lower glucose concentrations closer to the glucose inlet 114, and good sensitivity for higher glucose concentrations farther from the glucose inlet 114. This is analogous to taking pictures in bright sunlight with short exposures to avoid saturation, and taking pictures in dark rooms with long exposures to enable discrimination at low light levels. By taking oxygen consumption readings or glucose concentration readings via multiple waveguides at different distances from the glucose inlet 114, analogous to different camera exposures, the raw sensor readings may be used to determine glucose concentrations over a greater range of glucose levels than would be possible with a single sensor reading.

The four flexible waveguides 119 along the vertical dimension of middle layer 112 transmit sensor readings from regions 117A-C and oxygen reference 116 through sensor subassembly 110A to controller 120. In the case of a zero interstitial glucose concentration, the reference oxygen concentration and the working oxygen concentration are the same. In the case of a low glucose concentration, the majority of the glucose and oxygen consumption by the enzymatic reaction occurs in the first reaction region 117A volume of the enzymatic hydrogel 113 proximal to the glucose inlet 114. As the interstitial glucose concentration increases, the enzymatic reaction moves further into the second and third reaction region 117B, 117C volumes of the enzymatic hydrogel 113.

This progressive reaction to differing glucose concentrations depicted in FIG. 2C allows for high sensitivity to low glucose concentrations by monitoring the first reaction region 117A volume for oxygen concentration, and wide dynamic range by monitoring the second and third reaction region 117B, 117C volumes for oxygen concentration as well. When the interstitial glucose concentration is low and limited glucose diffuses through the glucose inlet 114 into the first reaction region 117A volume, the oxygen consumption in the enzymatic hydrogel 113 is primarily proximal to the glucose inlet 114. The interstitial glucose concentration is readily calculable from a set of oxygen concentration measurements. Given a reference oxygen level and three oxygen concentration measurements in the enzymatic hydrogel 113 in regions 117A-C, the glucose concentration is a linear function of the sum of the differences between each of the three oxygen concentration measurements and the reference oxygen concentration measurement. For each glucose concentration, there is a reference oxygen concentration measurement and a corresponding set of oxygen concentrations in the enzymatic hydrogel 113 and a corresponding oxygen concentration difference. There is a direct relationship of the net oxygen concentration difference measured from the enzymatic reaction chamber compared to the oxygen reference measurement versus the steady state glucose concentration. This direct relationship allows the sensor to be calibrated with a parameterized equation that yields a calculated glucose concentration based on the measured oxygen differences.

Depending on the parameterization, the calculated glucose concentration can be the concentration of glucose in the environment of the sensor. This can be an in vitro glucose concentration if the sensor is calibrated using in vitro glucose solutions, or an interstitial glucose concentration if the sensor is an implanted glucose biosensor. Alternatively, the parameterized equation may provide a direct calculation of blood glucose concentration, such as when the relationship between the blood and the interstitial tissue is assumed to be linear, and the parameterized equation is determined using a linear regression with blood glucose measurements as in FIG. 26. Alternatively, a second parameterized calculation may be used to calculate a blood glucose measurement from sensor calculated interstitial glucose measurements. For example, an enhanced Bayesian calibration method can be implemented using the Extended Kalman Filter to account for the existence of blood glucose-to-interstitial glucose kinetics by incorporating a population convolution model [Andrea Facchinetti, Giovanni Sparacino, and Claudio Cobelli. *Enhanced Accuracy of Continuous Glucose Monitoring by Online Extended Kalman Filtering*. Diabetes Technology & Therapeutics. May 2010, Vol. 12, No. 5: 353-363].

As the interstitial glucose concentration increases and the amount of glucose diffusing through the glucose inlet 114 increases, and more glucose is reacted in the second and third regions 117B, 117C, the oxygen consumption occurs farther within each reaction region 117B, 117C volume. The net oxygen consumed for a given glucose concentration is determined from the set of oxygen concentration differences. The total oxygen concentration difference is the sum of the net oxygen differences (reference-working as measured in regions 117A-C) from the three volumes compared to the reference oxygen concentration. The interstitial glucose concentration can therefore be determined from net oxygen consumption by means of a linear calibration.

The oxygen concentration measurement is based on the luminescence lifetime ($\tau$) of an oxygen-sensitive luminescent dye. The lifetime ($\tau$) expresses the amount of time the luminescent dye (or luminophore) remains in an excited state following excitation by light of a suitable frequency. The sensor 110 oxygen-sensitive luminescent dye lifetime measurement is made using a time domain approach in which the oxygen sensing polymer sample is excited with a pulse of light and then the time-dependent intensity is measured. The lifetime is calculated from the slope of the log of intensity versus time.

In another embodiment, the sensor 110 is pre-interrogated with an optical signal at a wavelength that does not excite the luminescent dye but with a known lifetime decay to calibrate the on body transmitter and optical system before each glucose measurement is made. The light is reflected by the dye instead of inducing a luminescent signal. In addition, the pre-interrogation pulse of light ensures that proper optical connections have been maintained before each measurement.

The difference in the reference and working oxygen concentrations are used to calculate the interstitial glucose concentration. In the case of a zero interstitial glucose concentration, the reference oxygen concentration and the working oxygen concentration are the same. In the case of a low glucose concentration, the majority of the glucose and oxygen consumption by the enzymatic reaction occur in the first reaction volume of the enzymatic hydrogel proximal to the glucose inlet. As the interstitial glucose concentration increases, the enzymatic reaction moves further into the second and third reaction volumes of the enzymatic hydrogel.

The relationship of the interstitial glucose concentration to oxygen consumed in the enzymatic reaction is a function of the distance from the glucose inlet 114. For example, a first reaction region 117A volume close to the glucose inlet 114 will be sensitive to low concentrations of glucose, and exhibit high dynamic range when differentiating among different, low glucose concentrations.

Figure 3B:
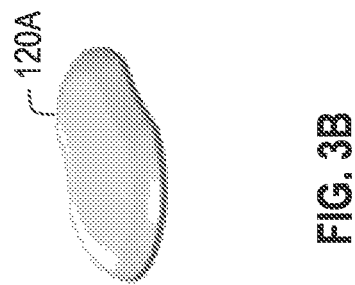
FIG. 3B is an illustration of the controller of FIG. 3A, according to an embodiment of the present invention.
Figure 3A:
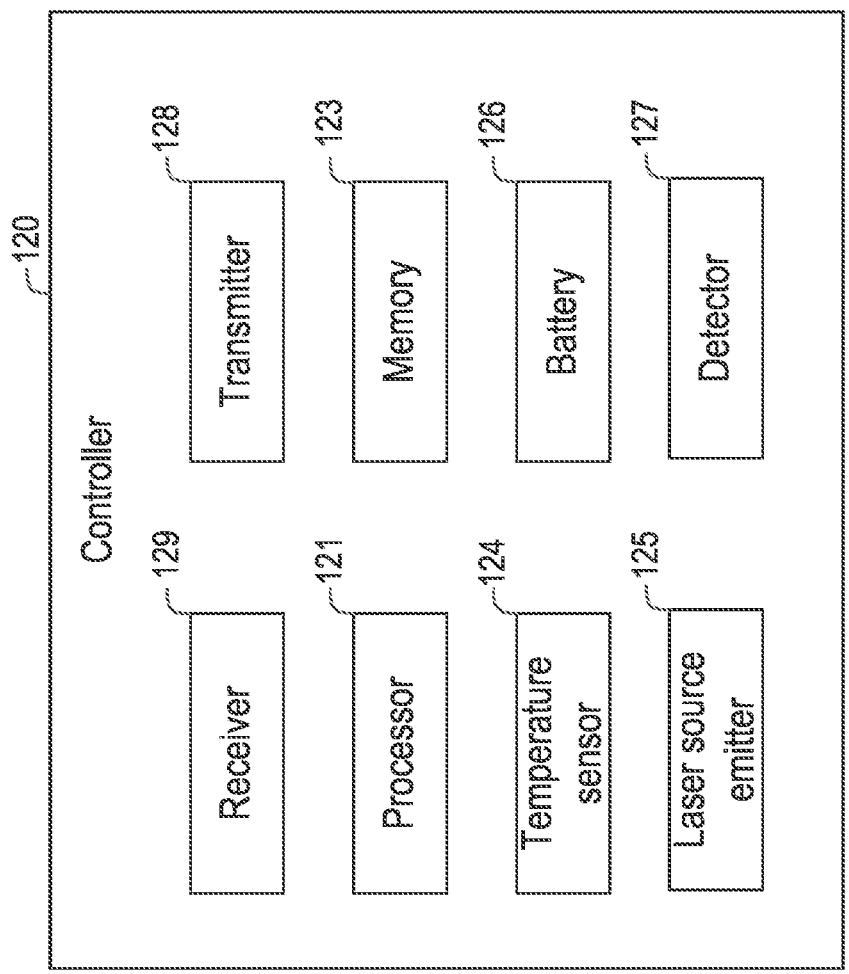
FIG. 3A is a functional block diagram of the controller in FIG. 1, according to an embodiment of the present invention

FIG. 3A is a functional block diagram of the controller 120 in FIG. 1A. FIG. 3B illustrates the controller housing 120A that is affixed to the patient's skin, and is connected via a connector and an optical pathway to waveguides 119 of sensor 110. The controller 120 includes a processing circuit 121, a controller memory circuit 123, a laser source 125, a battery 126, a detector 127, a transmitter 128, and a receiver 129, and may also include a temperature sensor 124. The controller 120 is embedded within a flexible housing 120A configured to be affixed on a patient's skin, and connected via an optical channel to sensor 110.

Processing circuit (processor) 121 converts the received raw optical signals into glucose measurements using the methods disclosed herein. Transmitter 128 transmits the measurements via a protocol to an external receiver using a wireless communication protocol. In an embodiment, the wireless communication protocol is a Bluetooth low energy protocol. Laser source 125 is an optical excitation source. In an embodiment, laser source 125 is a single stage laser diode. In an embodiment, laser source 125 emits light at a wavelength of substantially 405 nm, corresponding substantially to the peak absorption wavelength of the luminescent dye. The detector 127 is a multipixel, miniaturized silicon photomultiplier chip. The optical source emitter (laser source) 125 and the detector 127 silicon components are mounted in a high precision polymer housing within the durable transmitter 120.

The receiver 129 receives protocols, described below, from analysis engine 130. The controller processing circuit 121 determines timing, duration, and frequency to interrogate the sensor 110 via the optical pathway between the controller 120 and sensor 110. The laser source 125 interrogates the sensor 110 via the optical pathway (waveguide), and the detector 127 receives the sensed data via the optical pathway. The sensed data is stored in controller memory circuit 124. For example, based on the protocol, the optical transmitter 128 may interrogate sensor 110 every 30 seconds. The optical receiver may store sensed data in memory unit 124 and every five minutes while sensing an analyte level, the controller transmitter 129 transmits the sensed data stored since the previous burst transmission to analysis engine 130. This transmission may be over a wireless communication channel or any other communication means.

The processor 121 estimates glucose or other analyte levels based on the detections optically received by detector 127. The relationship of the interstitial glucose concentration to oxygen consumed in the enzymatic reaction is a function of the distance from the glucose inlet 114.

Processor 121 may monitor system components and trigger alarms. For example, processor 121 may trigger sensor status alarms, battery level alarms, controller connection to sensor alarms, and controller performance alarms. Processor 122 may command the laser source 125 to emit light to the sensor 110, and analyze the return light detected by the detector 127 to inspect the optical connection to the sensor, as well as the sensor status. The processor may also monitor battery 126 status and performance, including battery level.

The processor 121 may conduct calibration operations independently or in conjunction with the analysis engine 130. Calibration operations may include calibrating glucose measurements from raw sensor data and factory calibration factors, updating calibration based on self-monitoring of blood glucose (SMBG) data, determining when the user should recalibrated based on oxygen sensor data, and determining when the implanted sensor 110 should be replaced based on oxygen sensor data and gain. Calibration operations may trigger alerts related to calibration, such as "replace the sensor 110," or "time to recalibrate with SMBG data."

The processor 121 calibrates sensor readings detected by detector 127. The processor 121 may use factory calibration data to calibrate sensor readings. The factory calibration data may be retrieved from a smart card by reading 2D barcodes or by using near field communications or radio frequency ID to transmit the factory calibration data from the smart card to processor 121. In an embodiment, processor 121 may use linear calibration to calibrate raw sensor readings by multiplying the raw sensor reading by a scale factor and adding an offset factor to determine a calibrated sensor measurement. In an embodiment, processor 121 may use nonlinear calibration to calibrate raw sensor readings. In an embodiment, calibration may include modifying a calibrating factor (such as the scale factor, offset factor, or a coefficient for a nonlinear calibration factor) based on the measured temperature. Processor 121 may use self-monitoring of blood glucose (SMBG) data to update the calibration scale factors and calibration offset factory.

The linear calibration required to convert net oxygen consumed to interstitial glucose concentration will be determined by a factory calibration. Calibration data may be read from a smart tag. The factory calibration will be determined from the luminescent signals of the oxygen sensing polymer while the sensors are exposed to a well-mixed aqueous glucose solution under known conditions at the final stage of the manufacturing process.

Temperature sensor 124 measures temperature to ensure that the temperature is in the operating range of the sensor 110, since the enzymatic reactions in sensor 110 are temperature sensitive and temperature can impact the sensor calibration.

The controller 120 includes battery 126 which powers controller 120. In an embodiment, battery 126 may power controller 120 for period of time between charges. In an embodiment, the period of time between charges is 5 days, 7 days, or two weeks. In an embodiment, battery 126 may be recharged using inductive power transfer. In an embodiment, battery 126 may be recharged using a battery charger. In an embodiment, battery 126 is not rechargeable and may be replaced with a new battery.

FIG. 4 is a functional block diagram illustrating an example of a continuous health monitoring system 400, including a sensor 110, a controller 120, an analysis engine 130, a knowledge base 140, a smart card 150, and/or a portable computing device 160. In an embodiment, the sensor 110, controller 120, and analysis engine 130 are described above with reference to FIG. 1A. The analysis engine 130 is in wired or wireless communication with a knowledge base 140. The analysis engine 130 is in wireless communication with the smart card 150. The analysis engine is in wireless communication with a personal computing device.

In an embodiment, the knowledge base 140 may be implemented in a memory block or in a memory unit, for example, as a relational database. The knowledge base 140 may be included in the same housing as the analysis engine 130 (for example, in a handheld or laptop computing device or smartphone or any other portable device). In an implementation, the knowledge base 140 may be included in a memory block or memory unit in a computing device separate from the analysis engine. In an embodiment, the knowledge base 140 may be accessible to the analysis engine 130 over a network, such as a wired or wireless local area network, via a router (not shown), or over the internet. The knowledge base 140 may include patient specific information that identifies the patient, as well as patient data relevant to analyses performed by the analysis engine 130, and which may impact analyte monitoring, including patient conditions and patient history. Past sensed data such as, for example, glucose levels—sensed by the opto-enzymatic sensor 110, or other sensors, may also be included in the knowledge base 140. Data for trends, patterns and analysis, bounds to determine whether readings are within normal limits, and alert conditions may also be stored in the knowledge base 140.

The knowledge base 140 may include the detailed mapping of standard orders from a doctor, received via a health provider network and over the internet/cloud, to timing, frequency, and type of interrogations of the sensor, as well as other sensors. The knowledge base 140 may also track activity data and other bio sensed data, to enable multi-sensor fusion and analyses as well as to provide a health care provider or caregiver, a more complete picture of a patient's health status. The knowledge base 140 may include data that support analyses performed by the analysis engine. In some embodiments, the knowledge base 140 may be implemented in a distributed database. In an embodiment, the knowledge base 140 may, in addition to being in communication with the analysis engine, be in communication with the controller 120, the portable computing device 160, the smart card 150, one or more activity sensor systems, and one or more biosensor systems.

In an embodiment, the trends and graphs determined by the analysis engine 130 may include glucose measurements, glycemic history, a glycemic dynamics envelope, insulin on board/insulin levels, and normative glycemic profiles with an insulin overlay. Example profiles include a 24 hour average, based on 7 days, 24 hour averages on a daily basis based on the last 49 days, or a basal profile overlay with 24 hour average.

The analysis engine 130 may estimate whether a patient missed a meal bolus using piezo data, insulin data, time of day, and/or prior identified meal periods. The analysis engine 130 may use an algorithm to determine the likelihood of a missed bolus using the likelihood of an activity state, insulin bolus data, insulin data entered by a patient or caregiver, monitored data readings, and prior readings.

In an embodiment, the analysis engine 130 generates alerts when an analyte level, trend, statistic, or other measure falls outside normal limits, exceeds a threshold, or is less than a threshold. Alerts are state dependent, for example based on activity, time of day, and/or user inputs. Example alert conditions include: missed bolus if likely eating a meal (or not eating a meal), sustained hyperglycemia if during or after eating a meal (or not during or after a meal), developing and or severe hypoglycemia, (dependent on activity and/or time of day), or near hypoglycemia for an extended time period. The smart card 150 provide a visual monitor of analyte (for example, glucose) readings. The smart card 150 may be carried in the patient's wallet. The patient, or an aide or health care provider with the patient, interacts with the system via a smart card 150 and/or a portable computing device 160. The analysis engine 130 may transmit results to the smart card 150 and/or one or more portable computing devices 160.

Figure 5:
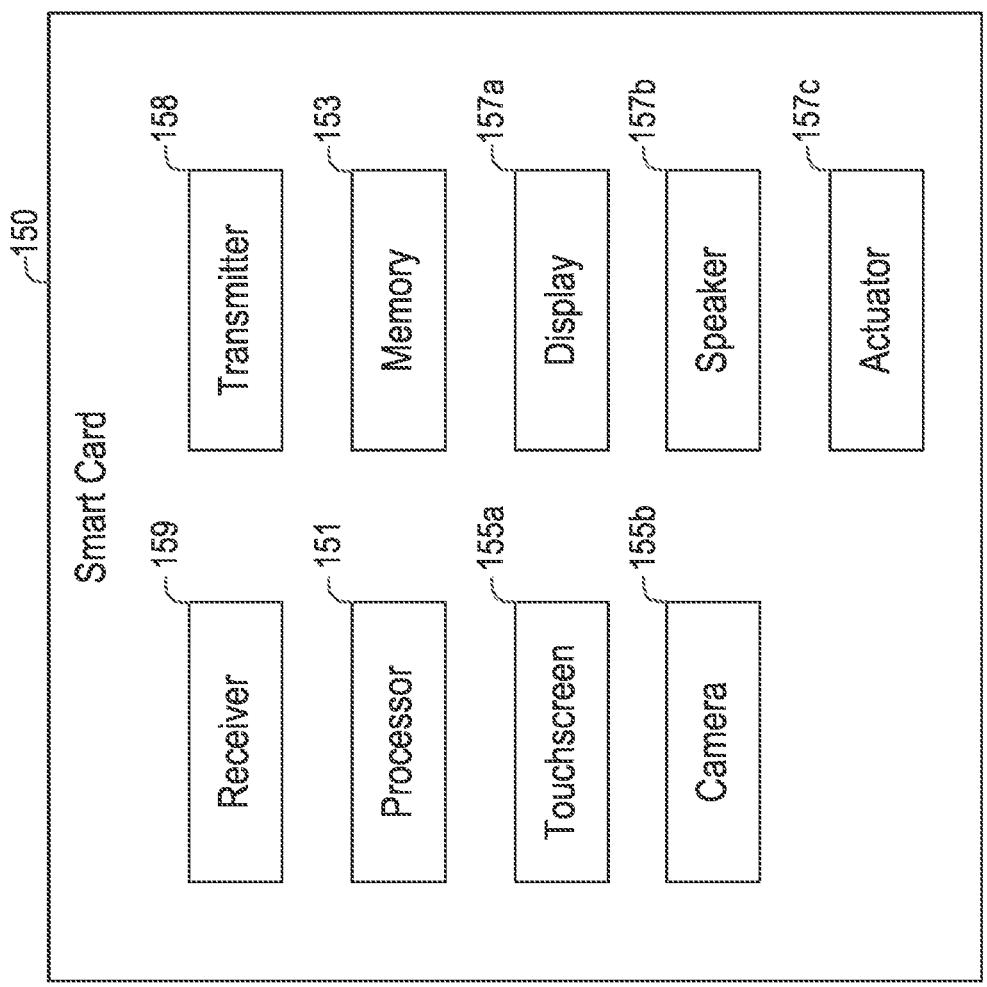
FIG. 5 is a functional block diagram of the smart card in FIG. 4, according to an embodiment of the present invention.

FIG. 5 is a functional block diagram of the smart card 150 in FIG. 4. The smart card 150 communicates queries and results to and from the analysis engine 130 using a transmitter 158 and receiver 159. In an embodiment, the transmitter 158 and receiver 159 may communicate over short distances using RFID and/or NFC technology with a smart card. In an embodiment, receiver 159 may include more than one receiver. For example, one for short distance reception using RFID or NFC, and another to receive results from analysis engine 130 over a distance varying from centimeters to meters. In an embodiment, transmitter 158 may include more than one transmitter. For example, one for short distance transmission using RFID or NFC, and another to transmit queries to analysis engine 130 over a distance varying from centimeters to meters. In an embodiment, transmitter 158 and receiver 159 may be combined in a transceiver (not shown).

The smart card 150 includes a processor circuit (processor) 151 in wired communication with memory circuit (memory) 153, transmitter 158, and receiver 159. The smart card 150 receives inputs via a touchscreen 155a and/or a camera 155b, each in wired communication with the processor 151. The smart card 150 includes a display 157a, speaker 157b, and/or actuator 157c, each in wired communication with the processor 151. The touchscreen 155a and display 157a may be integrated so that a user may select an item on display 157a by touching touchscreen 155a at one or more corresponding points on the touchscreen 155a. The display 157a outputs visual data and information, the speaker outputs audio data and information, and the actuator 157c outputs tactile data and information. Smart card 150 displays/transmits—numerically and/or graphically—analyte readings using display 157*a*, speaker 157*b*, and/or actuator 157*c*.

In an embodiment, the smart card 150 uses lights, sound, vibration, or its visual display 157*a* to "display" alarms when readings or trends are not within normal or preset/pre-identified limits. The processor 151 may be an embedded chip, such as a microcontroller circuit chip. In an embodiment, the microcontroller chip conforms to the ISO/IEC 14443 standard. The ISO/IEC 14443 standard is an international standard for contactless smart chips and cards that operate (i.e., can be read from or written to) at a distance of less than 10 centimeters (4 inches). This standard operates at 13.56 MHz and includes specifications for the physical characteristics, radio frequency power and signal interface, initialization and anti-collision protocols and transmission protocol. In an embodiment, the smart card may conform to the ISE/IEC 7816 standard for contact smart cards.

A smart tag (not shown) may use bar codes read by camera 155*b*, near field communications received by receiver 159, or RFID received by receiver 159. The smart tag may store sensor identity, sensor expiration, factory calibration data, and/or other device data. The smart tag may be read by other computing devices with a camera, an NFC receiver, and/or an RFID receiver, such as a smart phone, wearable computer, desktop computer, tablet, portable receiver, or charging platform.

Figure 6B:
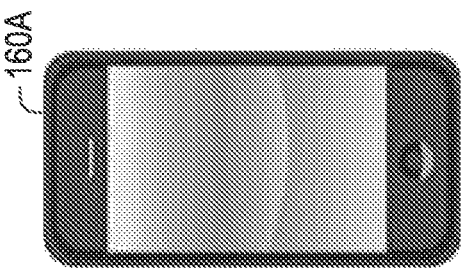
FIG. 6B is an illustration of an example the portable computing device of FIG. 6A, according to an embodiment of the present invention.
Figure 6A:
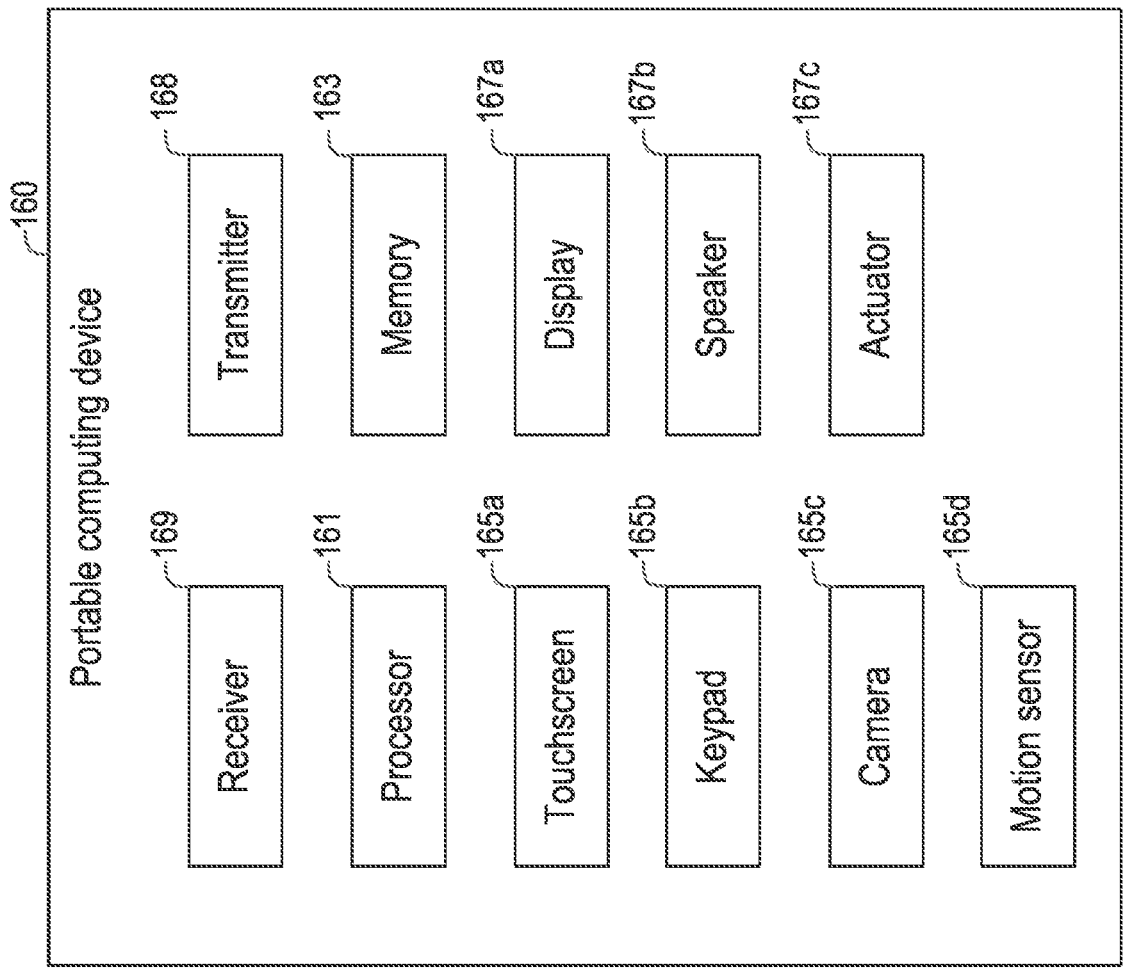
FIG. 6A is a functional block diagram of the portable computing device in FIG. 4, according to an embodiment of the present invention.

FIG. 6A is a functional block diagram of the portable computing device 160 in FIG. 4. FIG. 6B illustrates an example portable computing device 160A. The portable computing device 160 may be a cell phone, wearable computing device, tablet, personal digital assistant, or other computing device. Portable computing device 160 may include an application that enables viewing of results from the analysis engine 130 and/or knowledge base 140, as well as sending queries. For example, a query may include a request for trend data or a protocol to take additional data. Alerts may be viewed on the portable computing device 160, as well as system alarms. System alarms may include sensor status alarms, battery level alarms, controller connection to sensor alarms, and controller performance alarms.

A patient or health care provider may view results from the analysis engine 130 on one or more portable computing devices 160, using an application (app) that communicates queries and results to and from the analysis engine 130 using transmitter 168 and receiver 169. In an embodiment, transmitter 168 and receiver 169 may communicate over short distances using RFID and/or NFC with a smart card. In an embodiment, receiver 168 may include more than one receiver. For example, one for short distance reception using RFID or NFC, and another to receive results from analysis engine 130 over a distance varying from centimeters to meters. In an embodiment, transmitter 168 may include more than one transmitter. For example, one for short distance transmission using RFID or NFC, and another to transmit queries to analysis engine 130 over a distance varying from centimeters to meters. In an embodiment, transmitter 168 and receiver 169 may be combined in a transceiver (not shown).

The portable computing device 160 includes a processor circuit (processor) 161 in wired communication with memory circuit (memory) 163, transmitter 168, and receiver 169. The portable computing device 160 receives inputs via a touchscreen 165*a*, a keypad 165*b*, a camera 165*c*, and/or a motion sensor 165*d*, each in wired communication with the processor 161. A patient may enter a query using the touchscreen 165*a*, keypad 165*b*, or by speech entry via a microphone (not shown). The portable computing device 160 includes display 167*a*, speaker 167*b*, and/or actuator 167*c*, each in wired communication with the processor 161. The touchscreen 165*a* and display 167*a* may be integrated so that a user may select an item on display 167*a* by touching touchscreen 165*a* at one or more corresponding points on the touchscreen 165*a*. The display 167*a* outputs visual data and information, the speaker 167*b* outputs audio data and information, and the actuator 167*c* outputs tactile data and information. In an embodiment, portable computing device 160 may display a trend line on display 167*a*, output a high glucose reading over speaker 167*b*, and/or output tactile data using actuator 167*c* in case of an alarm or alert. The tactile alert may, for example, correspond to a tapping of a patient's wrist when the portable computing device 160 is a wearable computer worn on a patient's wrist, or a vibration when the portable computing device 160 is a phone or tablet.

The processor circuit 161 on portable computing device 160 may run a software application (app) to certain continuous health monitoring operations described herein, including displaying results, accepting user input, and communicating with other system components. The software application may include validation checks, tests, or other operations to validate data elements that are communicated, processed, stored, retrieved, displayed, or otherwise operated upon. For example, each function call may use cyclic redundancy checks (CRC), checksums, or other methods to detect errors and ensure data integrity. For example, cyclic redundancy checks may be applied for each function call. The CRC and/or checksum of each function may be determined in a preprocessing or software compilation step. These data integrity measures may be hard coded into a read only memory (ROM) image of the application. During runtime of the application, each function call may calculate a cyclic redundancy check of the function. The calculated value may be compared to the previously determined (and, possible, hard coded) value, and compared to see if they match. If they match, the function is validated and it is acceptable to run the function call. If not, the application may capture diagnostic data, report the validation error, mark the data for the process as invalid (and/or discard the data), and restart the process. If there are multiple errors in a row, or a particular error that repeats over time, system alerts may be recorded for diagnostic purposes by the system, as well as to the user. By including validation checking within the application itself, the mobile health software application may be validated independent of the operating system hosting the mobile health software application.

Figure 10:
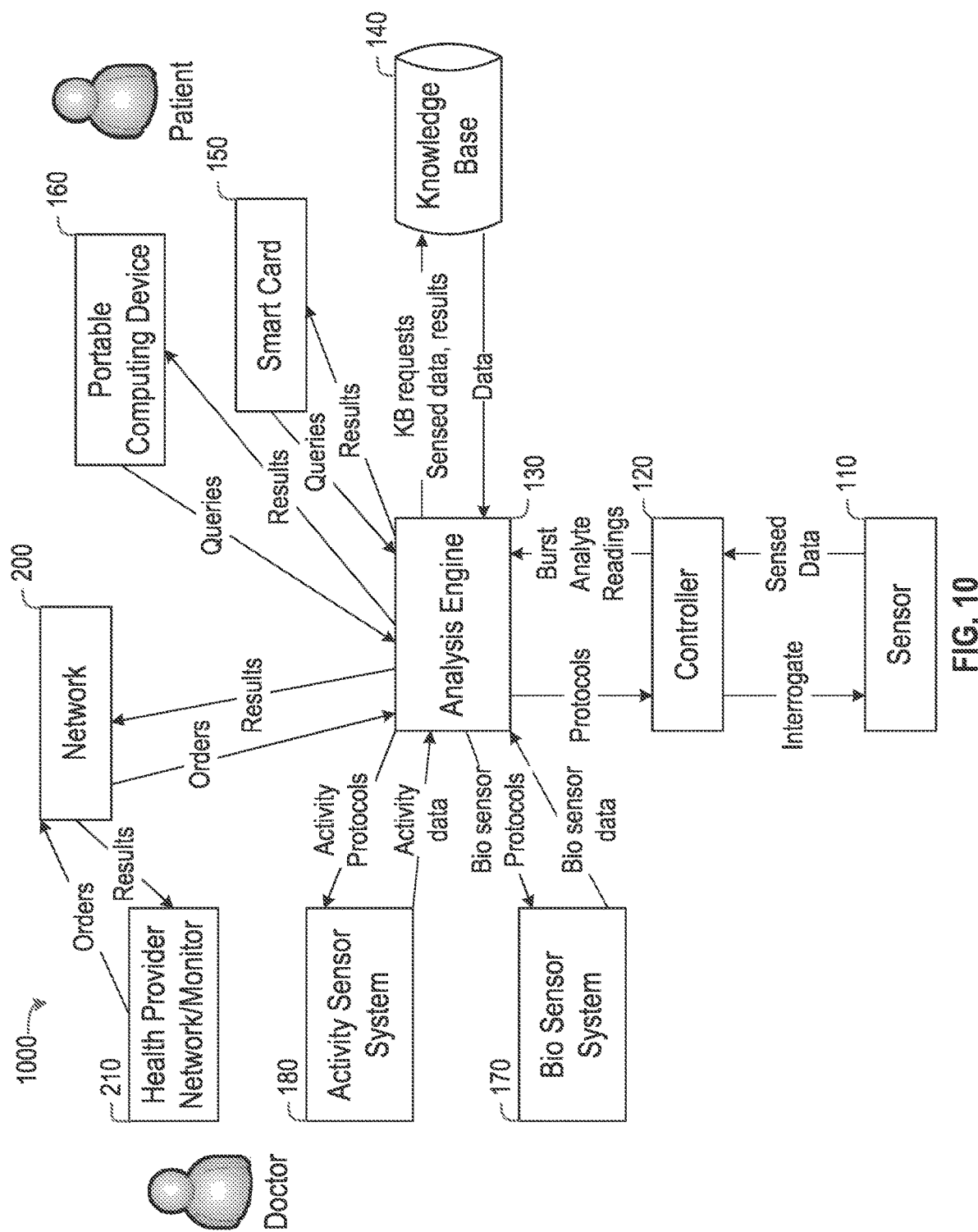
FIG. 10 is a functional block diagram illustrating an example of a continuous health monitoring system, including a sensor, a controller, an analysis engine, a knowledge base, a smart card, a portable computing device, a bio sensor system, an activity sensor system, a network, and/or a health provider network/monitor, according to an embodiment of the present invention.

Such self-validation may be applied not only to the portable computing device 160, but to smart card 150, analysis engine 130, controller 120, and an application hosted on health provider network/monitor 210 (see FIG. 10). The knowledge base 140 may incorporate data integrity or validation testing when conducting database transactions.

A smart tag (not shown) may use bar codes read by camera 165*b*, near field communications received by receiver 169, or RFID received by receiver 169. The smart tag may store sensor identity, sensor expiration, factory calibration data, and/or other device data.

Figure 7:
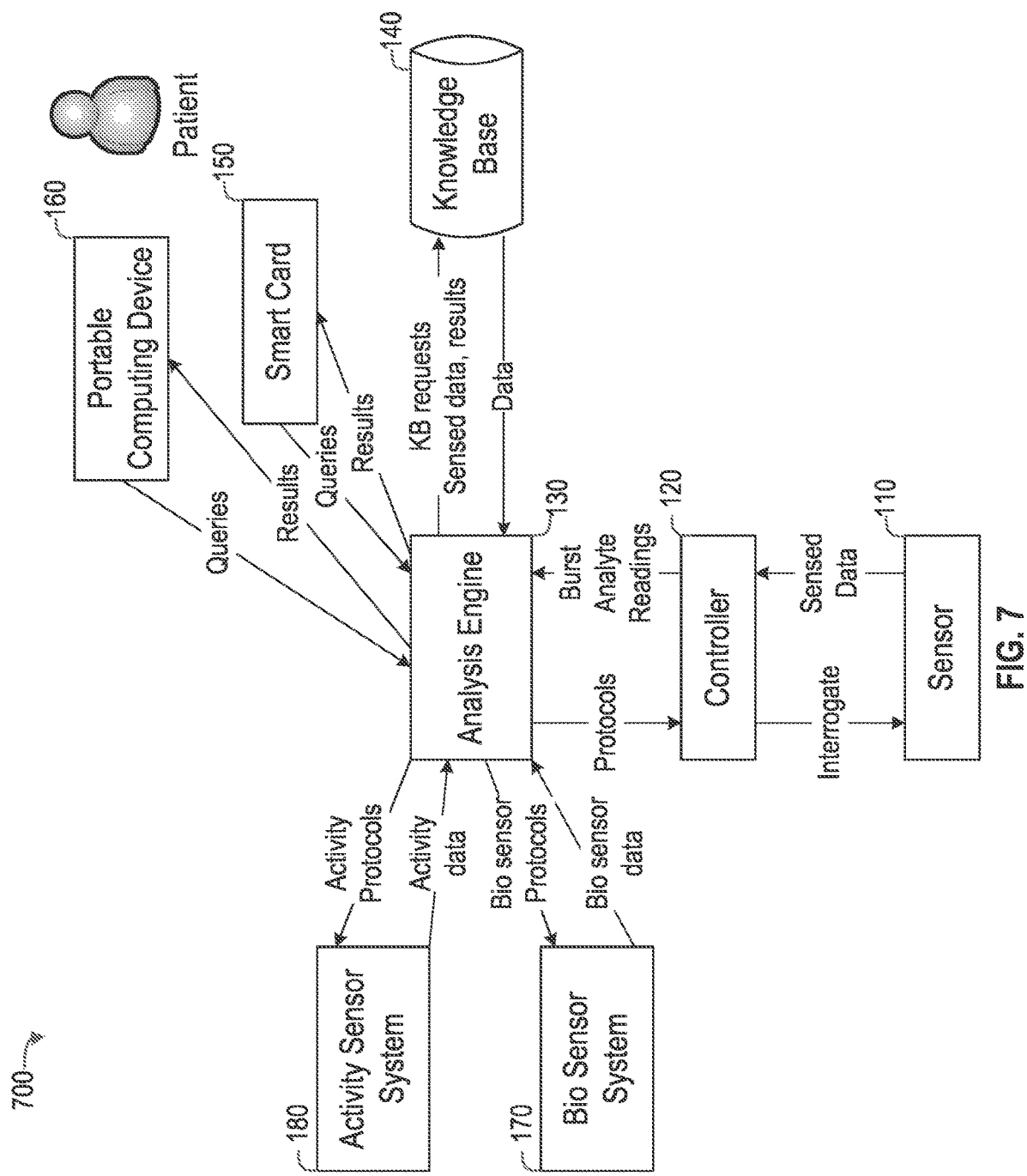
FIG. 7 is a functional block diagram illustrating an example of a continuous health monitoring system, including a sensor, a controller, an analysis engine, a knowledge base, a smart card, a portable computing device, a bio sensor system, and/or an activity sensor system, according to an embodiment of the present invention.

FIG. 7 is a functional block diagram illustrating an example of a continuous health monitoring system 700, including a sensor 110, a controller 120, an analysis engine 130, a knowledge base 140, a smart card 150, a portable computing device 160, a bio sensor system 170, and/or an activity sensor system 180. In an embodiment, the sensor 110, controller 120, and analysis engine 130 are described above with reference to FIG. 1A. In an embodiment, the knowledge base 140, smart card 150, and portable device 160 are described above with reference to FIG. 4.

The analysis engine 130 sends protocols to, and/or receives data from activity sensor system 180 and/or bio sensor system 170. Activity sensor systems include sensors, such as gyros or motion sensors, which enable estimation of patient activity (sleeping, resting, eating, strenuous exercising, etc.). In an embodiment, activity sensor system may be included in portable computing device 160, which include motion sensor 165d. Bio sensor systems 170 measure aspects of the patient's condition, such as pulse rate, temperature, respiration rate, pulse oximetry, or other analyte readings. The analysis engine 130 can also be configured to receive data from a third party activity sensor system such as, for example, a Fitbit® activity tracker.

The protocols indicate two types of information. The first type of information includes parameters, settings, and preferences for sensing, and the device for taking the data that are typically independent of sampling rate, duration, and timing. The second type of information includes sampling type, timing, rate, and duration. These protocols, and the two types of information, are used for analyte sensing (including glucose level), other bio sensors, and activity sensors. The activity data and bio sensor data that are communicated to the analysis engine 130 from activity sensor 180 and bio sensor system 170, respectively, may be stored in the knowledge base 140, and used to generate results (trends, patterns, alerts, sensor levels). The analysis engine may fuse the data from sensor 110, bio sensor system 170, activity sensor system 180, and data from knowledge base 140 to generate results.

For example, the analysis engine 130 may trigger an alarm when sensor 110 senses a blood glucose reading that is sustained over 150 mg/dl for 30 minutes when an activity sensor determines that a patient is not sleeping based on a reading from motion sensor 165d or data received from an activity sensor 180, which can be indicative of patient activity other than sleeping. However, the analysis engine 130 may not trigger an alarm when the sensor 110 senses a blood glucose reading that is sustained over 150 mg/dl for 30 minutes when an analysis engine determines that a patient is at rest based on a reading from motion sensor 165d or an activity sensor 180 in conjunction with the time of day and ambient light level; but the analysis engine 130 can be configured to trigger an alarm when sensor 110 senses a blood glucose reading has been sustained over 150 mg/dl for 2 hours if the analysis engine determines a patient is at rest.

In an embodiment, analysis engine 130 communicates with and/or interfaces to one or more bio sensor systems 170 and/or one or more activity sensor systems 180.

Figure 8:
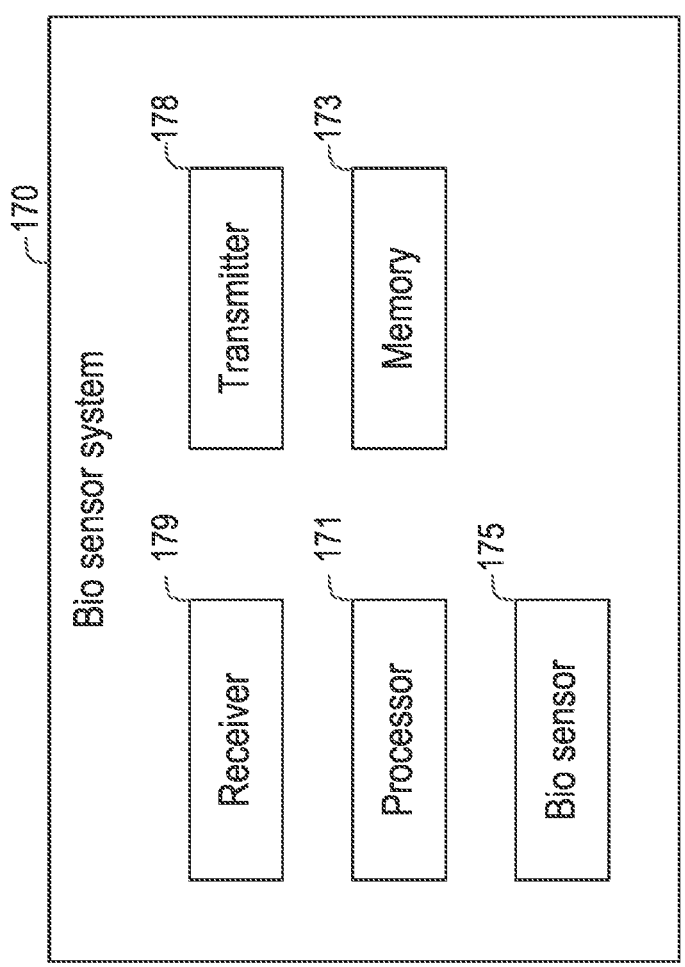
FIG. 8 is a functional block diagram of the bio sensor system in FIG. 7, according to an embodiment of the present invention.

FIG. 8 is a functional block diagram of the bio sensor system 170 in FIG. 7. The bio sensor system 170 communicates bio sensor data and bio sensor protocols to and from the analysis engine 130 using transmitter 178 and receiver 179. In an embodiment, transmitter 178 and receiver 179 may be combined in a transceiver (not shown). The bio sensor 170 includes a processor circuit (processor) 171 in wired communication with memory circuit (memory) 173, transmitter 178, and receiver 179. The bio sensor 170 measures/monitors an aspect of a patient's health/biology that may relate to a medical condition or otherwise characterize a patient, and communicates data based on these measures to the processor 171. Example data that can be obtained by these measurements or monitoring may include an analyte level, pulse rate, temperature, respiration rate, or pulse oximetry.

Figure 9:
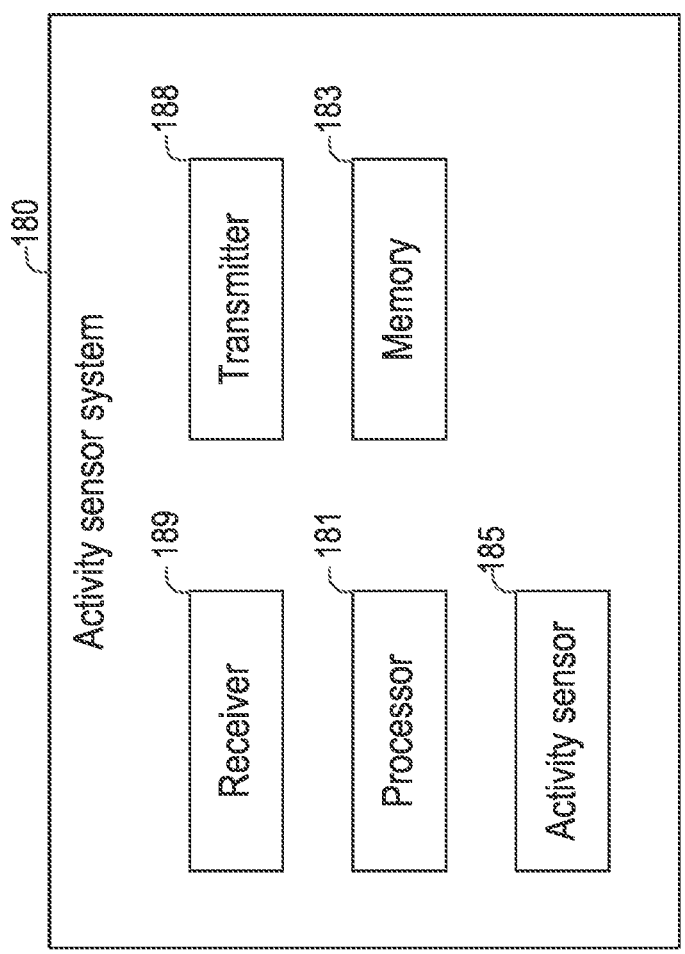
FIG. 9 is a functional block diagram of the activity sensor system in FIG. 7, according to an embodiment of the present invention.

FIG. 9 is a functional block diagram of the activity sensor system 180 in FIG. 7. The activity sensor system 180 communicates activity sensor data and activity sensor protocols to and from the analysis engine 130 using transmitter 188 and receiver 189. In an embodiment, transmitter 188 and receiver 189 may be combined in a transceiver (not shown). The activity sensor 180 includes a processor circuit (processor) 181 in wired communication with memory circuit (memory) 183, transmitter 188, and receiver 189. The activity sensor 180 measures an aspect of a patient's activity based on, for example, movement related to whether a patient is stationary, walking, running, or climbing stairs, and communicates data based on these measures to the processor 171. The activity sensor system 180 may, for example, use sensors and algorithms similar to the sensors and algorithms used by commercially available fitness tracking systems such as, for example, the Fitbit® activity tracker.

FIG. 10 is a functional block diagram illustrating an example of a continuous health monitoring system 1000, including a sensor 110, a controller 120, an analysis engine 130, a knowledge base 140, a smart card 150, a portable computing device 160, a bio sensor system 170, an activity sensor system 180, a network 200, and/or a health provider network/monitor 210. In an embodiment, the sensor 110, controller 120, and analysis engine 130 are described above with reference to FIG. 1A. In an embodiment, the knowledge base 140, smart card 150, and portable device 160 are described above with reference to FIG. 4. In an embodiment, the bio sensor system 170 and activity sensor system 180 are described above with respect to FIG. 7.

In addition to communicating results and data generated by analysis engine 130 to smart card 150 and/or portable computing device 160, the analysis engine 130 may communicate results and data to a network 200, and on to health provider network/monitor 210. Network 200 is connected by wire or wirelessly to the analysis engine 130. Network 200 is in wired or wireless communication with health provided network/monitor 210. In an embodiment, network 200 is an internetworking network (internet) enabling communication with a doctor via health provider network/monitor 210. In an embodiment, health provider network/monitor 210 includes electronic patient records (not shown) such as, for example, electronic health records and electronic medical records, medical databases (not shown), desktop physician workstations, and/or portable computing devices.

FIG. 11 is a functional block diagram of a health provider network/monitor 210. Health provider network/monitor 210 may include a computing device used by a physician or other provider. The health provider network/monitor 210 may run a software application (app) directed to monitoring the results of analysis engine 130, providing these results to a physician or another caregiver (nurse, spouse, etc.), recording results in a medical database, and/or enabling the physician to generate orders (such as the need for office visits, hospitalizations, changes in medications, etc.), based on the patient's history, condition, and/or results. The health provider network/monitor 210 includes a receiver 219 and transmitter 218 to receive results and transmit orders to and from the analysis engine 130 via network 200. The receiver 219 and transmitter 219 are in communication with processor 211.

The health provider network/monitor 210 includes a processor 211 in wired communication with memory 213, transmitter 218, and receiver 219. The health provider network/monitor 210 receives inputs via a touchscreen 215a, a keypad 215b (keyboard 215b), and/or a microphone 215c each in wired communication with the processor 161. A physician may enter a query using the touchscreen 215a, keypad/keyboard 215b, or by speech entry via microphone 215c. The health provider network/monitor 210 includes display 217a, speaker 217b, and/or actuator 217c, each in wired communication with the processor 211. The touchscreen 215a and display 217a may be integrated so that a physician may select an item on display 217a by touching touchscreen 215a at one or more corresponding points on the touchscreen 215a. The display 217a outputs visual data and information, the speaker 217b outputs audio data and information, and the actuator 217c outputs tactical data and information. In an embodiment, portable computing device 210 may display a trend line on display 217a, output a high glucose reading over speaker 217b, and/or output tactile data using actuator 217c (that can be, for example, by vibration), in case of an alarm or alert. The tactile alert may correspond to a tapping of a doctor's wrist when the health provider network/monitor 210 is a wearable computer worn on a doctor's or other healthcare provider's wrist, or a vibration when the health provider network/monitor 210 is a phone, tablet or other device.

A doctor may monitor a patient's progress by viewing results from the analysis engine via network 200. The network 200 (internet, cloud) may include a health provider network and/or monitoring station used by the physician. This enables communications of results, including glucose levels, trends, patterns, and alerts. Data may be stored in the patient's electronic medical record (not shown).

A doctor may also submit orders. These orders may impact alarm thresholds, and may set alarms or thresholds with respect to different patient activities. For example, an order may request frequent glucose readings at a predefined frequency, during and after a meal, or lower a glycemic alarm during strenuous exercise detected by an activity sensor The orders may be transmitted from the health provider network/monitor 210 via the network 200 to the analysis engine 130. The knowledge base 140 maps the order from the doctor to both types of protocol information that indicates, for example, when and how often to interrogate the sensor, as well as relationships with activity levels and/or other reading (from a bio sensor, etc.). The knowledge base 140 may store the mappings from order to protocol, as well as the form of analysis to perform on the sensed data. The doctor may query for data from the knowledge base 140.

Figure 12:
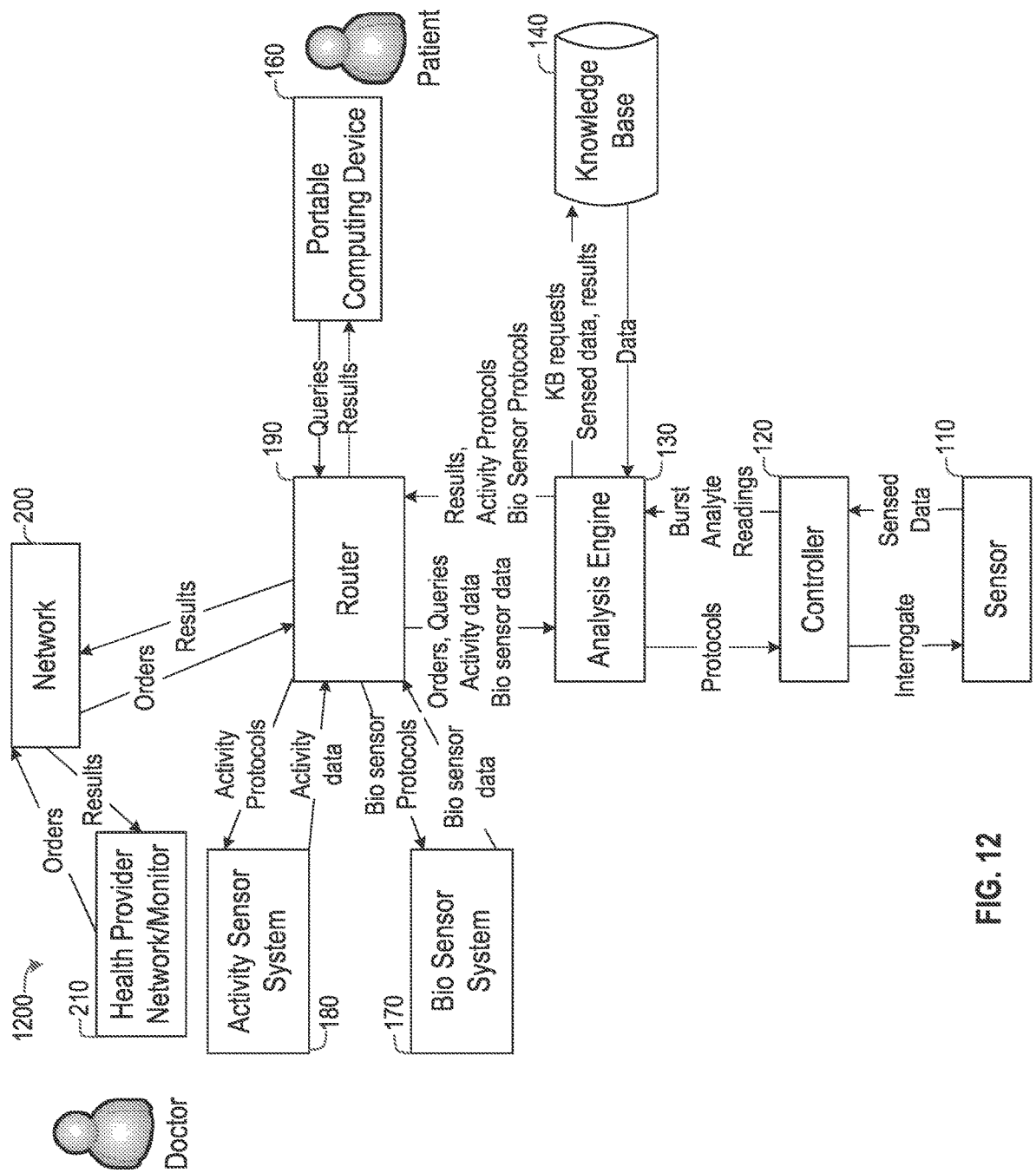
FIG. 12 is a functional block diagram illustrating an example of a continuous health monitoring system, including a sensor, a controller, an analysis engine, a knowledge base, a smart card, a portable computing device, a bio sensor system, an activity sensor system, a router, a network, and/or a health provider network/monitor, according to an embodiment of the present invention.

FIG. 12 is a functional block diagram illustrating an example of a continuous health monitoring system 1200, including a sensor 110, a controller 120, an analysis engine 130, a knowledge base 140, a smart card 150, a portable computing device 160, a bio sensor system 170, an activity sensor system 180, a router 190, a network 200, and/or a health provider network/monitor 210. In an embodiment, the sensor 110, controller 120, and analysis engine 130 are described above with reference to FIG. 1A.

In an embodiment, the knowledge base 140, smart card 150, and portable device 160 are described above with reference to FIG. 4. In an embodiment, the bio sensor system 170 and activity sensor system 180 are described above with respect to FIG. 7. In an embodiment, the network 190 and health provider network/monitor 210 are described above with reference to FIG. 10. The router 190 is in wireless or wired communication with the analysis engine 130, portable computing device 160, biosensor system 170, activity sensor system 180, and/or network 200.

The router 190 processes and routes information. The router 190 transmits orders, queries, activity data, and bio sensor data to the analysis engine 130. The router 190 receives results, activity protocols, and bio sensor protocols from the analysis engine 130. The router 190 receives queries from portable computing device 160 for analysis by analysis engine 130 and transmits results from analysis engine 130 to portable computing device 160. In an embodiment, the router receives queries from smart card 150 and sends results to smart card 150. In an embodiment, the router 190 transmits bio sensor protocols to bio sensor system 170, and receives bio sensor data from bio sensor system 170. In an embodiment, the router 190 receives orders from the network 200, and transmits results to the network 200.

In an embodiment, the router 190 is a smart card 150. In an embodiment, the router 190 includes multiple network elements and/or routers.

Figure 13:
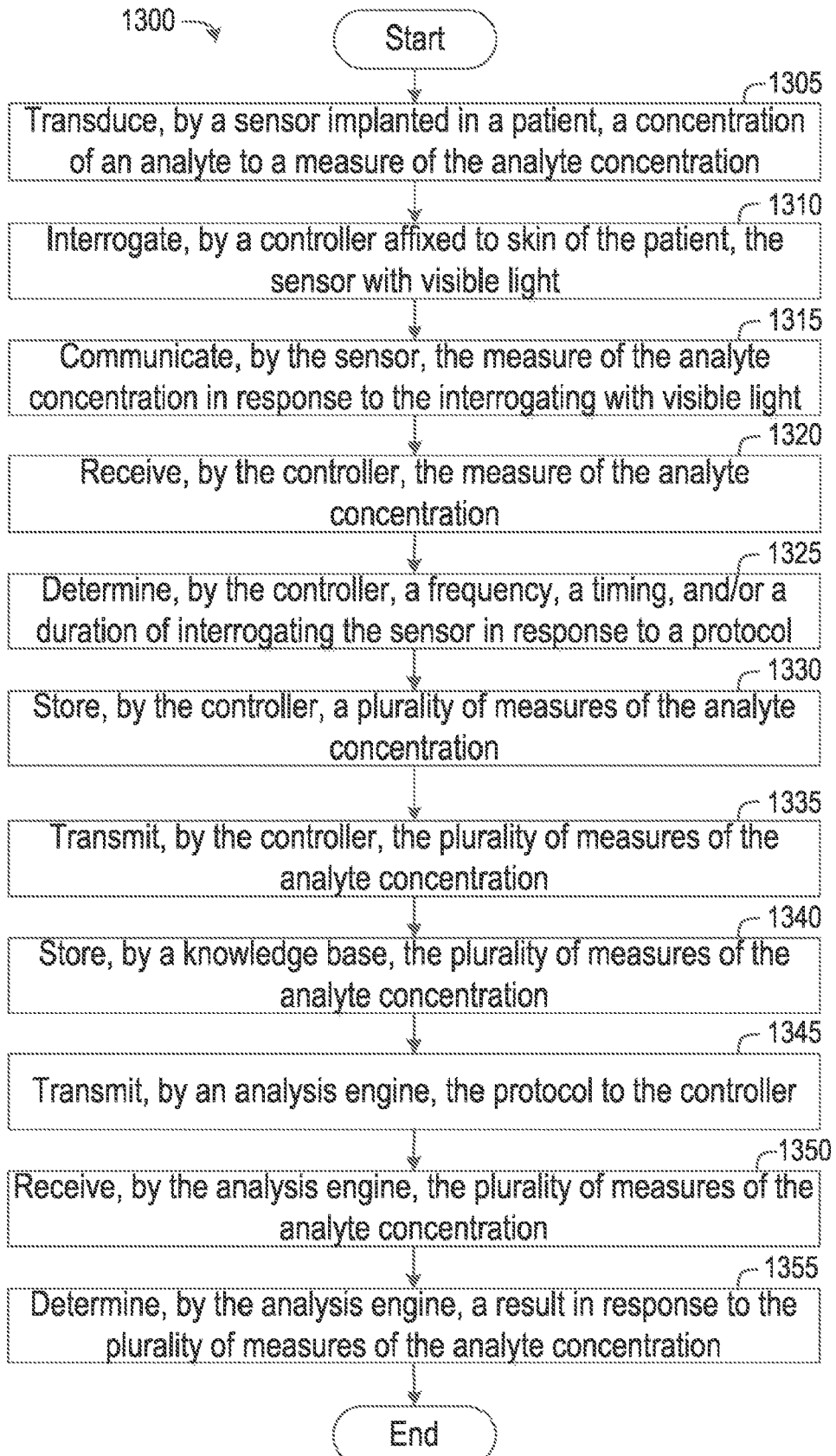
FIG. 13 is a flowchart that illustrates an example of a method of continuous health monitoring, according to an embodiment of the present invention.

FIG. 13 is a flowchart that illustrates an example of a method 1300 of continuous health monitoring. In some embodiments, the method 1300 may be performed by the system 100 in FIG. 1A. In some embodiments, the method 1300 may be performed by the system 400 in FIG. 4. In some embodiments, the method 1300 may be performed by the system 700 in FIG. 7. In some embodiments, the method 1300 may be performed by the system 1000 in FIG. 10. In some embodiments, the method 1300 may be performed by the system 1200 in FIG. 12.

In block 1305, method 1300 transduces, by a sensor implanted in a patient, a concentration of an analyte to a measure of the analyte concentration. In an embodiment, the analyte is glucose. In some implementations, the functionality of block 1305 is performed by the transducer 111 of the sensor 110 illustrated in FIGS. 1A, 2A, 4, 7, 10, and 12.

In block 1310, method 1300 interrogates, by a controller affixed to skin of the patient, the sensor with visible light. In some embodiments, the functionality of block 1310 is performed by optical transmitter 125 of the controller 120 illustrated in FIGS. 1A, 3A, 4, 7, 10, and 12.

In block 1315, method 1300 communicates, by the sensor, the measure of the analyte concentration in response to the interrogating with visible light. In some embodiments, the functionality of block 1315 is performed by an optical transmitter 118 of the sensor 110 illustrated in FIGS. 1A, 2, 4, 7, 10, and 12.

In block 1320, method 1300 receives, by the controller, the measure of the analyte concentration. In some embodiments, the functionality of block 1320 is performed by optical receiver 127 of the controller 120 illustrated in FIGS. 1A, 3A, 4, 7, 10, and 12.

In block 1325, method 1300 determines, by the controller, a frequency, a timing, and/or a duration of interrogating the sensor to determine a measure of the analyte concentration in response to a protocol. In some implementations, the functionality of block 1325 is performed by processor 121 of the controller 120 illustrated in FIGS. 1A, 3A, 4, 7, 10, and 12.

In block 1330, method 1300 stores, by the controller, a plurality of measures of the analyte concentration. In some embodiments, the functionality of block 1330 is performed by memory circuit (memory) 123 of the controller 120 illustrated in FIGS. 1A, 3A, 4, 7, 10, and 12.

In block 1335, method 1300 transmits, by the controller, the plurality of measures of the analyte concentration. In some embodiments, the functionality of block 1335 is performed by transmitter 128 of the controller 120 illustrated in FIGS. 1A, 3A, 4, 7, 10, and 12.

In block 1340, method 1300 stores, by a knowledge base, the plurality of measures of the analyte concentration. In some embodiments, the functionality of block 1340 is performed by knowledge base 140 illustrated in FIGS. 4, 7, 10, and 12.

In block 1345, method 1300 transmits, by an analysis engine, the protocol to the controller. In some embodiments, the functionality of block 1345 is performed by analysis engine 130 illustrated in FIGS. 1A, 4, 7, 10, and 12.

In block 1350, method 1300 receives, by the analysis engine, the plurality of measures of the analyte concentration. In some implementations, the functionality of block 1350 is performed by analysis engine 130 illustrated in FIGS. 1A, 4, 7, 10, and 12.

In block 1355, method 1300 determines, by the analysis engine, a result in response to the plurality of measures of the analyte concentration and the protocol. In some embodiments, the functionality of block 1350 is performed by analysis engine 130 illustrated in FIGS. 1A, 4, 7, 10, and 12. In an embodiment, the result is a glucose level, a glycemic history, a glycemic dynamics envelope, insulin levels, and/or normative glycemic profiles with insulin overlay.

Figure 14:
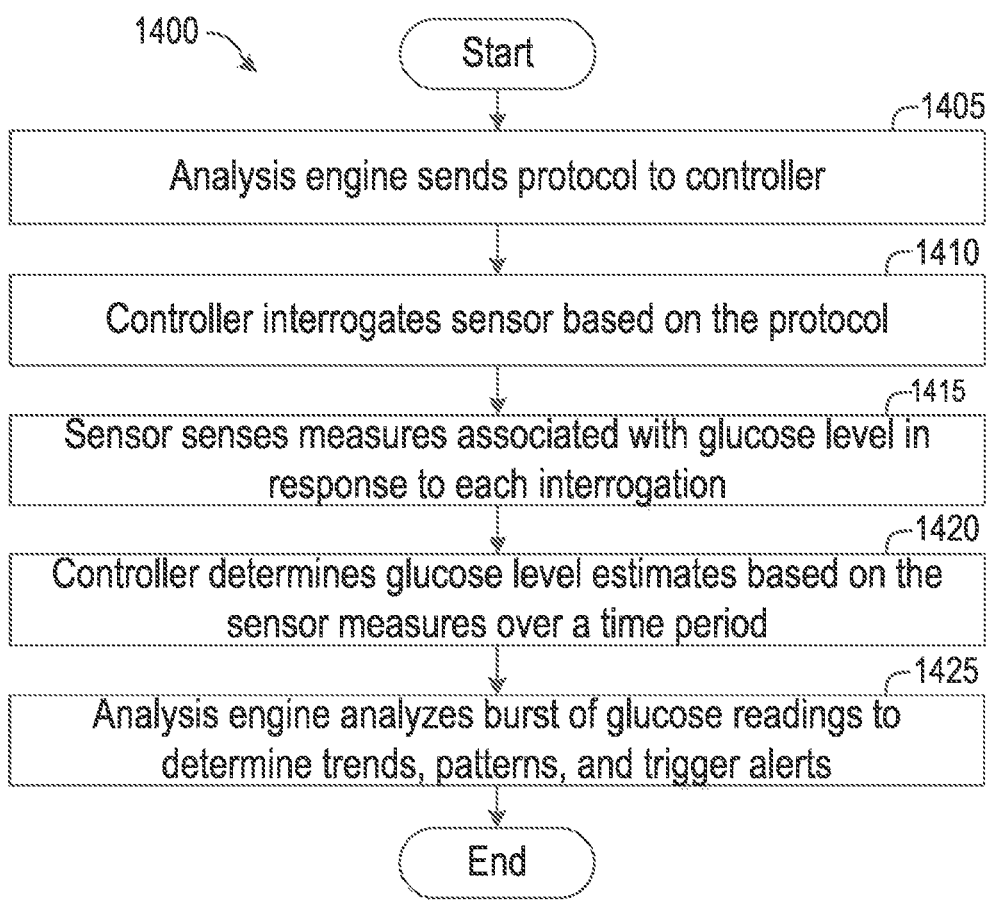
FIG. 14 is a flowchart that illustrates an example of a workflow of continuous health monitoring by a sensor, a controller, and an analysis engine, according to an embodiment of the present invention.

FIG. 14 is a flowchart that illustrates an example of a workflow 1400 of continuous health monitoring by a sensor, a controller, and an analysis engine. In some aspects, the workflow 1400 may be performed by the system 100 in FIG. 1A, the system 400 in FIG. 4, the system 700 in FIG. 7, the system 1000 in FIG. 10, and/or the system 1200 in FIG. 12. In block 1405, analysis engine 130 sends a protocol to controller 120. In block 1410, the controller 120 interrogates sensor 110 based on the protocol. In block 1415, sensor 110 senses measures associated with glucose levels in response to each interrogation. In block 1420, controller 120 determines glucose level concentration estimates based on the sensor measures over a time period. In block 1425, analysis engine 130 analyzes bursts of glucose level readings to determine trends, patterns, and trigger alerts.

Figure 15:
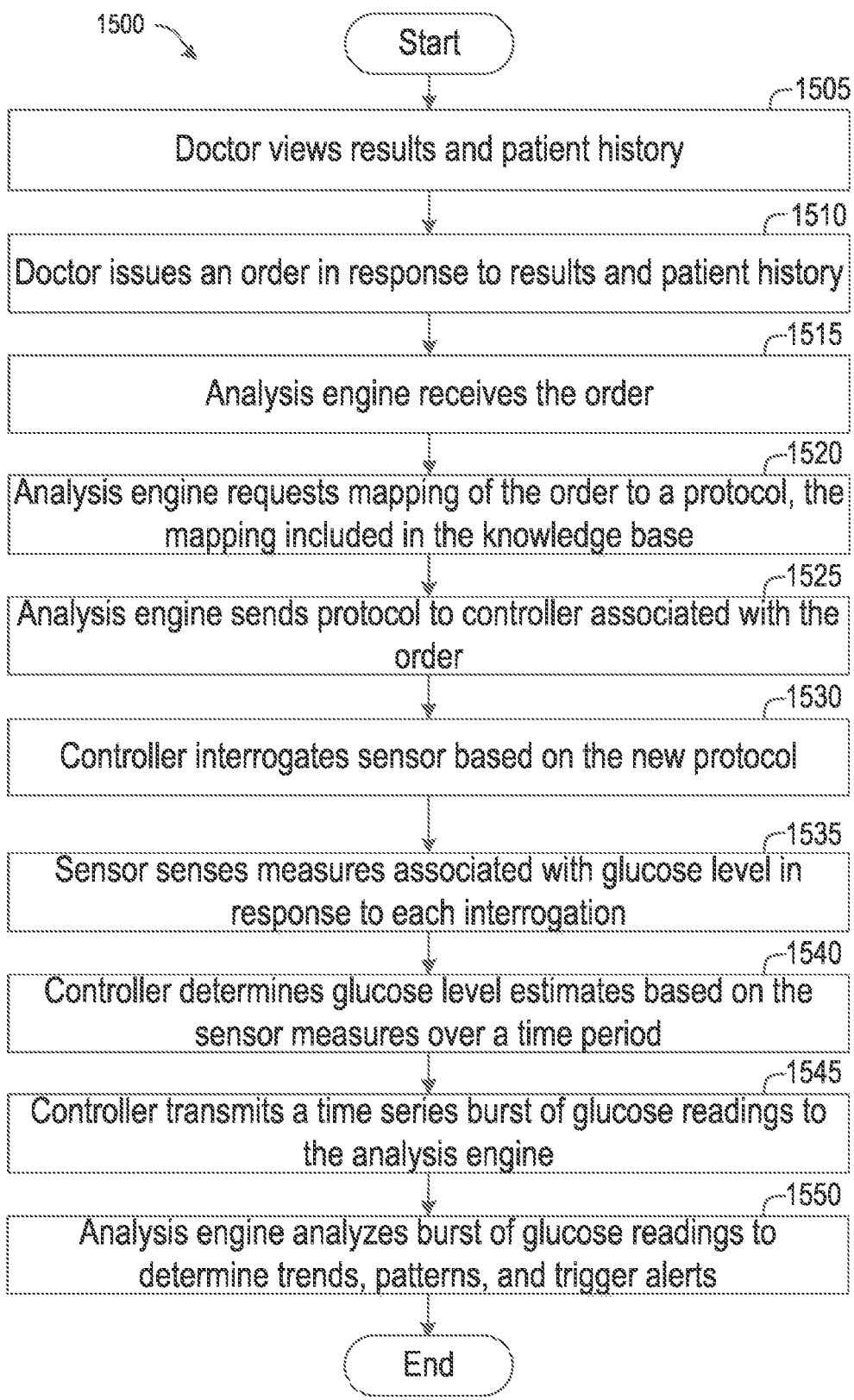
FIG. 15 is a flowchart that illustrates an example of a workflow of continuous health monitoring incorporating doctor orders, according to an embodiment of the present invention.

FIG. 15 is a flowchart that illustrates an example of a workflow 1500 of continuous health monitoring incorporating doctor orders. In some aspects, the workflow 1500 may be performed by the system 1000 in FIG. 10 and/or the system 1200 in FIG. 12. In block 1505, a doctor views results and patient history at health provider network/monitor 210. In block 1510, the doctor issues an order in response to results and patient history at health provider network/monitor 210 (FIGS. 10 and 12). In block 1515, analysis engine 130 receives the order. In block 1520, analysis engine 130 requests mapping of the order to a protocol, the mapping included in the knowledge base 140. In block 1525, the analysis engine 130 sends the protocol associated with the order to the controller 120. In block 1530, the controller 120 interrogates the sensor 110 based on the new protocol. In block 1535, the sensor 110 senses glucose concentrations associated with glucose levels in the interstitial fluid into which the sensor 110 is implanted in response to each interrogation. In block 1540, the controller 120 determines glucose level estimates based on the sensor measurements over a time period. In block 1545 the controller 120 transmits a time series burst of glucose readings to the analysis engine 130. In block 1550, the analysis engine 130 analyzes burst(s) of glucose readings to determine trends, patterns, and trigger alerts.

Figure 16:
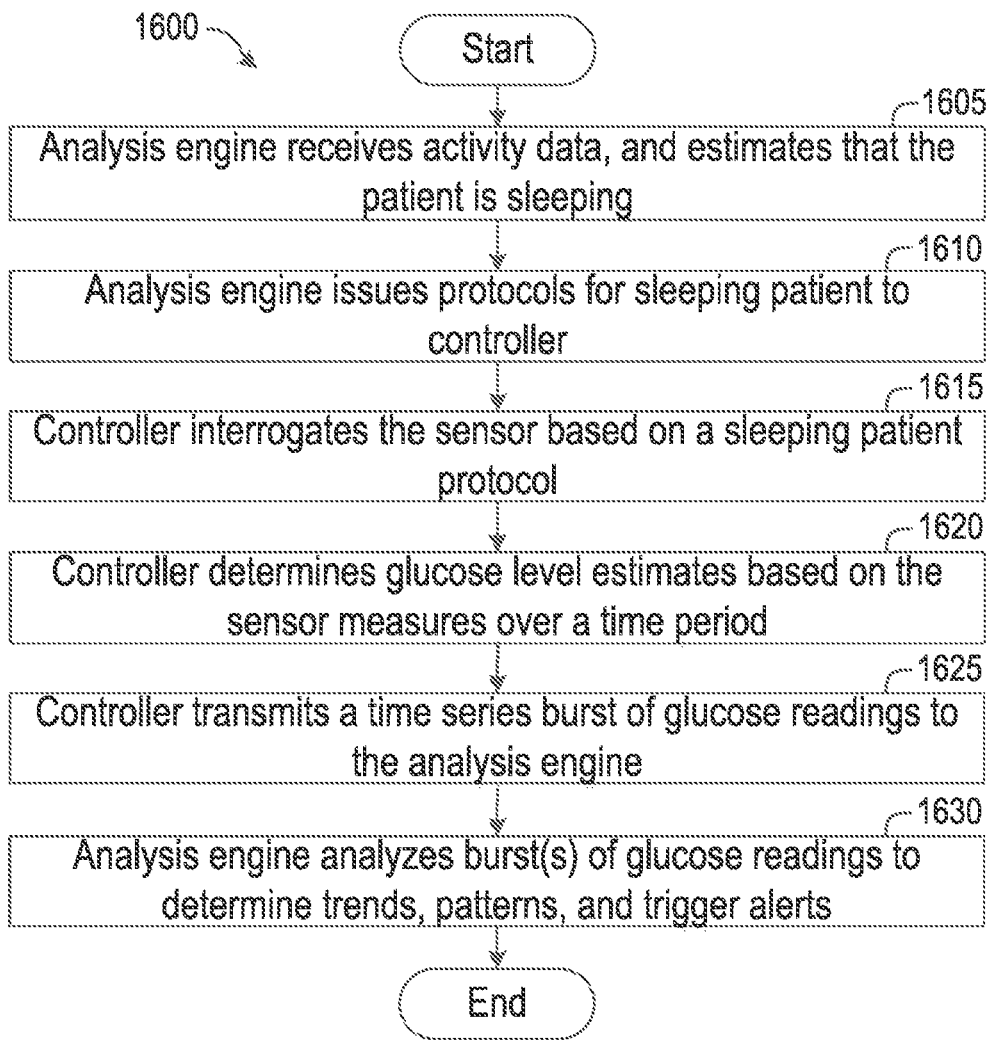
FIG. 16 is a flowchart that illustrates an example of a workflow of continuous health monitoring incorporating activity data, according to an embodiment of the present invention.

FIG. 16 is a flowchart that illustrates an example of a workflow 1600 of continuous health monitoring incorporating activity data. In some aspects, the workflow 1600 may be performed by the system 700 in FIG. 7, the system 1000 in FIG. 10, and/or the system 1200 in FIG. 12. In block 1605, the analysis engine 130 receives activity data from the activity sensor system 180, and estimates the patient's level of activity. In this embodiment, the analysis engine 130 determines that the patient is sleeping. In block 1610, the analysis engine 130 issues protocols for the sleeping patient to the controller 120. In block 1615, the controller 120 interrogates the sensor 110 based on a sleeping patient protocol that is included in the controller 120. In block 1620, the controller 120 determines glucose level estimates based on the sensor measures over a time period. In block 1625, the controller 120 transmits a time series burst of glucose readings to the analysis engine. In block 1630, the analysis engine 130 analyzes burst(s) of glucose readings to determine trends, patterns, and trigger alerts. The alerts are dependent on the protocol. For example, a patient who is sleeping may have the low glucose alert set to a lower threshold value than a patient that is not sleeping, but exercising. For example, in a sleeping patient, the alarm for a high glucose level may not be triggered if the glucose measurement is slowly climbing above a primary threshold but has not yet crossed a secondary threshold.

Other workflows may include incorporation of bio sensed data or inputs/queries from the patient.

Figure 17:
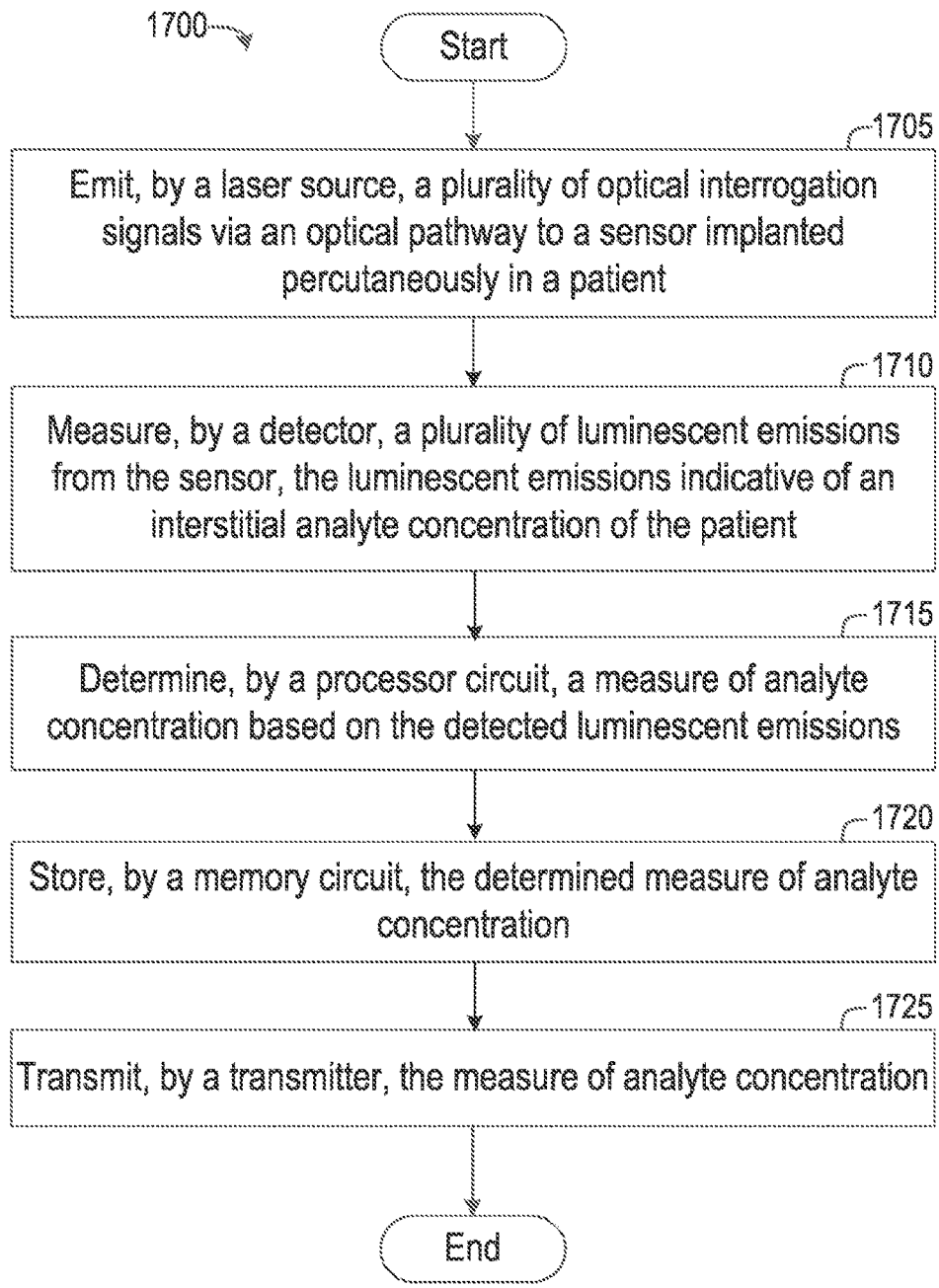
FIG. 17 is a flowchart that illustrates an example of a method of continuous health monitoring, according to an embodiment of the present invention.

FIG. 17 is a flowchart that illustrates an example of a method 1700 of continuous health monitoring. In some aspects, the method 1700 may be performed by the controller 120 in FIGS. 1A, 3A, 4, 7, 10, and 12.

In block 1705, method 1700 emits, by a laser source, a plurality of optical interrogation signals via an optical pathway to a sensor implanted percutaneously in a patient. In an embodiment, the analyte is glucose and the optical pathway is a waveguide. In some embodiments, the functionality of block 1705 is performed by the laser source emitter 125 of the controller 120 illustrated in FIGS. 1A, 3A, 4, 7, 10, and 12.

In block 1710, method 1700 measures, by a detector, a plurality of luminescent emissions from the sensor, the luminescent emissions indicative of an interstitial analyte concentration of the patient. In some embodiments, the functionality of block 1710 is performed by the detector 127 of the controller 120 illustrated in FIGS. 1A, 3A, 4, 7, 10, and 12.

In block 1715, method 1700 determines, by a processor circuit, a measure of analyte concentration based on the detected luminescent emissions. In some embodiments, the functionality of block 1715 is performed by the processor (processor circuit) 121 of the controller 120 illustrated in FIGS. 1A, 3A, 4, 7, 10, and 12.

In block 1720, method 1700 stores, by a memory circuit, the determined measure of analyte concentration. In some embodiments, the functionality of block 1720 is performed by the memory (memory circuit) 123 of the controller 120 illustrated in FIGS. 1A, 3A, 4, 7, 10, and 12.

In block 1725, method 1700 transmits, by a transmitter, the measure of analyte concentration. In some embodiments, the functionality of block 1725 is performed by the transmitter 128 of the controller 120 illustrated in FIGS. 1A, 3A, 4, 7, 10, and 12.

Analyte Sensor and Method of Manufacturing an Analyte Sensor

Disclosed and described herein are embodiments of a layered optical sensor such as, for example, sensor 110, that can be used to measure different analytes in a patient. A non-exhaustive list of example analytes that can be measured with embodiments of the present invention include, and are not limited to, glucose, galactose, lactose, peroxide, cholesterol, amino acids, fructose, alcohol, lactic acid, and mixtures of the preceding analytes. In particular, disclosed herein is a unique method for forming a layered optical sensor through a layering technique and capillary filling, as well as a method of mass manufacturing optical sensors. The disclosed sensors can advantageously be quickly and easily manufactured, allowing for mass production for embodiments of the sensor.

Laminate Structure

Figure 18:
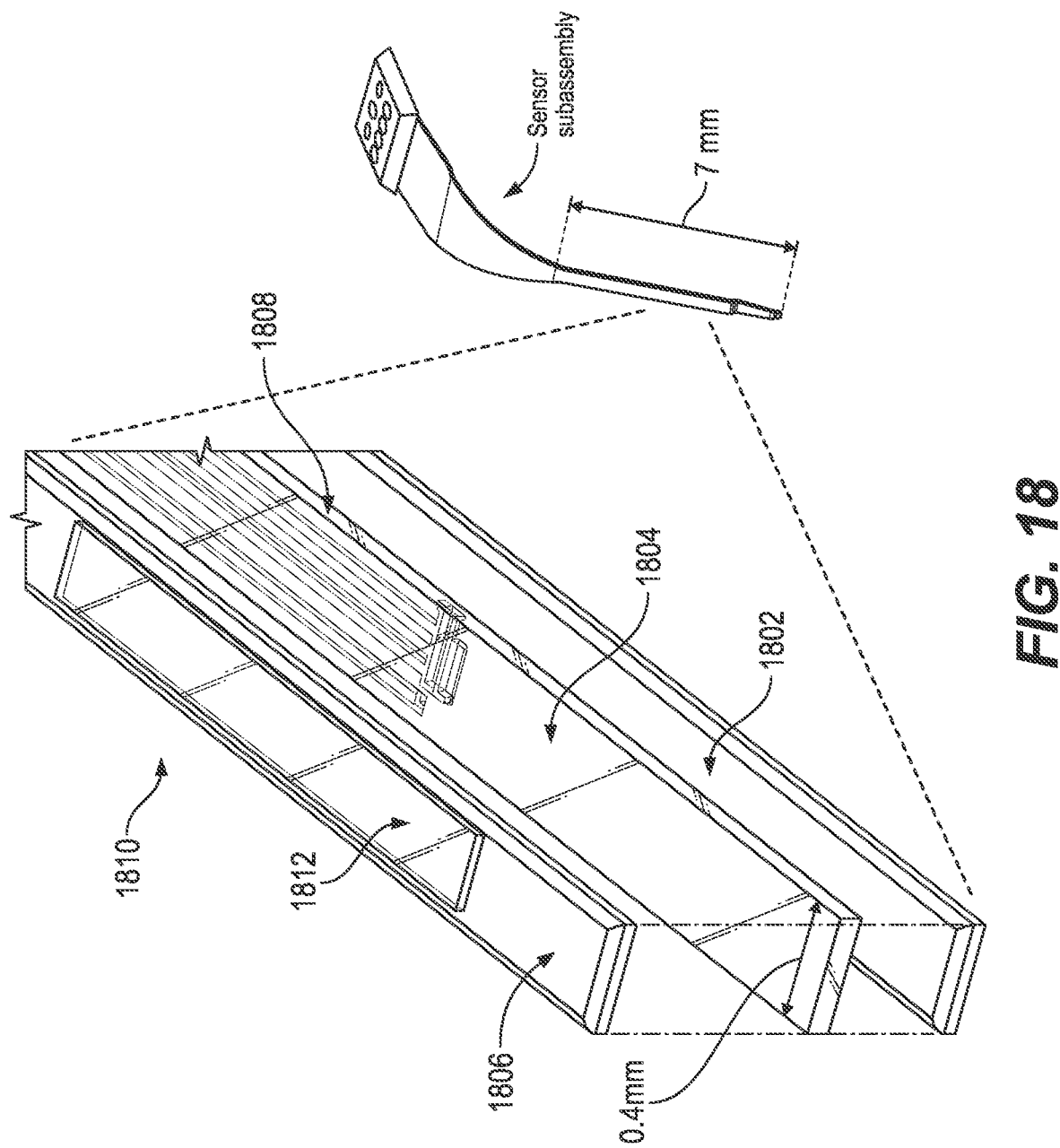
FIG. 18 illustrates different layers of an embodiment of a layered optical sensor, according to an embodiment of the present invention.

Accordingly, FIG. 18 illustrates an example embodiment of a layered optical sensor for measuring an analyte. The disclosure can relate to a sensor subassembly, and can be incorporated with other sensor features. The analyte can be, for example, glucose, galactose, lactose, peroxide, cholesterol, amino acids, fructose, alcohol, lactic acid, and mixtures of the preceding analytes, but the particular analyte to be measured is not limiting.

As shown, the layered optical sensor from sensor subassembly 110A can be composed of a plurality of different layers, where the layers can be located on top of one another. Each of the layers can provide a specific structure or purpose, though other types of layers can be used as well. While the below disclosure discusses the specifics of a three-layer configuration, it will be understood that other numbers of layers could be used (e.g., 2, 4, 5 or more), and the number of layers can vary depending on the internal components of the sensor and the requirements or functions of the sensor.

In some embodiments, a bottom layer 1802 can be generally stiff, thus allowing for mechanical modulation. Specifically, the bottom layer 1802 can provide for mechanical integrity of the layered optical sensor, and thus can be the strongest of the layers in some embodiments. Further, the bottom layer 1802 can have structural support features sufficient to mate with a lancet, or other implantation devices. For example, the bottom layer 1802 can include protrusions, notches, or attachment mechanisms. In some embodiments, the bottom layer 1802 can have a particular stiffness to provide durability to the layered optical sensor.

In some embodiments, the bottom layer 1802 may be formed from a structural polymer, such as a robust biocompliant polymer film of polyether ether ketone (PEEK). However, other materials can be used as well to form the bottom layer 1802, such as metals (e.g., Nitinol), plastics, rubbers, and the particular material is not limiting. Preferably, the material forming the bottom layer 1802 can be biocompatible in order to reduce a patient's response to implantation of the layered optical sensor. However, in some embodiments the material may not be biocompatible, such as if the sensor will only be inserted into a patient for a short period of time or if the sensor will be coated with a biocompatible coating.

In some embodiments, the bottom layer 1802 can be formed of a single piece of material formed in a generally rectangular shape. Thus, in some embodiments there are no cutouts, apertures, holes, or protrusions into the bottom layer 1802, unlike the other below disclosed layers, and the bottom layer 1802 can be generally flat on the top and bottom. In some embodiments, the bottom layer 1802 can have beveled and/or tapered edges, which can be advantageous for fitting of layers together.

In some embodiments, the bottom layer 1802 can have a width of about 0.1, 0.2, 0.3, 0.4, 0.5, 0.6, 0.7, 0.8, 0.9, or 1.0 mm. In some embodiments, the bottom layer 1802 can have a length of about 1, 2, 3, 4, 5, 6, 7, 8, 9, or 10 mm. However, the particular dimensions of the bottom layer 1802 are not limiting.

Next, at least one middle layer, or optical sensing layer, 1804 can be formed on top of bottom layer 1802. As mentioned, a plurality of middle layers can be used, each having the same or different configurations, though the use of a single middle layer 1804 is discussed herein.

The middle layer 1804 can include a distal section 1806 and a proximal section 1808. The distal section 1806 can be generally flat, and can be shaped similarly to the distal section of bottom layer 1802. In some embodiments, the distal section 1806 may not have any apertures cut out of it, and thus can be generally the same thickness throughout.

The proximal end 1808 can include a number of features for the construction of the layered optical sensor. A close-up view of the proximal end 1808 is shown in FIG. 19. As shown, the proximal end 1808 can include an enzymatic hydrogel cavity 1902 and an oxygen sensing polymer cavity 1904. While FIG. 19 shows the discussed features filled with the respective polymers, during construction of the layered optical sensor, and specifically, middle layer 1804, these portions are left as empty cavities, and will be filled in a manner as discussed in detail below. The middle layer 1804 can include other cavities as well, such as the oxygen reference cavity 1908 and a glucose inlet cavity 1906, which can be in fluid communication with the enzymatic hydrogel cavity 1902 and the oxygen sensing polymer cavity 1904. The particular amount and type of cavity in the middle layer 1804 is not limiting.

Further, as shown in FIG. 19, the proximal end 1808 can include a number of optical circuits or waveguides 1910 allowing for optical radiation, such as light, to pass into the oxygen sensing polymer cavity 1904 and oxygen reference cavity 1908.

In some embodiments, the middle layer 1804 may be formed from polymer, such as a polymer laminate. However, other materials can be used as well, such as metals (e.g., Nitinol), plastics, rubbers, and the particular material is not limiting. Preferably, the material forming the middle layer 1804 can be biocompatible in order to reduce a patient's response to implantation/insertion. However, in some embodiments the material may not be biocompatible, such as if the sensor will only be inserted for a short period of time. In some embodiments, the material of the middle layer 1804 is the same as the material of the bottom layer 1802. In some embodiments, the material of the middle layer 1804 is the different from the material of the bottom layer 1802.

In some embodiments, the dimensions of the middle layer 1804 are generally the same as that of the bottom layer 1802. In some embodiments, the middle layer 1804 is bigger than the bottom layer 1802. In some embodiments, the middle layer 1804 is smaller than the bottom layer 1802. In some embodiments, the middle layer 1804 can have a width of about 0.1, 0.2, 0.3, 0.4, 0.5, 0.6, 0.7, 0.8, 0.9, or 1.0 mm. In some embodiments, the middle layer 1804 can have a length of about 1, 2, 3, 4, 5, 6, 7, 8, 9, or 10 mm. However, the particular dimensions of the middle layer 1804 are not limiting.

Next, as depicted in FIG. 18, a top layer 1810 can be formed on top of middle layer 1804, or plurality of middle layers. The top layer 1810 can be generally flat, and can be shaped similarly to the bottom layer 1802 and/or middle layer 1804. In some embodiments, portions of the top layer 1810 may not have any apertures cut out of it, and thus can be generally the same thickness throughout. In some embodiments, the top layer 1810 may have portions cut out of it to form an oxygen conduit cavity 1812. Similar to the middle layer 1804, during construction of the layered optical sensor, these oxygen conduit cavities 1812 are left as empty cavities, and will be filled in a manner as discussed in detail below. In some embodiments, other cavities can be included in the top layer 1810. For example, the oxygen reference cavity 1908 can be moved from the middle layer 1804 to the top layer 1810.

In some embodiments, the top layer 1810 may be formed from a polymer, such as, for example, a polymer laminate. However, other materials can be used as well, such as metals (e.g., Nitinol), plastics, rubbers, and the particular material is not limiting. Preferably, the material forming the top layer 1810 can be biocompatible in order to reduce a patient's response to implantation/insertion. However, in some embodiments the material may not be biocompatible, such as if the sensor will only be inserted for a short period of time. In some embodiments, the material of the top layer 1810 is the same as the material of the bottom layer 1802 and/or the middle layer 1804. In some embodiments, the material of the top layer 1810 is the different from the material of the bottom layer 1802 and/or the middle layer 1804.

In some embodiments, the dimensions of the top layer 1810 are generally the same as that of the bottom layer 1802 and/or middle layer 1804. In some embodiments, the top layer 1810 is bigger than the bottom layer 1802 and/or middle layer 1804. In some embodiments, the top layer 1810 is smaller than the bottom layer 1802 and/or middle layer 1804. In some embodiments, the top layer 1810 can have a width of about 0.1, 0.2, 0.3, 0.4, 0.5, 0.6, 0.7, 0.8, 0.9, or 1.0 mm. In some embodiments, the top layer 1810 can have a length of about 1, 2, 3, 4, 5, 6, 7, 8, 9, or 10 mm. However, the particular dimensions of the top layer 1810 are not limiting.

Further, a top cap layer can be used to seal the top layer 1810. For example, the top cap layer can be formed from a silicone pressure sensitive adhesive (PSA). This can be oxygen permeable and glucose impermeable, thus allowing for oxygen to pass through the top cap layer and into the oxygen conduit cavity and preventing glucose or other analytes from passing through. In some embodiments, a conduit hydrogel is dispensed into shaped region in conduit structure. In some embodiments, PSA is directly shaped by embossing to create shaped region. In some embodiments, a punched structure is laminated to the PSA to create shaped region.

Figure 20A:
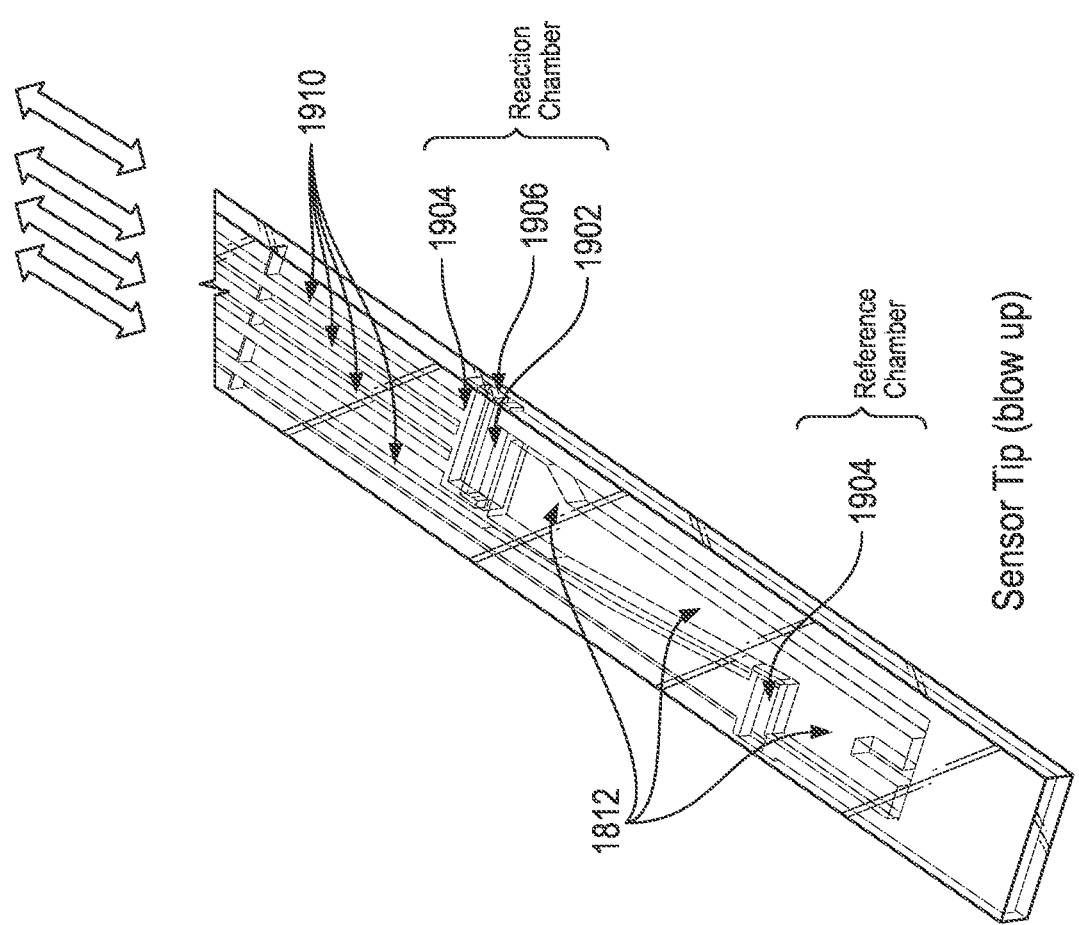
FIG. 20A illustrates a constructed layered optical sensor, according to an embodiment of the present invention.

FIG. 20A illustrates an embodiment of a layered optical sensor incorporating all layers discussed above and being filled by the respective polymers. However, as shown in FIG. 20A, the structures can have a slightly different configuration than discussed above. For example, the oxygen conduit cavity 1812 may not be generally rectangular shaped as discussed above, but can instead take a different configuration. In some embodiments, the oxygen conduit cavity 1812 may extend into and/or through the middle layer 1804.

FIG. 20B is a cross-section of the layered optical sensor of FIG. 20A incorporating all layers previously discussed and being filled by the respective polymers. As depicted, included is a base layer 1802, an optical sensing layer 1804, which includes a plurality of waveguides/optical circuits 1910, an oxygen sensing polymer 1904 and an enzymatic hydrogel 1902, and a conduit layer 1810, which includes a reversible oxygen binding protein hydrogel 1908.

As mentioned above, the different layers 1802, 1804, and 1810 can be bonded together to form a layered optical sensor. In some embodiments, adhesives can be used to bond the layers together. In some embodiments, the layers can be heated in order for the layers to adhere to one another.

Figure 20D:
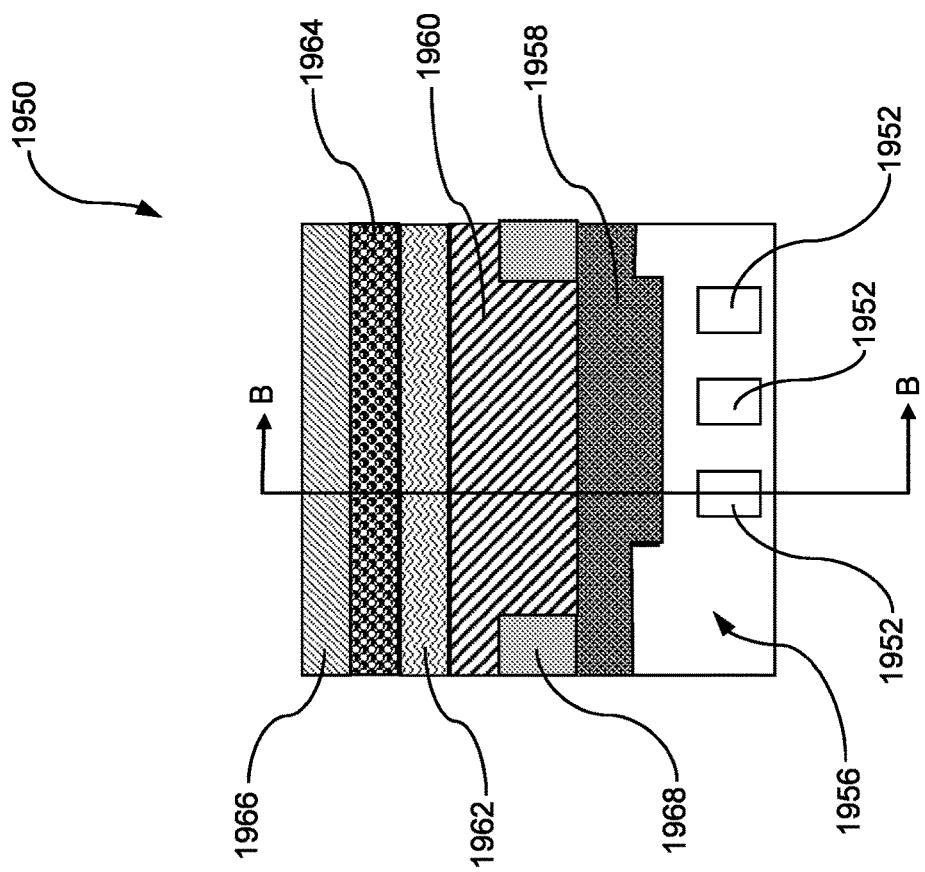
FIG. 20D is a cross-sectional view taken along line A-A in FIG. 20C.
Figure 20C:
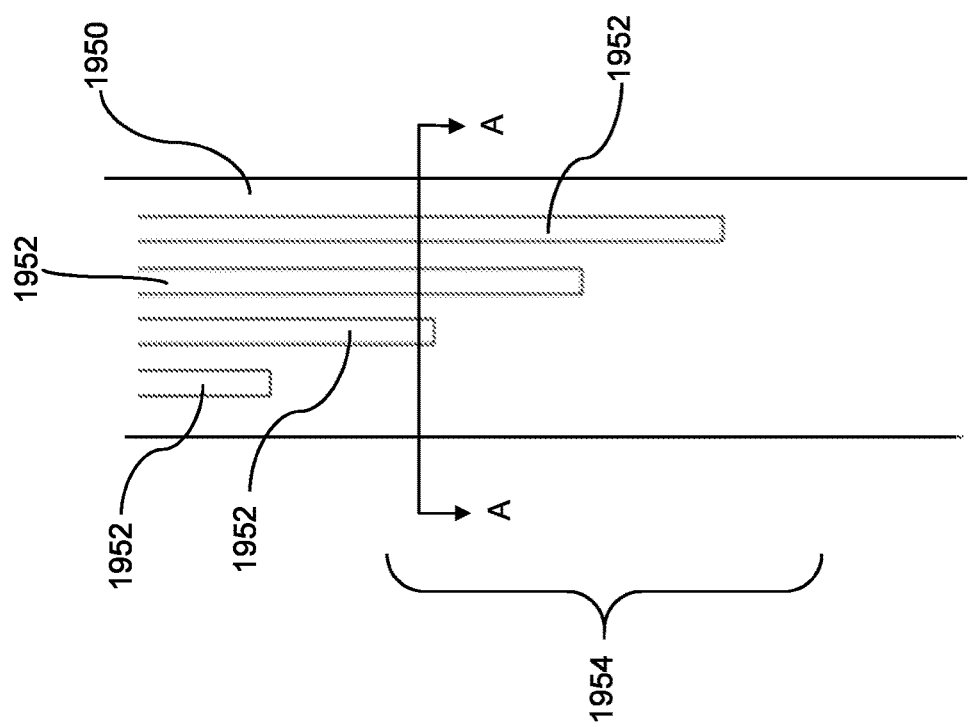
FIG. 20C illustrates a top view of a layered optical sensor, according to an embodiment of the present invention.
Figure 20E:
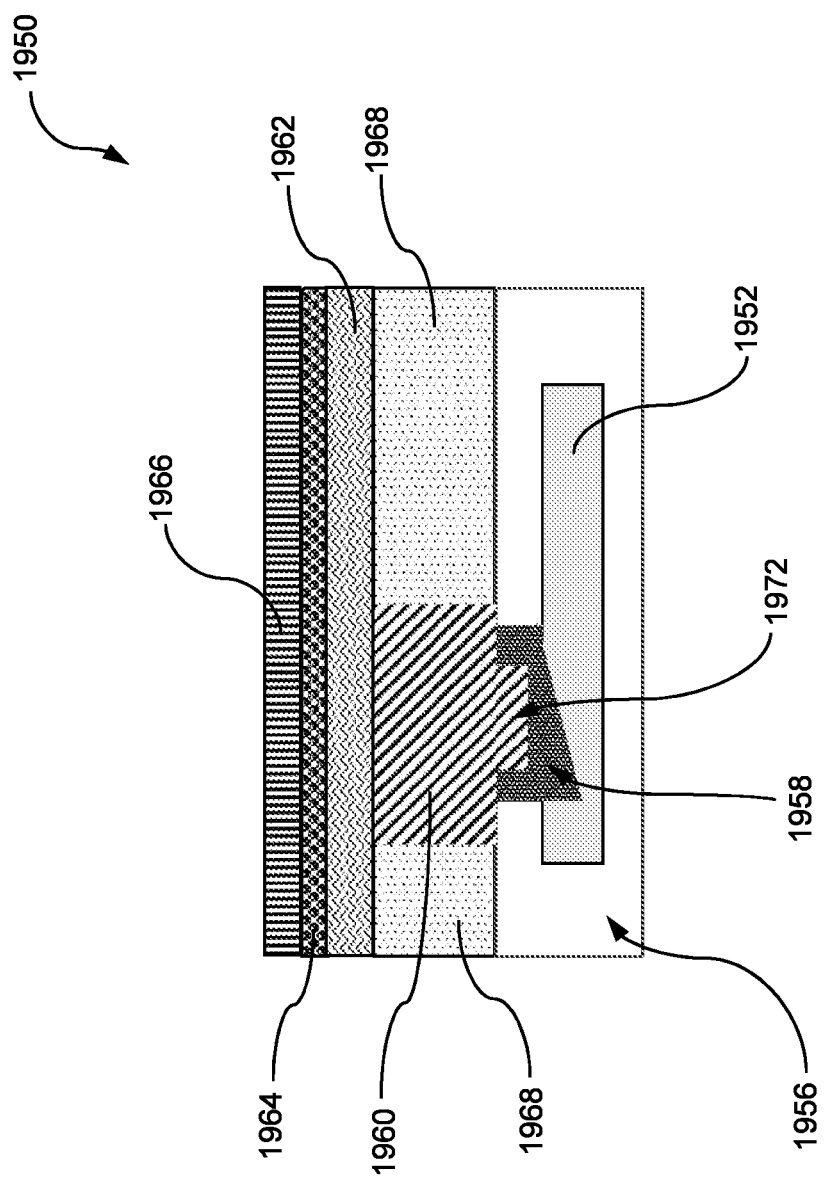
FIG. 20E is a cross-sectional view taken along line B-B in FIG. 20D

FIGS. 20C to 20E illustrate another embodiment of a layered optical sensor according to embodiments of the present invention. FIG. 20C is a partial top view of the layered optical sensor and FIGS. 20D and 20E are cross-sectional views, which are identified in FIG. 20C.

As depicted in FIG. 20C, the layered optical sensor 1950 includes multiple waveguide cores 1952. A reaction chamber 1954 is formed adjacent to the distal ends of select waveguide cores 1952. FIG. 20D is a cross-sectional view of the reaction chamber 1954 taken along line A-A in FIG. 20C and FIG. 20D is a cross-sectional view of the reaction chamber 1954 taken along line B-B is FIG. 20D.

The layered optical sensor of this embodiment includes a plurality of waveguide cores 1952 located in an optical sensing layer 1956, an oxygen sensing polymer region 1958, which is contiguous with and in direct communication with select waveguide cores 1952 in the optical sensing layer 1956, (i.e., the oxygen sensing polymer 1958 contacts at least a portion of the select waveguide cores 1952), an enzymatic reaction region 1960, where the region is geometrically defined by the contiguous portions of the enzymatic reaction layer 1968 and is in direct communication with the oxygen sensing polymer region 1958, an oxygen permeable polymer layer 1962, an oxygen transport layer 1964 and a capping layer 1966. In some embodiments, the optical sensing layer 1956 and/or the capping layer 1966 provide a biocompliant tissue interface.

As can be seen in FIGS. 20D and 20E, the oxygen sensing polymer region 1958 is constructed to contact select waveguide cores 1952 and to extend into and between the optical sensing layer 1956 and the enzymatic reaction layer 1968 of the sensor body such that the oxygen sensing polymer region 1958 contacts and is in communication with both the waveguide cores 1952 and the enzymatic hydrogel in the enzymatic reaction region 1960. Prior to filling the oxygen sensing polymer region 1958 with the oxygen sensing polymer, the waveguide cores 1952 are exposed to allow direct contact with the oxygen sensing polymer in the oxygen sensing polymer region 1958. The enzymatic hydrogel reaction region 1960 is formed such that a portion of the oxygen sensing polymer in the oxygen sensing polymer region 1958 will be contiguous with the enzymatic hydrogel in the enzymatic hydrogel reaction region 1960, such that the oxygen sensing polymer in the oxygen sensing polymer region 1958 will define part of the geometric boundary for the enzymatic hydrogel reaction region 1960.

In one embodiment, the oxygen sensing polymer region 1958 is formed and filled prior to the creation of the enzymatic reaction layer 1968, such that the oxygen sensing polymer region 1958 intersects with the plurality of waveguide cores 1952. The shape of the enzymatic hydrogel reaction region 1960 is defined in part by the shaping of the oxygen sensing polymer region 1958. The oxygen sensing polymer region 1958 can be filled with the oxygen sensing polymer using any filling methods disclosed herein, for example, see the capillary action filling section below. As can be seen in FIG. 20E, the oxygen sensing polymer region 1958 includes a surface 1972 (which may be an ablated or an embossed portion of the oxygen sensing polymer region 1958), which forms a contiguous portion of the enzymatic hydrogel reaction region 1960.

In some embodiments, the surface 1972 is formed along with the enzymatic hydrogel reaction region 1960. A gross opening larger than the desired shape for the enzymatic hydrogel reaction region 1960 is formed in the enzymatic reaction layer 1968 using a low tolerance method (such as $CO_2$ laser cutting), and then the enzymatic reaction layer 1968 is laminated to the optical sensing layer 1956. The oxygen sensing polymer is then dispensed into the gross opening in the enzymatic reaction layer 1968 and into the contiguous space of the oxygen sensing polymer region 1958, using any of the filling methods disclosed herein. In this embodiment, the surface 1972, which forms the base of the enzymatic hydrogel reaction region 1960 and the remainder of the enzymatic hydrogel reaction region 1960 in the enzymatic reaction layer 1968 are created by shaping the oxygen sensing polymer that fills the enzymatic reaction layer 1968 and oxygen sensing polymer region 1958.

In some embodiments, the enzymatic hydrogel reaction region 1960 along with surface 1972 are created by material displacement of the oxygen sensing polymer while uncured, using the embossing method discussed below, by placement of an embossing insert with a shape to create the enzymatic hydrogel reaction region 1960 with surface 1972, thus forming the enzymatic hydrogel reaction region 1960 and surface 1972 upon curing of the polymer.

In some embodiments, the enzymatic hydrogel reaction region 1960 and surface 1972 are formed by material removal of cured oxygen sensing polymer in the oxygen sensing polymer region 1958. The material removal of the oxygen sensing polymer may be accomplished by laser ablation using, for example, femtosecond, nanosecond, or UV laser systems.

In some embodiments, the surface 1972 is formed along with enzymatic hydrogel reaction region 1960. For this, a gross opening larger than the desired shape of the enzymatic hydrogel reaction region 1960 is formed in the lower portion of the enzymatic reaction layer 1968. In this embodiment, the upper portion of the enzymatic reaction layer 1968 above the enzymatic hydrogel reaction region 1960 remains intact, while the adhesive layer that comprises the lower portion of the enzymatic reaction layer 1968 is modified to form a gross opening larger than the desired enzymatic hydrogel reaction region 1960 using a low tolerance method (such as $CO_2$ laser cutting). The enzymatic reaction layer 1968 is laminated to the optical sensing layer 1956. The oxygen sensing polymer is dispensed into the lower portion of the gross opening in the enzymatic reaction layer 1968 and into the contiguous space of the oxygen sensing polymer region 1958 by means of microfluidic filling from an adjacent filling well and filling vent, i.e., capillary filling. In this embodiment, the enzymatic hydrogel reaction region 1960 and the surface 1972 in the oxygen sensing polymer are formed by ablation of the upper portion of the enzymatic reaction layer 1968 and the lower portion of enzymatic reaction layer 1968, which forms the walls of the enzymatic hydrogel reaction region 1960 and surface 1972, which forms the base of the enzymatic hydrogel reaction region 1960, which is contiguous with the oxygen sensing polymer in the oxygen sensing polymer region 1958. As can be seen in FIG. 20E, forming the surface 1972 in the oxygen sensing polymer in the oxygen sensing polymer layer 1958, ensures that the oxygen sensing polymer in the oxygen sensing polymer region 1958 and the enzymatic hydrogel in the enzymatic hydrogel reaction region 1960 are in physical contact with each other and therefore, in communication with each other.

In some embodiments, the surface 1972 is formed along with the enzymatic hydrogel reaction region 1960. The oxygen sensing polymer is dispensed into oxygen sensing polymer region 1958. The enzymatic reaction layer 1968 is then laminated to the optical sensing layer 1956 without first forming the enzymatic hydrogel reaction region 1960. In this embodiment, the enzymatic hydrogel reaction region 1960 and the surface 1972 in the oxygen sensing polymer are formed by ablation of select regions of the enzymatic reaction layer 1968 and the oxygen sensing polymer region 1958 to ensure that the base of the enzymatic hydrogel reaction region 1960 is contiguous with the oxygen sensing polymer by forming surface 1972. As can be seen in FIG. 20E, forming the surface 1972 in the oxygen sensing polymer in the oxygen sensing polymer layer 1958, ensures that the oxygen sensing polymer in the oxygen sensing polymer region 1958 and the enzymatic hydrogel in the enzymatic hydrogel reaction region 1960 are in physical contact with each other and therefore, in communication with each other.

In some embodiments, the oxygen sensing polymer region 1958 is formed along with the enzymatic hydrogel reaction region 1960. The enzymatic reaction layer 1968 is laminated to the optical sensing layer 1956 without first forming the enzymatic hydrogel reaction region 1960 or oxygen sensing polymer region 1958. In this embodiment, the enzymatic hydrogel reaction region 1960 is created by ablation of select regions of the enzymatic reaction layer 1968, and the oxygen sensing polymer region 1958 is created by ablation through the enzymatic hydrogel reaction region 1960. In this embodiment, the shape of the oxygen sensing polymer region 1958 does not intersect with the side walls of the enzymatic hydrogel reaction region 1960. The oxygen sensing polymer is then dispensed into the oxygen sensing polymer region 1958. The surface of the oxygen sensing polymer then serves as the direct surface 1972 that interfaces with the enzymatic hydrogel in the enzymatic hydrogel reaction region 1960.

After the oxygen sensing polymer is cured, the enzymatic hydrogel reaction region 1960 can now be filled with the enzymatic hydrogel using any of the filling methods disclosed herein. The enzymatic hydrogel is then crosslinked. In some embodiments, the enzymatic hydrogel is dehydrated prior to application of a subsequent contiguous polymer layer.

Next, an oxygen permeable polymer layer 1962 is laminated to the enzymatic hydrogel reaction layer 1968. The polymer for this oxygen permeable polymer layer 1962 must be one that is permeable to oxygen and impermeable to the analyte that is being sensed, which in some embodiments, is glucose. This creates an oxygen permeable, analyte impermeable membrane. In some embodiments, the oxygen permeable polymer layer 1962 is laminated along with an oxygen transport layer 1964. In some embodiments, the oxygen transport layer 1964 contains a reversible oxygen binding molecule. In some embodiments, the oxygen transport layer 1964 contains a hydrogel that includes a reversible oxygen binding molecule.

In some embodiments, a capping layer 1966 is laminated to the oxygen transport layer 1964. In some embodiments, the capping layer 1966 provides mechanical stabilization to oxygen transport layer 1964

After the lamination and filling of the polymer laminate structure of this embodiment with active hydrogels and the oxygen sensing polymer, the physical structure of individual optical sensors is attained by laser cutting the final shape of the individual sensors from the upper exposed layer through the bottom exposed layer.

In some embodiments, the enzymatic reaction layer 1968 also serves as a mechanical support for the sensor 1950 to enable implantation into and extraction from tissue. In some embodiments, the lower portion of the enzymatic reaction layer 1968 (the adhesive layer) in the region of the sensor tip is removed and this region used to form a looped sensor lancet interface 3140 as described below. In some embodiments, the oxygen permeable polymer layer 1962 in the region of the sensor tip is removed and this region used to form a looped sensor lancet interface 3140. In some embodiments, the oxygen permeable polymer layer 1962, and the oxygen transport layer 1964 in the region of the sensor tip are removed and this region used to form a looped sensor lancet interface 3140.

In some embodiments, the oxygen permeable polymer layer 1962, the oxygen transport layer 1964 and the capping layer 1966 are removed in the region of the optical input to form the optical sensing layer 1956. In some embodiments, the region of the optical input to the optical sensing layer is an optical microlens array.

In some embodiments, the layers comprising the optical sensors 1950 are laminated to create a plurality of optical sensors 1950 in a card, where the laminate layers each comprise at least 10, 20, 50, or at least 100 optical sensors 1950.

Embossing

As discussed above, the layered optical sensor can be formed by the combination of a number of different layers. Specifically, embossing can be used to produce precise internal structures by leveraging techniques from silicon wafer manufacturing.

During the manufacturing of the layers discussed above, inserts can be used to form specific cavities, such as those discussed above. Thus, the polymer of the particular layer will pass around the outside of the insert. For example, a rectangular mold can be used to form the top layer 1810. An insert can then be placed on the mold in the desired shape and desired location of the oxygen conduit cavity 1812. Then, when the layer 1810 is solidified, such as through curing, and the insert is removed, the oxygen conduit cavity 1812 will remain in the solidified layer. This can be done for all of the layers and cavities discussed above.

In some embodiments, embossing can also be used to fill specific cavities located within or next to other cavities. Thus, for example, an insert can be placed into the enzymatic hydrogel cavity 1902 in the shape of the oxygen sensing polymer cavity 1904 while the enzymatic hydrogel is filled. Once the hydrogel is solidified, for example through UV curing, the insert can be removed, and the oxygen sensing polymer can be filled in the oxygen sensing polymer cavity 1904 remaining adjacent to the enzymatic hydrogel cavity 1902. Thus, the enzymatic hydrogel and oxygen sensing polymer can be adjacent and in communication with one another. Further, a second insert can be used in a similar fashion to form the glucose inlet cavity 1906. Thus, the oxygen sensing polymer can be filled, followed by the enzymatic hydrogel, while still leaving the glucose inlet cavity 1906 in communication outside the sensor.

The embossing technique described is shown in FIG. 21. As shown, a portion of a hydrogel 2102 in the sensor can be embossed through placement of an insert, thus leaving a cavity 2104 formed. This cavity 2104 can then be filled with another type of hydrogel 2106, thus forming adjacent hydrogels in communication with one another.

Further, in some embodiments, embossing can be used to form the cavities for waveguides, ink well, and registration markings embossed into an ultraviolet curable optical polymer, such as, but not limited to, UV curable acrylate (bottom clad). In some embodiments, ink is deposited into the ink well and flows into the ink registration markings. Next, UV curable acrylate with a higher index of refraction than a base clad index of refraction is coated to fill the embossed cavities in the bottom CLAD (CORE). The CORE material may also fill the remainder of the ink well and registration markings that were not filled with ink. Next, the core material is cured. Next, the top clad material with an index of refraction lower than the CORE material is coated over the bottom clad and core material. In some embodiments, the top CLAD material may be embossed with a pattern for luminescent oxygen sensing dye or other registration marks. Next, the top clad material is cured.

In some embodiments, once the embossing procedures are performed, the different layers can be laminated together to form a layered optical sensor with empty cavities to be filled with the oxygen sensing polymer, etc.

Capillary Filling Methodology

In some embodiments, capillary action (e.g., wicking) can be used to fill the different cavities in the layered optical sensor. This action allows liquid to flow in narrow spaces without the assistance of (or in opposition to) external forces, such as gravity. Capillary action can occur as the combination of surface tension and adhesive force between the liquid and the surfaces contacting the liquid can act to move the liquid from one location into a narrower location or cavity.

In some embodiments, the oxygen sensing polymer cavity 1904 and the enzymatic hydrogel cavity 1902 can be accessible from the surface of the middle layer 1804 through the glucose inlet cavity 1906. In some embodiments, the oxygen sensing polymer cavity 1904 and the enzymatic hydrogel cavity 1902 can be shaped so that the accessible surface area of the oxygen sensing polymer cavity 1904 and the enzymatic hydrogel cavity 1902 is less than the cross sectional area of the oxygen sensing polymer cavity 1904 and the enzymatic hydrogel cavity 1902 in at least one substantially orthogonal dimension.

Figure 22:
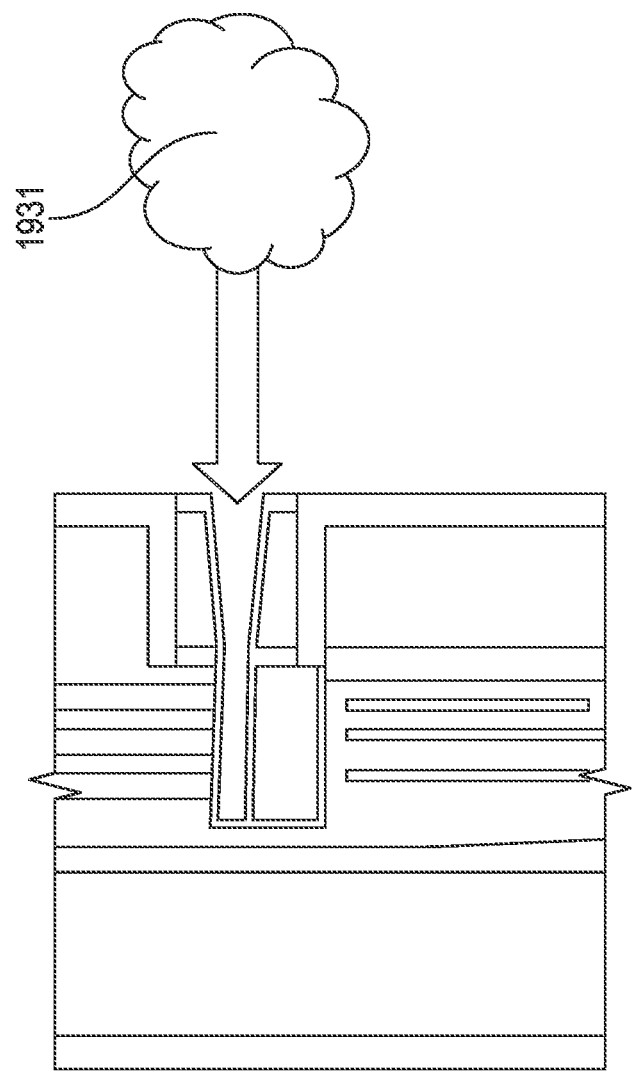
FIG. 22 illustrates a fill direction for capillary filling of a layered optical sensor, according to an embodiment of the present invention.

In some embodiments, the cavities discussed above (e.g., oxygen sensing polymer cavity 1904, enzymatic hydrogel cavity 1902, oxygen reference cavity 1908, and oxygen conduit cavity 1812) can be filled through the use of capillary action. For example, a larger volume of hydrogel/polymer, depending on what is to be filled, can be located adjacent to outlets of the different cavities, such as the glucose inlet cavity 1906. Capillary action can force and/or draw in a portion of the hydrogel/polymer from the larger volume of hydrogel/polymer 1931 into the particular cavity, as shown in FIG. 22. In some embodiments, the larger body volume of hydrogel/polymer 1931 can be a milliliter volume while the volume of cavities to be filled can be measured in picoliters.

In some embodiments, the larger volume can be pretreated in order to fill the cavities. For example, for hydrophobic or amphipathic surfaces, an amphipathic pretreatment solution is dispensed to allow hydrogel filling by capillary action. In some embodiments, the dispensing solution can be Hydroxyethylmethacrylate (HEMA) in water and ethanol. In some embodiments, the dispensing solution can be HEMA in water and isopropyl alcohol. In some embodiments, the dispensing solution is volatilized. In some embodiments, the dispensing solution is not volatilized.

In some embodiments, the cavities can be filled simultaneously. In some embodiments, the cavities can be filled one after another.

In some embodiments, the cavities can be laterally filled into picoliter volumes in hydrophobic, amphipathic, or hydrophilic surfaces from nanoliter or microliter adjacent volumes.

Method of Manufacturing

Advantageously, embodiments of the disclosed layered optical sensor can be mass manufactured, thus allowing the layered optical sensor to be produced cheaply as compared to other sensors in the art. Thus, consumers can experience the benefit of the mass production by being able to purchase and use sensors, particularly glucose sensors, without having to pay significant sums of money. Thus, low income users, such as elderly patients, will not have to worry as much about their ability to purchase high priced medical devices.

Figure 23:
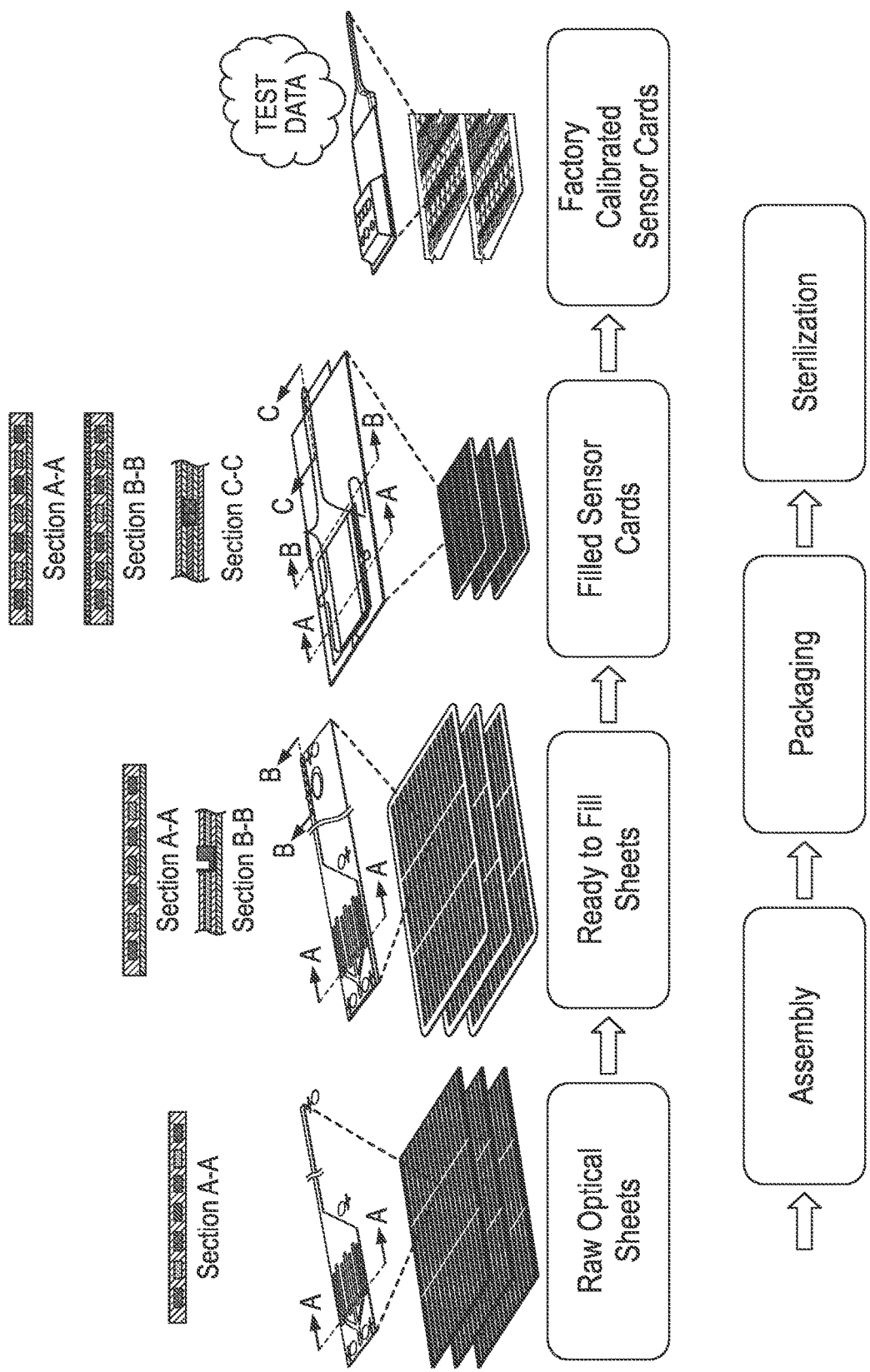
FIG. 23 illustrates a method of mass manufacturing of a layered optical sensor, according to embodiments of the present invention.
Figure 24:
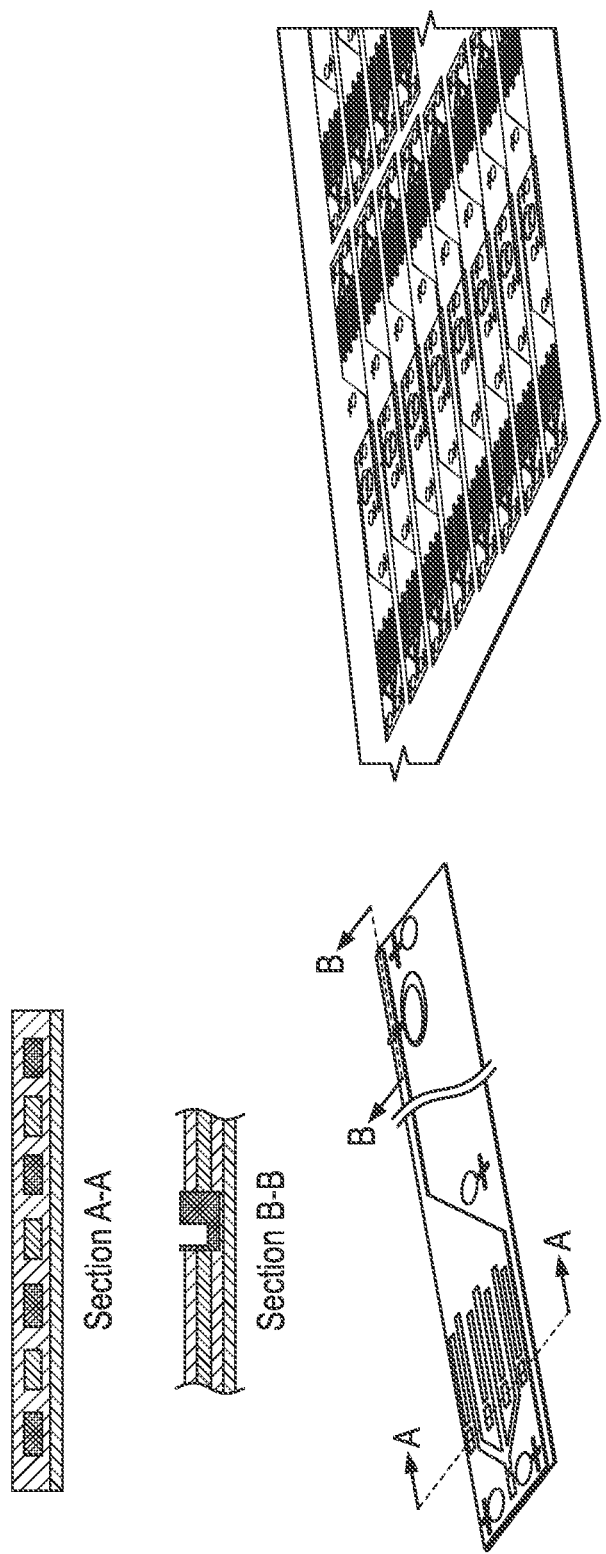
FIG. 24 illustrates a ready to fill sheet of a layered optical sensor, according to an embodiment of the present invention.

FIG. 23 illustrates an example of a method of manufacturing the layered optical sensor. First, raw optical sheets, which can be layers, can be produced into a sheet. As shown, a significant amount of the sensor can be formed at once from a single sheet. For example, 10, 20, 100, 200, 250, 300, 350, 400, 500, or 1000 sensor cards can be formed per sheet. The sensor cards can be semi-individuated, thus allowing for ease of splitting apart all the sensors on the sheet. A top layer can be attached to the raw optical sheets, thus forming ready to fill sheets shown in FIG. 24.

These ready to fill sheets can be filled with different hydrogels/polymers, such as described in detail above, to form a plurality of semi-individuated filled sensor cards.

Further, electronic components can be attached to the plurality of filled sensor cards. The sensor cards can be calibrated while they are in a semi-individuated form in an array. The sensor cards can be calibrated by exposing each of them to fluids under fixed test conditions with sterile glucose, or other analyte, and oxygen of known concentrations and monitoring each sensor card response. In some embodiments, semi-individuated sensors can be fully functional and can be optically interrogated to test the devices and to generate individual calibration parameters for each sensor at the card level.

Each sensor card in the array can have a unique identity that can be registered during calibration. Thus, calibration parameters for each sensor can be generated from these optical measurements associated with the specific card and stored for subsequent retrieval. In some embodiments, the use of retrieving calibration information from 2D barcodes, near field communications (NFC), and radio frequency identification (RFID) can be used to transmit and receive the calibration data and information.

After calibration, the sensor cards can be assembled with other devices, such as delivery devices. In some embodiments, the sensor cards are not assembled with delivery devices. The sensor cards can then be packaged as desired, and can be sterilized for use in a patient. In some embodiments, the sensor cards are sterilized before packaging. In some embodiments, the sensor cards are not sterilized.

Thus, as shown in FIG. 23 and described herein, hundreds of sensor cards can be quickly and easily manufactured and calibrated. Thus, the cost of the layered optical sensors can be drastically reduced, allowing easier access to patients.

Example

Sensors were assessed for lag time and warm-up time using a linear retrospective calibration maintained for the entirety of the sensor observation period during a clinic visit. Specifically, a single linear calibration for each sensor was determined for a selected lag time the end of the in-clinic observation period to estimate retrospective sensor performance after lag time adjustment. The median sensor lag time was five (5) minutes.

Figure 25:
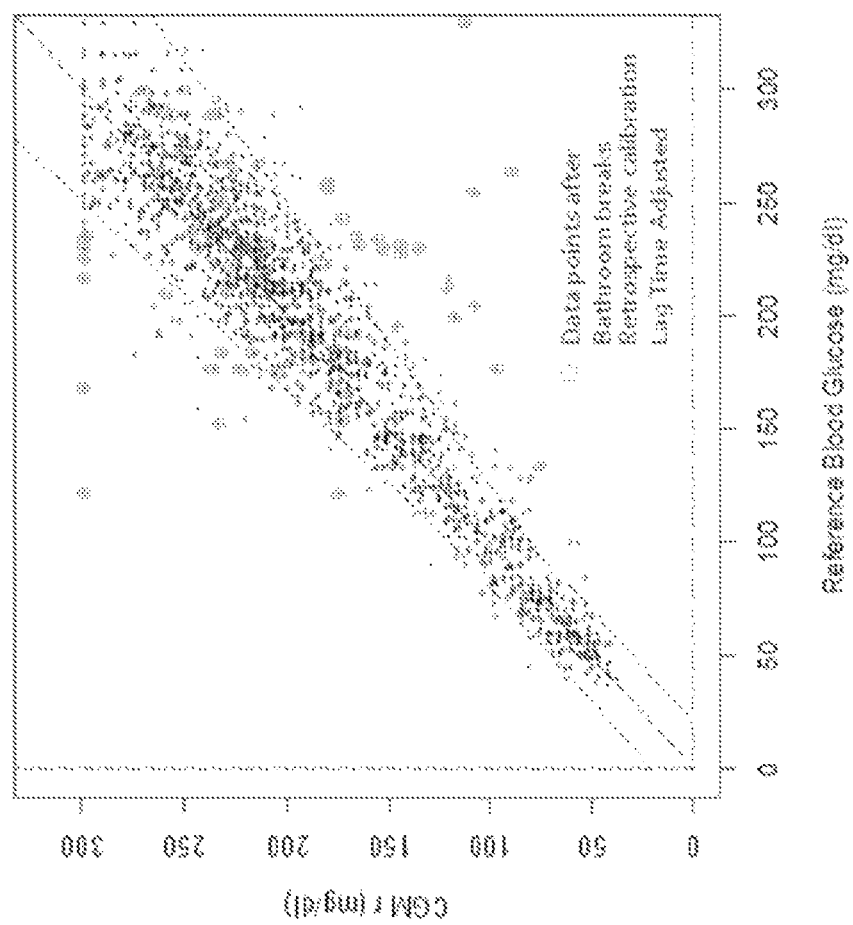
FIG. 25 illustrates a lag-adjusted retrospectively calibrated sensor 20/20 performance graph.
Figure 26:
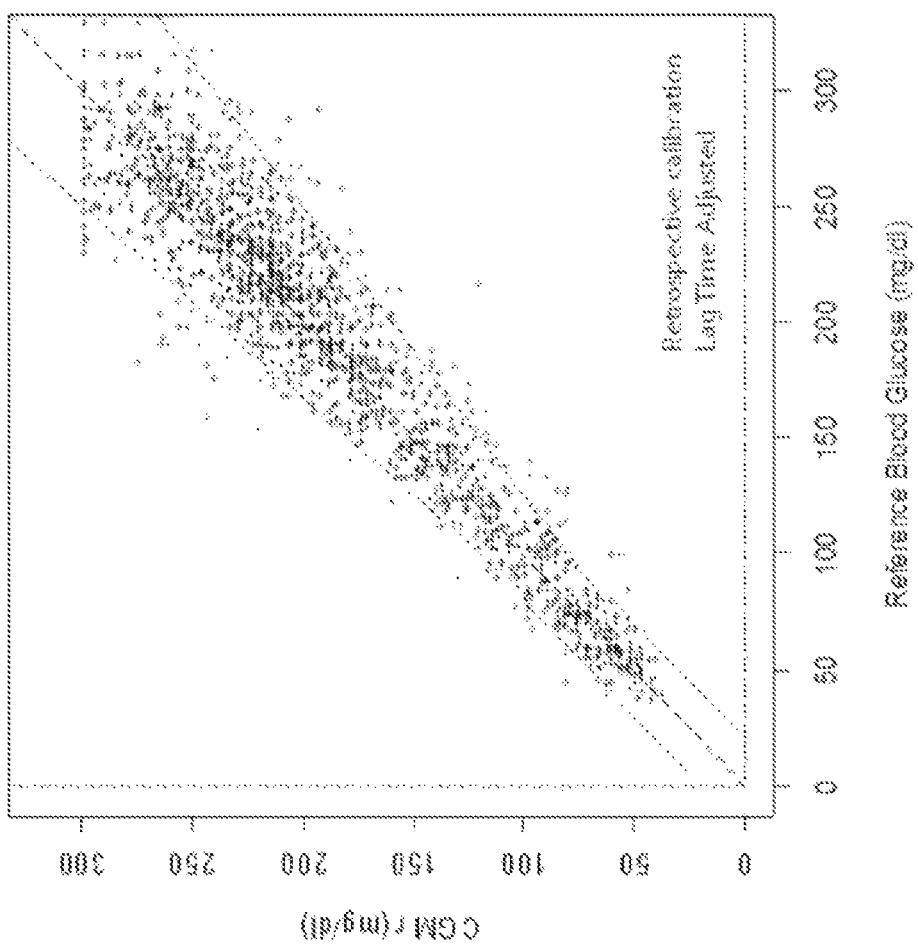
FIG. 26 illustrates a lag-adjusted retrospectively calibrated sensor 20/20 performance graph with outliers removed.

The optical instrumentation was not miniaturized for the prototype sensors used in the clinical study. The prototype sensors were connected to the optical instrumentation with an optical cable. The optical cable was connected at the start of the observation day and disconnected at the end of the observation day. However, the optical cable was disconnected and reconnected to the sensors during the observation day when required (bathroom breaks). The retrospectively assessed data was analyzed for outliers. It was identified that sensor measurements were often discrepant post disconnection/reconnection. These outliers related to the reconnection of the optical cable to the sensor were identified. The lag-adjusted retrospectively calibrated sensor 20/20 performance graph is provided in FIG. 25, with the outliers due to cable reconnection indicated by circles. These sensors measurements were identified, removed, and the analysis was repeated with these outliers. The lag-adjusted, retrospectively calibrated sensor performance characteristics with outliers removed are illustrated in FIG. 26 and listed in FIG. 27. Based on calibration that was determined retrospectively with an adjusted lag time for each in-clinic observation period for each sensor, the overall mean average relative deviation (MARD) with cable reconnection outliers removed was 9% and the overall 20/20 criteria performance was 94%.

From the foregoing description, it will be appreciated that an inventive product and manufacturing method for a laminated optical sensor are disclosed. While several components, techniques and aspects have been described with a certain degree of particularity, it is manifest that many changes can be made in the specific designs, constructions and methodology herein above described without departing from the spirit and scope of this disclosure.

Adhering a Medical Device to the Skin of a Patient

Disclosed herein are embodiments of a multilayer composite adhesive system, configured to adhere, in some embodiments, to an body wearable device, such as, for example, the opto-enzymatic analyte sensors disclosed and described herein, to the surface of skin. The multilayer composite adhesive systems disclosed herein can attach to the bottom of the body wearable device housing thereby allowing the device to be attached to the skin for an extended period of time, for example, 4 to 7 days, 7 to 10 days, 10 to 14 days or 14 to 21 days.

Current adhesive systems have difficulty remaining on the skin for extended periods of time because they do not address the differences in mechanical properties between the skin and the adhesive, i.e., stress/strain differentials that exist between skin and the adhesive systems. Skin typically has a low stress strain relationship that may be approximated as 0.05 MPa for strains of 1.0 or 0.02 MPa for strains of 0.4. The skin is viscoelastic and current adhesive systems are typically highly elastic. Because of the mechanical mismatch between the skin and current adhesive systems, when current adhesive systems are in place on skin and the skin moves (stretches/tension and compresses/compression), these adhesive systems do not move to the same extent as the skin and therefore, experience stress/strain mismatch between the adhesive system material and the skin. This mismatch results in high shear forces at the interface between the adhesive system adhesive layer and the skin upon which it is adhered. As a result of these shear forces, current adhesive systems experience edge peel, which eventually leads to peel off of the entire adhesive system.

Another issue with current adhesive systems is that they suffer from moisture loading (moisture trapped between the skin and the adhesive system) because they have an inadequate moisture vapor transmission rate ("MVTR"), which results in "float off" of the system. MVTR is a measure of the passage of water vapor through a substance and/or barrier. Because perspiration naturally occurs on the skin, if the MVTR of a material or adhesive system is low, this can result in moisture accumulation between the skin and the adhesive system that can promote bacterial growth, cause skin irritation, and can cause the adhesive system to peel away or "float off" from the skin.

Thus, adhesive systems must be designed to (1) address the mismatch of mechanical properties that exist between skin and the adhesive systems and (2) have a high MVTR. Prior adhesive systems have attempted to address the issue of mismatch of mechanical properties and the resulting edge peel, by using aggressive adhesives, i.e., adhesives that have high adhesion to skin. An adhesive's aggressiveness is defined by its initial bond strength and its sustained bond strength. However, these aggressive adhesives do not address the main problem of strain mismatch and the high shear forces that result between the skin and the adhesive and therefore, result in systems that do not expand and contract to the same extent as the skin and remain strongly attached to the skin resulting in very high shear forces leading to pain to the wearer, and which will eventually lead to edge peel and peel off. Additionally, using an aggressive adhesive is very difficult and painful to remove from the skin when a wearer desires to remove the adhesive system. However, an adhesive that is not sufficiently aggressive will not maintain attachment to the skin as the skin expands and contracts and will result in edge peel and peel off.

Accordingly, adhesive system embodiments of the present invention have been designed to address these deficiencies of prior adhesive systems.

In order to achieve the required sustained attachment to the skin while allowing the adhesive system have a high MVTR and to be easily removed from the skin when desired, embodiments of the present invention are directed to multilayer composite adhesive systems where the properties of the layers combine to form a system with a high MVTR that addresses the mismatch of mechanical properties and that uses a skin adhesive that provides sufficient adhesion to skin while allowing the adhesive system to be easily removed with little pain. Thus, each layer of the present adhesive systems can have different mechanical and material properties but when the properties of all layers are combined, they address the issues with prior systems by mimicking skin mechanics in order to address the strain mismatch between the skin and the adhesive system while providing a high MVTR.

To satisfy these requirements, the multilayer composite adhesive systems of the embodiments of the present invention have been designed to have a high MVTR and a low, effective Young's/elastic modulus. Further, the system can plastically deform when worn on the skin and has good adhesion to skin while being easily removed from the skin when desired. The MVTR of a material can be an inherent property of the material or a material's MVTR can be changed/adjusted by altering the material to include, for example, openings, slits, cuts or other perforations (collectively, "perforations") therein, resulting in a material that has a higher effective MVTR, thereby providing a pathway for moisture to escape through the material. As used herein, (1) "inherent" shall mean a property of an unmodified material and (2) "effective" shall mean the resulting property after a material or layer or multilayer adhesive system has been modified, for example, as disclosed herein to include modifications such as perforations or the resulting properties of a multilayer adhesive system constructed in accordance with the embodiments disclosed herein.

A material typically plastically deforms when its linear elastic force is exceeded as stress is developed in the material. Similar to a material's MVTR, a material's elastic modulus can be an inherent property of the material or it can be changed/adjusted by modifying the material to include, for example, perforations therein, resulting in a material that has an effective elastic modulus that is lower than its inherent elastic modulus. The shape, orientation, size and spacing of these perforations, can also be used to change a material's elastic in different directions, i.e., the web and cross-web directions of the material, depending on the size, orientation and spacing of the perforations.

For example, as discussed in detail below, a material that includes perforations that are longer in length than the gap/spacing between adjacent perforations will have a lower effective elastic modulus than a material that includes perforations that are shorter in length than the gap/spacing between adjacent perforations. Using perforations that have different lengths and spacing between in different directions allows tuning of the modulus of elasticity in the different directions, i.e. a first modulus of elasticity in a first direction and a second modulus of elasticity in a second direction where the first and second elastic modulus's can be the same or different. As discussed in more detail below, the length of the perforations and the spacing between adjacent perforations can be adjusted to tune the effective elastic modulus of the materials/layers and hence, the effective modulus of the embodiments of the adhesive systems disclosed and described herein. For example, the effective elastic modulus of an individual layer or the constructed multilayer adhesive system can be tuned/adjusted to be less than approximately 100 Kpa, 90 Kpa, 70 Kpa, 60 Kpa, 50 Kpa, 40 Kpa, 30 Kpa, 20 Kpa, and 10 Kpa, at 100% strain.

Thus, embodiments of the present adhesive systems have been designed to have a high MVTR and low elastic modulus, i.e., designed to have low elasticity, that undergo plastic deformation at low strains. Having an adhesive system that plastically deforms when attached skin, allows the system to use a less aggressive adhesive to attach the adhesive system to the skin as the shear forces between the adhesive and the skin are significantly reduced after the adhesive system plastically deforms. Adhesive systems that plastically deform when worn on the skin, solves the issue of edge peel and results in an adhesive system that remains attached to the skin for an extended period of time, for example, five (5) weeks.

The multilayer, composite adhesive system embodiments disclosed herein are also advantageous as they permit different system designs based on the intended use of the system while allowing one to design the system to have the required MVTR and elastic modulus properties. For example, one may desire to have an adhesive system with moisture wicking properties, or one may desire to have an adhesive system to absorb bodily fluid such as in the form of a bandage, or one may desire to an adhesive system with sufficient strength to attach medical devices and other medical items to the body. Different uses may require different properties or a combination of properties, which can be achieved through the use of layers of different materials, which individually may not meet the intended use requirements but when modified as discussed herein and combined, provide the required properties.

Material properties to consider in designing adhesive system embodiments of the present invention include, and are not limited to, Young's modulus, MVTR, hydrophobicity, hydrophilicity and moisture wicking, adhesive strength, adhesive hypoalgernicity and intact adhesive system removal.

FIGS. 28A-C illustrate exploded and side views of an embodiment of the adhesive system 2800. The adhesive system 2800 is a multilayer adhesive system that provides a high MVTR in general, especially under the housing of the attached device. In some examples, the adhesive system 2800 includes a first layer composed of a device adhesive

2830, a second layer composed of the outer ring 2820, and a top layer composed of the coin standard 2810. The adhesive system 2800 can be oriented such that the first layer device adhesive 2830 is attached to the bottom of the device and the third layer coin standard 2810 is attached to the surface of the skin.

Turning first to the coin standard 2810, in some examples the coin standard 2810 is attached to the skin. The surface of the coin standard 2810 can be composed of an acrylate pressure sensitive adhesive on a PET release. The pressure sensitive adhesive allows the coin standard 2810 to adhere to the skin when pressure is applied—thereby activating the adhesive without the use of a solvent, water or heat. The material of the coin standard 2810 can be composed of a spun lace non-woven material with a high MVTR. In some examples, the coin standard 2810 can have a thickness of 4 mm.

As illustrated in FIGS. 28A to 28C, the coin standard 2810 can include an opening 2812 that extends through the coin standard 2810. In some examples, the opening 2812 can have a diameter of 3 mm and can be placed a distance of 10 mm from the narrow end of the coin standard 2810.

Turning next to the outer ring 2820, in some examples, the outer ring 2820 is composed of a re-attachable pressure sensitive adhesive. The outer ring 2820 can be composed of a lined silicon/silicon pressure sensitive adhesive on a PTFE release.

In some examples, the outer ring 2820 can be joined to the coin standard 2810. The attachment between the two layers can form a gap 2822. The outer ring 2820 can be attached to the coin standard 2810 with acrylate pressure sensitive adhesive. In some examples, the acrylate pressure sensitive adhesive can be a polyurethane acrylate (P-UR acrylate). In some embodiments, the release liner of the outer ring 2820 is formed from a patterned PET and PTFE pattern. The PET can be bonded to the PTFE below the coin and the PTFE below the silicon. In some examples, the outer ring 2820 can have a base width of 30 mm and a length of 40 mm. In some embodiments, outer ring 2820 can have a width of 7 mm and a thickness of 6 mm.

FIGS. 29A-B illustrate a top and side view of another embodiment of the adhesive system 2860. The adhesive system 2860 illustrated in FIGS. 29A-B is a multi-layered system that includes a top layer 2840 with a top layer adhesive 2842 and a bottom layer 2844 with a bottom layer adhesive 2846. The top layer 2840 can be formed from a material having a low intrinsic elastic modulus or it can be made from a material that has been modified (as discussed in more detail below) to have a low effective elastic modulus. Example materials for the top layer include polyurethane and a silicone elastomer. The bottom layer 2844 includes an outer ring 2850, a middle ring 2852, a central portion layer 2854, and gaps 2856, which can be continuous or discontinuous. The outer ring 2850 can include a number of variations. In some examples, the outer ring 2850 is a high strength bio-compliant skin adhesive that can be connected to the top layer 2840 of the adhesive system 2860. The bottom layer 2844 can include a middle ring 2854 and a central portion 2854 of spun lace, non-woven material, which can be a material that wicks moisture, such as perspiration, away from under the device.

In other examples, the bottom layer 2844 can be a spun lace, non-woven material that includes a plurality of cuts or gaps 2856 therein that divide the bottom layer 2844 into an outer ring 2850, a middle ring 2852 and a central portion 2854. In this embodiment, the bottom layer adhesive 2844 can be more aggressive than the top layer adhesive 2842.

In another embodiment, the outer annular region 2850 can be a re-attachable bio-compliant skin adhesive connected to the top layer 2840 of the adhesive system 2860. The outer annular region 2850 can have a central portion 2854 of spun lace, non-woven material. The outer annular region 2850 may also have an additional adhesive layer above the central portion 2854 of spun lace, non-woven material. In other examples, the outer annular region 2850 can have the same materials as the central portion 2854. As well, the outer annular region 2850 can have an adhesive connected to the top layer 2840 of the adhesive system 2860.

In some examples, the adhesive system 2860 includes a top layer 2850 that can be a backing material that has a high MVTR, such as polyurethane. In some examples, the backing material is thin and complaint. In some embodiments, as illustrated in FIG. 29B, one or more layers can include one or more physical gaps 2856. In some examples, these gaps 2856 can be in the spun lace, non-woven material of the bottom layer 2844 and adhesive layer below the backing of the top layer 2852 creating discontinuous segments. The physical gaps 2856 provide strain relief in the adhesive system 2860 as the adhesive system 2860 is stretched, allowing the discontinuous segments of the annular region to move independently of one another. In some examples, additional gaps through the entire adhesive system 2860 can provide further strain relief. In some examples, these additional gaps in the spun lace and skin adhesive can provide further strain relief. While in the figures, these gaps 2854 are shown as extending completely through the material, it should be noted that these gaps can also be recessed, indented or embossed portions of the material, which create failure lines in the material that are designed to fail and hence, cause gaps to form in the material, when stress is applied to the material, thereby providing the required strain relief.

Figure 29D:
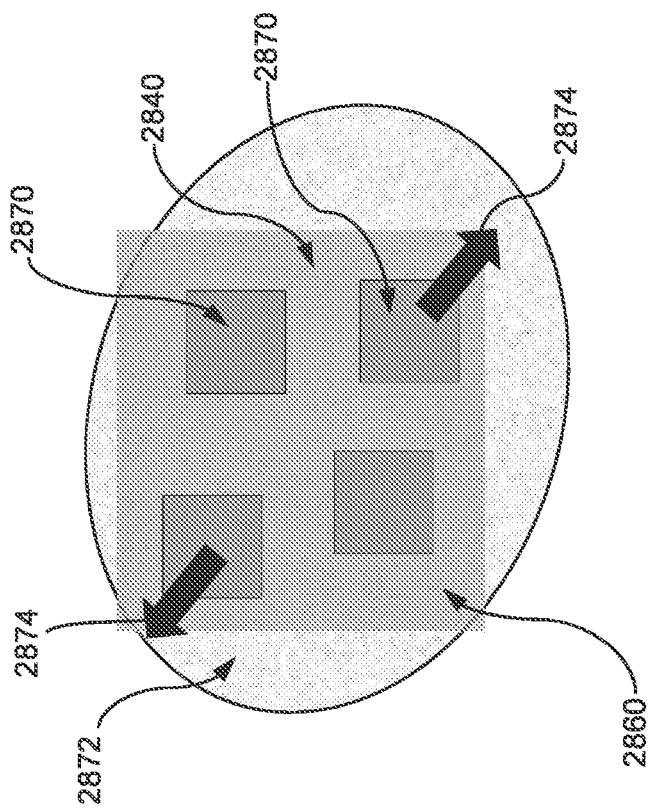
FIG. 29D is a top view of the adhesive system depicted in FIG. 29C on a skin when the skin is stretched, according to an embodiment of the present invention.
Figure 29C:
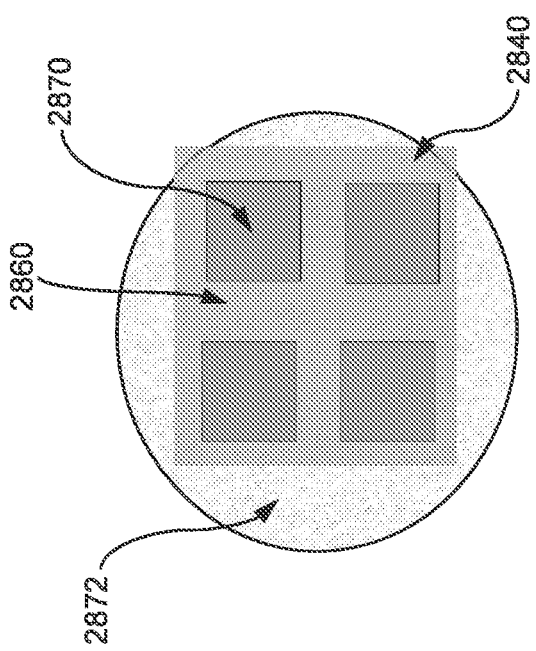
FIG. 29C is a top view of an adhesive system on skin in a relaxed state, according to an embodiment of the present invention.

In another embodiment of the adhesive system 2860 depicted in FIGS. 29C and 29D, instead of the bottom layer being divided into ring-shaped discontinuous portions, the bottom layer 2844 can be divided into polygonal-shaped discontinuous portions 2870. The top layer 2840 can be formed from a material having a low intrinsic elastic modulus or it can be made from a material that has been modified (as discussed in more detail below) to have a low effective elastic modulus. The top layer 2840 may be attached to the bottom layer 2844 with an adhesive. The bottom layer 2844 can be a spun lace, non-woven material that includes an adhesive for attaching to the skin 2872. FIG. 29C depicts the adhesive system 2860 adhered to skin 2872 when the skin is in a relaxed state. When adhered to the skin 2872, the discontinuous portions 2870 form discrete attachment points to the skin 2872. As depicted in FIG. 29D, when the skin 2872 is stressed/stretched as indicated by arrows 2874, because the top layer 2840 has a low elastic modulus either inherently or through modification as discussed herein, the discontinuous portions 2870 that are adhered to the skin 2872 easily move with the skin in the direction of arrows 2874. The combination of the bottom layer 2844 having discrete attachment points between the discontinuous portions 2870 and the skin 2872 and the top layer 2840 having a low elastic modulus that stretches and/or plastically deforms under stress, provides the required strain relief between the skin 2872 and the adhesive system 2860.

In the herein disclosed embodiments, dividing the bottom layer of the adhesive system into multiple annular regions or other discontinuous portions, helps to minimize the strain on the inner or central regions of the adhesive system by distributing stress across the annular regions or discontinuous portions. Adhesive systems constructed in this manner, create a stress-strain gradient between the inner or central regions and the ring or discontinuous portions that extend away from the inner or central regions. For example, the embodiment of the adhesive system depicted in FIGS. 29A and 29B includes a bottom layer 2844 with discontinuous portions (annular regions 2850, 2852) that are detached from a central portion (central portion 2854). In this embodiment, a device, such as an opto-enzymatic device as disclosed herein, may be included on the adhesive system in the area above central portion 2854 (a loaded portion). Thus, designing an adhesive system that has a central loaded portion with discontinuous portions extending away from the central loaded portion (see for example, FIGS. 29C and 29D), allows for the stresses on the loaded central portion to be distributed across the exterior discontinuous portions.

In some examples, the adhesive system 2800 is re-sealable and provides for comfortable adhesion. The illustrated adhesive system 2800 can include two zones of attached materials. In some embodiments, the outer layer can be elastic, with a low durimetry. The outer layer can allow the adhesive system 2800 and attached device to be re-sealable to the skin. In some embodiments, the inner layer can be composed of a material that is less elastic but has a high MVTR. As will be discussed in further detail below, the material properties of the inner layer can allow the skin to breath by allowing water and/or water vapor to evaporate off the surface of the skin.

Figure 29F:
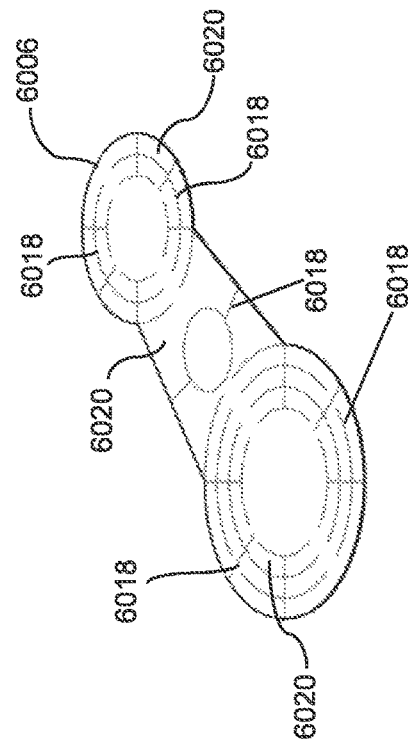
FIG. 29F is an exploded view of the adhesive system in FIG. 29E, according to an embodiment of the invention.
Figure 29H:
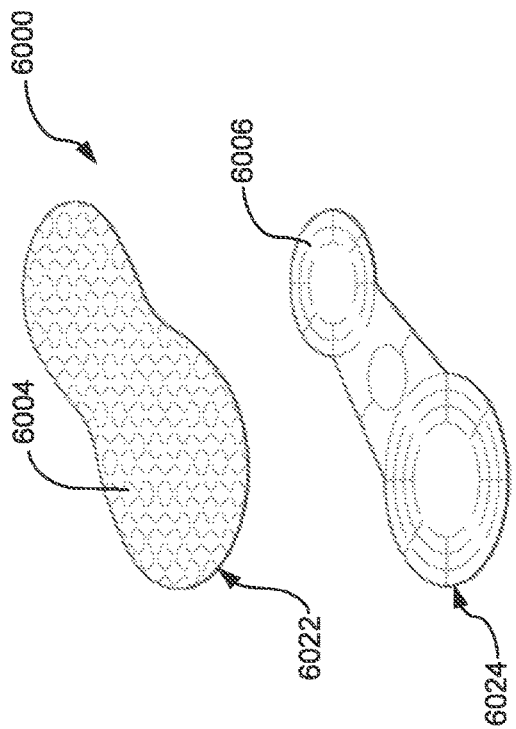
FIG. 29H is a front perspective view of the bottom layer of the adhesive system in FIG. 29E, according to an embodiment of the invention.
Figure 29E:
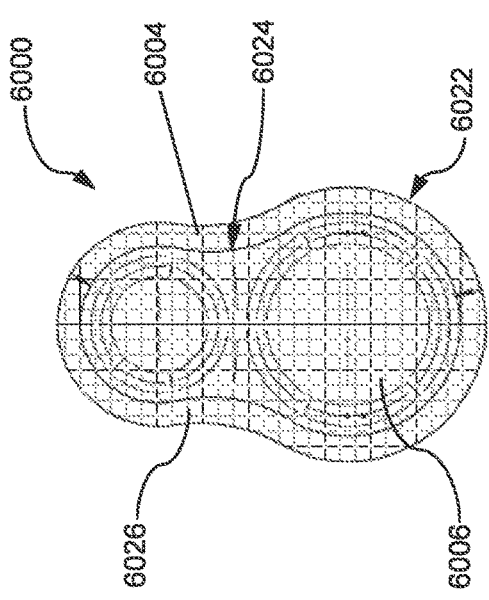
FIG. 29E is a top view of an adhesive system, according to an embodiment of the present invention.
Figure 29G:
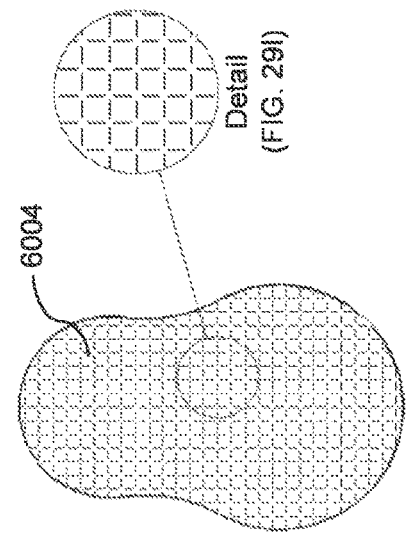
FIG. 29G is top view of the top layer of the adhesive system in FIG. 29E, according to an embodiment of the invention.
Figure 29J:
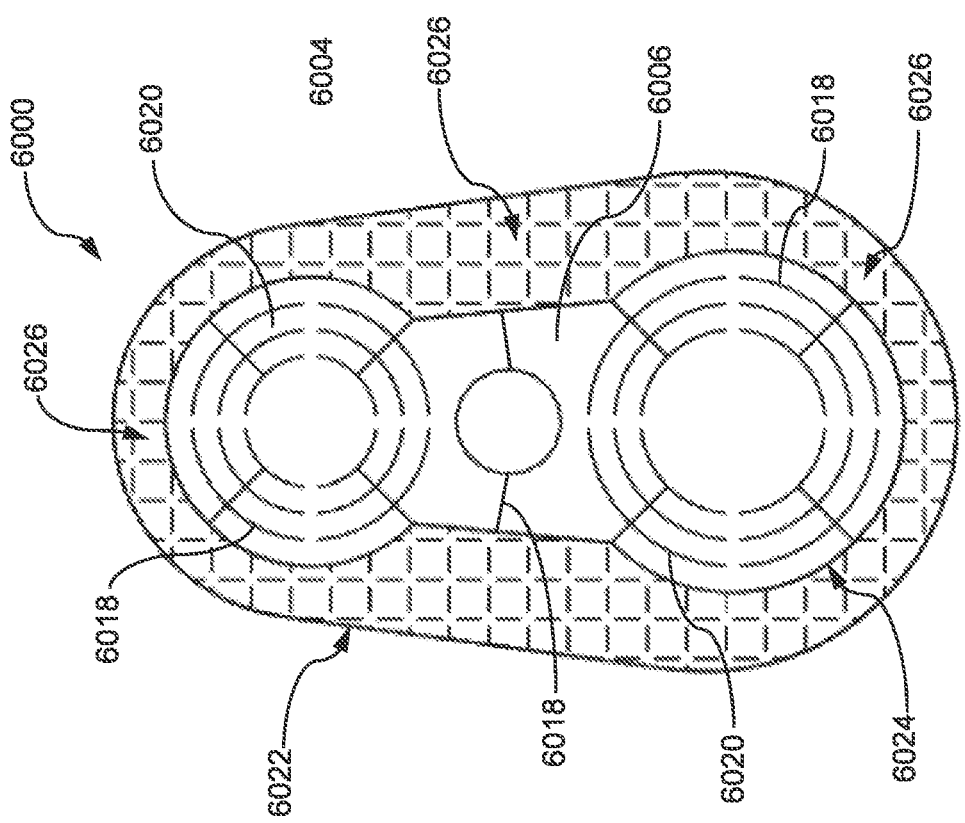
FIG. 29J is a bottom view of the adhesive system in FIG. 29E, according to an embodiment of the invention.
Figure 29I:
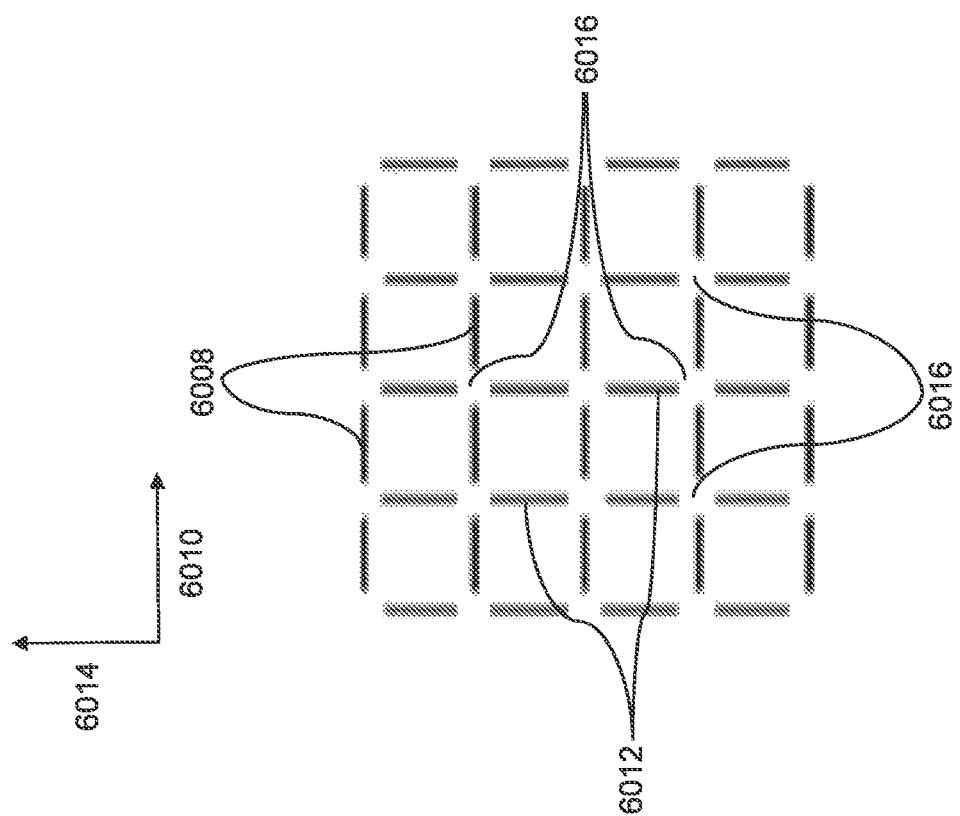
FIG. 29I is a detail of the perforations in the top layer of the adhesive system in FIG. 29G, according to an embodiment of the invention.

Depicted in FIGS. 29E to 29J is another embodiment of the present adhesive system. The adhesive system 6000 is a two-layer system that includes a top layer 6004 and a bottom layer 6006. The top layer 6004 can be made from a material having an intrinsic low elastic modulus and an intrinsic high MVTR or it can be made from a material that is modified to have an effective lower elastic modulus and/or an effective higher MVTR. The top layer 6004 can include an adhesive for attaching the top layer 6004 to the bottom layer 6006. Thus, a material having a higher elastic modulus and/or a lower MVTR than desired may be used but may be modified mechanically, for example, to include a plurality of modifications, such as, for example, perforations 6008, along a first direction 6010, and/or a plurality of modifications, such as, for example, perforations 6012, along a second direction 6014 (as depicted in FIGS. 29G and 29I, that extend through the thickness of the top layer 6004 and which can also extend through the adhesive.

The plurality of perforations 6008, 6012 transform the top layer material from a material having a high or first intrinsic elastic modulus and/or a low intrinsic MVTR into a material having an effective lower or second elastic modulus and/or an effective higher MVTR. The effective low elastic modulus is achieved by creating stress relaxing perforations that expand as the material is stretched. As the perforations expand, a plurality of concentrated areas of stress 6016 develop between adjacent perforations 6008, 6010, that undergo plastic deformation when stress is applied to the top layer 6004. Because any stress that is applied to the top layer 6004 is concentrated in areas 6016, these concentrated areas of stress 6016 plastically deform under external loads that are lower than stress that would cause an unmodified top layer 6004 material to plastically deform. This plastic deformation provides further strain relief between the top layer 6004 and the skin. The stress becomes lower for a given strain after deformation. Although the perforations 6008, 6012 in this embodiment are shown in a cross-hatch orthogonal pattern, the perforations 6008, 6012 can have any shape or pattern as long as they allow the material to separate creating a low elastic modulus response and preferentially create concentrated areas of stress 6016 between adjacent perforations. Additionally, in some embodiments, the plurality of perforations 6008, 6012 may extend completely through the top layer 6004 material while in other embodiments, they may not extend completely through the thickness of the material/layer and instead may be recessed, indented or embossed portions that fail when under stress and create the concentrated areas of stress 6016 between adjacent indentations causing the material layer to plastically deform under stress when applied to skin. In some embodiments, the top layer 6004 is a polyurethane material. In some embodiments, the top layer is a silicone elastomer.

The bottom layer 6006 can comprise any material (wicking materials, adhesives, etc.) and the material should be chosen based on the intended use of the adhesive system. In some embodiments, the material for the bottom layer 6006 is a wicking material such as, for example, a spun lace non-woven material, that includes an adhesive for adhering the bottom layer 6006 to skin. The wicking material of the bottom layer 6006, which contacts the skin, transports moisture laterally from areas of high moisture to areas of low moisture. As illustrated in FIGS. 29E, 29F, 29H and 29J, the bottom layer 6006 includes a plurality of perforations 6018 therein that form a plurality of discontinuous portions 6020. These perforations 6018 can be continuous or discontinuous. Accordingly, when the bottom layer 6006 is adhered to skin and is stressed, the plurality of discontinuous portions 6020 separate from each other, thereby providing strain relief in the bottom layer 6006. Because the discontinuous portions 6020 are adhered to the skin, as they separate and move away from the adjacent discontinuous portions 6020, they move with the skin, independently of one another. Although, in some embodiments, the plurality of perforations 6018 may extend completely through the bottom layer 6006 material, they may also be recessed, indented or embossed portions of the material, which create failure lines in the material that are designed to fail under stress and hence, cause adjacent discontinuous portions 6020 to separate from one another, when stress is applied to the material, thereby providing the required strain relief. In the present embodiment, the plurality of perforations 6018 that form a plurality of curvilinear discontinuous portions 6020 are depicted as curvilinear, however, the plurality of perforations 6018 need not be curvilinear and instead can be any geometry such as, for example, polygonal—square or rectangular, which form correspondingly-shaped discontinuous portions 6020, see for example, discontinuous portions 2870 in FIGS. 29C and 29D. It is only required that the plurality of perforations 6018 result in a plurality of discontinuous portions 6020 being formed in the bottom layer 6006 material that separate from each other and move with the skin, independent of one another.

As illustrated in the figures, the top layer 6004 is attached to the bottom layer 6006 with the first layer adhesive thereby sandwiching the bottom layer 6006 between the top layer 6004 and the skin when the adhesive system 6000 is attached to the skin. In this embodiment, because the perforations 6018 extend through the entire thickness of the bottom layer 6006, which create discontinuous portions 6020 that are adjacent to one another, the bottom layer 6006 typically has a lower effective elastic modulus than the top layer 6004. Therefore, the top layer 6004 provides structural reinforcement for the bottom layer 6004 and holds the adhesive system 6000 together.

As depicted in FIG. 29J, which is a bottom view of the adhesive system 6000, the top layer 6004 has a first perimeter 6022 that defines a first area and the bottom layer 6006 has a second perimeter 6024 that defines a second area. In some embodiments, the first area is greater than the second area, which results in portions 6026 of the first perimeter 6022 extending beyond the second perimeter 6024. Thus, when the adhesive system 6000 is attached to the skin, in addition to the bottom layer 6006 adhering to the skin with the bottom layer adhesive, the portions 6026 of the top layer 6004 that extend beyond the perimeter 6022 of the bottom layer 6006 (i.e., overhang the bottom layer 6006), result in a portion of the top layer 6004 also adhering to the skin with the top layer adhesive. In some embodiments, the bottom layer adhesive can be less aggressive than the top layer adhesive. In the present embodiment, a less aggressive adhesive may be used to adhere the bottom layer 6006 to the skin as the plurality of discontinuous portions 6020 transform the bottom layer into a very low elastic modulus layer. Because the discontinuous portions 6020 separate under low stress and therefore, move with the skin independently of one another, the bottom layer adhesive can be less aggressive as the shear forces between the discontinuous portions 6020 and the skin, are low. The lower shear forces result from the smaller contact area between the bottom layer adhesive on the discontinuous portions 6020 and the skin. Thus, smaller area discontinuous portions 6020 allow less aggressive adhesives to be used resulting in reduced skin irritation and easier and less painful removal from the skin. In this embodiment, the top layer 6004 and the bottom layer 6006, are attached to the skin with an adhesive.

In some embodiments, the top layer adhesive used to attach the top layer 6004 to the bottom layer 6006 and the portions 6026 of the top layer that extend beyond the perimeter 6022 of the bottom layer 6006 to the skin, is a more aggressive adhesive than the bottom layer adhesive. This more aggressive adhesive is necessary to keep the top layer attached to the bottom layer 6006 and the skin when stress is applied to the adhesive system 6000 due to movement (expansion and contraction) of the skin. That is, the top layer 6004 must expand and contract to the same extent as the skin in order to cause the perforations 6008, 6012 to open and preferentially induce formation of the concentrated areas of stress 6016 and hence, plastic deformation of the top layer 6004, thereby minimizing stress in the top layer 6004. Thus, the top layer 6004 must remain attached to the skin.

In addition to using an aggressive adhesive to impart a higher initial and sustained bond strength between the portions 6026 of the top layer 6004 that extend beyond the perimeter 6024 of the bottom layer 6006 that attach to the skin with the top layer adhesive, the area of the portions 6026 of the top layer 6004 that extend beyond the perimeter 6024 of the bottom layer 6006 can be increased such that a larger area of the top layer 6004 is attached to the skin with the top layer adhesive. The increased area of the top layer 6004 that adheres to the skin allows a less aggressive adhesive to be used while keeping the adhesive system 6000 attached to the skin and causing the adhesive system 6000 to plastically deform under the stress imparted due to movement of the skin.

Figure 29L:
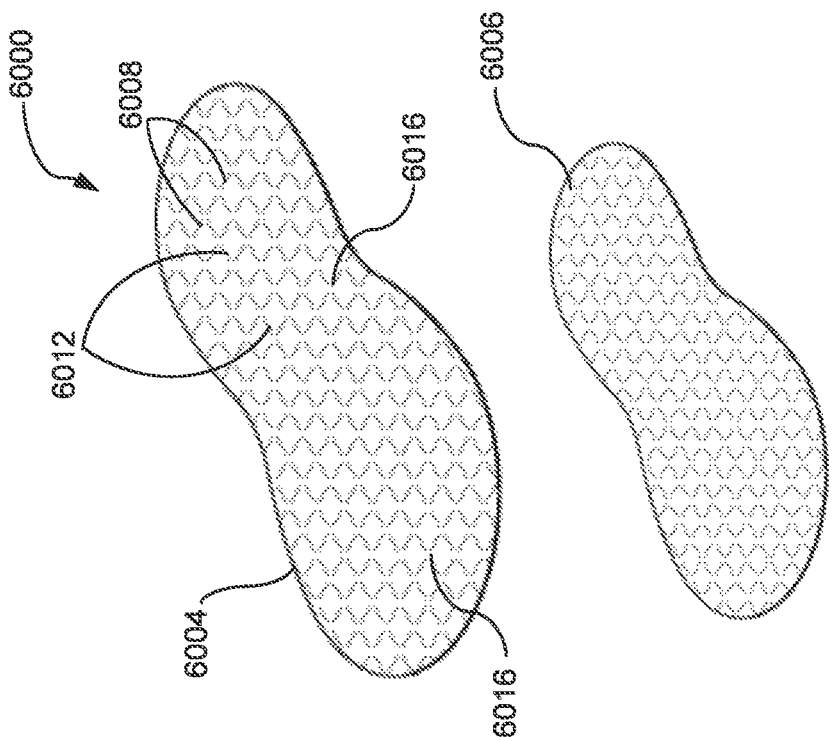
FIG. 29L is an exploded view of an adhesive system, according to an embodiment of the invention.
Figure 29K:
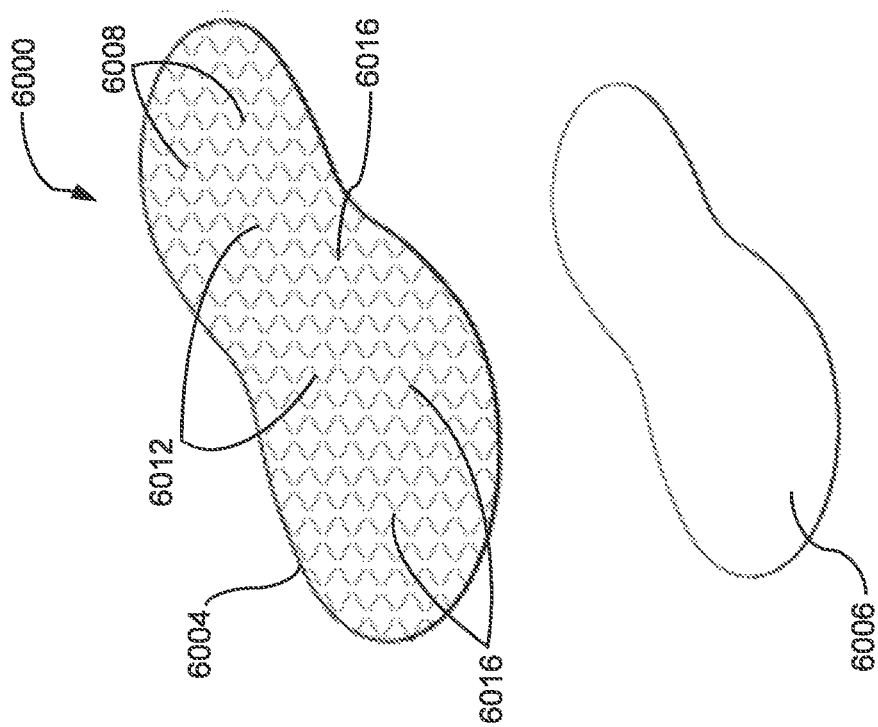
FIG. 29K is an exploded view of an adhesive system, according to an embodiment of the invention.

In additional embodiments of a two-layer adhesive system according to the present invention, as depicted in FIGS. 29K and 29L, the adhesive system 6000 includes a top layer 6004, which can be constructed in accordance with embodiments herein to include, for example, a plurality of perforations 6008, along a first direction, and/or a plurality of perforations 6012, along a second direction that create openings in the material and concentrated areas of stress 6016 between adjacent perforations as depicted in FIG. 29I.

The bottom layer 6006 can comprise a hydrocolloid. Because hydrocolloids are low elastic modulus materials with high MVTRs, in these embodiments, the bottom layer 6006 may (FIG. 29L) or may not (FIG. 29K) include the plurality of perforations 6004, 6008 therein that the top layer 6004 includes.

Depicted in FIGS. 29M to 29R are additional embodiments of the present multilayer adhesive system. The adhesive systems 6500, 6600 are three-layer systems that include a top layer 6504, 6604, middle layer 6508, 6608 and bottom layer 6512, 6612. The top layer 6504 can be made from a material having an intrinsic low elastic modulus and an intrinsic high MVTR or it can be formed of a material that is modified to have an effective lower elastic modulus and/or an effective higher MVTR. The modifications can be, for example, a plurality of perforations 6008 along a first direction, and/or a plurality of perforations 6012 along a second direction that create concentrated areas of stress 6016 between adjacent perforations as depicted in FIG. 29F. In some embodiments, the top layer is a polyurethane material. In some embodiments, the top layer is a silicone elastomer.

Figure 29N:
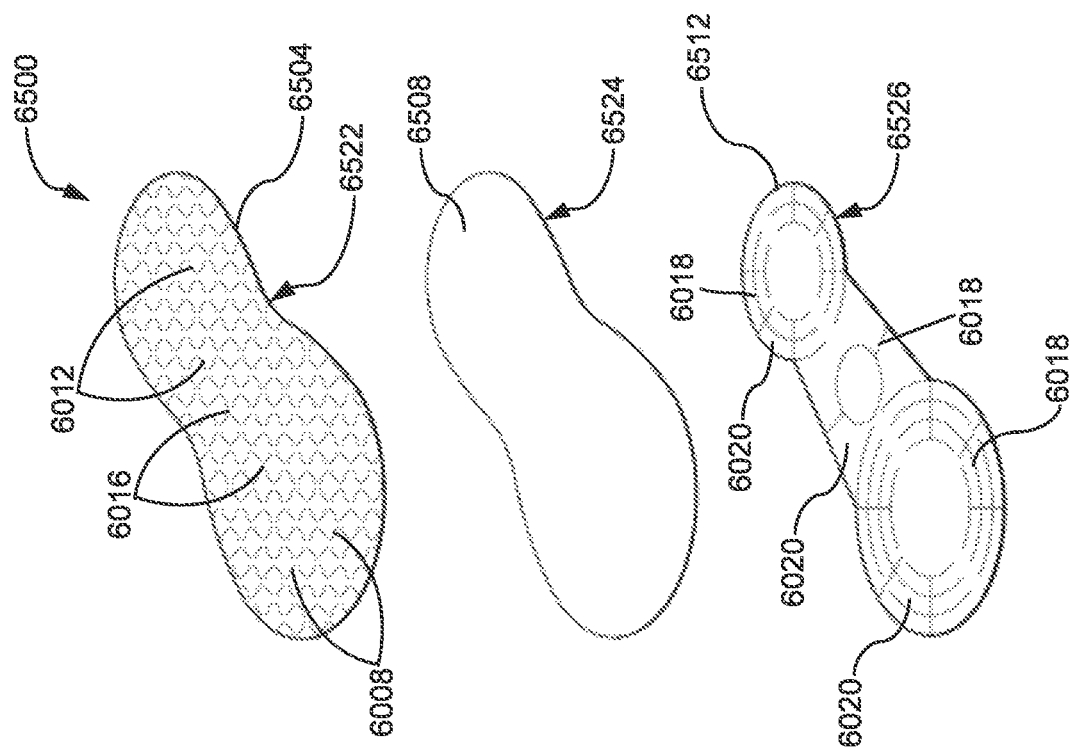
FIG. 29N is an exploded view of the adhesive system in FIG. 29M, according to an embodiment of the invention.
Figure 29M:
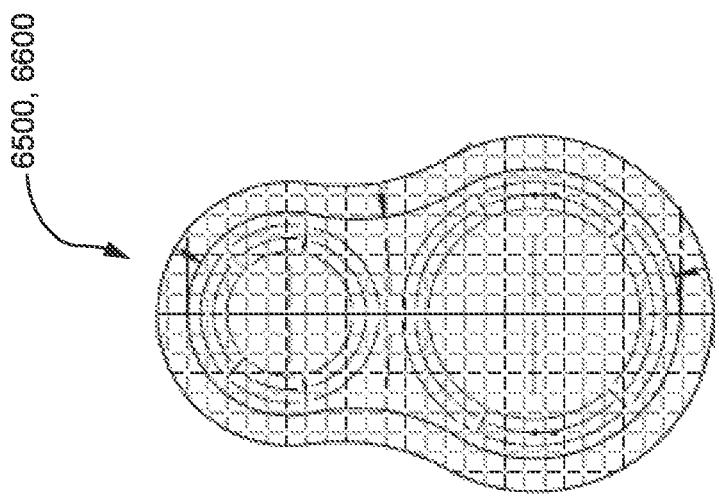
FIG. 29M is a top view of an adhesive system, according to an embodiment of the present invention.
Figures 29O, 29P:
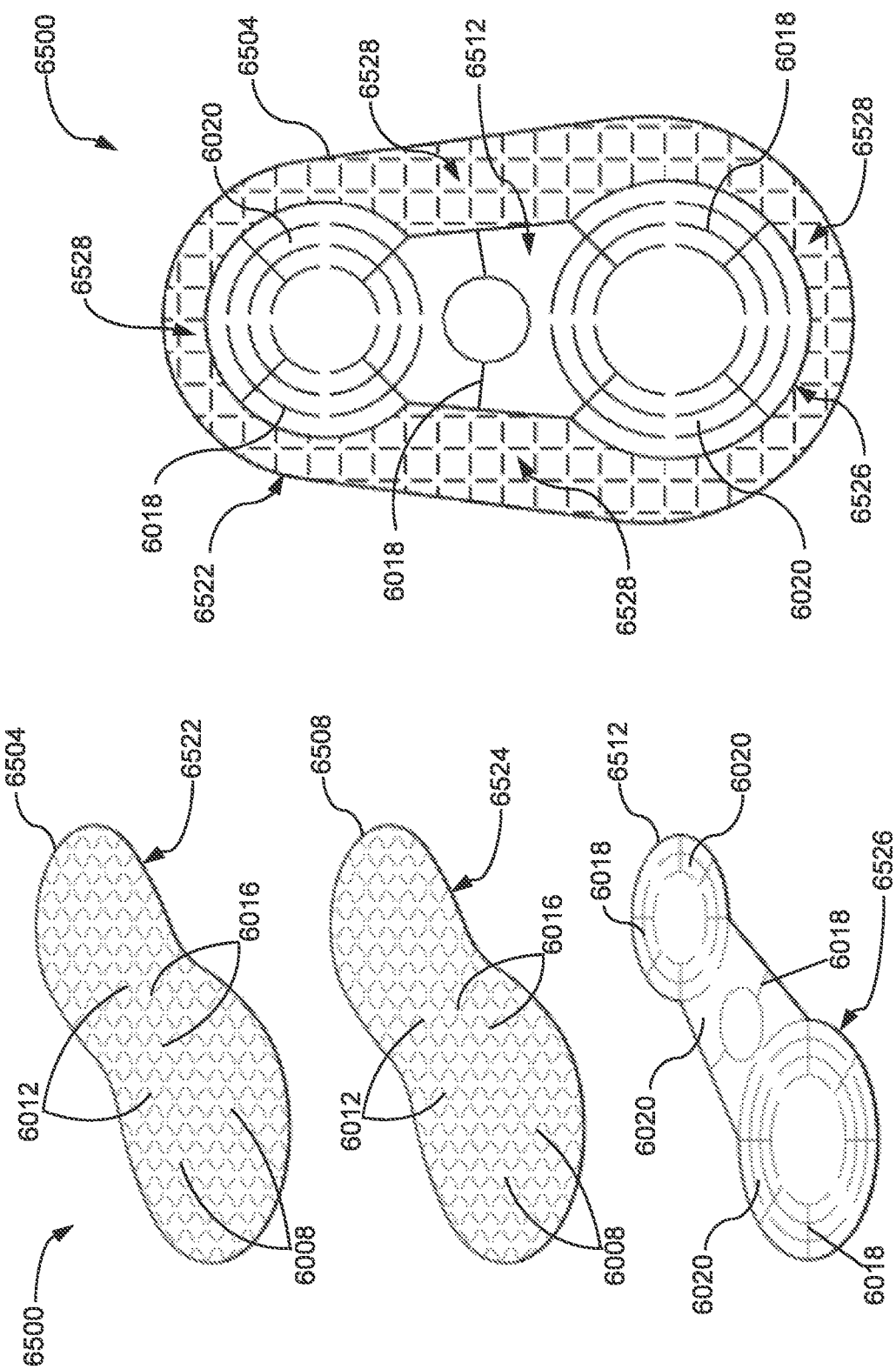
FIG. 29O is an exploded view of an adhesive system, according to an embodiment of the invention.
FIG. 29P is a bottom view of the adhesive system in FIG. 29O, according to an embodiment of the invention.

In the embodiment depicted in FIG. 29N, the middle layer 6508 can be a separate adhesive to attach the top layer 6505 to the bottom layer 6512. In some embodiments, the middle layer 6508 can be a fiber reinforced adhesive, such as, for example, a polyester fiber reinforced acrylate adhesive. Because fiber reinforced adhesives typically have a higher elastic modulus than desired, as depicted in FIGS. 29O and 29P where FIG. 29P is a bottom view of the adhesive system 6500, the middle layer 6508 in these embodiments can also include the plurality of perforations 6008 along a first direction, and/or the plurality of perforations 6012 along a second direction, similar to the top layer 6504, in order to reduce the elastic modulus of the middle layer 6508. In some embodiments, as depicted in FIG. 29N, the middle layer 6508 is unmodified.

As depicted in FIGS. 29 N to 29P, the bottom layer 6512 can comprise a hydrophobic material or a wicking material such as, for example, a spun lace non-woven material, that includes and adhesive for adhering the bottom layer 6512 to skin. As illustrated in the figures, the bottom layer 6512 in these embodiments, can be constructed in a similar manner with similar properties as the bottom layer 6006 for the two layer embodiments of the present adhesive system (see for example. FIG. 29H), to include a plurality of perforations 6018 therein that form a plurality of discontinuous portions 6020. Accordingly, when the bottom layer 6512 is adhered to skin and is stressed, the plurality of discontinuous portions 6020 separate from each other, thereby providing strain relief in the bottom layer 6512. Because the discontinuous portions 6020 are adhered to the skin, once they separate from the adjacent discontinuous portions 6020, they move with the skin, independently of one another. Thus, the same wicking material designs disclosed above for the bottom layer 6006 of the two-layer adhesive system embodiments, can be used for the three-layer adhesive system embodiments.

Figure 29R:
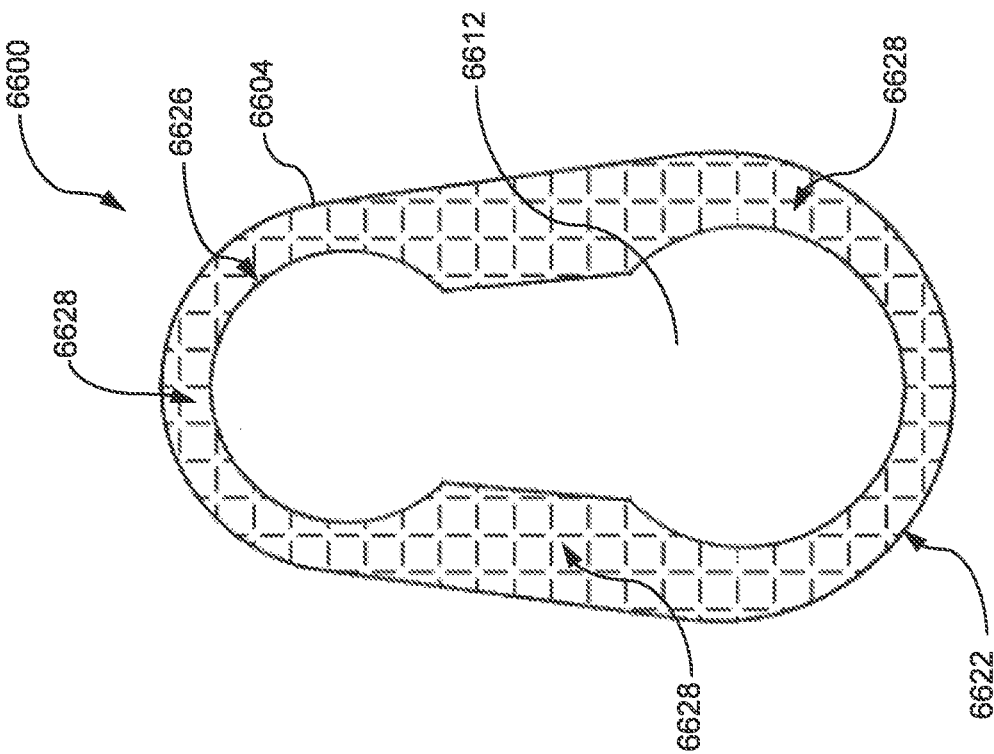
FIG. 29R is a bottom view of the adhesive system in FIG. 29Q, according to an embodiment of the invention.
Figure 29Q:
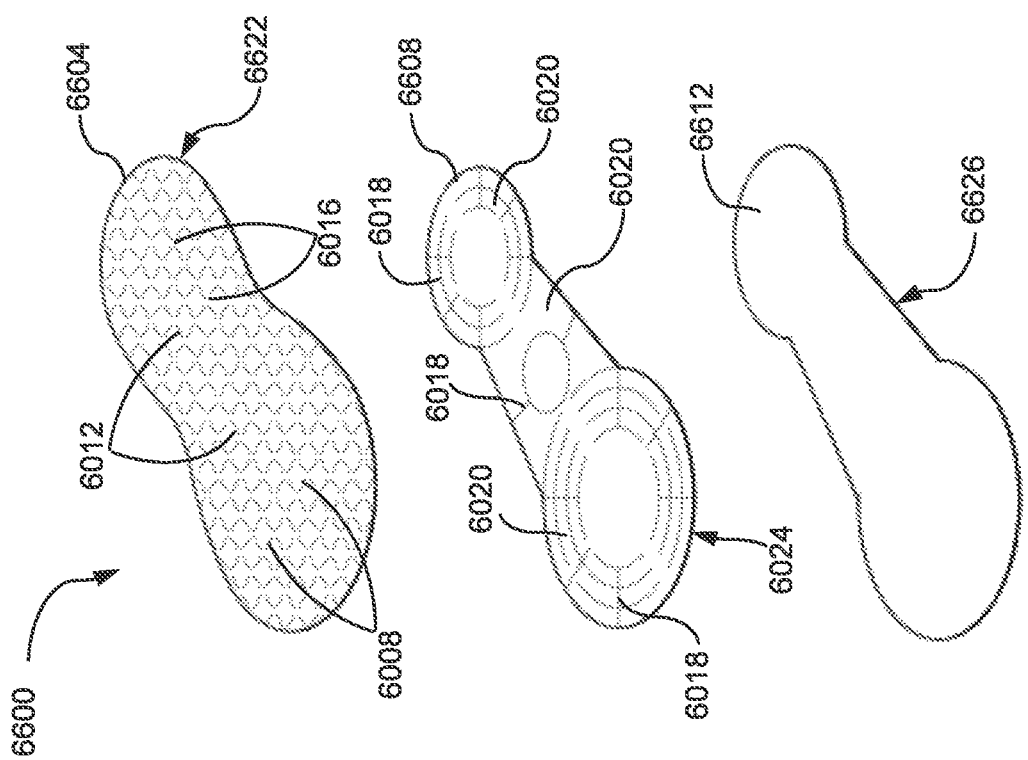
FIG. 29Q is an exploded view of an adhesive system, according to an embodiment of the invention.

In another embodiment of the three-layer adhesive system 6600, as depicted in FIGS. 29Q and 29R, the system includes a top layer 6604, middle layer 6608 and bottom layer 6612. The top layer 6604 can be, similar to previous embodiments, made from a material having an intrinsic low elastic modulus and an intrinsic high MVTR or it can be formed of a material that is modified to have an effective lower elastic modulus and/or an effective higher MVTR. The modifications can be, for example, a plurality of perforations 6008 along a first direction, and/or a plurality of perforations 6012 along a second direction that create concentrated areas of stress 6016 between adjacent perforations as depicted in FIG. 29I. In some embodiments, the top layer is a polyurethane material. In some embodiments, the top layer is a silicone elastomer.

In the embodiment depicted in FIG. 29Q, the middle layer 6608 can comprise a hydrophobic material or a wicking material such as, for example, a spun lace non-woven material. As illustrated, the middle layer 6608 in these embodiments, can be constructed in a similar manner with similar properties as the bottom layer 6006 for the two layer embodiments of the present adhesive system depicted in FIG. 29I, to include a plurality of perforations 6018 therein that form a plurality of discontinuous portions 6020. In this embodiment, the bottom layer 6612 can comprise a hydrocolloid, which attaches to the middle layer 6608 and the skin. Accordingly, when the three-layer adhesive system 6600 is adhered to skin and is stressed, the plurality of discontinuous portions 6020 of the middle layer 6608 to move with the hydrocolloid, which moves with the skin because it is a low elastic modulus material, and separate from each other, thereby providing strain relief in the middle layer 6608. Because the discontinuous portions 6020 are adhered to the skin through the hydrocolloid, once they separate from the adjacent discontinuous portions 6020, they move with the skin, independently of one another. Thus, the same wicking material designs disclosed above for the bottom layer 6006 of the two-layer adhesive system embodiments, can be used for the middle layer 6608 in this embodiment of the three-layer adhesive system.

In the three-layer adhesive system embodiments 6500, 6600 depicted in FIGS. 29M-29R, the top layer 6504, 6604 has a first perimeter 6522, 6622 that defines a first area, the middle layer 6508, 6608 has a second perimeter 6524, 6624 that defines a second area and the bottom layer 6512, 6612 has a third perimeter 6526, 6626 that defines a third area. In some embodiments, the first area is greater than the second and third areas, which results in portions 6528, 6628 of the first perimeter 6522, 6622 extending beyond the second and third perimeters 6524, 6624, 6526, 6626 (see FIGS. 29P and 29R). Thus, when the adhesive systems 6500, 6600 are attached to the skin, in addition to the bottom layer 6512, 6612 adhering to the skin, the portions 6528, 6628 of the top layer 6504, 6604 that extend beyond the perimeters 6524, 6624, 6526, 6626 of the middle layer 6508, 6608 and bottom layer 6512, 6612 (i.e., overhang the middle layer 6508, 6608 and bottom layer 6512, 6612), result in a portion of the top layer 6504, 6604 also adhering to the skin. Accordingly, adhesives with similar properties to those disclosed above for the two-layer adhesive system embodiments, can be used to attach the three-layer adhesive system embodiments to skin.

As previously disclosed, the length of the perforations 6008, 6012 and the spacing between adjacent perforations in the embodiments of the adhesive systems disclosed herein, can be changed/adjusted to tune the effective elastic modulus of the materials/layers and hence, the effective modulus of the completed multilayer adhesive systems.

Figure 29S:
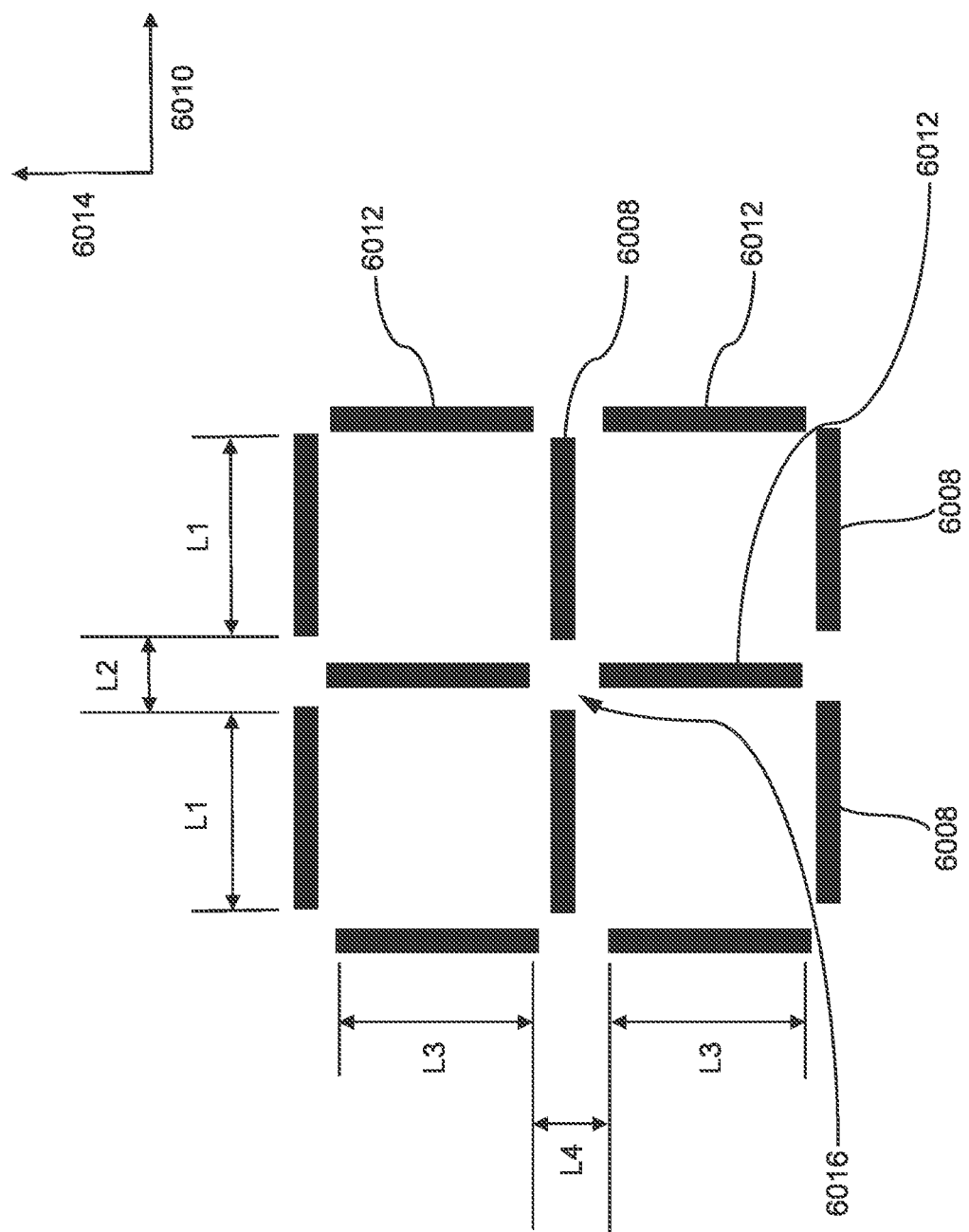
FIG. 29S is a detail of the modifications to the adhesive system layers, according to an embodiment of the present invention.

As illustrated in FIG. 29S, embodiments of the present adhesive systems can include layers that have been modified to include a plurality of first perforations 6008 along a first direction 6010 and a plurality of second perforations 6012 along a second direction 6014. In some embodiments, (a) the plurality of first perforations 6008 have a length L1 and adjacent first perforations 6008 are separated by a distance L2 and (b) the plurality of second perforations 6012 have a length L3 and adjacent second perforations 6012 are separated by a distance L4. The lengths L1 and L3 and the distances L2 and L4 can be chosen to change the size of the concentrated areas of stress 6016 that are created between adjacent first perforations 6008 and adjacent second perforations 6012, which changes the effective elastic modulus of the layer that includes the first and second perforations 6008, 6012. Thus, for example, when L1 and L3 have lengths that are longer than the distances L2 and L4, the layer will have an effective elastic modulus that is lower than a layer having an L1 and L3 with lengths that are shorter than the distances L2 and L4. Accordingly, adhesive system layer embodiments that include first and second perforations 6008, 6012 having lengths L1 and L3, respectively, that are significantly longer than the distances L2 and L4, will have a much lower elastic modulus than adhesive system layer embodiments that include first and second perforations 6008, 6012 having lengths L1 and L3, respectively, that are not significantly longer than the distances L2 and L4. In some embodiments, L1 is substantially equal to L3 and L2 is substantially equal to L4, which results in a layer/adhesive system having an effective elastic modulus that is substantially the same in both the first and second directions 6010, 6014. In some embodiments, L1 is not substantially equal to L3 and L2 is not substantially equal to L4, which results in a layer/system having an effective elastic modulus that is not substantially the same in both the first and second directions 6010, 6014. In some embodiments, L1 and L3 can range from approximately 1.0 mm to 3.0 mm and L2 and L4 can range from approximately 0.25 mm to 1.0 mm. Also, in some embodiments, adhesive system layers may only include perforations along one direction so as to only substantially change the effective elastic modulus of the layer/material in one direction.

Although the plurality of perforations in the disclosed embodiments are shown in a cross-hatch pattern or are orthogonal to one another, any pattern of a plurality of perforations that create concentrated areas of stress in a layer or multilayer adhesive system, may be used. The type of patterned perforations used will affect the effective elastic modulus of the layer and/or adhesive system.

Modifying L1, L2, L3, and L4 as outlined above, allows the effective elastic modulus of an individual layer or the constructed multilayer adhesive system to be tuned/adjusted to be less than approximately 100 Kpa, 90 Kpa, 70 Kpa, 60 Kpa, 50 Kpa, 40 Kpa, 30 Kpa, 20 Kpa, and 10 Kpa, at 100% strain. Thus, modifying the individual layers or the constructed multilayer adhesive system as outlined above, allows the effective elastic modulus to be maintained for strains up to 0.4 and preferably, up to 1.0.

In some embodiments of the two-layer adhesive systems disclosed herein, the top layer can have an effective elastic modulus less than 0.02 Mpa (20 Kpa) that is maintained for strains up to 0.4 and preferably, for strains up to 1.0. In some embodiments, the bottom layer can have an effective elastic modulus less than 0.02 Mpa (20 Kpa) that is maintained for strains up to 0.4 and preferably, for strains up to 1.0. In some embodiments, the two-layer adhesive system can have an effective elastic modulus less than 0.02 Mpa (20 Kpa) that is maintained for strains up to 0.4 and preferably, for strains up to 1.0. In some embodiments, the concentrated areas of stress plastically deform when an external load is applied to achieve a net strain of up to 0.4 in the two-layer adhesive system. In some embodiments, when the multilayer adhesive system is deformed by an external load to a strain of up to 0.4, the multilayer adhesive system deforms resulting in >90% of the achieved strain being retained when the external load is removed.

In some embodiments of the three-layer adhesive systems disclosed herein, the top layer can have an effective elastic modulus less than 0.02 Mpa (20 Kpa) that is maintained for strains up to 0.4 and preferably, for strains up to 1.0. In some embodiments, the middle layer can have an effective elastic modulus less than 0.02 Mpa (20 Kpa) that is maintained for strains up to 0.4 and preferably, for strains up to 1.0. In some embodiments, the bottom layer can have an effective elastic modulus less than 0.02 Mpa (20 Kpa) that is maintained for strains up to 0.4 and preferably, for strains up to 1.0. In some embodiments, the three-layer adhesive system can have an effective elastic modulus less than 0.02 Mpa (20 Kpa) that is maintained for strains up to 0.4 and preferably, for strains up to 1.0. In some embodiments, the concentrated areas of stress plastically deform when an external load is applied to achieve a net strain of up to 0.4 in the two-layer adhesive system. In some embodiments, when the multilayer adhesive system is deformed by an external load to a strain of up to 0.4, the multilayer adhesive system deforms resulting in >90% of the achieved strain being retained when the external load is removed.

Figure 29T:
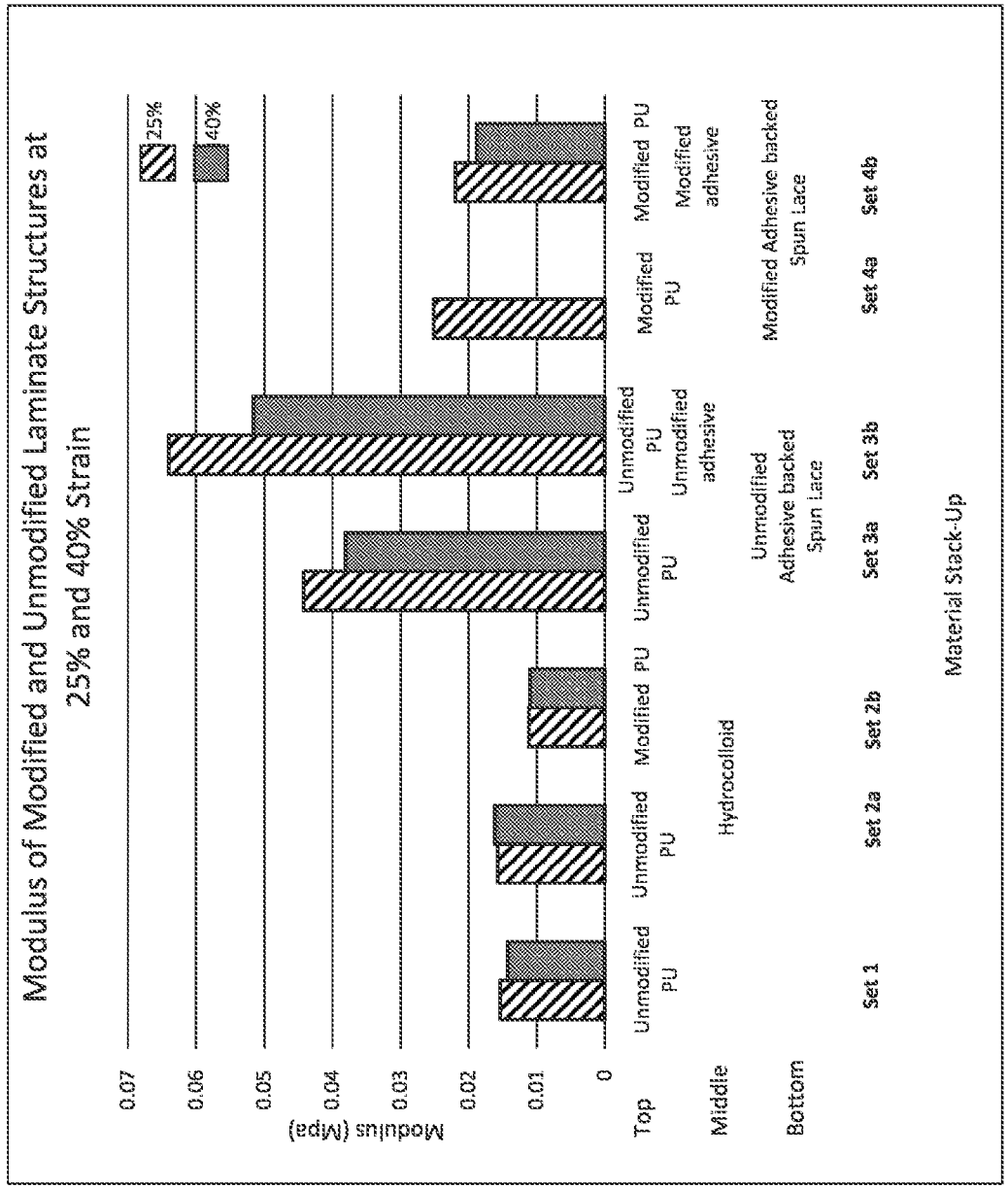
FIG. 29T is a chart summarizing strain test results for different adhesive system embodiments according to the present invention.

Depicted in FIG. 29T is a chart showing the results of strain tests that were performed on adhesive systems constructed in accordance with the embodiments disclosed herein. As used in the description of FIG. 29T, unmodified means that the layer was not modified as disclosed herein to include any perforations therein and modified means that the layer was modified to include either a plurality of perforations in the first and second directions (for the polyurethane (PU) top layer and the adhesive middle layer) or a plurality of perforations that form a plurality of discontinuous portions therein (the adhesive-backed spun lace, non-woven bottom layer). It should be noted that the adhesive systems identified in the chart started to plastically deform at 40% strain, reducing the slope calculation of the modulus.

The following seven adhesive systems were tested. Set 1 comprised an adhesive system having an unmodified polyurethane top layer. At 25% strain, the elastic modulus was approximately 15 Kpa and at 40% strain, the elastic modulus was approximately 14 Kpa. Set 2a comprised an unmodified polyurethane top layer and an unmodified hydrocolloid bottom layer. At 25% strain, the elastic modulus was approximately 15 Kpa and at 40% strain, the elastic modulus was approximately 16 Kpa. Set 2b comprised a modified polyurethane top layer and an unmodified hydrocolloid bottom layer. At 25% strain, the elastic modulus was approximately 10 Kpa and at 40% strain, the elastic modulus was approximately 10 Kpa. Set 3a comprised an unmodified polyurethane top layer and an unmodified adhesive backed spun lace, non-woven bottom layer. At 25% strain, the elastic modulus was approximately 44 Kpa and at 40% strain, the elastic modulus was approximately 38 Kpa. Set 3b comprised an unmodified polyurethane top layer, an unmodified adhesive middle layer and an unmodified adhesive backed spun lace, non-woven bottom layer. At 25% strain, the elastic modulus was approximately 64 Kpa and at 40% strain, the elastic modulus was approximately 51 Kpa. Set 4a comprised a modified polyurethane top layer and a modified adhesive backed spun lace, non-woven bottom layer. At 25% strain, the elastic modulus was approximately 25 Kpa and at 40% strain, the elastic modulus was approximately 0 Kpa. Set 4b comprised a modified polyurethane top layer, a modified adhesive middle layer and a modified adhesive backed spun lace, non-woven bottom layer. At 25% strain, the elastic modulus was approximately 22 Kpa and at 40% strain, the elastic modulus was approximately 19 Kpa.

As can clearly be seen in FIG. 29T. modifying the adhesive layers as disclosed herein, reduces the materials and hence, the adhesive system's elastic modulus.

Figure 29U:
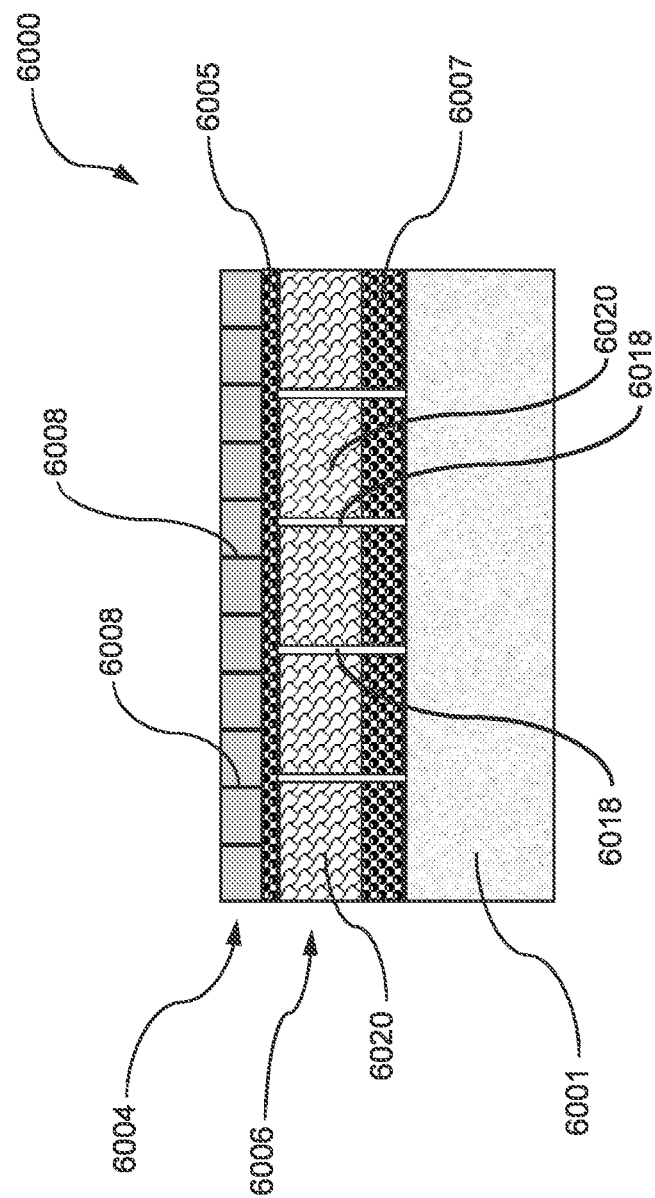
FIG. 29U is an illustration of an adhesive system according to an embodiment of the invention, attached to relaxed skin.
Figure 29W:
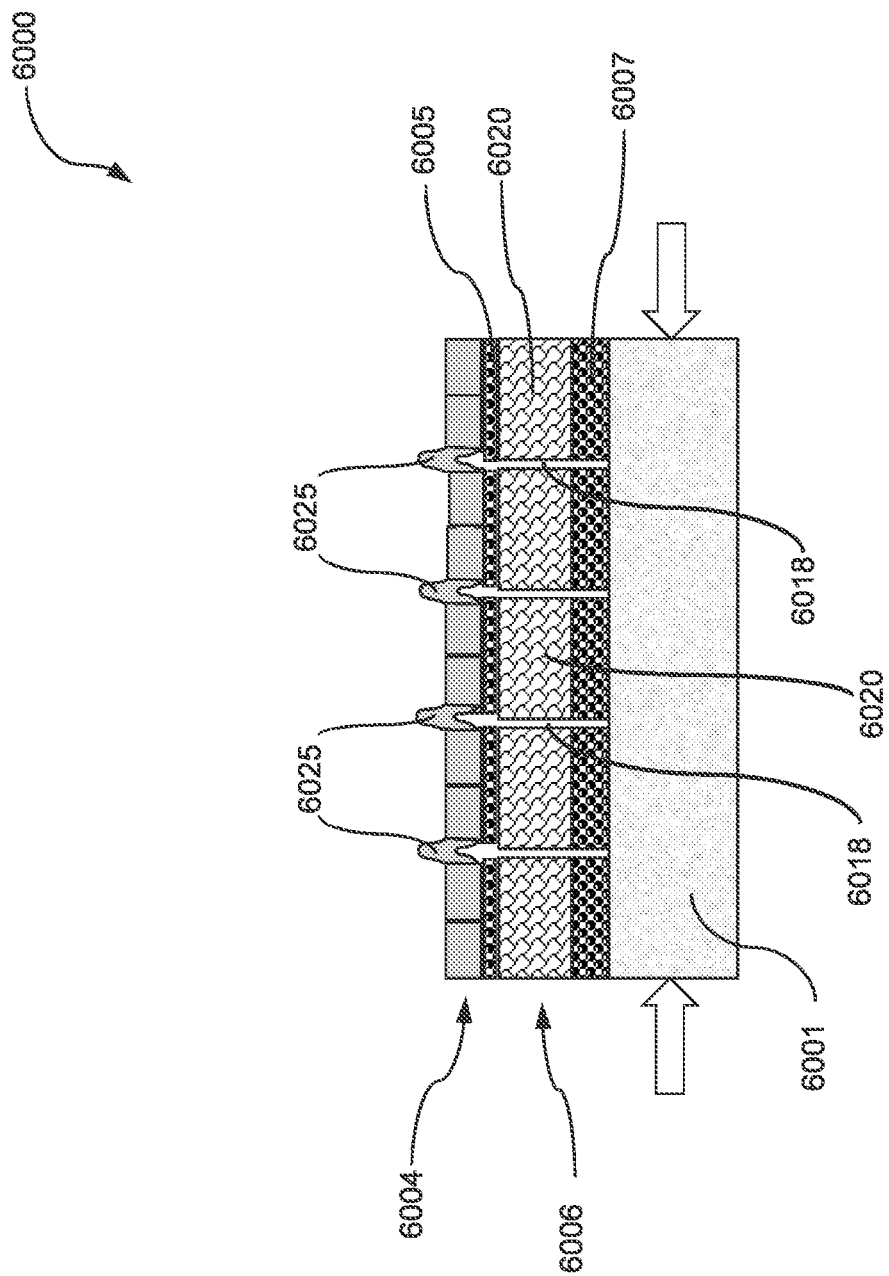
FIG. 29W is an illustration of the adhesive system depicted in FIG. 29V on skin when the skin returned to a relaxed state.

Depicted in FIGS. 29U to 29W is an illustration of how adhesive systems according to embodiments of the present invention react and respond when attached to skin. FIGS. 29U to 29W are cross-sectional views through a two-layer adhesive system according to embodiments of the present invention, for example, the embodiments associated with FIGS. 29E to 29I. Although a two-layer system adhesive system is depicted, three-layer adhesive systems of the embodiments of the present invention, will react and respond in a similar manner.

FIG. 29U depicts the adhesive system 6000 when initially attached to the skin 6001. As can be seen in the figure, the adhesive system 6000 includes a top layer 6004 with a plurality of perforations 6008 along a first direction that is attached to a middle layer 6006 with a top layer adhesive 6005. The bottom layer 6006 attaches to the skin 6001 with a bottom layer adhesive 6007 and includes a plurality of perforations 6018 that form a plurality of discontinuous portions 6020 in the bottom layer 6006.

As depicted in FIG. 29V, when the skin 6001 stretches in the direction indicated by arrows 6021, the discontinuous portions 6020 of the bottom layer 6006, which are attached to the skin 6001 with bottom layer adhesive 6007, also move in direction 6021 causing any discontinuous portions 6020 that are connected to adjacent discontinuous portions 6020 to separate. Accordingly, movement of the discontinuous portions 6020 away from each other causes the material of the top layer 6004, which is attached to the bottom layer 6006 with top layer adhesive 6005, to move in a corresponding manner. This movement imparts stress on the top layer 6004, which causes the concentrated areas of stress 6016 to form in the areas between adjacent perforations 6008 in the top layer 6004. These concentrated areas of stress 6016 plastically deform and elongate under the stress applied by movement of the skin 6001 as a result of the top layer 6004 being stretched beyond its elastic limit. This plastic deformation provides strain relief between the adhesive system 6000 and the skin 6001.

Once the skin 6001 is unstressed or returned to its relaxed state, which is depicted in FIG. 29W, the concentrated areas of stress 6016 in the top layer 6004 that plastically deformed and hence, elongated, now form wrinkles 6025 in the adhesive system 6000. As a result of top layer's 6004 plastic deformation and the discontinuous portions 6020 separating from each other, the shear forces/stress between the skin 6001 and bottom layer adhesive 6007 is reduced. In subsequent movement/stretching of the skin 6001 and the adhesive system 6000, the discontinuous portions 6020 of the bottom layer 6006 and the material of the top layer 6004 can now move freely with the skin as the wrinkles 6025 or elongated material of the top layer 6004, freely elongate allowing the adhesive system 6000 to move with the skin 6001 with very minimal shear forces between the adhesive system 6000 and skin 6001. Thus, there is minimal "pulling" on the adhesive system, which drastically reduces the occurrence of edge peel. If the wrinkled portions 6025 are elongated past there previously deformed length, these wrinkled portions 6025 again undergo plastic deformation and elongate, thereby creating larger wrinkles 6025, which again reduce shear forces between the adhesive system 6000 and skin 6001.

In addition, this reduction in shear forces/stress after plastic deformation, permits the use of an adhesive that has a high initial bond strength with a lower sustained bond strength, which results in an adhesive system that is easy to remove with less pain and that is able to be removed as an intact system (in one piece).

In some examples, the bottom of the device housing can have channels or other disruptions 2845 that allow air flow under the device housing and also allow moisture to flow away from the skin and adhesive system 6000. The device can therefore be bonded to the underlying adhesive system 6000 in a disrupted manner. The device can be attached to the adhesive system 6000 in a plurality of ways. For example, the device housing 2832 can be attached to the adhesive system 6000 using heat staking, an adhesive layer (e.g. device adhesive 2830 discussed above or any other type of adhesive) or through ultrasonic welding.

Figure 30:
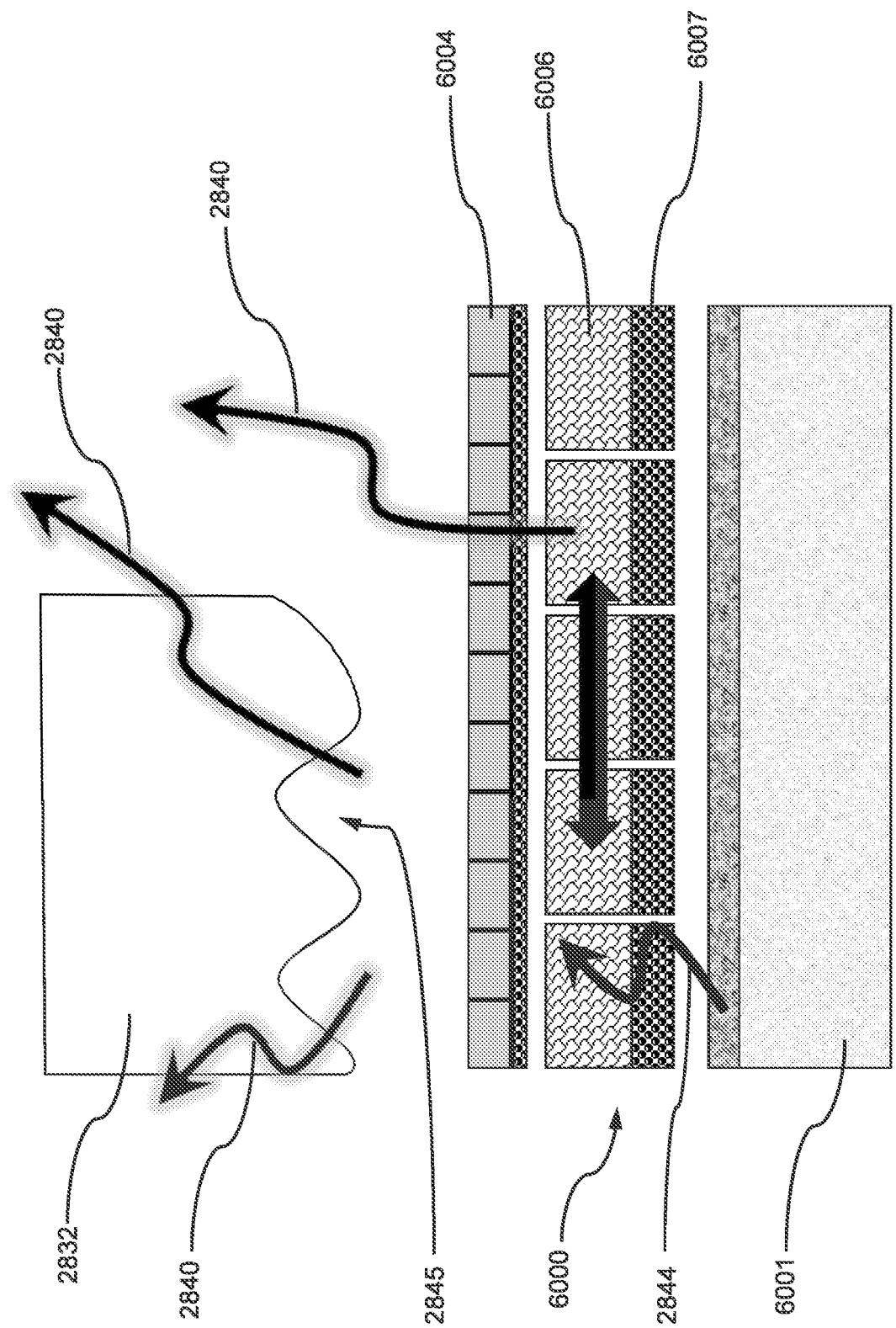
FIG. 30 is a schematic view of the flow of moisture from the surface of the skin through an adhesive system and attached opto-enzymatic sensor system, according to an embodiment of the present invention.

FIG. 30 illustrates a schematic view of the device 2832 attached to the skin 6001 with the adhesive system 6000. As discussed above, the material layers of the adhesive system 6000 can provide a high MVTR under the housing of the device 2832 such that water does not accumulate under the device 2832.

FIG. 30 includes a plurality of arrows that illustrate the movement of moisture from the skin 6001 and through the adhesive system 6000. As denoted by the arrow, the skin 6001 can perspire, generating sweat 2844 that moves to the surface of the skin 6001. The high MVTR material of the adhesive system 6000 can transfer the sweat 2844 the bottom layer 6006, which can be a wicking material. The wicking material of the adhesive system 6000 can pull the moisture away from the skin 6001. The adhesive system 6000 can then allow the water vapor 2840 to evaporate from the skin 6001 by causing it to travel laterally through the wicking material of the adhesive system 6000. In some embodiments, the material of the adhesive system 6000 can also serve to repel water from the top surface of the adhesive system 6000. Additionally, any disruptions 2845 on the bottom of the device housing 2832 also helps aid sweat and other water vapor to evaporate from under the adhesive system 6000 and device housing 2832.

Turning briefly to the embodiments of the adhesive systems illustrated in FIG. 29, in some examples, the moisture will wick through the layer of spun lace non-woven material and will evaporate through the top layer, which, in some embodiments, is a modified polyurethane. Evaporation may occur through the plurality of perforations in the top layer of the adhesive systems. In some examples, the moisture will evaporate form the top of the adhesive system and diffuse out from under the sensor housing 2832, 3110 through the disruptions 2845 on the bottom of the sensor housing 2832, 3110.

Implanting a Sensor in a Patient

Disclosed is an inserter system and associated methods for transdermally inserting a sensor for a continuous glucose monitoring system.

The sensor inserter system is a single-use device that can allow the patient to safely and reliably place the sensing element of the sensor assembly into the skin with little or no pain. The sensor inserter system can be sterile packaged such that it can provide a simple and safe way to handle the sensor assembly during sensor insertion. In some examples, the sensor inserter is preassembled with the disposable sensor and sterilized as a system. The disposable sensor is ready for insertion when the sensor inserter is removed from its packaging.

In some examples, the disposable sensor can be inserted on the abdomen or the dorsal upper arm. The sensor insertion process is simple and reliably inserts the sensor. The sensor inserter system can enable the proper depth placement of the percutaneous sensor. The sensor insertion process using the sensor inserter system can be simple, intuitive, and brief. After the sensor is attached to the skin of the patient, the sensor inserter can be withdrawn and disposed. In some embodiments, the sensor inserter may be reusable—up to 20 times, with replaceable, one-time-use lancets.

As will be described in more detail below, the sensing element of the sensor assembly is inserted into the subcutaneous tissue using the sensor inserter system. The sensor inserter system is preassembled with the sensor assembly and can be provided to the user using a sterile sensor inserter assembly to facilitate easy sensor placement. The percutaneous sensing element of the sensor assembly is inserted into the tissue by means of an insertion lancet. The sensor inserter assembly can be removed after the sensor assembly is placed and discarded. As discussed in previous sections above, the on-body transmitter can be connected to the sensor assembly after the sensor is placed. The on-body transmitter can interrogate the sensor assembly in order to obtain sensor measurements that can be transmitted to the primary display. The primary display can contain a receiver and microprocessor to convert the transmitted measurements into calibrated glucose measurements.

Figure 31A:
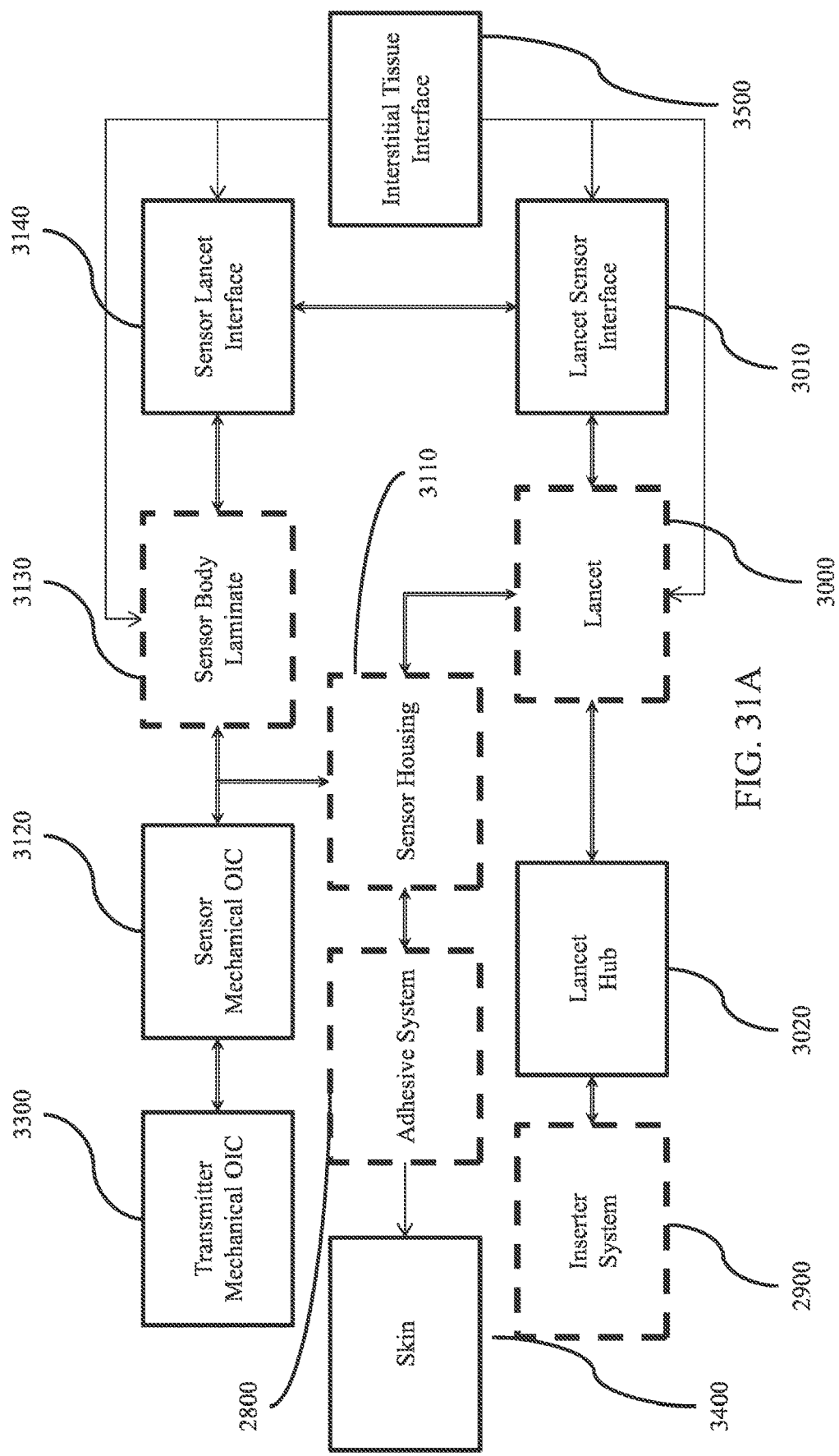
FIG. 31A is a schematic view of the connection between the sensor system and inserter system, according to an embodiment of the present invention.
Figure 31B:
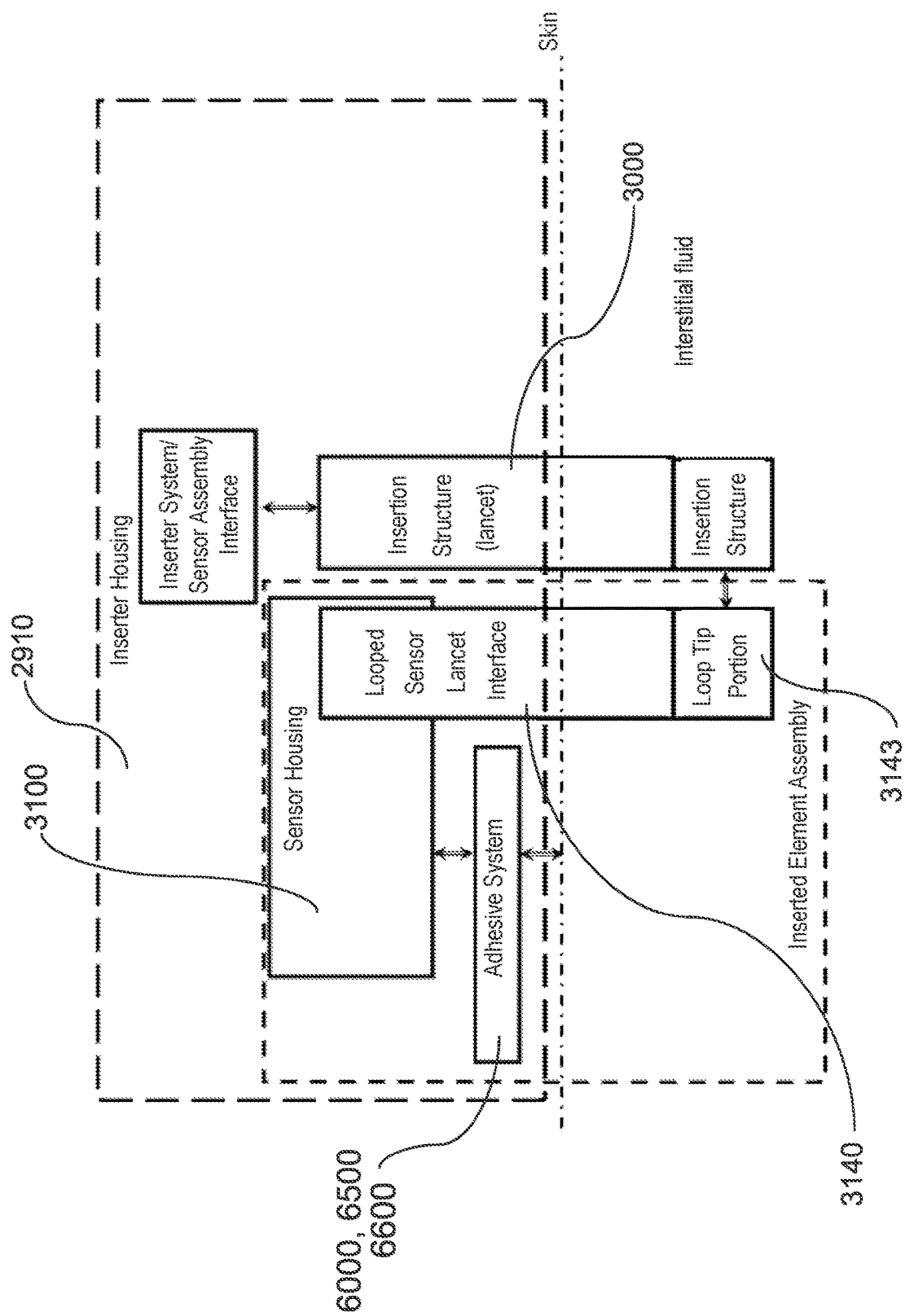
FIG. 31B is a schematic view of the connection between the sensor system and inserter system, according to an embodiment of the present invention.

FIGS. 31A and 31B provide a schematic illustration of the interaction between the sensor assembly, the inserter system, and the interaction with the tissue of a patient. Turning first to the sensor assembly, in some embodiments, the sensor assembly can include a sensor housing 3110. The sensor housing 3110 can include a sensor mechanical optical interconnect (OIC) 3120. As discussed above, the sensor mechanical optical interconnect 3120 can be mechanically connected to a transmitter mechanical optical interconnect 3300. In some embodiments, a surface of the sensor housing 3110 can include an adhesive system 2800 that can allow the sensor assembly to be attached to a surface of the patient's skin 3400.

In order to deliver the percutaneous portion of the device, such the sensing element of the sensor assembly into the skin, an inserter system 2900 can be provided. The inserter system 2900 can include a lancet hub 3020 that includes a lancet 3000 or other insertion structure. As will be described in more detail below, the lancet 3000 can include a lancet sensor interface 3010 that is configured to retain a portion of the looped sensor lancet interface 3140. As shown in FIG. 31A, the sensor housing 3110 can include a body laminate 3130 with looped sensor lancet interface 3140 that can be retained on the lancet sensor interface 3010. The lancet 3000 is configured to insert a portion of the sensor assembly (at least the sensor looped distal portion 4004 as disclosed and described below), into the interstitial fluid/tissue interface 3500. As will be described in more detail below, the inserter system 2900 can be configured to allow the lancet 3000 to be removed from the patient's tissue while leaving a portion of the sensor assembly (e.g. the sensing element) implanted in the tissue of the patient.

Figure 32:
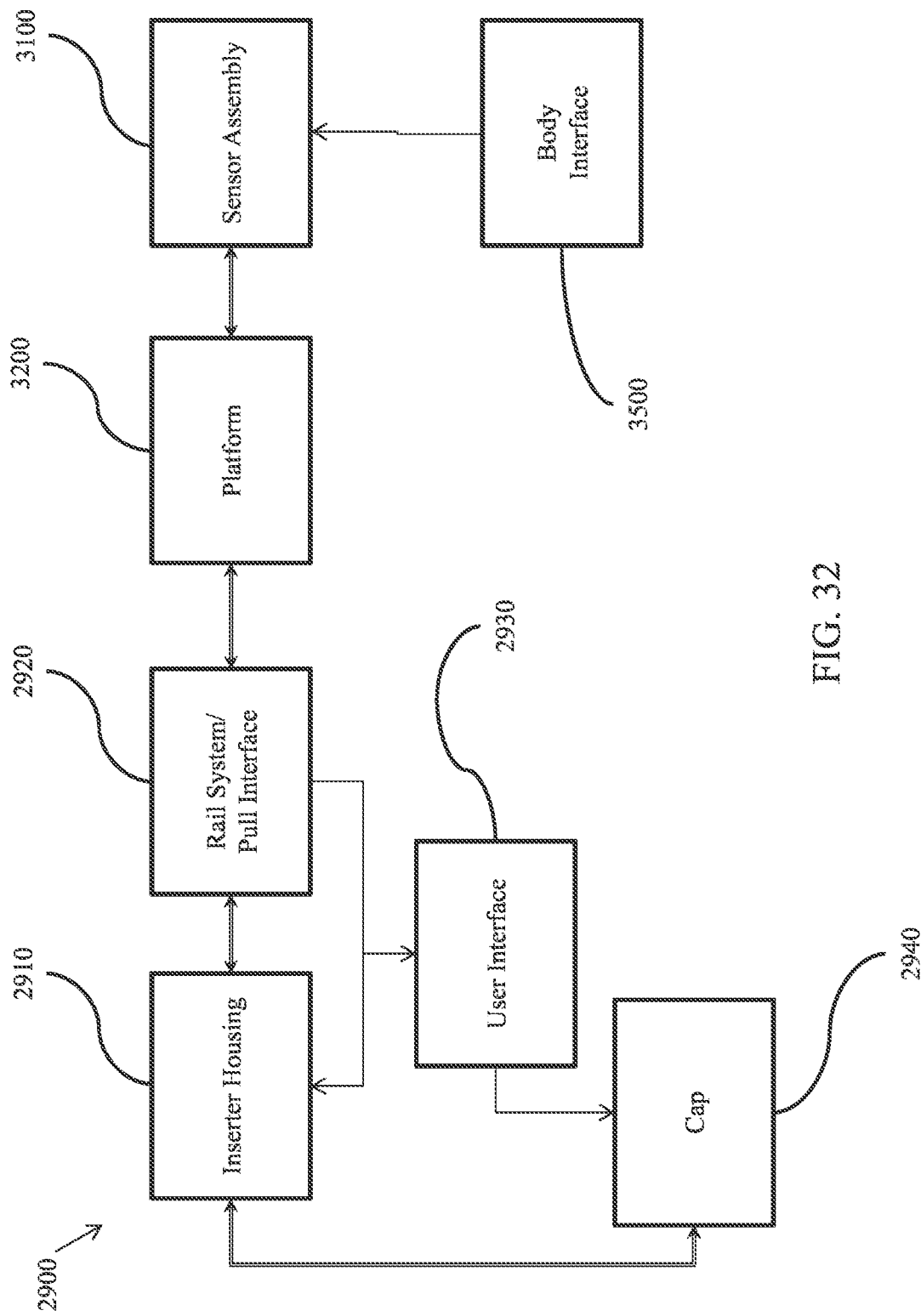
FIG. 32 is a schematic view of an inserter system for the sensor, according to an embodiment of the present invention.
Figure 33A:
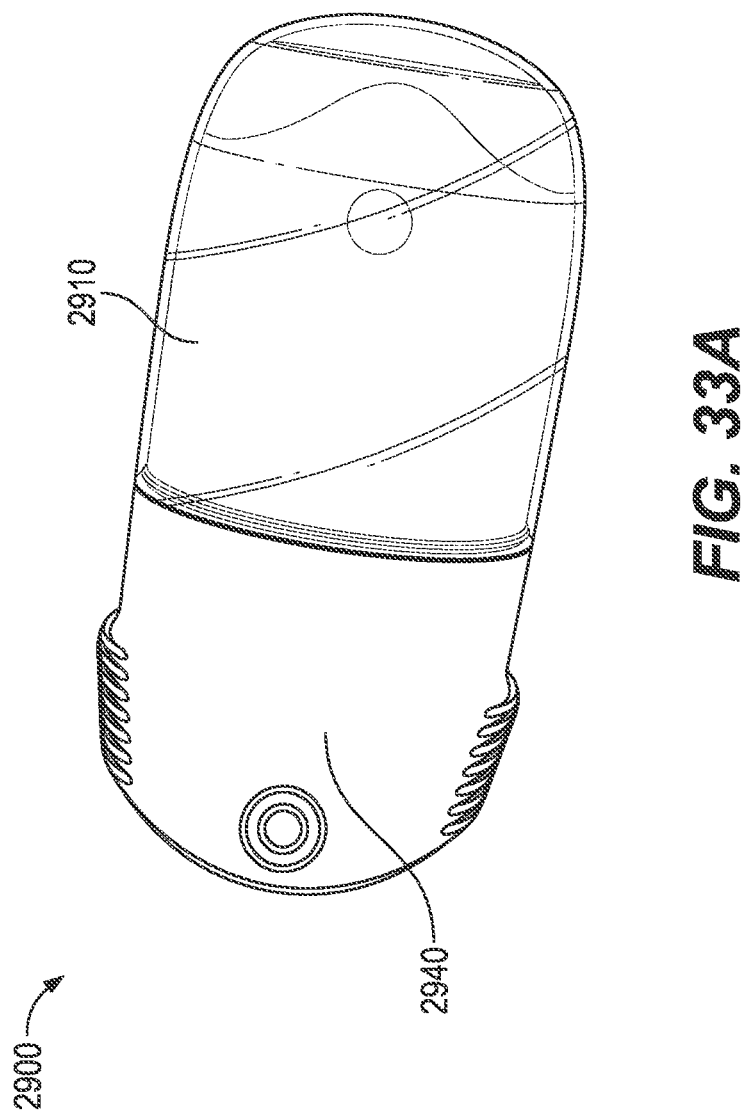
FIG. 33A is a side view of the inserter system, according to an embodiment of the present invention.
Figure 33C:
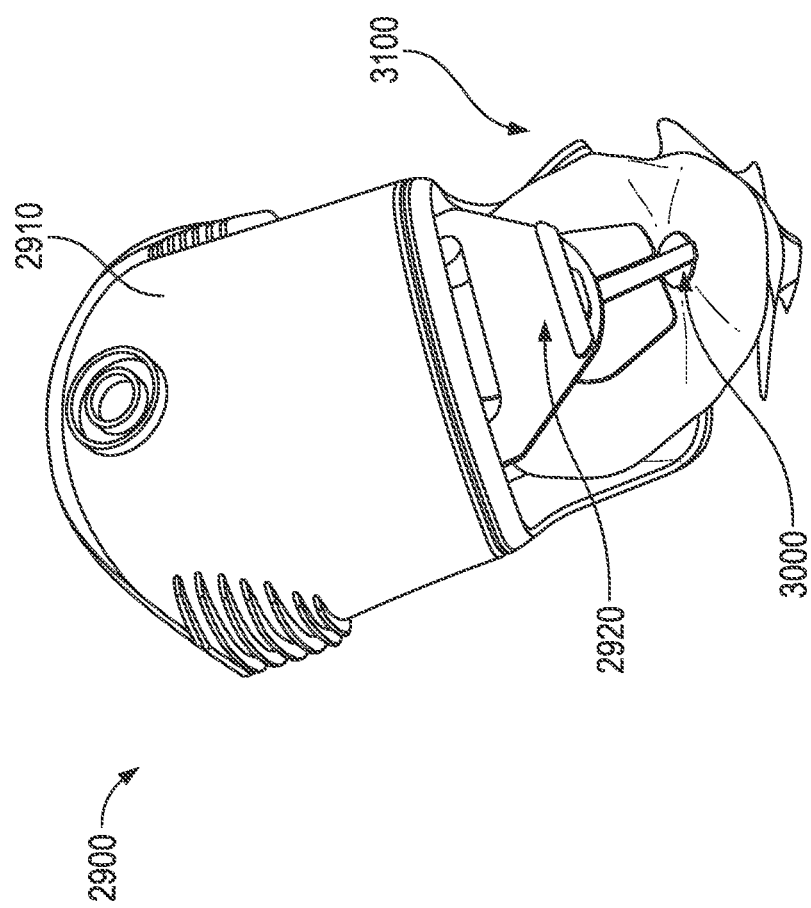
Figure 33D:
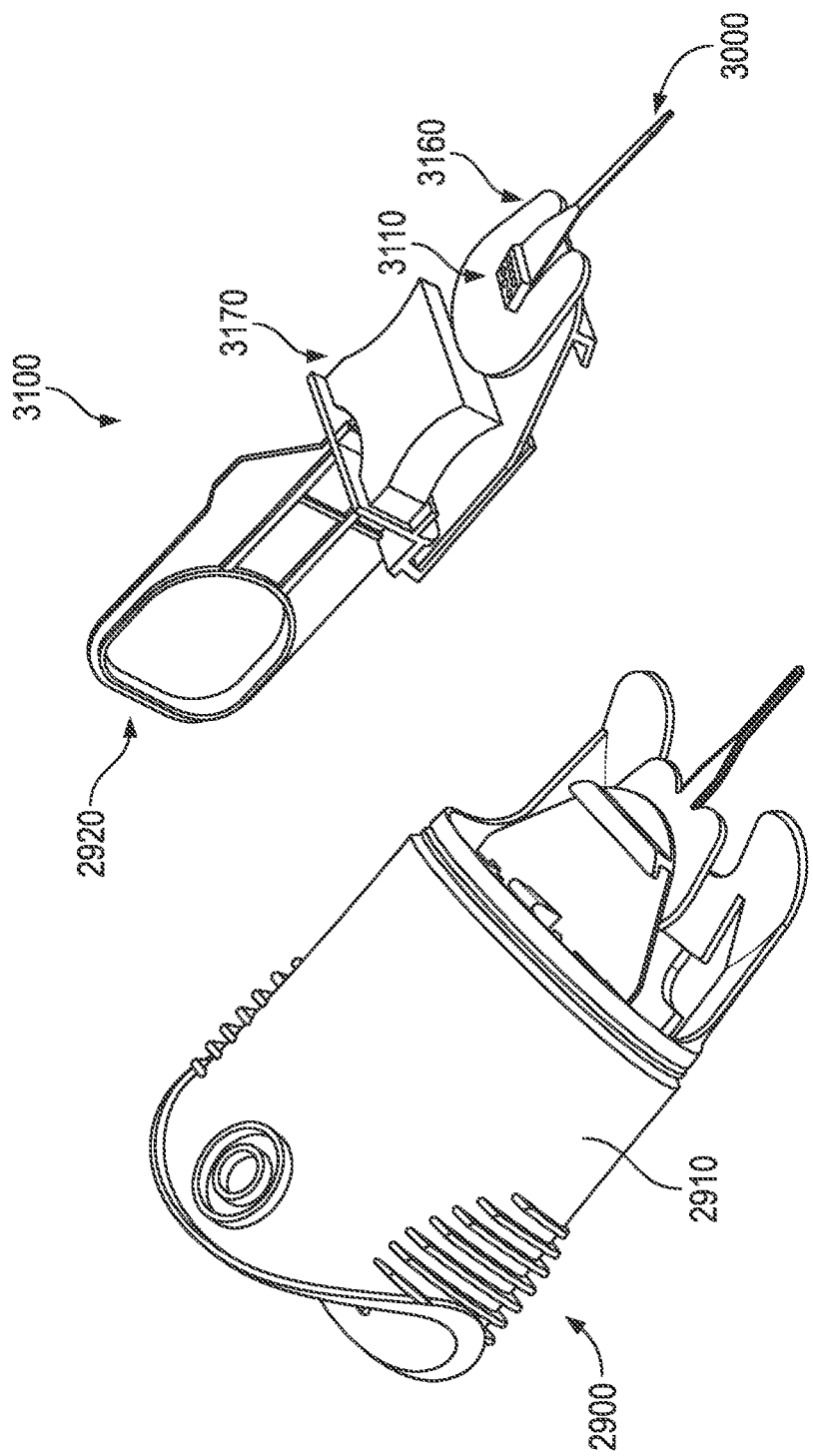
FIG. 33D is a frontal view of the outside and inside components of the inserter assembly, according to an embodiment of the present invention.

FIG. 32 illustrates a schematic illustration of the inserter system 2900 that are further illustrated in FIGS. 33A-D. FIGS. 33A-C illustrate an embodiment of the inserter system 2900 and sensor assembly 3100. In some embodiments, the inserter system 2900 can include an inserter housing 2910 and a cap 2940. The cap 2940 can be provided to prevent unintentional contact of the patient with the lancet 3000. FIG. 33D illustrates a perspective view of the complete inserter system 2900 and a perspective view of the internal sensor assembly 3100 removed from its internal location within the inserter housing 2910.

The sensor assembly 3100 consists of a sensor housing 3110, a lancet 3000, an adhesive system 2800, and a sensor subassembly 3160. As noted above, in some embodiments, the sensor subassembly 3160 can include the sensing element described above. As well, in some embodiments, the sensor subassembly 3160 does not contain any electronics.

As will be described in more detail below, the inserter system 2900 can include a housing and a rail system 2920. To insert the sensor subassembly 3160 into the tissue, the inserter system 2900 can include a lancet assembly 3170 that can include a lancet 3000 and a lancet hub 3010 (FIG. 33D). The sensor assembly 3100 can include a sensor housing 3110, the sensor subassembly 3160, the adhesive system (described in more detail above), and the lancet assembly 3170.

As illustrated in FIG. 33B, the sensor subassembly 3160 can be adhered to the upper surface of the sensor housing 3110. In some embodiments, the insertion lancet 3000 can be adhered to the bottom surface of the sensor housing 3110. As will be described in more detail below, the tip of the lancet 3000 can be mechanically mated to the tip of the sensor subassembly 3160. The tip of the lancet 3000 can be shaped like a suture cutting needle so as to allow the sensor subassembly to be cleanly inserted into the patient's tissue with minimal trauma and little or no pain. With such a shape, the tip of the lancet 3000 cuts skin and other body tissue instead of tearing through skin and body tissue. Embodiments of the lancet 3000 design will be discussed in more detail below. After the lancet 3000 is delivered through the skin, upon withdrawal of the lancet 3000 from the skin, the sensor is released from the tip of the lancet 3000 and remains implanted. Embodiments of the lancet 3000 disclosed herein can be used to deliver and implant sensors for analyte monitors, including the glucose monitors disclosed herein as well as to deliver and implant micro catheters and drug eluting implants. The micro catheters can be for infusion pumps to deliver, for example, insulin, therapeutic agents and other treatments (chemotherapy, for example) to a patient.

As depicted in FIG. 34A and FIG. 34B, lancets/insertion structures 3000 according to embodiments of the present invention comprise a substantially planar, non-rigid, non-frangible, elongate member having a proximal portion 3003, an intermediate portion 3004, a distal portion 3005 for piercing the skin for subcutaneous insertion and a longitudinal axis 3051. In some embodiments, the elongate member may not be planar and may be rigid. The elongate member can have a thickness "T" ranging between approximately 100 μm to approximately 400 μm depending on the material used and the depth of insertion (as discussed below). This thickness can be uniform along the length of the elongate member or the thickness can vary. The thickness "T" of the elongate member can be chosen to ensure that the elongate member remains in a configuration that permits successful insertion through skin and into subcutaneous tissue and this thickness may be dependent on the Young's modulus of the material from which the elongate member is constructed. That is, the Young's modulus of the elongate member material will correspond to the thickness of the material required to ensure successful insertion through the skin. In some embodiments, the elongate member is constructed from fully tempered stainless steel as SS1.4028. SS1.4028 is a martensitic stainless steel. Martensitic stainless steels are ones with high hardness and high carbon content. These steels are generally fabricated using methods that require hardening and tempering treatments is used in the quenched and tempered condition in a host of constructional where corrosion resistance is required. Due to its higher carbon content, 1.4028 is more hardenable than 1.4021, with a 50HRC and a Young's modulus of 200 GPa. As for other martensitic grades, optimal corrosion resistance is attained when the steel is in the hardened condition and the surface is finely ground or polished.

Also, the thickness "T" of the material used and which material (Young's modulus) used for the elongate member may be dependent on the depth of insertion of the elongate member's distal portion 3005 into subcutaneous tissue, i.e., the distance that the tip 3030 of the elongate member's distal portion 3005 is inserted into the subcutaneous tissue as measured from the surface of the tissue to the deepest point of the tip 3030 within the tissue. This distance is also known as the insertion length of the elongate member.

In some embodiments, for an insertion length of the elongate member ranging between approximately 5 mm to approximately 9 mm, the thickness "T" of the elongate member is approximately 200 μm. In some embodiments, for an insertion length of the elongate member of approximately 9 mm, the thickness "T" of the elongate member is approximately 180 μm. In some embodiments, for an insertion length of the elongate member of approximately 9 mm, the thickness "T" of the elongate member is approximately 250 μm. In some embodiments, for an insertion length of the elongate member ranging between approximately 4 mm to approximately 10 mm, the thickness "T" of the elongate member ranges between approximately 180 μm and approximately 250 μm.

The elongate member includes a first surface 3001 and a second surface 3002. As depicted in the figures, the first surface 3001 and the second surface 3002 are opposite each other and can be a top and a bottom surface of the elongate member. The proximal portion 3003 of the elongate member provides a mechanical interconnect between the lancet 3000 and the sensor assembly 3100 for attaching the lancet 3000 to the sensor assembly 3100.

Figure 35A:
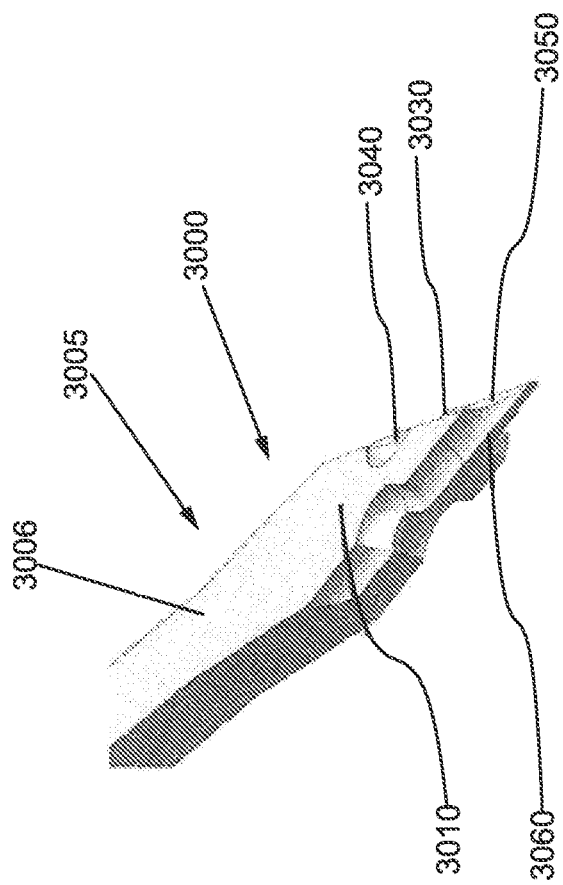
FIG. 35A is a top perspective view of the distal portion of a lancet, according to an embodiment of the present invention.
Figure 35B:
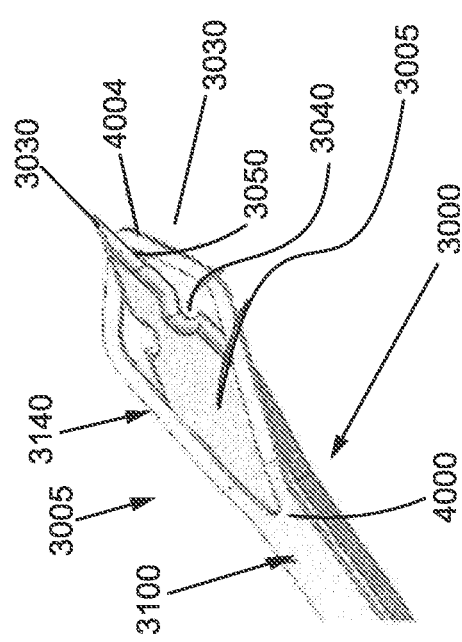
FIG. 35B is a top perspective view of the distal portion of the lancet depicted in FIG. 35A with a sensor attached, according to an embodiment of the present invention.
Figure 35C:
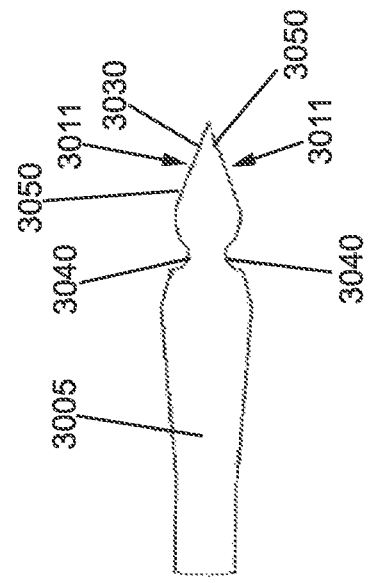
FIG. 35C is a top perspective view of the distal portion of a lancet, according to an embodiment of the present invention.
Figure 35D:
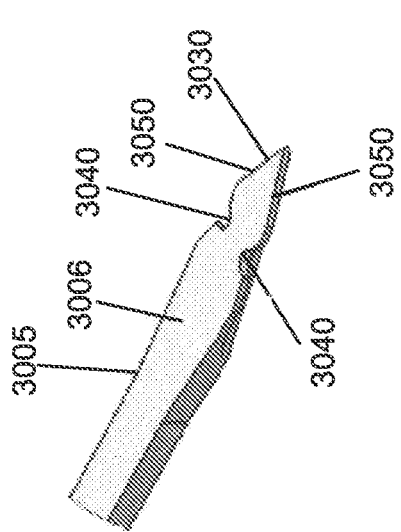
FIG. 35D is a top view of the distal portion of the lancet depicted in FIG. 35C, according to an embodiment of the present invention.
Figure 35E:
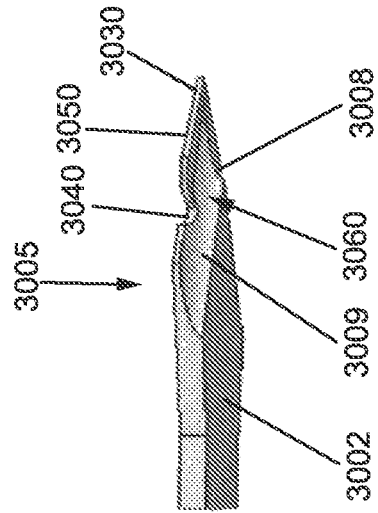
FIG. 35E is a side view of the distal portion of the lancet depicted in FIG. 35C, according to an embodiment of the present invention.
Figure 35F:
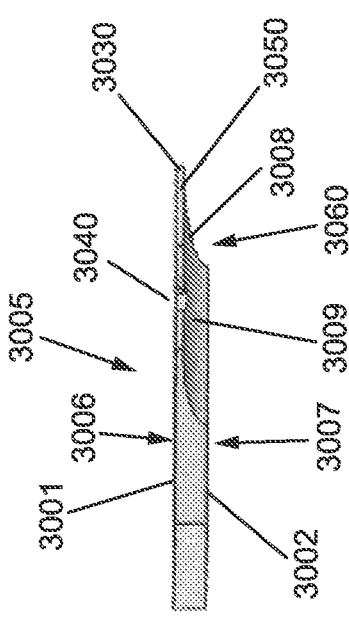
FIG. 35F is a bottom perspective view of the distal portion of the lancet depicted in FIG. 35C, according to an embodiment of the present invention.
Figure 35G:
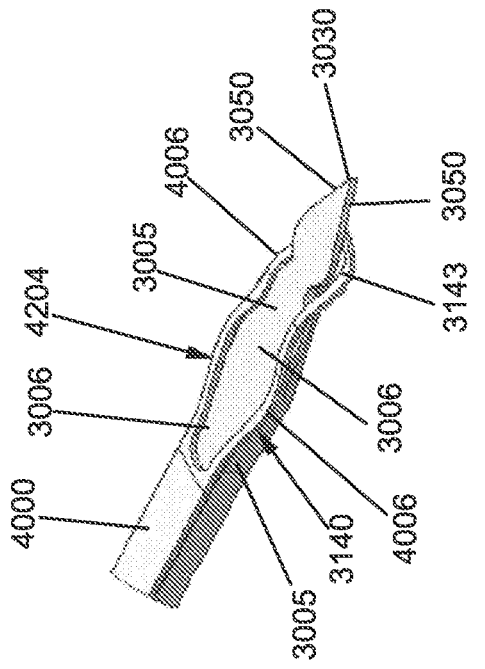
FIG. 35G is a bottom perspective view of the distal portion of the lancet depicted in FIG. 35C, according to an embodiment of the present invention.
Figure 35H:
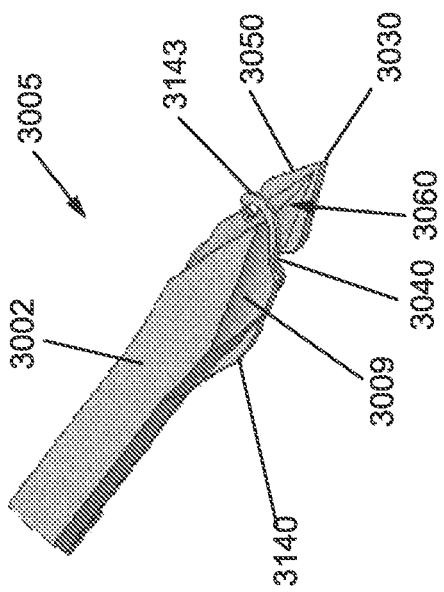
FIG. 35H is a top perspective view of the distal portion of the lancet depicted in FIG. 35C with a sensor attached, according to an embodiment of the present invention.
Figure 35I:
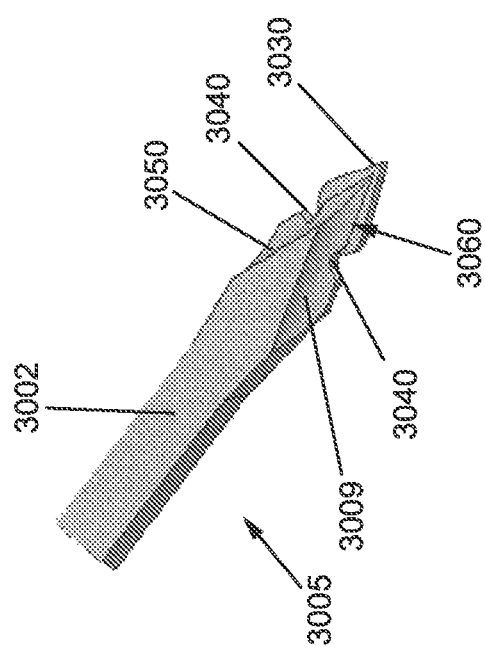
FIG. 35I is a side view of the distal portion of the lancet depicted in FIG. 35H, according to an embodiment of the present invention.
Figure 35J:
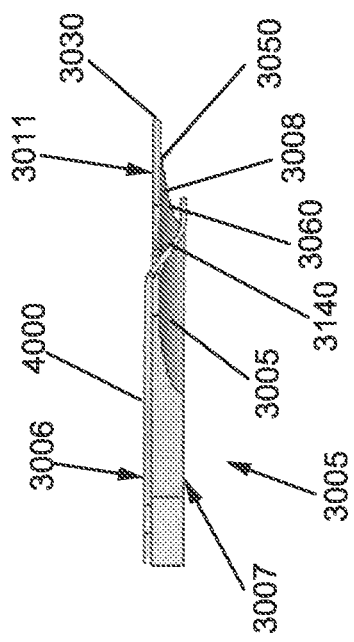
FIG. 35J is a bottom perspective view of the distal portion of the lancet depicted in FIG. 35H, according to an embodiment of the present invention.
Figure 35L:
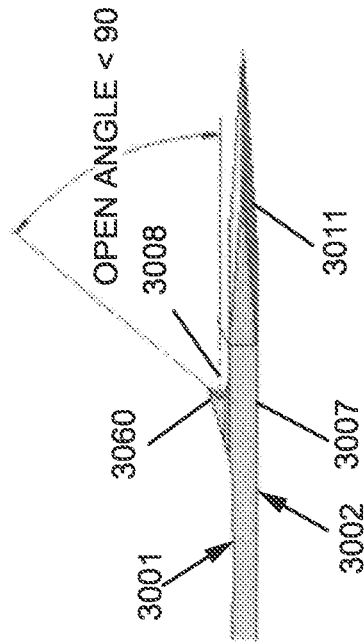
FIG. 35L is a top perspective view of the distal portion of a lancet, according to an embodiment of the present invention.
Figure 35N:
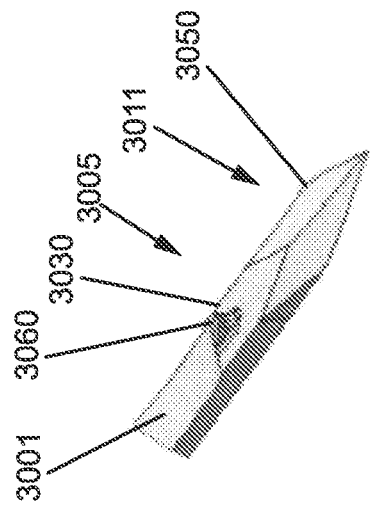
FIG. 35N is a side view of the distal portion of the lancet depicted in FIG. 35L, according to an embodiment of the present invention.
Figure 35K:
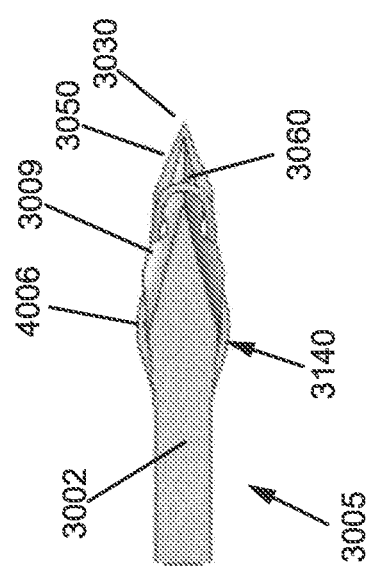
FIG. 35K is a bottom view of the distal portion of the lancet depicted in FIG. 35H, according to an embodiment of the present invention.
Figure 35M:
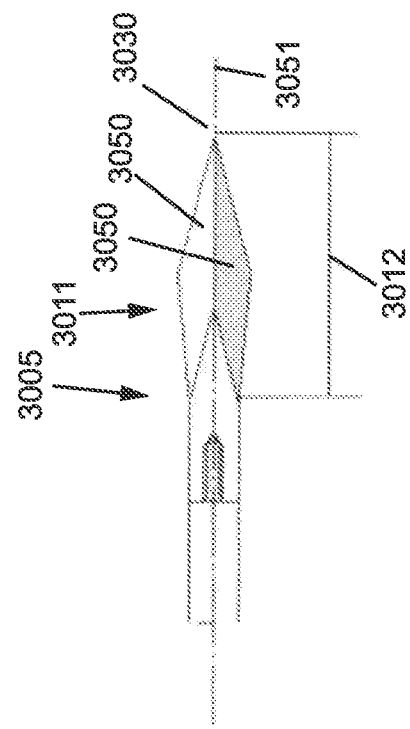
FIG. 35M is a top view of the distal portion of the lancet depicted in FIG. 35L, according to an embodiment of the present invention.
Figure 35O:
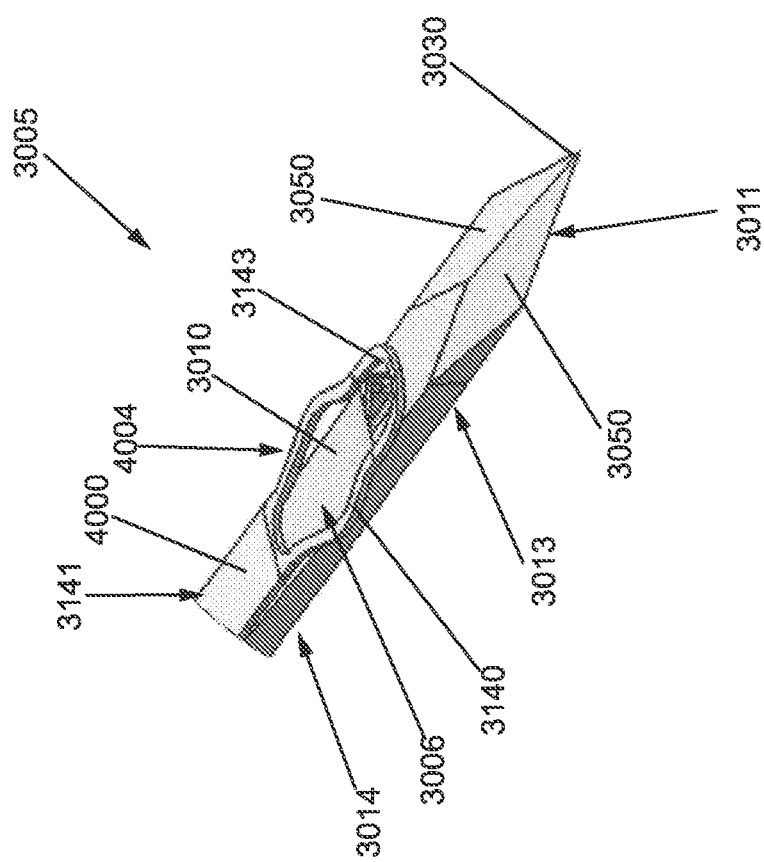
FIG. 35O is a top perspective view of the distal portion of the lancet depicted in FIG. 35L with a sensor attached, according to an embodiment of the present invention.
Figure 35P:
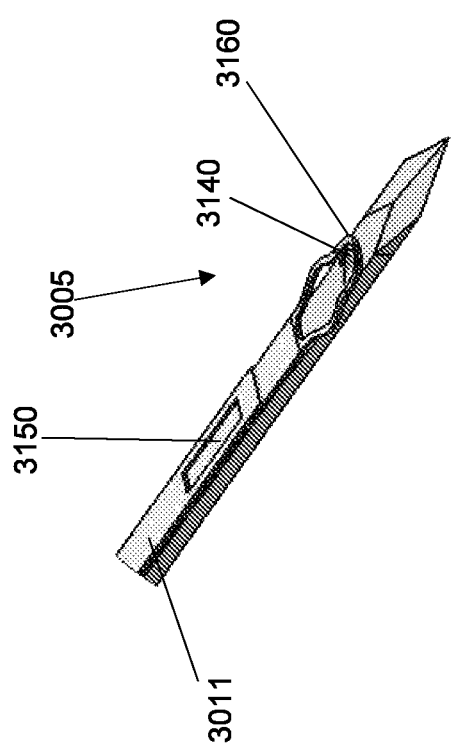
FIG. 35P is a top perspective view of the distal portion of the lancet depicted in FIG. 35L with a sensor attached, according to an embodiment of the present invention.
Figure 35Q:
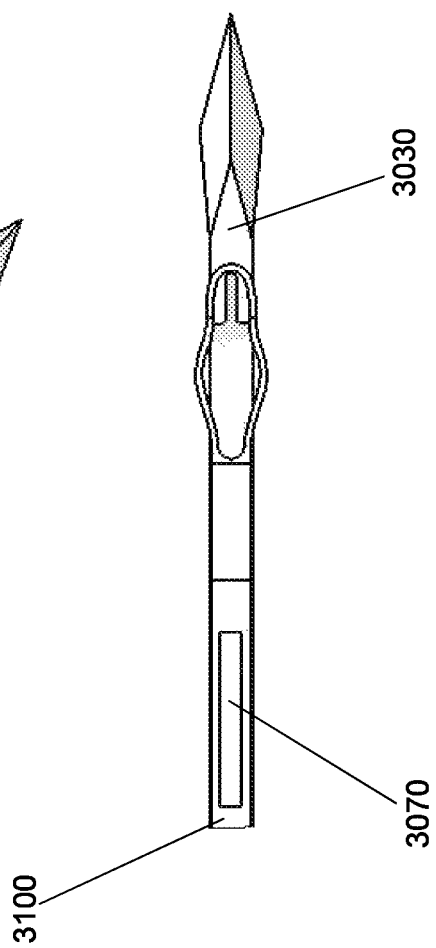
FIG. 35Q is a top view of the distal portion of the lancet depicted in FIG. 35L with a sensor attached, according to an embodiment of the present invention.

FIGS. 35A-35Q depict various embodiments of the distal portion 3005 of the elongate member. The distal portion 3005 includes a first surface 3006, a second surface 3007 that is substantially opposite the first surface 3006 and a tip 3030. In order to cut through the skin and subcutaneous tissue during insertion, the distal portion 3005 includes at least one cutting surface/edge 3050. This cutting surface 3050 can be, for example, a positive convex surface that forms a cutting surface/edge. In some embodiments, the distal tip portion includes a plurality of cutting surfaces 3050 that can be adjacent to the distal portion first surface 3006 and/or the distal portion second surface 3007 or that can be disposed between the distal portion first surface 3006 and the distal portion second surface 3007.

In some embodiments, as depicted in FIGS. 36A-36E, the cutting surface 3050 extends from the tip 3030 along at least a portion of the length of the distal portion 3005 thereby creating a cutting portion 3011 having a cutting surface length 3012. This cutting surface length 3012 may be dependent on the angle (a) of the cutting surface 3050 and the desired width of the cutting surface 3050. In some embodiments, the cutting surface 3050 forms an acute angle (a) that is defined by the intersection of a plane that is substantially parallel to the first surface 3006 and a line that is tangent to the cutting surface 3050. In some embodiments, the acute angle (a) ranges between approximately 15° and 45°. In some embodiments, the cutting surface length 3012 ranges between approximately 300 μm and 1,000 μm.

The location and the design of the cutting surfaces 3050 allow the lancet 3000 to be inserted into the skin and subcutaneous tissue of the patient with low trauma and/or pain as these surfaces cause the distal portion 3005 to cut through the skin and subcutaneous tissue instead of tearing through the tissue. In some embodiments, the cutting surfaces 3050 can be formed by chemical etching, laser milling, mechanical grinding or micro electric discharge machining (EDM).

In some embodiments, the perimeter of the distal portion 3005 can be sized for the sensor package and elongate member with a tissue stretch that can be 20%, 30%, 40%, or 50%.

In some embodiments of the lancet 3000, as depicted in the figures, the distal portion 3005 can include one or more insets or recessed portions 3040 that extend between the first surface 3006 of the distal portion 3005 and the second surface 3007 of the distal portion 3005. The one or more insets or recesses 3040 are designed to receive at least a portion of a looped sensor lancet interface 3140 located in the percutaneous portion of the sensor (discussed further below) to be inserted/implanted into the skin and can be, for example, circular or curvilinear. In some embodiments, the one or more insets or recessed portions 3040 form an area on the distal portion 3005 that has a narrower width than other portions of the distal portion 3005. This narrower area provides a recess to receive portions of the looped sensor lancet interface 3140. In addition to the one or more insets or recessed portions 3040 that extend between the first surface 3006 of the distal portion 3005 and the second surface 3007, in some embodiments, the distal portion 3005 can include a recessed area 3009 on each side of the distal portion 3005 that extend along at least a portion of the length of the distal portion 3005. These recessed areas 3009 can also receive a portion of the sensor lancet interface 3140.

In some embodiments, as depicted in FIG. 34A, the distal portion first surface 3006 can include surface recesses 3041, which can also receive at least a portion of the looped sensor lancet interface 3140. Because the looped sensor lancet interface 3140 can be received in insets/recessed portions 3040, recessed areas 3009 and surface recesses 3041, these elements help retain the sensing element on the distal portion and can also help to reduce the profile of the distal portion 3005 during insertion, which aids in reducing pain and trauma during implantation.

In order to help retain the looped sensor lancet interface 3140 on the distal portion 3005 prior to and during insertion of the distal portion 3005 into subcutaneous tissue, a retaining element/structure 3060 is included. In some embodiments, the retaining element/structure 3060 is on the first surface 3006 and in some embodiments the retaining element 3060 is on the second surface 3007. The retaining element/structure 3060 is designed to retain the looped sensor lancet interface 3140 on the distal portion 3005 during insertion into the tissue and to release the sensing element 3140 from the distal portion 3005 upon removal of the distal portion 3005 from the tissue, thereby leaving the looped sensor lancet interface 3140 implanted within the subcutaneous tissue along with the percutaneous portion of the sensor. Retaining of the looped sensor lancet interface 3140 on the distal portion 3005 before and during subcutaneous tissue insertion (i.e., when there is no movement of the distal portion 3005 and when there is forward movement of the distal portion 3005) and release of the looped sensor lancet interface 3140 upon removal of the distal portion 3005 from the skin (backward movement of the distal portion 3005), can be achieved by (1) designing the distal facing front surface 3008 of the retaining element/structure 3060 to have a certain shape/geometry and/or (2) a combination of the geometry of the distal facing front surface 3008 of the retaining element/structure 3060 and the orientation of the looped sensor lancet interface 3140 with respect to the distal facing front surface 3008.

Figure 36A:
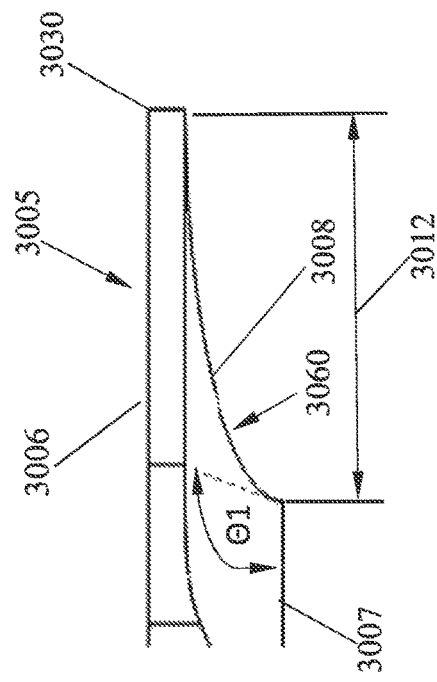
FIG. 36A is a side view of the distal portion of a lancet depicting the retaining structure, according to an embodiment of the present invention.
Figure 36B:
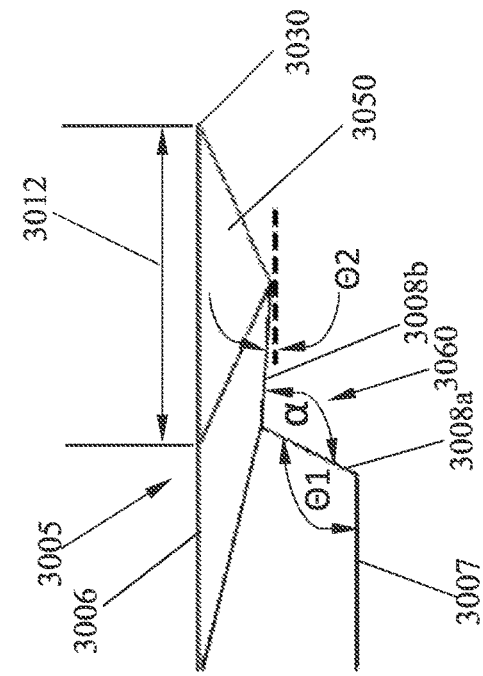
FIG. 36B is a side view of the distal portion of a lancet depicting the retaining structure, according to an embodiment of the present invention.
Figure 36C:
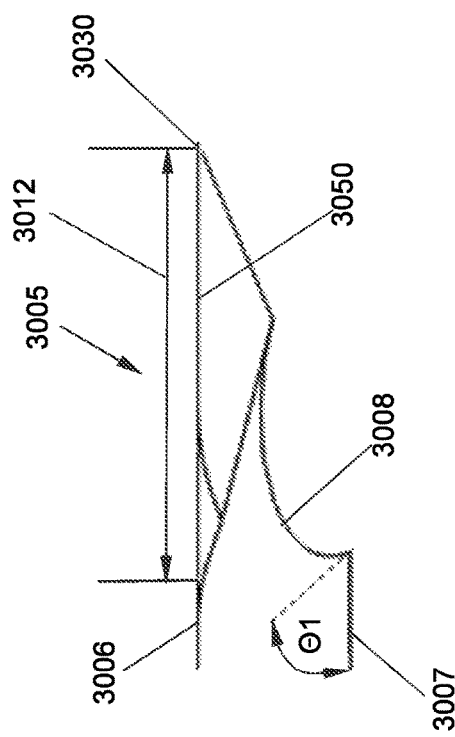
FIG. 36C is a side view of the distal portion of a lancet depicting the retaining structure, according to an embodiment of the present invention.
Figure 36D:
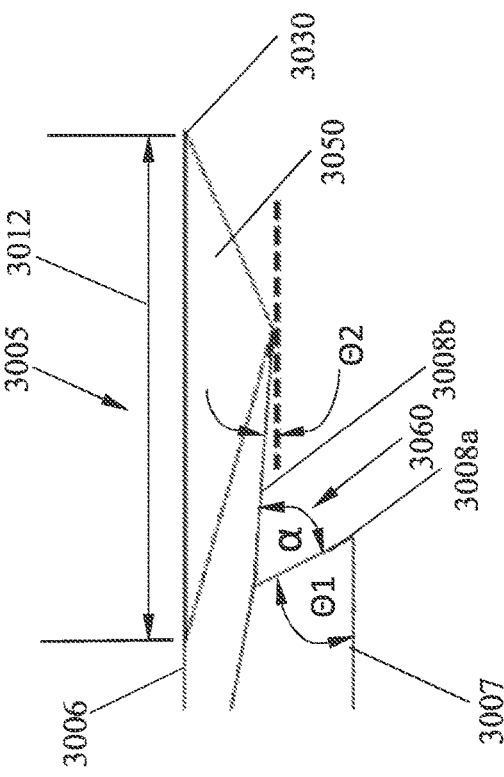
FIG. 36D is a side view of the distal portion of a lancet depicting the retaining structure, according to an embodiment of the present invention.
Figure 36E:
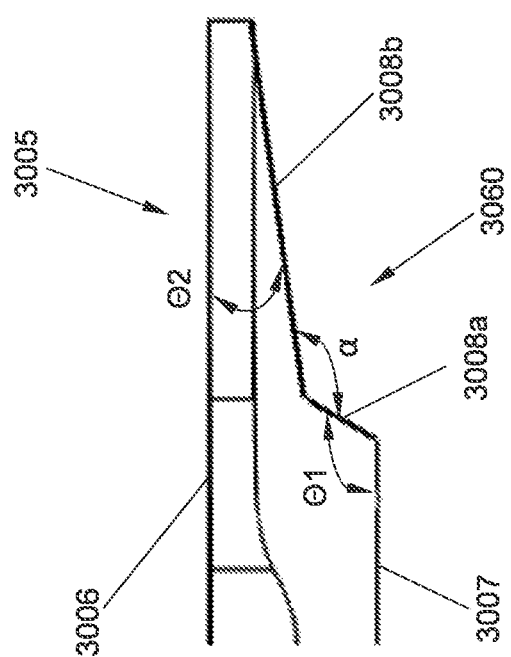
FIG. 36E is a side view of the distal portion of a lancet depicting the retaining structure, according to an embodiment of the present invention.

FIGS. 36A-36E depict various embodiments of the distal portion 3005 of the elongate member having retaining elements/structures 3060 with different shapes/geometries for the distal facing front portion 3008. As used herein, a "substantially forward facing front portion" of the engagement/retaining structure 3060 is defined by the below description and depicted in FIGS. 36A-36E. FIG. 36A depicts a distal facing front portion 3008 having a curved geometry with an angle θ1 of between approximately 20° and approximately 90° formed between a tangent of the curved distal facing front portion 3008 and a plane that is parallel to the distal portion second surface 3007. FIG. 36B depicts a distal facing front portion 3008 having a curved geometry with an angle θ1 of between approximately 90° and approximately 160° formed between a tangent of the curved distal facing front portion 3008 and a plane that is parallel to the distal portion second surface 3007. FIG. 36C depicts a distal facing front portion 3008 having an acute angled geometry where the acute angle (a) is defined by the intersection of (1) a plane tangent to a first portion 3008a of the distal facing front portion 3008 that forms an angle θ1 with the distal portion second surface 3007 of between approximately 20° and approximately 90° and (2) a plane that forms an angle θ2 of up to ±20° with the first surface 3006a. FIG. 36D depicts a distal facing front portion 3008 having an obtuse angled geometry where the obtuse angle (a) is defined by the intersection of (1) a plane tangent to a first portion 3008a of the distal facing front portion 3008 that forms an angle θ1 with the distal portion second surface 3007 of between approximately 90° and approximately 160° and (2) a plane that forms an angle θ2 of up to ±20° with the first surface 3006a. FIG. 36E depicts a distal facing front portion 3008 having an obtuse angled geometry where the obtuse angle α is defined by the intersection of (1) a plane tangent to a first portion 3008a of the distal facing front portion 3008 that forms an angle θ1 with the distal portion second surface 3007 of between approximately 90° and approximately 160° and (2) a plane tangent to a second portion 3008b of the distal facing front portion 3008 that forms an angle θ2 with the distal portion first surface 3006 of between approximately 10° and approximately 45°.

Depicted in FIG. 36F is a looped sensor lancet interface 3140 of a sensor assembly 3100, according to an embodiment of the invention. The looped sensor lancet interface 3140 includes an elongate sensing portion 4000 and a sensor looped distal portion 4004 that is defined and bounded by a sensor transmission element 4006. As depicted in FIG. 36F, the elongate sensing portion 4000 extends to a proximal end 4008 of the sensor looped distal portion 4004 where it divides into two legs of the sensor transmission element 4006, which form the sensor looped distal portion 4004. The sensor looped distal portion 4004 includes a first opening 4010 that is adjacent to the loop tip portion 3143 with a maximum first width 4012 and a second opening 4014 disposed between the proximal end 4008 and the first opening 4010. The second opening 4014 has a maximum second width 4016 that is greater than the maximum first width 4012. The first opening 4010 and the second opening 4014 are contiguous. As can be seen in FIG. 36F, the sensor transmission element 4006 includes sensor looped transition portions 4018 (*a*) between the first opening 4010 and the second opening 4014 and (b) between proximal end 4008 and the second opening 4014 of the sensor looped distal portion 4004, that are thicker than the other portions of the sensor transmission element 4006. As discussed in more detail below, the thicker portions of the sensor looped transition portions 4018 aid in the unloading of the sensor looped distal portion 4004 from the distal portion 3005 and also helps in anchoring of the sensor in subcutaneous tissue. After implantation, the looped sensor lancet interface 3140 along with the percutaneous portion of the sensor, provides the required interstitial fluid information to the sensor assembly 110A and hence, the analyte sensors of the embodiments of the present invention.

Depicted in FIG. 35B and FIGS. 35H-35K, are embodiments of a looped sensor lancet interface 3140 loaded in place on the distal portion 3005 of an elongate member. As can be seen in the figures, the elongate sensing portion 4000 extends along the distal portion first surface 3006 and the sensor looped distal portion 4004 loops over the tip 3030 in order for the loop tip portion 3143 to engage the retaining structure 3060. Once the loop tip portion 3143 is engaged on the retaining structure 3060, portions of the sensor transmission element 4006 that define the first opening 4010 of the sensor looped distal portion 4004 are received within the insets/recessed portions 3040. To cause the portions of the sensor transmission element 4006 that define the first opening 4010 of the sensor looped distal portion 4004 to be received within the insets/recessed portions 3040, once the sensor looped distal portion 4004 is looped over the tip 3030, the elongate sensing portion 4000 is tensioned or pulled proximally away from the tip 3030, causing (1) the loop tip portion 3143 to engage the retaining structure 3060 and (2) the portions of the sensor transmission element 4006 that define the first opening 4010 of the sensor looped distal portion 4004 to seat or be received within the insets/recessed portions 3040. Further proximal movement/tensioning of the elongate sensing portion 4000, causes the sensor transition element 4006 portions that define the second opening 4014 of the sensor looped distal portion 4004 to collapse inwards, reducing the width of the second opening 4014. Thus, when sensor looped distal portion 4004 is loaded onto the elongate member, the width of the second opening 4014 is reduced causing the sensor transition element 4006 to deform. This deformation, however, is elastic and therefore, once the sensor looped distal portion 4004 is unloaded from the distal portion 3005, the sensor transition element 4006 springs back to its original shape, which causes the second opening 4014 to return to its original shape and width. The thicker sensor looped transition portions 4018 on the sensor transition element 4006, aid in helping the second opening 4014 return to its original shape and width.

Depicted in FIG. 35O is another embodiment of a looped sensor lancet interface 3140 loaded in place on the distal portion 3005 of an elongate member. In this embodiment, the retaining structure 3060 is disposed on the same surface as the elongate sensing portion 4000. As can be seen in FIG. 35O, the elongate sensing portion 4000 extends along the distal portion first surface 3006 and the sensor looped distal portion 4004 is placed over the retaining structure 3060 such that the loop tip portion 3143 is positioned distally of the retaining structure 3060. Once the loop tip portion 3143 is positioned distally of the retaining structure 3060, the elongate sensing portion 4000 is tensioned or pulled proximally away from the tip 3030, causing, as discussed above, (a) the loop tip portion 3143 to engage the retaining structure 3060 and (b) the sensor transition element 4006 portions that define the second opening 4014 of the sensor looped distal portion 4004 to elastically deform and collapse inwards. As also discussed above, once the sensor looped distal portion 4004 is unloaded from the distal portion 3005, the sensor transition element 4006 springs back to its original shape, which causes the second opening 4014 to return to its original shape and width.

Although in the embodiments of the lancet 3000 disclosed and described herein, all of the features associated with retaining and releasing the looped sensor lancet interface 3140, i.e., the insets/recesses 3040, recessed area 3009, surface recesses 3041 and the retaining element/structure 3060, are depicted as being on the distal portion 3005 of the elongate member, these need not be limited to the distal portion 3005. Instead, these features can be located at any location along the elongate member, for example, they can be located at the intermediate portion 3004 of the elongate member, such that the looped sensor lancet interface 3140 can be loaded onto and delivered into subcutaneous tissue from this portion of the elongate member.

Figure 37:
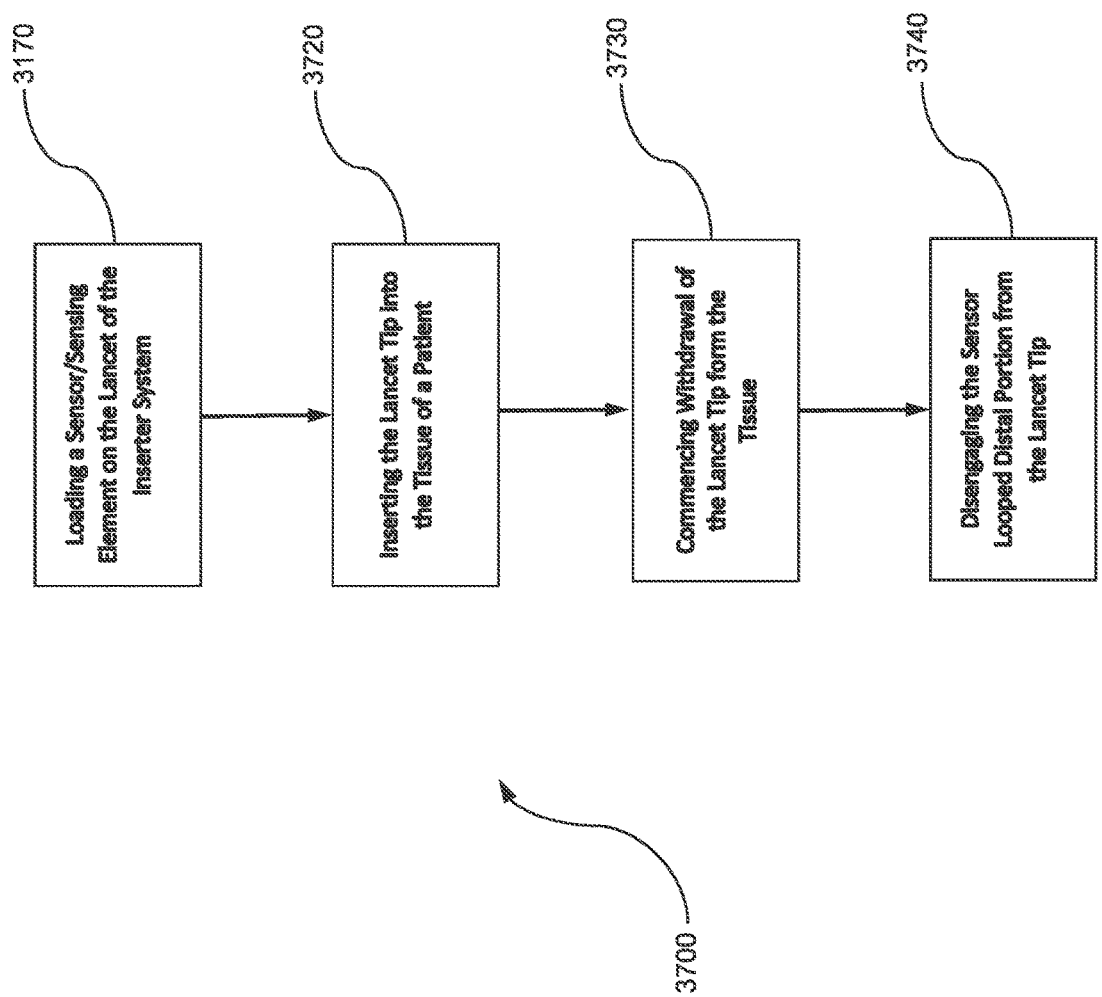
FIG. 37 is a schematic of the method for inserting a sensor system for continuous glucose monitoring, according to an embodiment of the present invention.

FIG. 37 illustrates an embodiment of a method 3700 of inserting/implanting a sensing element into subcutaneous tissue. Prior to insertion/implantation of the sensing element 3141 into subcutaneous tissue, the sensing element is loaded onto the lancet 3000 (block 3710). The sensing element 3141 and hence, the sensor looped distal portion 4004 are loaded in the manner described above such that the sensor transition element 4006 portions that define the second opening 4014 of the sensor looped distal portion 4004 are elastically deformed and collapse inwards. During insertion, the distal portion 3005 of the elongate member is advanced distally or forward into the subcutaneous tissue (block 3720). After the distal portion 3005/tip 3030 is delivered to its desired depth within the subcutaneous tissue, i.e., the depth of insertion for the sensing element 3141, the distal portion 3005/tip 3030 is retracted proximally or backwards away from or out of the subcutaneous tissue (block 3730). Because, as illustrated in the figures, the looped sensor lancet interface 3140 is engaged with the distal portion 3005/tip 3030 in a manner that only restricts backward movement of the looped sensor lancet interface 3140 on the elongate member, backward movement of the distal portion 3005/tip 3030 causes the loop tip portion 3143 to disengage from the retaining structure 3060, which permits the sensor looped distal portion 4004 to disengage and unload from the distal portion 3005 of the elongate member (block 3740). As the sensor looped distal portion 4004 disengages and unloads from the distal portion 3005, the inwardly-tensioned sensor transition element 4006 portions that define the second opening 4014, spring back outwardly to substantially assume their original shape and width, which now help to anchor the sensor looped distal portion 4004 and hence, the sensing element 3141, at the correct depth within the subcutaneous tissue. As the distal portion 3005/tip 3030 continues to retract from the skin or body tissue, the remaining components of the sensing element 3141 disengage from the elongate member leaving the sensing element 3141 implanted in the subcutaneous tissue.

Although, embodiments of the lancet 3000 disclosed herein have been described for delivering/implanting a sensing element in body tissue, embodiments of the lancet 3000 can be used for other medical applications. For example, embodiments of the lancet 3000 can be used to implant drug delivery cannulas (micro catheters) or other delivery lumens for infusion pumps to deliver, for example, insulin and other therapeutic agents/treatments to a patient. Additionally, items that can be delivered with the embodiments of the lancet 300 disclosed herein include, and are not limited to, drug eluting implants. In some embodiments, these delivery lumens and other implants can be combined with the sensor looped distal portion 4004 to allow the delivery lumens and other implants to be implanted in a similar manner to how embodiments of the looped sensor lancet interface 3140 are implanted.

Figure 35R:
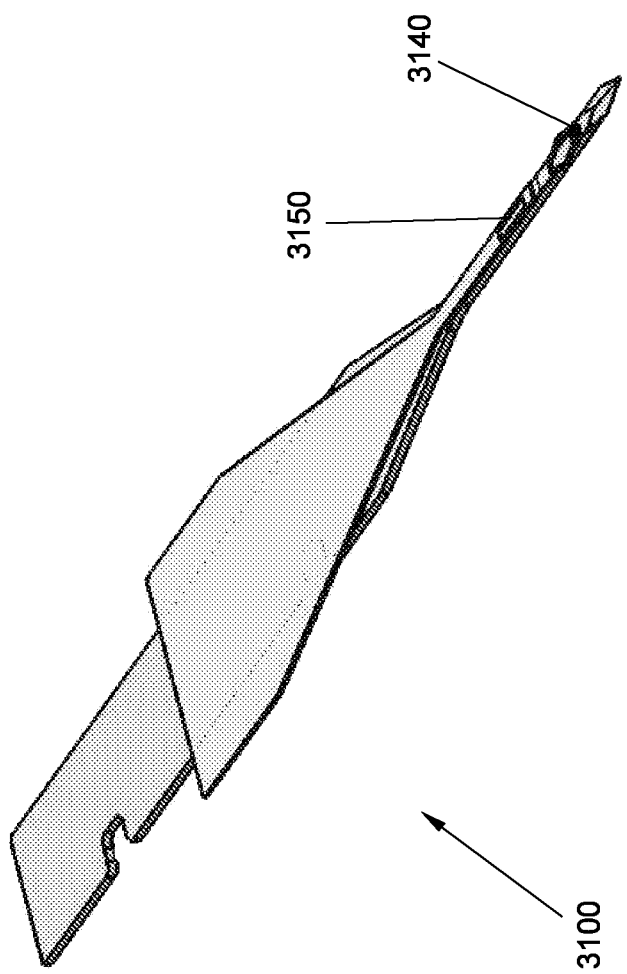
FIG. 35R is a top perspective view of a sensor loaded onto a lancet, according to an embodiment of the present invention.

FIGS. 35P-35Q depict additional embodiments of the sensor assembly 3100 and the sensor assembly 3100 retained on the lancet 3000. FIGS. 35P and 35R illustrate the sensor assembly 3100. In some embodiments, the sensor assembly 3100 can include an opening 3150 that extends along the length of the body of the sensor assembly 3100. As illustrated in FIG. 35Q, the lancet 3000 can include a corresponding convex horn 3070 that extends from the surface of the lancet 3000. In some examples, the convex horn 3070 of the lancet 3000 can engage the opening 3150 such that the opening 3150 is disposed about the convex horn 3070. This configuration can help to properly retain the sensor assembly 3100 along the lancet 3000.

Analyte Sensor and its Operation

The biosensor of the present invention does not utilize an electrochemical sensing modality and does not require the immobilization of the enzyme to an electrode. Rather the present biosensor requires the formation of active hydrogels within the sensor. Therefore, there is a need to consistently formulate an active hydrogel with controlled active macromer, such as glucose oxidase, loading and hydrogel permeability properties. Preferably, the active hydrogel material is formulated so that it can be characterized during sensor manufacturing without destructive sensor testing.

In some embodiments, methods of preparing a sensor tip for a glucose monitoring device are described. In some embodiments, the methods pertain to fabricating a sensor tip that is small enough to be inserted subcutaneously into a patient with little or no pain. In some embodiments, the sensor tip and its components are adapted and configured to be mass-produced at small-length scale.

Figure 38:
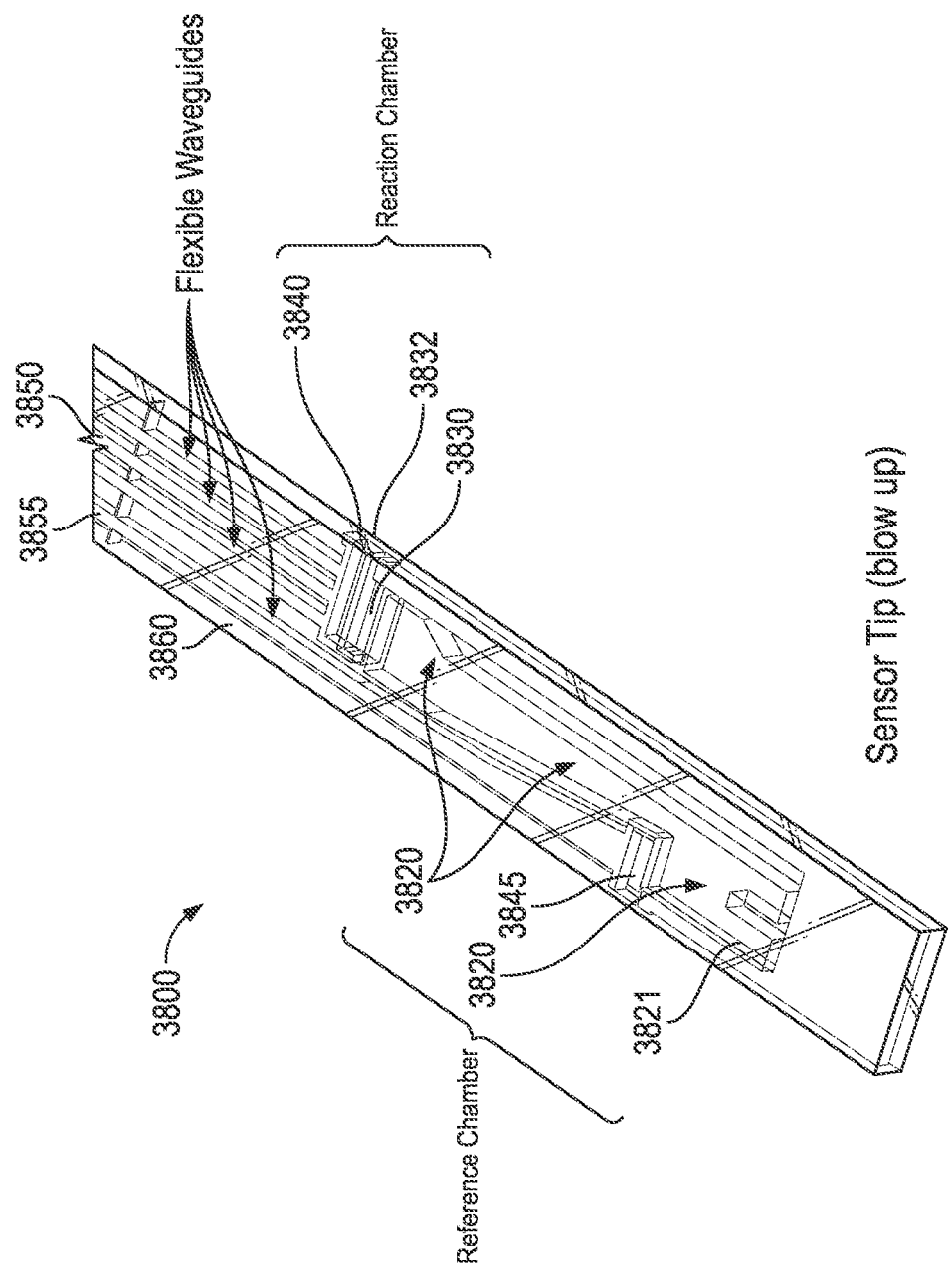
FIG. 38 illustrates an expanded view of a sensor tip for a glucose monitoring device, according to an embodiment of the present invention.

In some embodiments, the sensor tip (e.g., sensing system) comprises one or more components (e.g., regions, layers, sections, etc.). In some embodiments, as shown in FIG. 38, the individual components of the glucose sensor tip 3800 include an oxygen conduit 3820, an oxygen inlet surface 3821, an enzymatic region 3830, and a sensor region 3840 (e.g., an oxygen sensing polymer). In some embodiments, the oxygen conduit 3820, enzymatic region 3830, and sensor region 3840 can be combined to provide the sensing portion of a glucose sensor system. In some embodiments, the glucose sensor tip further comprises a base support 3860. In some embodiments, the base support 3860 is configured to provide a substrate on which one or more components of the glucose sensor tip 3800 can reside.

In some embodiments, each region (e.g., the oxygen conduit, the enzymatic region, and/or the oxygen sensing polymer region) is a distinct layer within a glucose sensing device. In some embodiments, a region can be embedded within, or supported by another region. In some embodiments, multiple regions serving each function can be provided. For example, in some embodiments, there are multiple oxygen conduit regions, enzymatic regions, and/or sensor regions. In some embodiments, there 1, 2, 3, 4, 5, or more oxygen conduit regions, enzymatic regions, and/or sensor regions. In some embodiments, each region serves a discrete function (e.g., one region acts as an oxygen conduit, one acts as the enzymatic region, and one acts as a sensor).

In some implementations, regions can serve similar, overlapping, or the same function.

Figure 39:
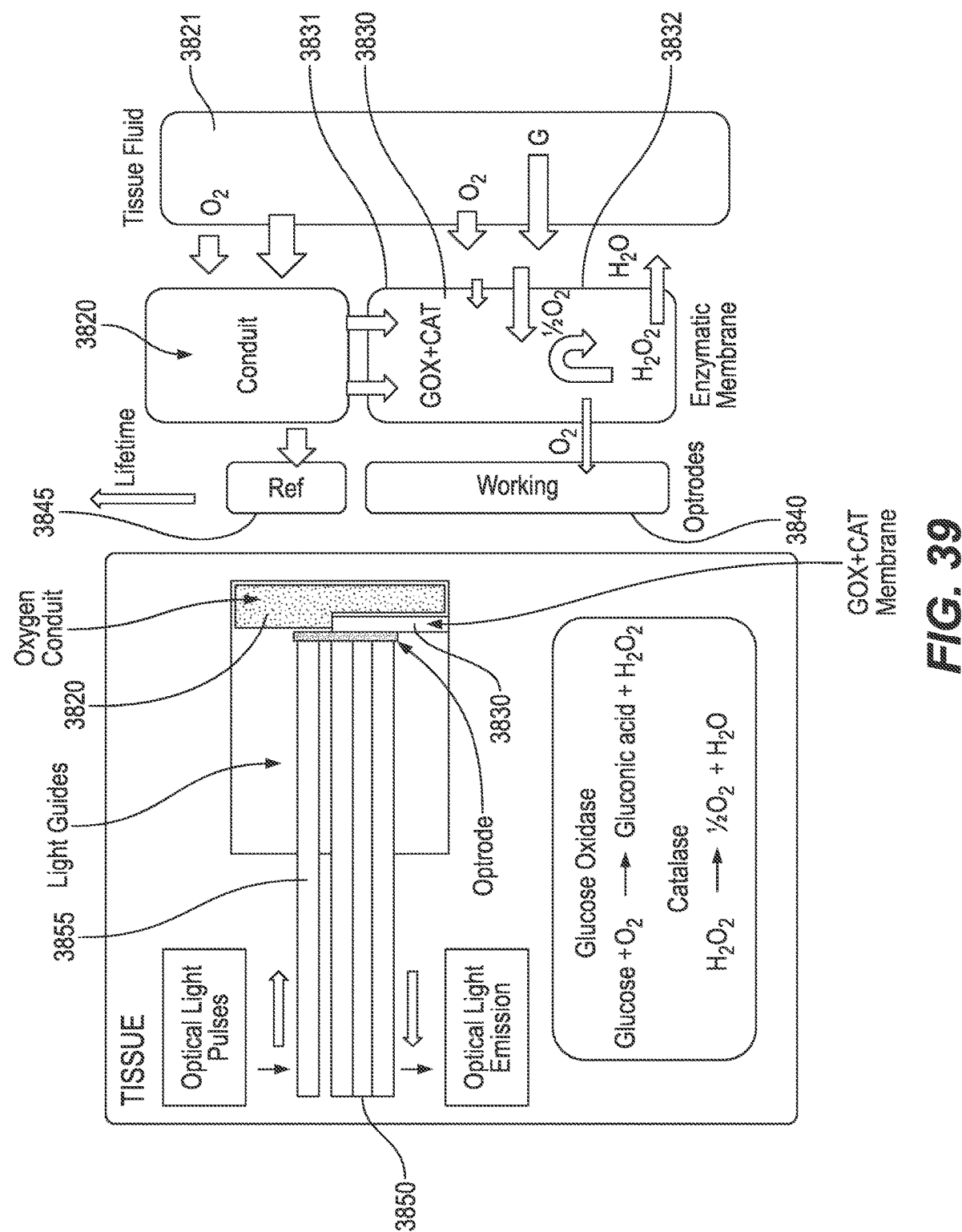
FIG. 39 illustrates a diagram of a functioning sensor tip, according to an embodiment of the present invention.
Figure 40:
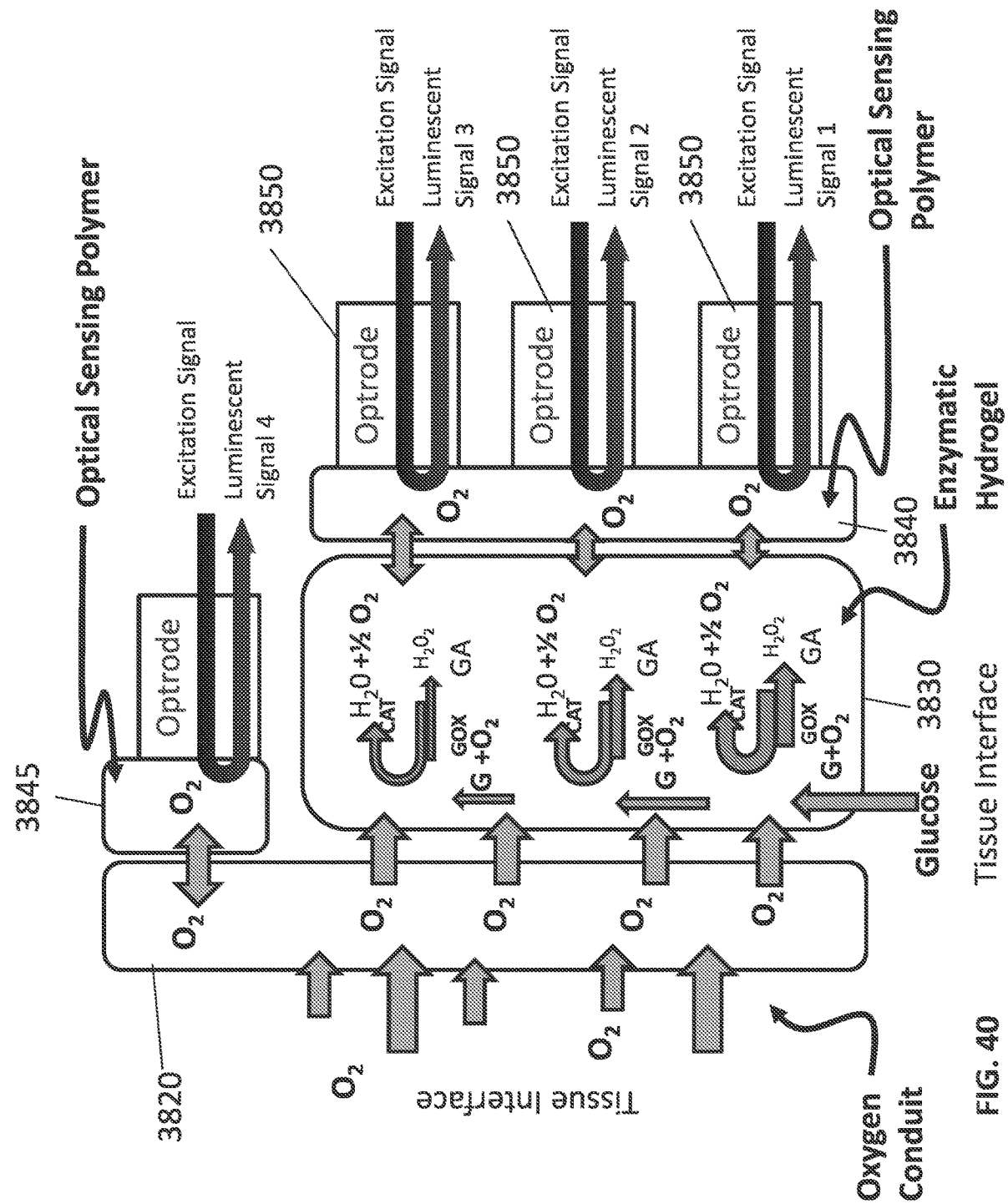
FIG. 40 illustrates a second diagram of a functioning sensor tip, according to an embodiment of the present invention.

In some embodiments, as shown in FIGS. 39 and 40, the oxygen conduit region 3820 comprises a species that binds and releases oxygen, transporting it through or within the region. In some embodiments, also as shown in FIGS. 39 and 40, the enzymatic region 3830 comprises one or more enzymes that catalyze a reaction to convert one or more species within the enzymatic region into identifiable products. As shown in FIGS. 39 and 40, glucose oxidase (GOx) and catalase (CAT) can be used together in the enzymatic region 3830. While GOx and CAT used as exemplary enzymes throughout this disclosure, other enzymes or enzyme combinations can be employed keeping in mind the goal of the enzymatic layer is to produce a measurable species for analytical data.

As shown in FIGS. 38, 39, and 40, in some embodiments, the oxygen conduit is configured to receive environmental oxygen (e.g., from the tissue of a patient or some other environment proximal to the tip) and to transport it. In some embodiments, as shown, the enzymatic region 3830 (i.e., enzymatic hydrogel), is configured to receive oxygen from a portion of the oxygen conduit 3820 through an enzymatic region oxygen inlet 3831. Also as shown, in some embodiments, the enzymatic region 3830 is configured to receive environmental glucose (e.g., from the tissue of a patient) via a glucose inlet 3832.

As shown in FIGS. 39 and 40, the one or more enzymes can, for example, catalyze reactions to convert reactants (e.g., analytes) into identifiable products. In some embodiments, the enzymatic region comprises combinations of enzymes that catalyze reactions to convert analytes and other enzymes that catalyze reactions to convert the byproducts of the primary reaction. For example, as shown in FIGS. 38 and 39, in some embodiments, the GOx can convert glucose and oxygen into gluconolactone and $H_2O_2$:

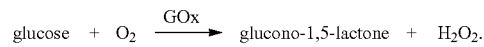

$H_2O_2$ can then be converted back to oxygen and water in the presence of water and CAT to afford product oxygen:

As shown above, this reaction scheme causes a net decrease in the amount of oxygen (by ½ of a mole compared to environmental oxygen). This decrease in oxygen can be detected using an oxygen sensing polymer 3840 and by comparing the amount of product oxygen to the amount of oxygen in a reference sample.

As shown in FIGS. 38, 39, and 40, a reference oxygen sensing polymer 3845 is provided to provide a measure of the amount of environmental oxygen present. In some embodiments, the difference between the oxygen present at the reference oxygen sensing polymer 3845 and the oxygen sensing polymer 3840 can be used to provide an indirect measure of glucose. In some embodiments, this indirect measurement allows, highly sensitive glucose monitoring.

In some embodiments, as discussed elsewhere herein, the oxygen sensing polymer regions 3840 and 3845 comprise an oxygen detecting dye. In some embodiments, the dye is a luminescent dye. In some embodiments, the dye is a porphyrin dye. In some embodiments, the porphyrin dye is platinum tetrakis pentafluorophenyol porphyrin (pT-TFPP).

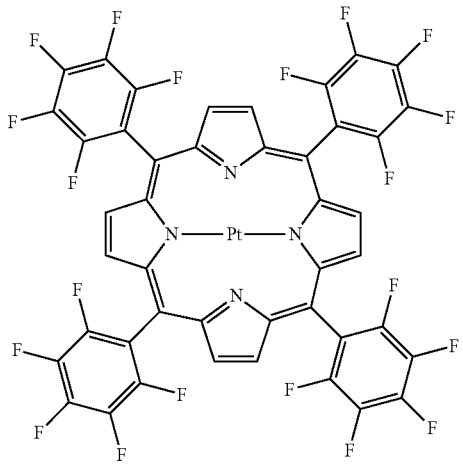

In some embodiments, the luminescent dye emits a measurable signal dependent on the amount of oxygen present. Thus, interrogating the oxygen in the oxygen sensing polymer of the reaction region 3840 and the reference oxygen sensing polymer 3845 give a measure of the amount of glucose present.

In some embodiments, the working oxygen sensing polymer 3840 and the reference oxygen sensing polymer 3845 are interrogated by test waveguides 3850 and reference waveguides 3855, respectively, as shown in Figured 38, 39, 40, and 41. Information gathered by these waveguides can be gathered, processed, and used to provide information to a patient or doctor regarding glucose levels in the patient.

Certain embodiments disclosed herein provide methods for making glucose monitoring device components and methods of combining components to yield devices that provide a convenient means of continuous glucose monitoring. In some embodiments, the methods disclosed herein are especially suited for preparing devices that have very small dimensions. For example, in some embodiments, a given sensor feature comprises a three dimensional shape having an x-dimension, a y-dimension, and a z-dimension. In some embodiments, the smallest dimension of the x-, y-, and z-dimensions feature is less than about 0.05 mm. In some embodiments, the glucose sensor tip 3800 shown in FIG. 41A has dimensions of about 0.05 mm by about 0.3 mm by about 1.5 mm in the x-, y-, and z-directions. In some embodiments, the glucose sensor tip has dimensions less than about 0.05 mm by about 0.3 mm by about 1.5 mm. In some embodiments, the small features of the sensor tip minimize the size of the device and maximize the efficiency and accuracy at which these devices can measure analytes.

Figure 42:
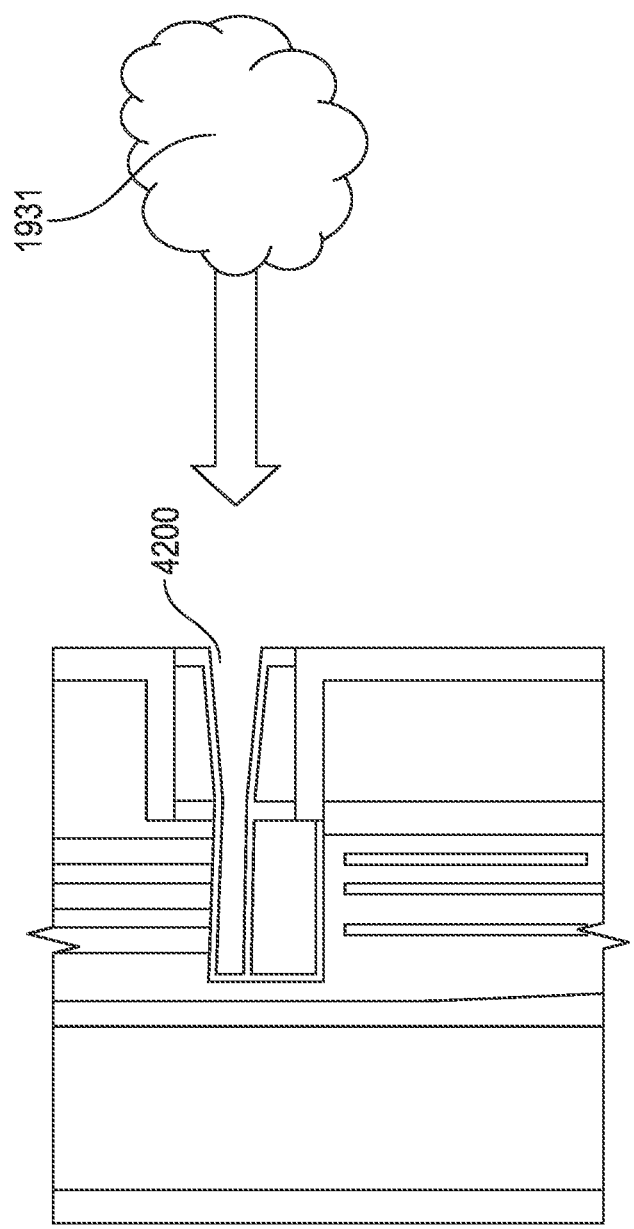
FIG. 42 illustrates a top view of a mold for preparing different components of the sensor tip, according to an embodiment of the present invention.

In some embodiments, these small dimensions can be achieved by the unique polymer systems and fabrication methods disclosed herein (as shown in FIG. 41B). For instance, these small features can be provided by supplying solutions of crosslinkable (or crosslinked) materials that can be taken-up by spaces (e.g., channels, tunnels, paths, etc.) in molds (e.g., dye casts, lithography plates, etc.) by capillary action to produce features of less than about 0.05 mm, in some cases as small as about 10 μm, at their smallest dimension (as shown in 41C). For example, as shown in FIG. 42, solutions can be taken up through capillary action into mold 4200 ports 4210. These ports are configured to distribute the material solutions via channels throughout sensing tip 3800. These solutions, as discussed in more detail elsewhere herein, can then be cured (e.g., crosslinked with crosslinkers) and/or concentrated to afford individual sensor components (e.g., an oxygen conduit 3820, an enzymatic region 3830, and/or an oxygen sensing polymer region 3840, 3845).

In the mass production of the present biosensor, active hydrogels are preferably consistently prepared and located within a specified region inside the sensor. The volume of the regions for locating the active hydrogels for oxygen transport or enzymatic reduction of an analyte are small for devices that will be minimally invasive. For example, an active hydrogel region may be <200 pL, <500 pL, <1 nL, <5 nL, <10 nL, or <50 nL. The controlled immobilization of a target macromer (e.g., oxygen binding molecule or enzyme) and incorporation of the target macromer into the hydrogel polymer network is difficult to consistently accomplish in such small reaction volumes using prior art methods, and direct placement of a membrane or hydrogel that must be cut to size is difficult. Further, the characterization of the extent of crosslinking of the hydrogel and macromer to be immobilized is difficult to assay in the sensor given the small volumes present, particularly in a non-destructive manner. The methods for making the present biosensor disclosed herein address these manufacturing issues.

According to the present invention, in order for the active hydrogel to have stable properties and to prevent immobilized macromer from diffusing from the sensor, the immobilized macromer is preferably retained by a stable linkage in a hydrogel, rather than being entrapped passively into a hydrogel as is typically the case in prior art biosensors. In some embodiments of the present methods, this process of macromer stabilization and immobilization may be facilitated by crosslinking the target macromer to a nanostructure (e.g., a carrier protein such as albumin) and conjugation of the macromer-nanostructure complex to a polymer network to form a nanogel particle. According to the present invention, the nanogel particle is used as a precursor or interim form from which the active hydrogel regions (e.g., the oxygen conduit region and the enzymatic region) may be formulated within a biosensor. In contrast to prior hydrogel formation methods, the nanogel particles of the present invention may be more fully characterized and formulated in a controlled and consistent manner. Moreover, it has been found that the characteristics of the nanogel particles primarily determine the properties of the active hydrogel.

Thus, embodiments of the present methods are able to overcome the complex challenges of consistently crosslinking a macromer to a nanostructure while conjugating the complex to a polymer network in very small volumes inside individual sensors amenable to minimally invasive application. Furthermore, embodiments of the present methods may be used to execute multistep formulation chemistry while maintaining quality control of the resulting active hydrogels.

In some embodiments, in order to improve quality control in a biosensor application, the extent of the target macromer crosslinking with the nanostructure is preferably controlled to achieve consistent crosslinking to form a reproducible nanogel particle with the desired stability and activity. For example, enzymatic activity is inversely proportional to the concentration of linker used to link enzyme to the nanostructure because extensive crosslinking may result in a distortion of the enzyme structure (i.e., the active site conformation) [Chuff, W. K. and L. S. Wan. 1997. Prolonged retention of cross-linked trypsin in calcium alginate microspheres. J. Microencapsulation 14:51-61]. With this distortion, the accessibility and accommodation of the active substrate may be reduced, thus affecting the retention of biological activity. In some embodiments of the present methods, for example where the nanostructure is a protein with a given number of crosslinking sites (such as lysine (Lys) residues on albumin), the extent of the crosslinking between the nanostructure and the target macromer may be controlled by reducing the number of available crosslinking sites on the protein available to the crosslinking reaction between the target macromer and the protein.

For example, in some embodiments, an oxygen conduit component is prepared using a dispensable, UV-curable nanogel solution. In some embodiments, the dispensable, UV-curable nanogel solution can be prepared by first interconnecting (e.g., covalently bonding, complexing, etc.) a nanostructure with one or more reversible oxygen binding molecules thereby forming a reversible oxygen binding nanoparticle. In some embodiments, the oxygen conduit nanostructure comprises a macromolecular structure capable of supporting one or more oxygen binding molecules. In some embodiments, the nanostructure is albumin and the oxygen binding molecule is hemoglobin. For purposes of summarizing the disclosure, certain features have been described herein using albumin (with Lys residues that act as the crosslinking sites) and hemoglobin. While albumin and hemoglobin used to describe features herein, these molecules are exemplary and other nanostructures or oxygen binding molecules are envisioned. For example, in some embodiments, the nanostructure is any suitable protein. In some embodiments the reversible oxygen binding molecule comprises any suitable oxygen binding protein (e.g., hemoglobin, myoglobin, a synthetic oxygen carrier, etc.).

In some embodiments, the nanoparticle comprises a plurality of hemoglobin molecules functionalized to each albumin molecule. In some embodiments, the nanoparticle comprises less than one hemoglobin molecules per albumin molecule. In some embodiments, the ratio of hemoglobin to albumin is at least about 0.5:1, about 1:1, about 2:1, about 5:1, about 10:1, or about 15:1.

In some embodiments, hemoglobin is bound to albumin covalently. In some embodiments, the covalent link between hemoglobin is formed using a difunctional linker. In some embodiments the difunctional linker is selected a dialdehyde, a dicarboxylic acid, a diepoxide, or the like. In some embodiments, the difunctional linker is represented by one or more of the following structures:

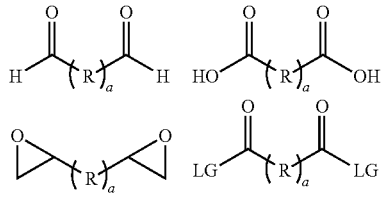

where R is selected from the group consisting of —CH$_2$—, —(CH$_2$O)CH$_2$, —(CH$_2$CH$_2$O)—CH$_2$CH$_2$—, and —(CH$_2$CH$_2$CH$_2$O)—CH$_2$CH$_2$CH$_2$—, and "a" is an integer between 0 and 10. In some embodiments, the hemoglobin and albumin are functionalized via amine groups residing on the hemoglobin and albumin molecules. In some embodiments, when a dialdehyde, a dicarboxylic acid, or a diepoxide are used as the difunctional linkers, diimines, diamides, and diamines, respectively, result through reaction with the hemoglobin and albumin amines. In some embodiments, combinations of difunctional linkers can be used.

The crosslinking of hemoglobin and albumin may involve multiple site reactions. For example, albumin is rich in Lys residues. One common and versatile technique for crosslinking or labeling peptides and proteins such as antibodies involves the use of chemical groups that react with primary amines (—NH$_2$). Primary amines exist at the N-terminus of each polypeptide chain and in the side-chain of lysine (Lys) amino acid residues. These primary amines are positively charged at physiologic pH; therefore, they occur predominantly on the outside surfaces of native protein tertiary structures where they are readily accessible to conjugation reagents introduced into the aqueous medium. Furthermore, among the available functional groups in typical biological or protein samples, primary amines are especially nucleophilic; this makes them easy to target for conjugation with several reactive groups. Formaldehyde and glutaraldehyde are aggressive carbonyl (—CHO) reagents that condense amines via Mannich reactions and/or reductive amination.

The following represents a hemoglobin molecule linked to albumin using a dialdehyde (i.e., via a diimine linker):

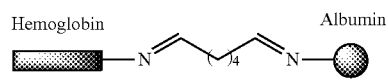

In some embodiments, as shown above, the difunctional linker is glutaraldehyde (or another dialdehyde) and forms a diimine link via the aldehydes of glutaraldehyde and amines from hemoglobin and albumin That configuration is also represented by the depiction:

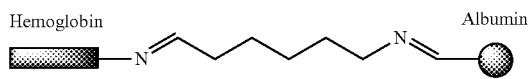

In some embodiments, the hemoglobin is covalently linked to albumin by incubation with gluteraldehyde, at low temperature, low to no oxygen concentration, pH of between about 7.0 and 8.0, for an incubation time to complete the reaction, which is preferably at least about 24 hours, to form hemoglobin-albumin nanoparticles.

In some embodiments, the incubation time with glutaraldehyde is at least about 10 hours, about 24 hours, about 36 hours, or about 48 hours. In some embodiments, the glutaraldehyde (or other difunctional linker) is provided to the albumin/hemoglobin solution at a low concentration. In some embodiments, the reaction is performed at low temperature and is below about 30° C., about 20° C., about 10° C., about 5° C., about 2° C.

In some embodiments, after incubation with glutaraldehyde and formation of the diimine linker, the hemoglobin-albumin nanoparticles are subjected to a borohydride reduction to convert the diimine linkages to diamine linkages. For example, the hemoglobin-albumin nanoparticle is diluted with a coupling buffer (e.g., 0.1 M sodium phosphate, 0.15 M NaCl, or standard phosphate buffer solution) and a borohydride (e.g., sodium cyanoborohydride, or sodium borohydride) is added. Unreacted aldehyde sites are blocked by the addition of a quenching buffer solution (e.g., 1 M Tris-HCl, pH 7.4), and the reaction solution filtered to remove unreacted borohydride. The resulting reduced nanoparticles may be characterized using SDS Page.

In some embodiments, mixed difunctional linkers can be used (for example a linker having an aldehyde and a carboxylic acid). For example, in some embodiments, the hemoglobin (or albumin) can first be decorated with a linker under a first set of reaction conditions. This decorated molecule can then be exposed to albumin (or hemoglobin) under a set of second reaction conditions to create a bond through the linker.

In some embodiments, the reversible oxygen binding molecules are not covalently bound to the nanostructure and instead are bound via electrostatic interactions or complexation.

In some embodiments, after functionalization of the hemoglobin to the albumin via, e.g., a diimine linker, the reversible oxygen binding nanoparticle is further functionalized and/or decorated with a nucleophilic species (e.g., —NH$_2$, —OH, —SH, etc.). In some embodiments, the functionalization of the albumin with a nucleophilic species (e.g., —NH$_2$, —OH, —SH, etc.) to form an albumin carrier may occur prior to the functionalization of the hemoglobin to the albumin carrier. For purposes of the following discussion, the hemoglobin is shown having already been functionalized to the albumin, though the discussion may encompass functionalization of albumin to form an albumin carrier prior to functionalization of the hemoglobin to albumin.

In some embodiments, the nucleophilic species is a thiol (i.e., —SH) and the nanoparticle is thiolated. In some embodiments, the nanoparticle (e.g., the nanostructure, the reversible oxygen binding molecule, or both) is thiolated using a thiolating agent. In some embodiments, the thiolating agent is selected from the group consisting of:

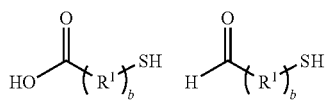

where R$^1$ is selected from the group consisting of —CH$_2$—, —(CH$_2$O)CH$_2$—, —(CH$_2$CH$_2$O)—CH$_2$CH$_2$—, and —(CH$_2$CH$_2$CH$_2$O)—CH$_2$CH$_2$CH$_2$—, and "b" is an integer between 0 and 10. In some embodiments, Traut's reagent (2-iminothiolane) is used as the thiolating agent.

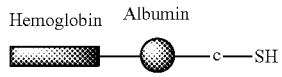

wherein c is selected from the group consisting of —C(O)(CH$_2$)$_p$— and —N═CH(CH$_2$)$_p$—, wherein p is an integer ranging from 1 to 10. In other embodiments, N-succinimididyl S-acrylthioacetate or succinimidyl acetyl-thiopropionate is used as the thiolating agent. [Hermanson, G. T. Bioconjugate Techniques; Academic Press: New York, 2013].

Traut's reagent reacts with primary amines (—NH$_2$) to introduce sulfhydryl (—SH) groups while maintaining charge properties similar to the original amino group. Once added, sulfhydryl groups can be specifically targeted for reaction in a variety of useful labeling, crosslinking and immobilization procedures.

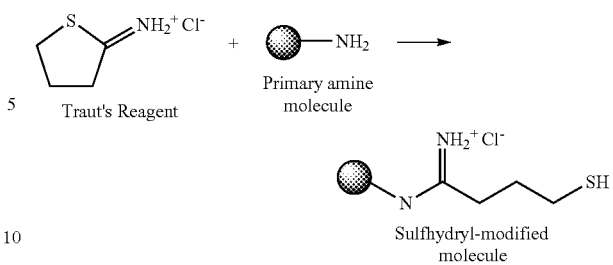

Preferably, the 2-iminothiolane reacts with primary amines at pH 7 to 10, creating aminidine compounds with a sulfhydryl group. More preferably, the 2-iminothiolane reaction is at pH 7 to 9. This allows for crosslinking or labeling of molecules such as proteins through use of disulfide or thioether conjugation. In some embodiments, thiol-ene polymerization conditions are typically chosen to minimize side reactions. In particular, disulfide formation can present a challenge in the consistent formation of thiol-ene hydrogels. For example, thiol-functionalized macromers can react with each other to form disulfide linkages, making them inaccessible for subsequent reaction with alkenes. Additionally, thiols on macromers can react with various functional groups that are present on biologics (i.e., off-target reactions leading to oxidation of cysteine residues on proteins).

According to some embodiments of the present methods, the extent of the nucleophilic functional groups (e.g., sulfhydryls) introduced onto the lysine (Lys) residues of albumin can be controlled by the availability of an initiator, such as 2-iminothiolane (Traut's reagent). For example, in embodiments where the functionalization of the albumin with a nucleophilic species (e.g., —NH$_2$, —OH, —SH, etc.) occurs prior to crosslinking the hemoglobin to the albumin, depending on the reaction of the initiator and the albumin, the remaining unreacted lysine residues on the albumin are then available for crosslinking with hemoglobin for stabilization. In some embodiments, a bifunctional linker chemistry may then be selected to allow an alternative crosslinking approach for crosslinking of the hemoglobin to albumin, such as a reaction using glutaraldehyde, so that the nucleophilic group functionalized Lys residues are excluded from the crosslinking reaction and may alter the conformation of binding between the albumin and hemoglobin.

The functionalization of the Lys residues is a process that can be monitored (e.g., by $^1$H NMR or by fluorescence-based assay) and tuned to achieve the desired number of lysine residues to be excluded from a subsequent crosslinking reaction between the hemoglobin and albumin. The extent of the lysine residues that are converted to nucleophilic groups can be monitored as can the conjugation of a linker to the nucleophilic group. This allows the crosslinking reaction between the hemoglobin and albumin to be regulated.

For purposes of summarizing the discussion that follows, certain features of the present methods are described using Traut's reagent and sulfhydryls (thiol groups). While Traut's reagent and sulfhydryls are used herein to discuss certain features, these molecules and groups are exemplary and other initiators and nucleophilic groups, as well as other nanostructures and oxygen binding agents, are envisioned within the scope of the present invention.

In some embodiments, the number of lysine residues that are converted into thiol functional groups (sulfhydryls) may be set by the molar ratio the primary amines (e.g., Lys residues on albumin) and 2-iminothiolane (Traut's reagent). In some embodiments, for example where the nanostructure has many lysine residues, adjusting the molar ratio of Traut's reagent in the reaction allows one to control the level of thiolation. For example, for IgG molecules (150 kDa), reaction with a 10-fold molar excess of Traut's reagent ensures that all antibody molecules will be modified with at least 3-7 sulfhydryl groups. By comparison, nearly all available primary amines (~20 in the typical IgG) could be thiolated using a 50-fold molar reagent excess.

The extent of the thiolation may be monitored using any method known in the art so that the desired level of thiolation is achieved in the bulk reaction. In some embodiments, the active thiol groups on the protein surface may be assayed by the disulfide exchange reaction with 2,2'-dithiopyridine (2,2'-DTP) to produce 2-thiopyridinone (2-TP) with an absorption at 343 nm (molar absorption coefficient: $8.1 \times 10^3$ $M^{-1}$ $cm^{-1}$) [Pedersen, A. O., and Jacobsen, J. (1980) Reactivity of the thiol group in human and bovine albumin at pH 3-9, as measured by exchange with 2,2-dithiodipyridine. Eur. J. Biochem. 106, 291-295].

In some embodiments, quantitative spectroscopic measurements may be used to conveniently provide the thiol concentration. For example, the parent protein may show a small absorption band in this range, which should be subtracted from the spectrum after the disulfide exchange reaction, where the difference in the thiol groups per protein before and after the modification corresponds to the mean of the sulfhydryl-functionalized chains on the protein surface.

In some embodiments, a fluorescence-based assay may be used, such as the method described by Udenfriend [Udenfriend, S., Stein, S., Bohlen, P., Dairman, W., Leimgruber, W. & Weigele, M. Fluorescamine: A Reagent for Assay of Amino Acids, Peptides, Proteins, and Primary Amines in the Picomole Range Science 178 871-872 (1972)], which is based on the rapid reaction of fluorescamine (4-phenyl-spiro [furan-2(3H), 1'-phthalan]-3,3'-dione) with primary amines in proteins, such as the terminal amino group of peptides and the e-amino group of lysine, to form highly fluorescent moieties

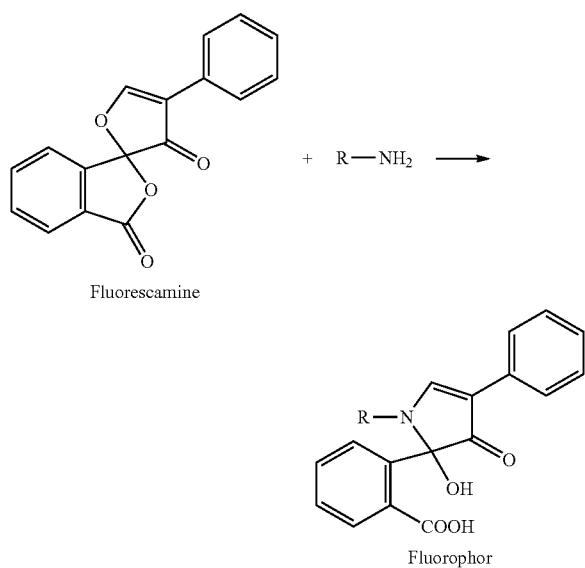

Fluorescamine

Fluorophor

Fluorescamine reacts with the primary amino groups found in terminal amino acids and the e-amine of lysine to form fluorescent pyrrolinone type moieties.

In some embodiments, the protein assay of Udenfriend [Udenfriend, S., Stein, S., Bohlen, P., Dairman, W., Leimgruber, W. & Weigele, M. Fluorescamine: A Reagent for Assay of Amino Acids, Peptides, Proteins, and Primary Amines in the Picomole Range Science 178 871-872 (1972)], may be modified for microplates as described by Lorenzen [Lorenzen, A. & Kennedy, S. W. A Fluorescence-Based Protein Assay for Use with a Microplate Reader Anal. Biochem. 214 346-348 (1993)]. For example, a series of dilutions of Bovine Serum Albumin (BSA) ranging from 0 to 500 g/ml was made using phosphate buffered saline (PBS) pH 7.4 as the diluent. After dilution, 150 μl aliquots of samples and standards were pipetted into microplate wells in replicates of eight. The microplate was placed on a microplate shaker and 50 μl of 1.08 mM (3 mg/ml) fluorescamine dissolved in acetone was added to each well. Following the addition of fluorescamine the plate was shaken for one minute. The fluorescence was then determined using a FL600 fluorescence plate reader (BioTek Instruments, Inc., Winooski, Vt.) with a 400 nm, 30 nm bandwidth, excitation filter and a 460 nm, 40 nm bandwidth emission filter. The sensitivity setting was at 29, and the data collected from the bottom with a 5 mm probe using static sampling with a 0.35 second delay, 50 reads per well. When lower protein concentrations (0-500 μg/ml) were examined, the reaction was found to be linear. Using a least means squared regression analysis, a straight line was generated and utilized for the determination of protein concentrations. This allowed for determination of an equation describing the standard curve.

Various buffers may be used for thiolation with Traut's reagent. In some embodiments, the buffer is preferably a phosphate buffered saline (PBS) solution (PBS, Thermo Fisher). In other embodiments, a 0.1M borate buffer adjusted to pH 8 may be used for thiolation. Other buffers devoid of primary amines that maintain solubility of the nanostructure (e.g., carrier protein) may also be used. Traut's reagent is very stable in acidic or neutral buffers that are devoid of primary amino groups. Even in alkaline conditions, hydrolysis is slow compared to the rate of reaction with primary amines. Because hydrolysis is slow relative to the amine reaction rate, thiolation with Traut's reagent does not require as large a molar excess of reagent as other types of modification reagents, such as SATA.

In some embodiments, the nucleophilic species (e.g., the thiol) may be used to further functionalize a portion of the nanoparticle (e.g., the nanostructure, the reversible oxygen binding molecule, or both) with a hydrophilic species. In some embodiments, the nucleophile of the nanoparticle is used to attack an electrophilic group (e.g., a carboxylic acid, epoxide, succinimidyl group, maleimide, etc.) situated on a hydrophilic species thereby coupling the hydrophilic species to the nanoparticle. In some embodiments, this functionalization can be performed in the presence of coupling reagents to facilitate coupling (e.g., EDC, DCC, etc.).

In some embodiments, the hydrophilic species is coupled to albumin via a thiol of the albumin and a maleimide of the hydrophilic species, as shown below:

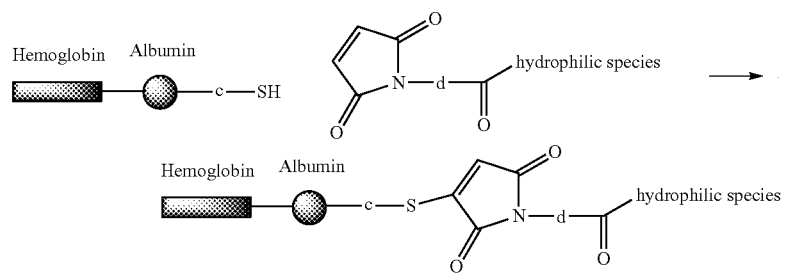

wherein c is selected from the group consisting of —C(O)(CH$_2$)$_p$— and —N=CH(CH$_2$)$_p$—, wherein p is an integer ranging from 1 to 10 and wherein d is —(CH$_2$)$_q$—, wherein q is an integer ranging from 1 to 10.

Thiol-maleimide reactions offer a number of advantages: (1) at neutral pH, maleimides react with high selectivity for thiols; (2) thiol-maleimide reactions occur rapidly under physiological conditions; and (3) the thiol-maleimide linkage formed with aryl thiols can undergo retro-Michael reaction under reducing conditions for controlled degradation and release applications. However, it is important to note that maleimide groups undergo ring hydrolysis under aqueous conditions, yielding maleamic acid that is not reactive with thiols. Solution pH, temperature, neighboring functional groups, and hydroxyl ion concentration affect the rate of ring hydrolysis (k=500-1600 M-1 s-1).[ref 78] Although maleimide ring hydrolysis after formation of succinimide thioether linkages will not significantly change the properties of an existing hydrogel, ring hydrolysis in the precursor solution before hydrogel preparation can significantly increase network defects; such defects typically increase mesh size and reduce network retention of loaded therapeutics, affecting release characteristics. In addition, because unreacted small-molecule maleimides can be cytotoxic, so thorough purification of maleimide-functionalized macromers after synthesis is typically preferred.

In some embodiments, the nanostructure may be decorated with one or more hydrophilic polymers selected from the group consisting of PEG (e.g., PEGylated), poly(N-isopropylacrylamide) (PNIPAM), polyacrylamide (PAM), polyvinyl alcohol (PVA), polyacrylic acid, polyethyleneimine (PEI), poly(2-oxazoline), poly(vinylpyrrolidone), and copolymers thereof.

In some embodiments, as shown below, the nanostructure is PEGylated. In some embodiments, as shown below, the nanostructure is PEGylated using a maleimide of PEG. For example, human serum albumin may be modified by reacting 2-iminothiolane (IMT) with the amino groups of Lys to create active thiol groups and then binding the active thiol groups with maleimide-terminated poly(ethylene glycol) (PEG).

In some embodiments, the quantitative fluorescence-based assays discussed above may be utilized to tune the number of free lysine residues remaining and the number of sulfhydryls ready for functionalization, e.g., with MAL-PEG conjugation. After functionalization, the number of unreacted sulfhydryls can be determined by labeling them with fluorescein-5-maleimide in excess and filtering unreacted fluorescein-5-maleimide prior to quantitation. The degree of labeling with fluorescein-5-maleimide can be determined either by absorption using (ε'=fluor molar extinction coefficient: 68,000 M-1 cm-1) or by fluorescence emission (excitation at 491 nm and emission at 518 nm).

For example, albumin (0.25 mM) (BSA Sigma-Aldrich, St. Louis, Mo.) was incubated overnight with 5 mM 2-iminothiolane (BioAffinity Systems, Rockford, Ill.) and 7.5 mM maleimide PEG-5000 in phosphate buffer saline (PBS). The surface amino groups were thiolated, and thiol groups generated on the protein in situ were derivatized by the maleimide-PEG in the reaction mixture. The single step reaction limited the oxidation of the thiols of the thiolated protein to generate dimers and polymers of BSA, and is the preferred approach to generate PEGylated proteins. Excess reagents were removed by tangential flow filtration using the Minim System (Pall Life Sciences, Ann Arbor, Mich.) after overnight incubation. A 70 kDa membrane was used for diafiltration for removal of unreacted PEG and excess iminothiolane, and PEG-BSA was concentrated to 2.5 gms/dL (protein based). This example yielded an average of 12 copies of PEG 5K chains conjugated to a BSA molecule, a molecular weight of 130 kDa and a molecular radius of 8-9 nm.

In order to retain the hemoglobin-albumin complex in a polymer network, the bonds between the linker and the hemoglobin-albumin complex and within the polymer network preferably have little to no biodegradation. In some embodiments of the present invention, acrylate bonds are preferably used within the polymer network, and a stable thioether linkage between a polymer linker and the hemoglobin-albumin complex is preferably used to immobilize the complex in the polymer network. In some embodiments, a maleimide-activated PEG, which may be reacted with the thiols of cysteine residues or the sulfhydryls derived from Lys residues, is preferably used to form stable thioether linkages because it exhibits a much higher stability against hydrolysis a NHS ester of PEG acid.

Accordingly, in some embodiments, the one or more of the hydrophilic species further comprises a polymerizable unit (e.g., an acrylate, methacrylate, etc.). In some embodiments, the hydrophilic species and polymerizable unit are functionalized to the nanoparticle using maleimide-PEG-methacrylate (mal-PEG-MA) as shown below:

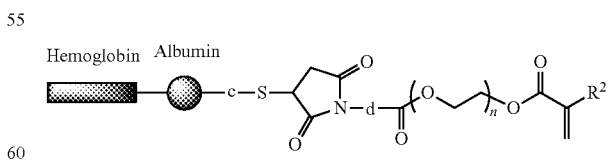

wherein c is selected from the group consisting of —C(O)(CH$_2$)$_p$— and —N=CH(CH$_2$)$_p$—, wherein p is an integer ranging from 1 to 10, wherein d is —(CH$_2$)$_q$—, wherein q is an integer ranging from 1 to 10, wherein n is an integer ranging from 1 to 1000 and wherein R$^2$ is selected from the group consisting of —C$_{1-4}$alkyl and H.

The extent of acryl group coupling to the macromer complex may be monitored using any monitoring method known in the art, e.g., $^1$H NMR. Alternatively, an iodine (Wijs solution) assay, as disclosed in Lubrizol Test Procedure, TP-TM-005C, may be used to determine the number of acrylate groups coupled to the macromer complex. For example, a 10 mg sample may be dissolved in water and an excess of Wijs solution (0.1M iodine monochloride, Sigma Aldrich), for example, 50-60% excess of titrateable double bonds, added. The resulting solution then may be incubated in the dark for about 30 minutes at room temperature. After further dilution with deionized water, 4-20 mL aqueous 1 M potassium iodide solution may be added, and the resulting solution immediately titrated using 0.1 N sodium thiosulfate. 1-2 mL 1% aqueous starch indicator solution may be added and the titration continued till completion. The iodine value then may be calculated to indicate the number of acrylate groups present in the sample.

In some embodiments, the polymerizable group of the hydrophilic species unit can be co-polymerized in a first crosslinking solution (which can contain one or more crosslinkers) to form a nanogel:

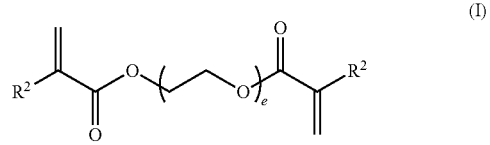

In some embodiments, the first crosslinking solution comprises the following structure (Formula I):

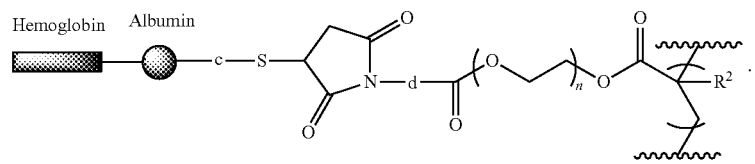

where e is an integer ranging from 1 to 10 and $R^2$ is selected from the group consisting of —$C_{1-4}$alkyl and H. In some embodiments, a plurality of differing crosslinkers having the Formula I structure can be used to form the nanogel.

In some embodiments, the first crosslinking solution comprises tetraethyleneglycol diacrylate (TEGDA). In some embodiments, the crosslinking solution comprises TEGDA at a weight % (weight of TEGDA/weight of solution) ranging from about 0% to about 5%, about 5% to about 15%, about 15% to about 25%, about 25% to about 50%, about 50% to about 75%, or about 75% to about 100%.

In some embodiments, the first crosslinking solution comprises the hemoglobin-albumin nanoparticle at a weight % (weight of nanoparticle/weight of solution) ranging from about 0% to about 0.5%, about 0.5% to about 1.5%, about 1.5% to about 2.5%, about 2.5% to about 5.0%, about 5.0% to about 7.5%, or about 7.5% to about 10.0%.

In some embodiments, the nanogel formation is performed in water or neat using UV light and a UV initiator (e.g., AIBN, etc.). In some embodiments, the nanogel is a matrix of polymer that retains water within the matrix. In some embodiments, the nanogel is a hydrogel particle. In some embodiments, the nanogel is a particle having a size of less than about 1 µm, 500 nm, about 100 nm, about 10 nm, about 5 nm, or about 2 nm.

In some embodiments, the nanogel can further be diffused in a liquid medium (i.e., an oxygen conduit fluid) to provide an emulsion, suspension, mixture, or solution. In some embodiments, the liquid of the oxygen conduit fluid comprises one or more of crosslinking agents and water. In some embodiments, the oxygen conduit fluid comprises a second crosslinker (or a second combination of crosslinkers). In some embodiments, the second crosslinker is also represented by Formula I above. In some embodiments, the second crosslinker is ethylene glycol dimethacrylate (EGDMA). In some embodiments, the EDGMA is present at a weight % (weight of EGDMA/weight of liquid medium) ranging from about 0% to about 5%, about 5% to about 15%, about 15% to about 25%, about 25% to about 50%, about 50% to about 75%, or about 75% to about 100%. In some embodiments, the second crosslinker is (TEGDA). In some embodiments, the TEGDA is present at a weight % (weight of TEGDA/weight of liquid solution) ranging from about 0% to about 5%, about 5% to about 15%, about 15% to about 25%, about 25% to about 50%, about 50% to about 75%, or about 75% to about 100%.

In some embodiments, the liquid medium and nanogel are configured to flow into the glucose sensor tip via capillary action. In some embodiments, the viscosity of the liquid medium and nanogel is sufficiently low to allow this capillary uptake. In some embodiments, the nanogel solution is introduced to a template via a port 4210, as shown in FIG. 42.

In some embodiments, when the nanogel is dispersed in ethylene glycol dimethacrylate at about 0.25 g gel wt./1 mL, the oxygen conduit fluid has a viscosity of less than about 2000 cP, about 1000 cP, about 500 cP, about 250 cP, about 100 cP, about 50 cP, about 25 cP, about 10 cP, about 5 cP, about 1 cP, or about 0.5 cP. In some embodiments, when the nanogel is dispersed in ethylene glycol dimethacrylate at about 0.25 g gel wt./1 mL, the oxygen conduit fluid is characterized by an ability to pass through a 20 g needle using less than 60 N pressure.

In some embodiments, as discussed above, the oxygen conduit fluid is configured to be dispensed as a solution into sub-millimeter features of the glucose sensor tip. Small features of the glucose sensor tip can be provided by supplying solutions of the nanogels which are taken-up by spaces (e.g., channels, tunnels, paths, etc.) in molds (e.g., dye casts) by capillary action. The oxygen conduit fluid can fill these device features and, upon filling, be cured using UV light (in the presence of a second crosslinker) and/or concentrated (to remove any volatile liquids) to afford the oxygen conduit 3820.

In some embodiments, where applicable, the second crosslinking step is performed while the nanogel is suspended in an oxygen conduit fluid (e.g., the second crosslinker, water, combinations thereof, etc.). In some embodiments, the second crosslinking step affords a hydrogel capable of rapidly transporting oxygen (e.g., diffusion controlled) from the oxygen conduit to other regions of the sensor tip.

Some embodiments pertain to a crosslinked hemoglobin-based material represented by the following structure:

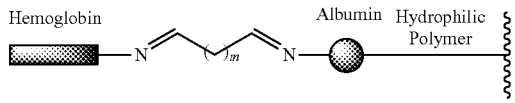

where "⁓" represents a hydrogel or nanogel matrix and m is an integer from 0 and 8. In some embodiments, these materials are used as an oxygen conduit. In some embodiments, the hemoglobin-albumin material comprises PEG-based linker and is represented by the following structure:

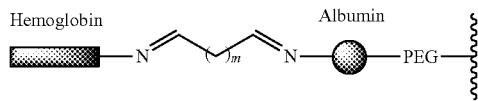

wherein m is an integer between 0 and 8.

In some embodiments, the crosslinked hemoglobin-based material is represented by the following structure:

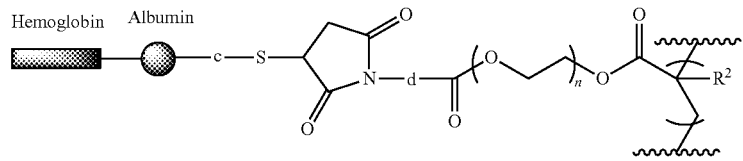

wherein c is selected from the group consisting of —C(O)(CH$_2$)$_p$— and —N═CH(CH$_2$)$_p$—, wherein p is an integer ranging from 1 to 10; wherein d is —(CH$_2$)$_q$—, wherein q is an integer ranging from 1 to 10; wherein n is an integer ranging from 1 to 1000; and wherein R$_2$ is selected from the group consisting of —C$_{1-4}$alkyl and H.

In some embodiments, the nanogel or hydrogel matrix of the crosslinked hemoglobin-based material comprises:

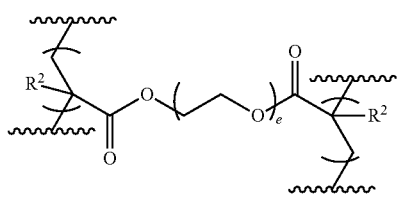

wherein e is an integer ranging from 1 to 10; and wherein R$^2$ is selected from the group consisting of —C$_{1-4}$alkyl and H. In some embodiments, the nanogel or hydrogel matrix of the crosslinked hemoglobin-based material comprises:

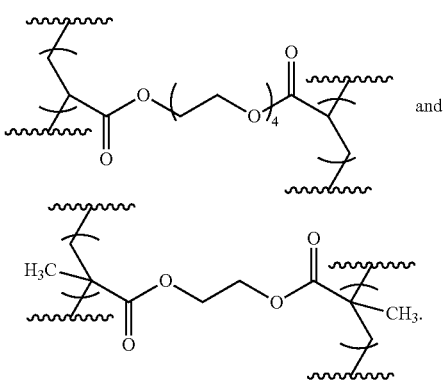

In some embodiments, after curing or concentrating, the crosslinked hemoglobin-based material is dense. In some embodiments, the crosslinked material has a modulus of at least about 8 GPa at a total material concentration of less than about 10 mg/mL. In some embodiments, after curing or concentrating, the crosslinked hemoglobin-based material has a storage modulus of at least about 0.01 GPa, about 0.1 GPa, 0.5 GPa, 1.0 GPa, 2.0 GPa, 4.0 GPa, or about 6.0 GPa at a total material concentration of about 10 mg/mL.

In some embodiments, the crosslinked hemoglobin-based material has a water content of at least about 70%, about 80%, about 90%, about 95%, about 97.5%, about 99%, or about 99.5% of the total dry weight of the crosslinked hemoglobin-based material.

Some embodiments pertain to a method of making a dispensable, UV-curable enzyme-albumin nanogel solution. In some embodiments, the method of making a UV-curable enzyme-albumin nanogel comprises linking a nanostructure to an enzyme. In some embodiments, the nanostructure is as described above. In some embodiments, the nanostructure is albumin. In some embodiments, the enzyme is GOx or CAT. In some embodiments, like the oxygen conduit described above, the method of making a UV-curable enzyme-albumin nanogel comprises incorporating a hemoglobin-albumin nanostructure. In some embodiments, the hemoglobin-albumin nanostructure is provided using the methods previously described to afford a crosslinkable nanostructure.

In some embodiments, the nanogel of the enzyme-albumin nanogel further comprises GOx linked to an albumin molecule and/or CAT linked to an albumin nanostructure. In some embodiments, GOx-albumin nanoparticles and CAT-albumin nanoparticles are provided (with the separate GOx-albumin and CAT-albumin molecules). In some embodiments, GOx and CAT enzymes are functionalized to the same albumin molecule. In some embodiments, where present, hemoglobin-albumin nanoparticles are also provided prior to nanogel formation. In some embodiments, each of GOx, CAT, and/or hemoglobin are functionalized to a single albumin nanostructure prior to nanogel formation.

As stated above, for purposes of summarizing the disclosure, certain features of enzymatic-albumin nanogels have been described herein using albumin and GOx or CAT. While albumin and GOx and albumin and CAT nanoparticles are described herein, any nanostructure or enzymatic molecule is envisioned. Similarly, when the more general term enzyme is used, both GOx and CAT are envisioned.

Similar to the hemoglobin-albumin nanoparticles above, in some embodiments, the nanoparticle comprises one or more enzyme molecules functionalized to each albumin molecule. In some embodiments, the nanoparticle comprises less than one enzyme molecule per albumin molecule. In some embodiments, the ratio of enzyme molecules to albumin is at least about 0.5:1, about 1:1, about 2:1, about 5:1, or about 10:1.

In some embodiments, the enzyme is bound to albumin covalently. In some embodiments, the covalent link to the enzyme is formed using a difunctional linker. In some embodiments the difunctional linker is selected a dialdehyde, a dicarboxylic acid, a diepoxide, or the like. In some embodiments, the difunctional linker is represented by one or more of the following structures:

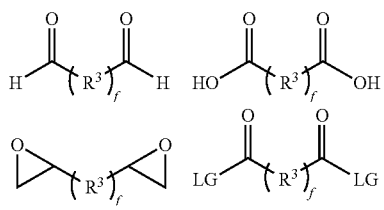

where $R^3$ is selected from the group consisting of —$CH_2$—, —$(CH_2O)CH_2$—, —$(CH_2CH_2O)$—$CH_2CH_2$—, and —$(CH_2CH_2CH_2O)$—$CH_2CH_2CH_2$, and f is an integer ranging from 0 and 10.

In some embodiments, mixed difunctional linkers can be used (for example a linker having an aldehyde and a carboxylic acid). For example, in some embodiments, the enzyme (or albumin) can first be decorated with a linker under a first set of reaction conditions. This decorated molecule can then be exposed to albumin (or enzyme) under a set of second reaction conditions to create a bond through the linker.

The crosslinking of enzyme and albumin may involve multiple site reactions. For example, albumin is rich in Lys residues. One common and versatile technique for crosslinking or labeling peptides and proteins such as antibodies involves the use of chemical groups that react with primary amines (—$NH_2$). Primary amines exist at the N-terminus of each polypeptide chain and in the side-chain of lysine (Lys) amino acid residues. These primary amines are positively charged at physiologic pH; therefore, they occur predominantly on the outside surfaces of native protein tertiary structures where they are readily accessible to conjugation reagents introduced into the aqueous medium. Furthermore, among the available functional groups in typical biological or protein samples, primary amines are especially nucleophilic; this makes them easy to target for conjugation with several reactive groups.

In some embodiments, the enzyme and albumin are functionalized via amine groups from each of the albumin and enzyme molecules. For example, in some embodiments, when a dialdehyde, a dicarboxylic acid, or a diepoxide is used as the difunctional linkers, diimines, diamides, and diamines, respectively, result from coupling of the enzyme to the albumin. In some embodiments, combinations of difunctional linkers can be used. The following represents an enzyme molecule linked to albumin using a dialdehyde (i.e., via a diimine linker):

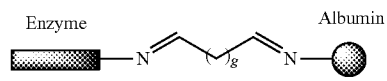

In some embodiments, the difunctional linker is glutaraldehyde and forms a diimine link via the aldehydes of the linker and amines from enzyme and albumin (where g is an integer ranging from 0 and 8). A glutaraldehyde-based linker configuration is represented by the depiction:

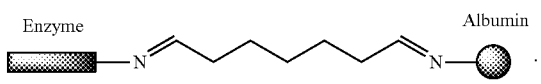

In some embodiments, the enzyme is covalently linked to albumin by incubation with gluteraldehyde, at low temperature, low oxygen concentration, pH of between about 7.0 and 8.0, for at least about 24 hours to form enzymatic nanoparticles.

In some embodiments, the incubation time with glutaraldehyde is at least about 10 hours, about 24 hours, about 36 hours, or about 48 hours. In some embodiments, the incubation time is at least about 10 hours, about 24 hours, about 36 hours, or about 48 hours. In some embodiments, the glutaraldehyde (or other difunctional linker) is provided to the albumin/hemoglobin or albumin/enzyme solution at a low concentration, e.g., at a wt % below about 0.0001 wt. % or at a molar ratio below about 0.1. In some embodiments, the temperature is below about 30° C., about 20° C., about 10° C., about 5° C., about 0° C. or lower than −5° C.

Glutaraldehyde has been widely used as a mild crosslinking agent for the immobilization of enzymes because the reaction proceeds in aqueous buffer solution under conditions close to physiological pH, ionic strength, and temperature. Essentially, two methods have been used: (i) the formation of a three-dimensional network as a result of intermolecular crosslinking and (ii) the binding to an insoluble carrier (e.g., nylon, fused silica, controlled pore glass, crosslinked proteins such as gelatin and bovine serum albumin (BSA), and polymers with pendant amino groups).

In some embodiments, after incubation with glutaraldehyde and formation of the diimine linker, the enzyme-albumin nanoparticles may be subjected to a borohydride reduction to convert the diimine linkages to diamine linkages. For example, the enzyme-albumin nanoparticle may be diluted with a coupling buffer (e.g., 0.1 M sodium phosphate, 0.15 M NaCl, or standard phosphate buffer solution) and a borohydride (e.g., sodium cyanoborohydride, or sodium borohydride) may be added. Unreacted aldehyde sites may be blocked by the addition of a quenching buffer solution (e.g., 1 M Tris-HCl, pH 7.4), and the reaction solution filtered to remove unreacted borohydride. The resulting reduced nanoparticles may be characterized using, e.g., SDS-polyacrylamide (SDS Page) electrophoresis.

Figure 49:
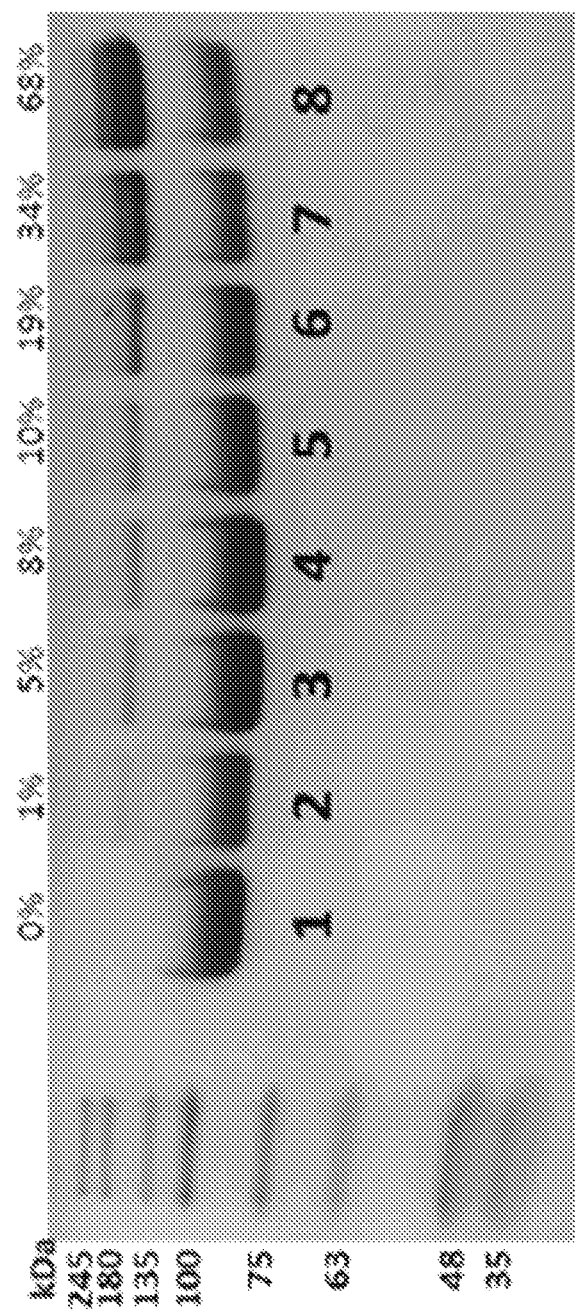
FIG. 49 is an SDS-PAGE after EDC coupling reaction with GOx and amine.
Figure 50:
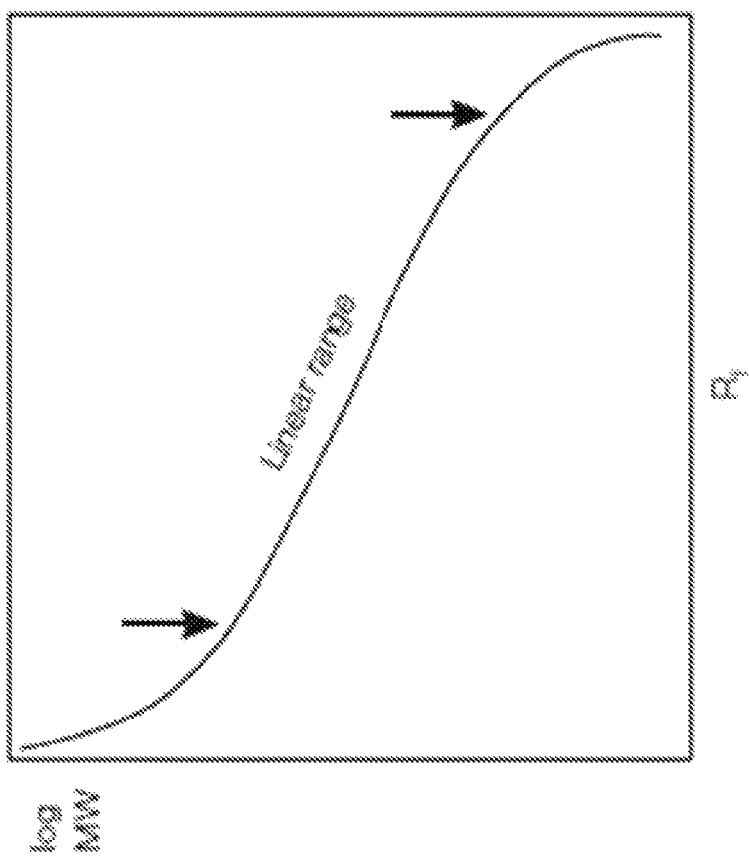
FIG. 50 is a graph of log Molecular Weight (MW) vs. $R_f$ using the values obtained for the protein standards in FIG. 49.

FIG. 49 shows an example of SDS Page of reduced nanoparticles after EDC coupling reaction with GOx and amine. Using the values obtained for the protein standards, a graph of log Molecular Weight (MW) vs. $R_f$ is plotted in FIG. 50.

The plot should be linear for most proteins, provided that the proteins are fully denatured and the gel percentage is appropriate for the MW range of the sample. The reaction efficiency is demonstrated in going from 1 to 8 with no coupling reagent present in 1 and increased amounts of reagent from 2 to 8, thus showing an increase in molecular weight as the coupling of the amine occurs.

In some embodiments, the enzyme molecules are not covalently bound to the nanostructure and instead are bound via electrostatic interactions or complexation.

In some embodiments, after functionalization of the enzyme to the albumin via, e.g., a diimine linker, the enzymatic nanoparticle is further functionalized and/or decorated with a nucleophilic species (e.g., —NH$_2$, —OH, —SH, etc.). In some embodiments, the functionalization of the albumin with a nucleophilic species (e.g., —NH$_2$, —OH, —SH, etc.) form an albumin carrier may occur prior to the functionalization of the enzyme to the albumin carrier. For purposes of the following discussion, the enzyme is shown having already been functionalized to the albumin, though the discussion may encompass functionalization of albumin to form an albumin carrier prior to functionalization of the hemoglobin to albumin.

In some embodiments, the nucleophilic species is a thiol (i.e., —SH) and the nanoparticle is thiolated. In some embodiments, the nanoparticle (e.g., the nanostructure, the enzyme, or both) is thiolated using a thiolating agent. In some embodiments, the thiolating agent is selected from the group consisting of:

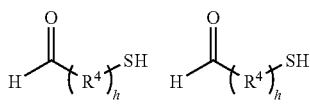

where R$^5$ is selected from the group consisting of —CH$_2$—, —(CH$_2$O)CH$_2$—, —(CH$_2$CH$_2$O)—CH$_2$CH$_2$—, and —(CH$_2$CH$_2$CH$_2$O)—CH$_2$CH$_2$CH$_2$—, and "h" is an integer between 0 and 10.

In some embodiments, Traut's reagent (2-iminothiolane) is used as the thiolating agent.

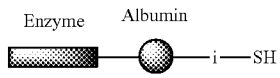

wherein i is selected from the group consisting of —C(O)(CH$_2$)$_r$— and —N═CH(CH$_2$)$_r$, wherein r is an integer ranging from 1 to 10. In other embodiments, N-succinimididyl S-acrylthioacetate or succinimidyl acetyl-thiopropropionate is used as the thiolating agent. [Hermanson, G. T. Bioconjugate Techniques; Academic Press: New York, 2013].

Traut's reagent reacts with primary amines (—NH$_2$) to introduce sulfhydryl (—SH) groups while maintaining charge properties similar to the original amino group. Once added, sulfhydryl groups can be specifically targeted for reaction in a variety of useful labeling, crosslinking and immobilization procedures.

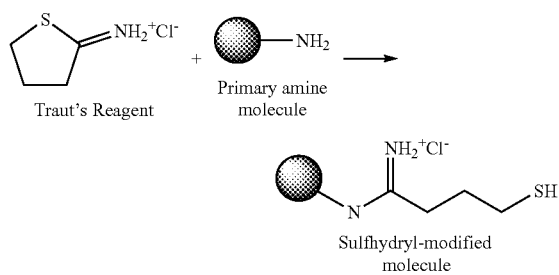

Preferably, the 2-iminothiolane reacts with primary amines at pH 7 to 10, creating aminidine compounds with a sulfhydryl group. More preferably, the 2-iminothiolane reaction is at pH 7 to 9. This allows for crosslinking or labeling of molecules such as proteins through use of disulfide or thioether conjugation. Thiol-ene polymerization conditions are typically chosen to minimize side reactions. In particular, disulfide formation can present a challenge in the consistent formation of thiol-ene hydrogels. For example, thiol-functionalized macromers can react with each other to form disulfide linkages, making them inaccessible for subsequent reaction with alkenes. Additionally, thiols on macromers can react with various functional groups that are present on biologics (i.e., off-target reactions leading to oxidation of cysteine residues on proteins).

According to some embodiments of the present methods, the extent of the nucleophilic functional groups (e.g., sulfhydryls) introduced onto the lysine (Lys) residues of albumin can be controlled by the availability of an initiator, such as 2-iminothiolane (Traut's reagent). In embodiments where the functionalization of the albumin with a nucleophilic species (e.g., —NH$_2$, —OH, —SH, etc.) occurs prior to crosslinking the enzyme to the albumin, depending on the reaction of the initiator and the albumin, the remaining unreacted lysine residues on the albumin are then available for crosslinking with the enzyme for stabilization. In some embodiments, a bifunctional linker chemistry may then be selected to allow an alternative crosslinking approach for crosslinking of the enzyme to albumin, such as a reaction using glutaraldehyde, so that the nucleophilic group functionalized Lys residues are excluded from the crosslinking reaction and may alter the conformation of binding between the albumin and enzyme.

The functionalization of the Lys residues is a process that can be monitored (e.g., by $^1$H NMR or by fluorescence-based assay) and tuned to achieve the desired number of lysine residues to be excluded from a subsequent crosslinking reaction with the enzyme and albumin. The extent of the lysine residues that are converted to nucleophilic groups can be monitored as can the conjugation of a linker to the nucleophilic group. This allows the crosslinking reaction between the enzyme and albumin to be regulated.

For purposes of summarizing the discussion that follows, certain features of the present methods are described using Traut's reagent and sulfhydryls (thiol groups). While Traut's reagent and sulfhydryls are used herein to discuss certain features, these molecules and groups are exemplary and other initiators and nucleophilic groups, as well as other nanostructures and enzymes, are envisioned within the scope of the present invention.

In some embodiments, the number of lysine residues that are converted into thiol functional groups (sulfhydryls) may be set by the molar ratio the primary amines (e.g., Lys residues on albumin) and 2-iminothiolane (Traut's reagent). In some embodiments, for example where the nanostructure has many lysine residues, adjusting the molar ratio of Traut's reagent in the reaction allows one to control the level of thiolation. For example, for IgG molecules (150 kDa), reaction with a 10-fold molar excess of Traut's reagent ensures that all antibody molecules will be modified with at least 3-7 sulfhydryl groups. By comparison, nearly all available primary amines (~20 in the typical IgG) could be thiolated using a 50-fold molar reagent excess.

The extent of the thiolation may be monitored using any method known in the art so that the desired level of thiolation is achieved in the bulk reaction. In some embodiments, the active thiol groups on the protein surface may be assayed by the disulfide exchange reaction with 2,2'-dithiopyridine (2,2'-DTP) to produce 2-thiopyridinone (2-TP) with an absorption at 343 nm (molar absorption coefficient: $8.1 \times 10^3$ M$^{-1}$ cm$^{-1}$) [Pedersen, A. O., and Jacobsen, J. (1980) Reactivity of the thiol group in human and bovine albumin at pH 3-9, as measured by exchange with 2,2-dithiodipyridine. Eur. J. Biochem. 106, 291-295].

In some embodiments, quantitative spectroscopic measurements may be used to conveniently provide the thiol concentration. For example, the parent protein may show a small absorption band in this range, which is subtracted from the spectrum after the disulfide exchange reaction, where the difference in the thiol groups per protein before and after the modification corresponds to the mean of the sulfhydryl-functionalized chains on the protein surface.

In some embodiments, a fluorescence-based assay may be used, such as the method described by Udenfriend [Udenfriend, S., Stein, S., Bohlen, P., Dairman, W., Leimgruber, W. & Weigele, M. Fluorescamine: A Reagent for Assay of Amino Acids, Peptides, Proteins, and Primary Amines in the Picomole Range Science 178 871-872 (1972)], which is based on the rapid reaction of fluorescamine (4-phenyl-spiro [furan-2(3H), 1'-phthalan]-3,3'-dione) with primary amines in proteins, such as the terminal amino group of peptides and the e-amino group of lysine, to form highly fluorescent moieties

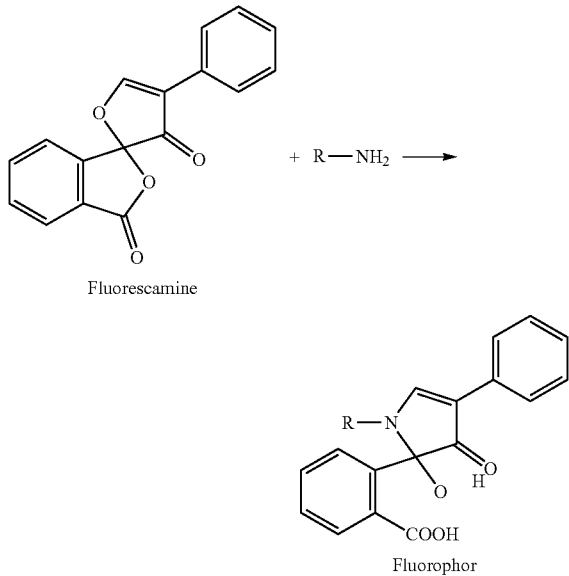

Fluorescamine reacts with the primary amino groups found in terminal amino acids and the e amine of lysine to form fluorescent pyrrolinone type moieties. In some embodiments, the protein assay of Udenfriend [Udenfriend, S., Stein, S., Bohlen, P., Dairman, W., Leimgruber, W. & Weigele, M. Fluorescamine: A Reagent for Assay of Amino Acids, Peptides, Proteins, and Primary Amines in the Picomole Range Science 178 871-872 (1972)], may be modified for microplates as described by Lorenzen [Lorenzen, A. & Kennedy, S. W. A Fluorescence-Based Protein Assay for Use with a Microplate Reader Anal. Biochem. 214 346-348 (1993)] and as discussed previously.

Various buffers may be used for thiolation with Traut's reagent. In some embodiments, the buffer is preferably a phosphate buffered saline (PBS) solution (PBS, Thermo Fisher). In other embodiments, a 0.1M borate buffer adjusted to pH 8 may be used for thiolation. Other buffers devoid of primary amines that maintain solubility of the nanostructure (e.g., carrier protein) may also be used. Traut's reagent is very stable in acidic or neutral buffers that are devoid of primary amino groups. Even in alkaline conditions, hydrolysis is slow compared to the rate of reaction with primary amines. Because hydrolysis is slow relative to the amine reaction rate, thiolation with Traut's reagent does not require as large a molar excess of reagent as other types of modification reagents, such as SATA.

In some embodiments, the nucleophilic species (e.g., the thiol) may be used to further functionalize the nanoparticle (e.g., the nanostructure, the enzymatic molecule, or both) with a hydrophilic species. In some embodiments, the nucleophile of the nanoparticle is used to attack an electrophilic group (e.g., a carboxylic acid, epoxide, succinimidyl group, etc.) situated on a hydrophilic species thereby coupling the hydrophilic species to the nanoparticle. In some embodiments, this functionalization can be performed in the presence of coupling reagents to facilitate coupling (e.g., EDC, DCC, etc.).

In some embodiments, the hydrophilic species is coupled to albumin via a thiol of the albumin and a maleimide of the hydrophilic species, as shown below:

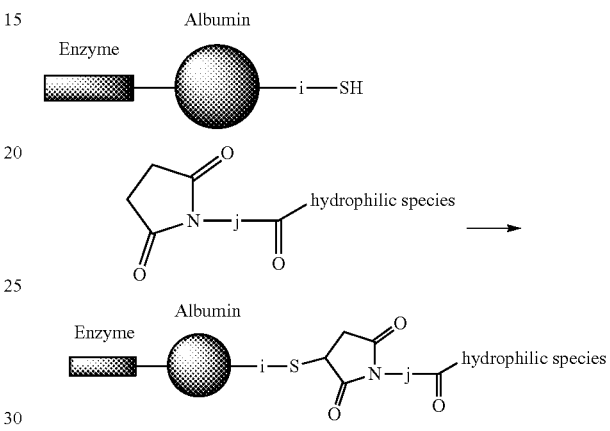

wherein i is selected from the group consisting of —C(O)(CH$_2$)$_r$— and —N=CH(CH$_2$)$_r$—, wherein r is an integer ranging from 1 to 10 and wherein j is —(CH$_2$)$_s$—, wherein s is an integer ranging from 1 to 10.

In some embodiments, the nanostructure may be decorated with one or more hydrophilic polymers selected from the group consisting of PEG (e.g., PEGylated), poly(N-isopropylacrylamide) (PNIPAM), polyacrylamide (PAM), polyvinyl alcohol (PVA), polyacrylic acid, polyethyleneimine (PEI), poly(2-oxazoline), poly(vinylpyrrolidone), and copolymers thereof.

In some embodiments, as shown below, the nanostructure is PEGylated. In some embodiments, as shown below, the nanostructure is PEGylated using a maleimide of PEG. For example, human serum albumin may be modified by reacting 2-iminothiolane (IMT) with the amino groups of Lys to create active thiol groups and then binding the active thiol groups with maleimide-terminated poly(ethylene glycol) (PEG).

In some embodiments, the quantitative fluorescence-based assays discussed above may be utilized to tune the number of free lysine residues remaining and the number of sulfhydryls ready for functionalization, e.g., with MAL-PEG conjugation. After functionalization, the number of unreacted sulfhydryls may be determined by labeling them with fluorescein-5-maleimide in excess and filtering unreacted fluorescein-5-maleimide prior to quantitation. The degree of labeling with fluorescein-5-maleimide may be determined either by absorption using (ε'=fluor molar extinction coefficient: 68,000 M-1 cm-1) or by fluorescence emission (excitation at 491 nm and emission at 518 nm).

In order to retain the enzyme-albumin complex in a polymer network, the bonds between the linker and the enzyme-albumin complex and within the polymer network preferably have little to no biodegradation. In some embodiments of the present invention, acrylate bonds are preferably used within the polymer network, and a stable thioether linkage between a polymer linker and the enzyme-albumin complex is preferably used to immobilize the complex in the polymer network. In some embodiments, a maleimide-activated PEG, which may react with the thiols of cysteine residues or the sulfhydryls derived from Lys residues, is preferably used to form stable thioether linkages because it exhibits a much higher stability against hydrolysis a NHS ester of PEG acid.

In some embodiments, the one or more of the hydrophilic species further comprises a polymerizable unit (e.g., an acrylate, methacrylate, etc.). In some embodiments, the hydrophilic species and polymerizable unit are functionalized to the nanoparticle using maleimide-PEG-methacrylate (mal-PEG-MA) as shown below:

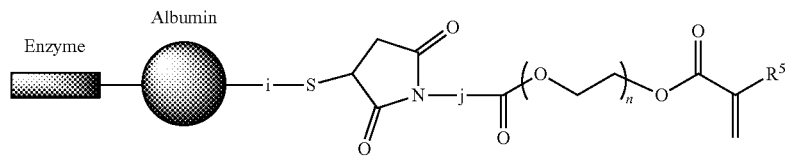

wherein n is an integer ranging from 1 to 1000 and wherein $R^5$ is selected from the group consisting of $—C_{1-4}alkyl$ and H.

The extent of acryl group coupling to the macromer complex may be monitored using, e.g., $^1H$ NMR. Alternatively, an iodine (Wijs solution) assay, as disclosed in Lubrizol Test Procedure, TP-TM-005C, may be used to determine the number of acrylate groups coupled to the macromer complex. For example, a 10 mg sample may be dissolved in water and an excess of Wijs solution (0.1M iodine monochloride, Sigma Aldrich), for example, 50-60% excess of titrateable double bonds, added. The resulting solution is then incubated in the dark for about 30 minutes at room temperature. After further dilution with deionized water, 4-20 mL aqueous 1 M potassium iodide solution is added, and the resulting solution immediately titrated using 0.1 N sodium thiosulfate. 1-2 mL 1% aqueous starch indicator solution is added and the titration continued till completion. The iodine value then may be calculated to indicate the number of acrylate groups present in the sample.

In some embodiments, the polymerizable group of the hydrophilic species unit can be co-polymerized with a first enzymatic crosslinking solution to form an enzymatic nanogel:

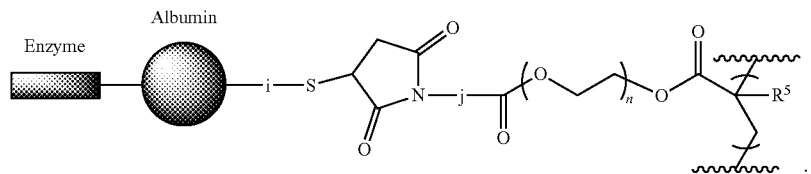

where  denotes an attachment to the nanogel matrix.

In some embodiments, the first enzymatic crosslinking solution comprises the following structure (Formula II):

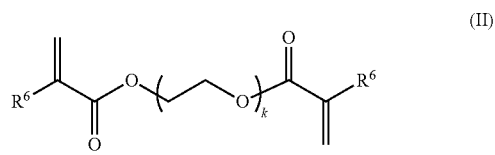

(II)

where e is an integer ranging from 1 to 10 and $R^2$ is selected from the group consisting of $—C_{1-4}alkyl$ and H. In some embodiments, the first crosslinking solution comprises a plurality of differing crosslinkers having the Formula II structure.

In some embodiments, the first crosslinking solution comprises TEGDA. In some embodiments, the crosslinking solution comprises TEGDA at a weight % (weight of TEGDA/weight of solution) ranging from about 0% to about 5%, about 5% to about 15%, about 15% to about 25%, about 25% to about 50%, about 50% to about 75%, or about 75% to about 100%.

In some embodiments, the first enzymatic crosslinking solution comprises the following structure:

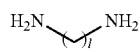

where l is an integer ranging from 1 to 10. In some embodiments, the first crosslinking solution comprises hexamethylenediamine (HMDA).

In some embodiments, the crosslinking solution comprises HMDA at a weight % (weight of HMDA/weight of solution) ranging from about 0% to about 5%, about 5% to about 15%, about 15% to about 25%, about 25% to about 50%, about 50% to about 75%, or about 75% to about 100%.

In some embodiments, the first enzymatic crosslinking solution comprises polymer additives. In some embodiments, the polymer additives are added to the crosslinking milieu to afford various copolymer enzymatic nanogels. For instance in some embodiments, the following monomer is added to the enzymatic nanoparticle and crosslinking solution:

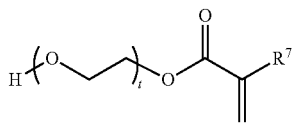

where $R^7$ is is selected from the group consisting of —$C_{1-4}$alkyl and H and t is an integer ranging from 1 to 1000.

In some embodiments, the first enzymatic crosslinking solution comprises PEG methacrylate (PEGMA). In some embodiments, the crosslinking solution comprises PEGMA at a weight % (weight of PEGMA/weight of solution) ranging from about 0% to about 5%, about 5% to about 15%, about 15% to about 25%, about 25% to about 50%, about 50% to about 75%, or about 75% to about 100%.

In some embodiments, the first enzymatic crosslinking solution comprises hydroxyethyl methylacrylate (HEMA). In some embodiments, the crosslinking solution comprises HEMA at a weight % (weight of HEMA/weight of solution) ranging from about 0% to about 5%, about 5% to about 15%, about 15% to about 25%, about 25% to about 50%, about 50% to about 75%, or about 75% to about 100%.

In some embodiments, the first enzymatic crosslinking solution comprises: HEMA, TEGDA, and PEGMA. In some embodiments, the first enzymatic crosslinking solution comprises: HMDA, TEGDA, and PEGMA. In some embodiments, the first enzymatic crosslinking solution comprises: HMDA, TEGDA, HEMA, and PEGMA.

In some embodiments, the first enzymatic crosslinking solution comprises the hemoglobin-albumin nanoparticle at a weight % (weight of nanoparticle/weight of solution) ranging from about 0% to about 0.5%, about 0.5% to about 1.5%, about 1.5% to about 2.5%, about 2.5% to about 5.0%, about 5.0% to about 7.5%, or about 7.5% to about 10.0%.

In some embodiments, the first enzymatic crosslinking solution comprises the enzyme-albumin nanoparticles at a weight % (weight of nanoparticle/weight of solution) ranging from about 0% to about 0.5%, about 0.5% to about 1.5%, about 1.5% to about 2.5%, about 2.5% to about 5.0%, about 5.0% to about 7.5%, or about 7.5% to about 10.0%.

In some embodiments, the crosslinking of the nanoparticle, crosslinker, and/or other additives comprising the first enzymatic crosslinking solution is performed in water or neat using UV light and a UV initiator (e.g., AIBN). In some embodiments, the enzymatic nanogel forms as a matrix of polymer that retains water within the matrix. In some embodiments, the enzymatic nanogel is a hydrogel particle. In some embodiments, the nanogel is a particle having a size of less than about 1 μm, about 0.5 μm, about 0.1 μm, about 0.05 μm, about or about 0.02 μm.

In some embodiments, the enzymatic nanogel can further be diffused in a liquid medium (i.e., an enzymatic nanogel fluid) to provide an emulsion, suspension, mixture, or solution. In some embodiments, the liquid of the enzymatic nanogel fluid comprises one or more of crosslinking agents and/or water. In some embodiments, the enzymatic nanogel fluid comprises a second crosslinker (or a second combination of crosslinkers). In some embodiments, the second crosslinker is also represented by Formula II. In some embodiments, the second crosslinker is EGDMA. In some embodiments, the second crosslinker is TEGDA. In some embodiments, the enzymatic nanogel fluid comprises EGDMA dissolved in TEGDA. In some embodiments, the enzymatic nanogel liquid with the nanogel is configured to flow into the glucose sensor tip via capillary action (see, e.g., FIG. 42). In some embodiments, the viscosity of the liquid medium and enzymatic nanogel is sufficiently low to allow this capillary uptake.

In some embodiments, the EDGMA is present at a weight % (weight of EGDMA/weight of solution) ranging from about 0% to about 5%, about 5% to about 15%, about 15% to about 25%, about 25% to about 50%, about 50% to about 75%, or about 75% to about 100%. In some embodiments, the TEGDA is present at a weight % (weight of TEGDA/weight of solution) ranging from about 0% to about 5%, about 5% to about 15%, about 15% to about 25%, about 25% to about 50%, about 50% to about 75%, or about 75% to about 100%.

In some embodiments, when the enzymatic nanogel is dispersed in dispensing solution at about 0.25 g gel wt./1 mL, the enzymatic nanogel fluid has a viscosity of less than about 2000 cP, about 1000 cP, about 500 cP, about 250 cP, about 100 cP, about 50 cP, about 25 cP, about 10 cP, about 5 cP, about 1 cP. In some embodiments, when the enzymatic nanogel is dispersed in the dispensing solution at about 0.25 g gel wt./1 mL, the enzymatic nanogel fluid is characterized by an ability to pass through a 20 g needle using less than 60 N pressure.

In some embodiments, as discussed above, the enzymatic nanogel fluid is configured to be dispensed as a solution into sub-millimeter features of the glucose sensor tip. Small features of the glucose sensor tip can be provided by supplying solutions of the enzymatic nanogel which are taken-up by spaces (e.g., channels, tunnels, paths, etc.) in molds (e.g., dye casts) by capillary action. The enzymatic nanogel fluid can fill these device features and, upon filling, be cured using UV light (in the presence of a second crosslinker) and/or concentrated (to remove any volatile liquids) to afford the enzymatic region 3830.

In some embodiments, where applicable, the second crosslinking step is performed while the enzymatic nanogel is suspended in the enzymatic nanogel fluid (e.g., comprising a second crosslinker, water, combinations thereof, etc.). In some embodiments, the second crosslinking step affords a hydrogel capable of rapidly transporting oxygen (e.g., diffusion controlled) from the oxygen conduit to other regions of the sensor tip.

Some embodiments pertain to forming a crosslinked enzymatic material using the methods disclosed above. In some embodiments, the enzymatic material comprises one or more of the following structures:

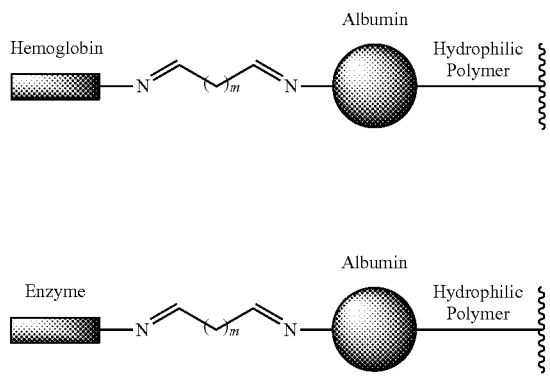

where the variables are as defined above and wherein "⌇" represents a hydrogel or nanogel matrix.

In some embodiments, the enzymatic material comprises one or more enzymatic nanostructures and hemoglobin-albumin nanostructures. In some embodiments, the enzymatic material comprises one or more of the following structures:

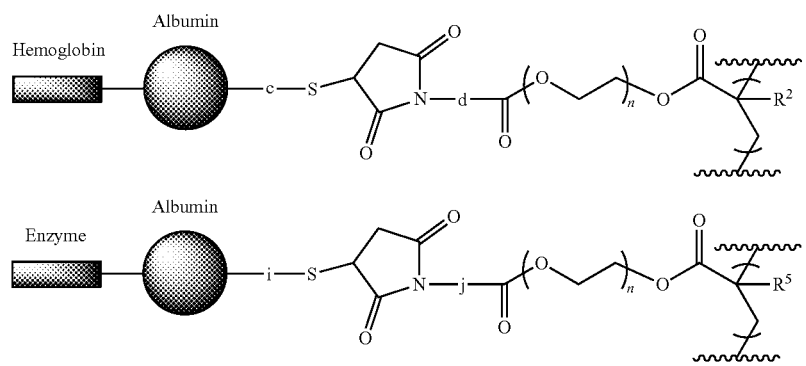

where the variables are as defined above and wherein "⌇⌇⌇" represents a hydrogel or nanogel matrix.

In some embodiments, the hydrogel or nanogel matrix of the enzymatic material is represented by one or more of the following:

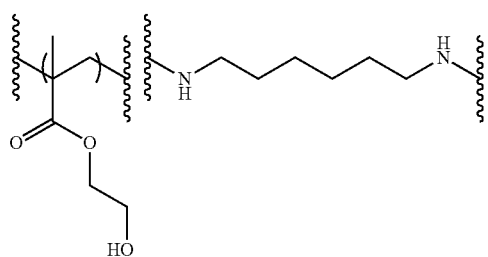

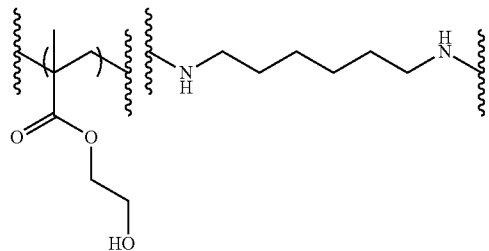

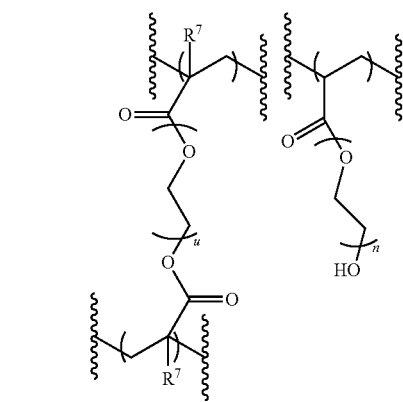

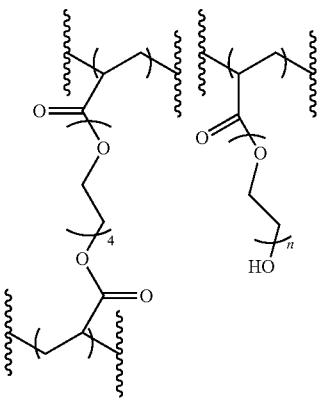

where u is an integer ranging from 1 to 10 and $R^7$ is selected from the group consisting of —$C_{1-4}$alkyl and H.

In some embodiments, the hydrogel or nanogel matrix of the enzymatic material is represented by each of the following:

where the variables are as defined above.

In some embodiments, the hydrogel or nanogel matrix of the enzymatic material is represented by each of the following:

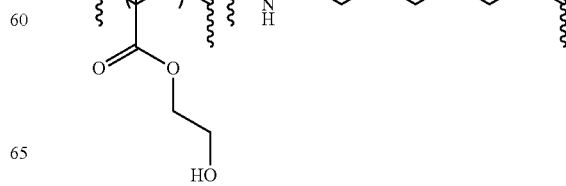

-continued

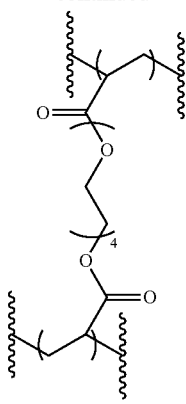

where the variables are as defined above.

In some embodiments, the hydrogel or nanogel matrix of the enzymatic material is represented by each of the following:

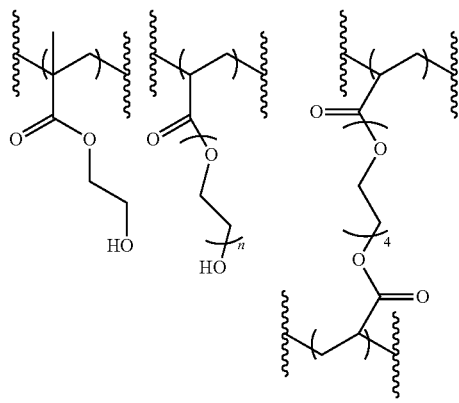

where the variables are as defined above.

In some embodiments, the enzymatic material comprises one of the above combinations where n is as described above, u is 4, and $R^7$ is H.

Thus, according to the present invention, controlling the extent of the crosslinking between the target macromer and nanostructure, and so the number of polymerization sites available to build the polymer network around the macromer-nanostructure complex, may be achieved by setting the number of residues that are available for crosslinking and by the molar ratios of target macromer and nanostructure and the amount of linker (such as glutaraldehyde).

For example, assume 59 lysine residues are available on the albumin. For a solution prepared with 1.244 μmols albumin, 0.050 mmols Traut's reagent, and 0.0376 mmol Acryl-PEG-MAL, the ratio of Lys residues to be converted with a sulfhydryl is 0.050 mmol/(59*1.244 μmols), which is approximately 68%. The reaction is allowed to proceed overnight. Assuming a theoretically complete reaction, the percentage of the sulfhydryl sites that are PEGylated is 0.0376 mmol/0.050 mmols, or approximately 75%. Therefore, 40 of the 59 Lys residues will be converted to sulfhydryls, and 30 of the 59 Lys residues will be PEGylated. As discussed previously, the actual number of Lys residues converted to sulfhydryls can be assayed, and the remainder of non-PEGylated sulfhydryls can be assayed, as the reactions proceed. These measurements allow one of ordinary skill in the art to adjust the reaction conditions to achieve a desired degree of Lys residues that are either converted to sulfhydryls or capped with a linker such as PEG.

The extent of the crosslinking of the nanostructure to the target macromer can be dictated then by the number of free sites on the nanostructure and the amount of the target macromer. For example, hemoglobin (Hb) may be added to the carrier albumin at a 3:1 molar ratio (e.g., 3.733 μmol Hb with 1.244 μmol Alb-MAL-PEG-Acryl) with excess glutaraldehyde. If, continuing with the example above, the number of free Lys residues on the carrier albumin is 19, and the number of free Lys residues on Hb that are modified by glutaraldehyde is 14 [Michael P. Doyle, Izydor Apostol and Bruce A. Kerwin, Glutaraldehyde Modification of Recombinant Human Hemoglobin Alters Its Hemodynamic Properties. Journal of biologic chemistry 274, 2583-2591. Jan. 22, 1999], then the average number of binding sites between Hb and the carrier albumin is approximately 6, or approximately 45% of the available sites. Adjusting the stoichiometric ratio of Hb to carrier albumin allows the percentage of the sites of the Hb that are crosslinked to the carrier albumin to be controlled. For example, increasing the molar ratio of Hb to carrier albumin to 5:1 would decrease the extent of Hb crosslinking by glutaraldehyde to approximately 27%.

This approach thus allows one to control the extent of crosslinking of a target macromer (e.g., hemoglobin, GOx, CAT) with a nanostructure (e.g., albumin) using available crosslinking sites (e.g., Lys residues on carrier albumin) and the number of target macromers that are crosslinked to a nanostructure. The PEGylated (hydrophilic polymer species functionalized) crosslinking sites include a polymerizable unit (e.g., Acryl) to which additional monomers may be linked and crosslinked, so the number of polymerization sites available for building a polymer network around a macromer-nanostructure complex may also be controlled using the approach of the present invention.

The macromer-nanostructure complex may be polymerized with a network of biocompliant (linear) monomers (such as HEMA and PEGMA) and crosslinker monomers (such as TEGDA and EDGMA). Additionally, the polymer network can be modified by incorporation of a hydrophilic compounds, such as methacrylic acid (MAA) or acrylic acid (AA). The resulting polymer network around the macromer-nanostructure complex primarily determines the bulk properties of the active hydrogel regions of the biosensor. For example, the polymerization of HEMA may be realized in the presence of acrylic acid (AA) in order to enhance the hydrophilicity of the active hydrogel; however, incorporation of a hydrophilic compound may also decrease the mechanical strength of the active hydrogel. In order to avoid the hydrosolubilization of the hydrogel, a crosslinker, such as TEGDA, that can form stable, non-biodegradable bonds, may be incorporated with the crosslinking solution.

Typically, each linear monomer, crosslinker and/or hydrophilic compound incorporated is first purified, for example by passing through the exchange ion columns, to remove any impurities that may inhibit the polymerization/crosslinking reaction. A hydrophilic compound may be incorporated into a crosslinking solution at a weight % (weight of hydrophilic compound/weight of solution) up to about 5%, to about 10%, to about 15%, to about 20%, to about 25%, to about 30% or to about 35%. A crosslinker may be incorporated in a molar % of up to about 0.5% (mol/mol linear monomer). Other components, such as an initiator (e.g. tetramethylethylenediamine (TEMED)) and/or an activator (e.g., ammonium persulfate (APS)), may be added into the crosslinking solution.

The characteristics of the polymer network around the macromer-carrier complex, and so the characteristics of the final active hydrogel, can be adjusted by the ratios of linear and crosslinking monomers. The ratio of the monomers to the macromer-carrier complex increases the extent of the polymer network that can encompass the macromer-carrier complex. By adjusting the relative amounts of linear and crosslinking monomers, the porosity and permeability of the active hydrogel matrix may be adjusted. In general, increasing the relative amount of crosslinker will decrease the pore size in the active hydrogel and so decrease its permeability to solutes. With more extensive crosslinking, the extent of water absorption and swelling be limited, and an increase in hydration time will also be observed. Thus, the relative ratios of monomers (linear and crosslinker), as well as the relative amount of hydrophilic compounds, can be used to adjust the permeability of the hydrogel network formed from the nanogel particles.

For example, a nanogel particle may be formed by crosslinking Albumin-GOx-CAT-PEG-Acryl (this chemical formula is intended to include multiple repeats of GOx, CAT, PEG-Acryl on a single albumin molecule) with HEMA, PEGMA and TEGDA. In some embodiments, the nanogel particle may comprise: GOx:Albumin in a molar ratio of about 10 to 0.5:1, or about 5 to 1:1; CAT:Albumin in a molar ratio range of about 2 to 0.02:1, or about 1.5 to 0.05:1; PEG-Acryl:Albumin in a molar ratio range of about 30 to 2:1, or about 10 to 2:1; HEMA:Albumin in a molar ratio range of about 400 to 40:1, or about 200 to 40:1; PEGMA: HEMA in a molar ratio range of about 10 to 2:1, or about 10 to 4:1; and (HEMA+PEGMA):TEGDA in a molar ratio range of about 200 to 20:1, or 150 to 50:1.

In another example, a nanogel particle may be formed by crosslinking Albumin-Hb-PEG-Acryl (this chemical formula is intended to include multiple repeats of Hb and PEG-Acryl on a single albumin molecule) with TEGDA. In some embodiments, the nanogel particle may comprise: Hb:Albumin in a molar ratio range of about 20 to 1:1, or about 10 to 1:1; PEG-Acryl:Albumin in a molar ratio range of about 40 to 4:1, or about 30 to 10:1; and TEGDA:PEG in a molar ratio range of about 3 to 0.1:1, or about 2 to 0.5:1.

Nanogel particles according to the present invention are used as a precursor, or interim, to form the active hydrogel on the sensor. One advantage to the use of the nanogel particles according to the present invention is that the activity and chemical and structural properties (e.g., particle size, number of available acryl-terminus sites, etc.) of the nanogel particle can be assayed and characterized in a consistent manner prior to the formation of the active hydrogel areas on the sensor. Moreover, the activity of the active hydrogel areas may be adjusted in a consistent, measurable way by manipulating and characterizing the polymer network around the macromer-nanostructure complex. For example, the bulk enzymatic reaction of glucose oxidase follows the ping-pong kinetics, while alternative effective reaction kinetics can be achieved by incorporation of a diffusion limiting polymer network around a core enzymatic-carrier complex to limit substrate availability to the enzymatic reaction.

Some embodiments pertain to a dispensable, UV-curable enzyme-albumin nanogel solution, configured to form a hydrogel upon UV curing, the enzyme-albumin nanogel comprising a hemoglobin-albumin nanoparticle, wherein the hemoglobin and albumin are interconnected with diimine linkers, wherein the hemoglobin-albumin nanoparticle is coupled to poly(ethylene glycol) (PEG) through a thio-linkage, and wherein the hemoglobin-albumin nanoparticle is functionalized to the nanogel matrix via a PEG-based linker and glucose oxidase-albumin nanoparticles, wherein the glucose oxidase and albumin are interconnected with diimine linkers, wherein the glucose oxidase-albumin nanoparticle is coupled to poly(ethylene glycol) (PEG) through a thio-linkage, and wherein the glucose oxidase-albumin nanoparticles is functionalized to the nanogel matrix via a PEG-based linker.

In some embodiments the dispensable, UV-curable enzyme-albumin nanogel solution further comprises a catalase-albumin nanoparticle, wherein catalase and albumin are interconnected via diimine linkers, wherein the catalase-albumin nanoparticle is coupled to poly(ethylene glycol) (PEG) through a thio-linkage, and wherein the catalase-albumin nanoparticle is functionalized to the nanogel matrix via a PEG-based linker.

In some embodiments, the crosslinked, enzymatic-nanoparticle-based material, comprising a hydrogel matrix; an enzyme-functionalized albumin nanoparticle having an albumin molecule covalently linked to at least one enzyme via a diimine-based linker, wherein the enzyme-albumin nanoparticles are PEGylated, and wherein the enzyme-albumin nanoparticles are functionalized to a hydrogel matrix and a hemoglobin-albumin nanoparticle having an albumin molecule covalently linked to at least one hemoglobin molecule via a diimine linker, wherein the hemoglobin-albumin nanoparticle is PEGylated, and wherein the hemoglobin-albumin nanoparticles are functionalized to the hydrogel matrix via a PEG-based linker.

In some embodiments, the crosslinked, enzymatic-nanoparticle-based material described above, have a p50 of at least about 0.1 kPa, about 1.0 kPa, about 1.5 kPa, about 2.0 kPa, about 2.5 kPa, or about 3.5 kPa.

In some embodiments, after curing or concentrating, the crosslinked, enzymatic-nanoparticle-based material has a storage modulus of at least about 8 GPa at a total material concentration of less than about 10 mg/mL. In some embodiments, after curing or concentrating, the crosslinked hemoglobin-based material has a storage modulus of storage modulus of at least about 0.01 GPa, about 0.1 GPa, 0.5 GPa, 1.0 GPa, 2.0 GPa, 4.0 GPa, or about 6.0 GPa at a total material concentration of about 10 mg/mL.

In some embodiments, the crosslinked, enzymatic-nanoparticle-based material has a water content of at least about 70%, about 80%, about 90%, about 95%, about 97.5%, about 99%, or about 99.5% of the total dry weight of the crosslinked hemoglobin-based material.

Some embodiments pertain to preparing a dispensable, UV-curable oxygen-sensing mixture, comprising an analyte detecting dye. In some embodiments, the analyte is oxygen and the dye is an oxygen detecting dye. In some embodiments, the dye is luminescent. In some embodiments, the dye is a porphyrin dye. In some embodiments, the porphyrin dye is configured to reversibly bind oxygen and to emit light when oxygen is bound. In some embodiments, the porphyrin dye is platinum tetrakis pentafluorophenyl porphyrin.

In some embodiments, the dye is prepared in a crosslinkable solution that can be distributed adjacent to or within the enzymatic layer of the glucose sensing tip. In some embodiments, the dye is distributed within a dispensable solution of polymer precursors. In some embodiments, the dispensable solution of polymer precursors is configured to crosslink or polymerize when exposed to UV light. In some embodiments, the solution comprises a polymerization initiator.

In some embodiments, the dispensable polymer precursor solution comprises one or more vinyl containing monomers. In some embodiments, the vinyl containing monomer is selected from the group consisting of: vinyl alcohol and vinyl acrylate. In some embodiments, the dispensable polymer precursor solution comprises styrene. In some embodiments, the styrene monomer (or other vinylic monomer or mixture of monomers) is present in the polymer precursor solution at a weight % (e.g., wt styrene/wt precursor solution) ranging from about 0% to about 5%, about 5% to about 15%, about 15% to about 25%, about 25% to about 50%, about 50% to about 75%, or about 75% to about 100%. In some embodiments, the dispensable polymer precursor solution comprises acrylonitrile. In some embodiments, the acrylonitrile monomer is present in the polymer precursor solution at a weight % (e.g., wt acrylonitrile/wt precursor solution) ranging from about 0% to about 5%, about 5% to about 15%, about 15% to about 25%, about 25% to about 50%, about 50% to about 75%, or about 75% to about 100%.

In some embodiments, the dispensable polymer precursor solution comprises a silanol. In some embodiments, mixtures of silanols are used. In some embodiments, the silanol is present in the polymer precursor solution at a weight % ranging from about 0% to about 5%, about 5% to about 15%, about 15% to about 25%, about 25% to about 50%, about 50% to about 75%, or about 75% to about 100%.

In some embodiments, the dispensable polymer precursor comprises an acrylate monomer selected from the group consisting of: HMDA, TEGDA, HEMA, and PEGMA. In some embodiments, mixtures of multiple acrylates are used. In some embodiments, the acrylate(s) are present in the polymer precursor solution at a weight % ranging from about 0% to about 5%, about 5% to about 15%, about 15% to about 25%, about 25% to about 50%, about 50% to about 75%, or about 75% to about 100%.

In some embodiments, the dye is present in the polymer precursor solution at a weight % ranging from about 0% to about 0.5%, about 0.5% to about 1.5%, about 1.5% to about 2.5%, about 2.5% to about 5.0%, about 5.0% to about 7.5%, or about 7.5% to about 10.0%.

In some embodiments, the dispensable polymer precursor solution comprises one or more of the porphyrin dye, styrene, the silanol, and acrylonitrile.

In some embodiments, the dispensable polymer precursor solution (or emulsion) is of low viscosity. In some embodiments, the precursor solution has a viscosity of less than about 2000 cP, about 1000 cP, about 500 cP, about 250 cP, about 100 cP, about 50 cP, about 25 cP, about 10 cP, about 5 cP, about 1 cP, or about 0.5 cP.

In some embodiments, after curing the oxygen sensing material has a storage modulus of at least about 8 GPa at a total material concentration of less than about 10 mg/mL. In some embodiments, after curing or concentrating, the oxygen sensing material has a storage modulus of at least about 0.01 GPa, about 0.1 GPa, 0.5 GPa, 1.0 GPa, 2.0 GPa, 4.0 GPa, or about 6.0 GPa at a total material concentration of about 10 mg/mL.

In some embodiments, an oxygen sensor polymer system formed using one of the polymer precursor solutions described above has high quantum efficiency. In some embodiments, the quantum efficiency is greater than about 50%, about 40%, or about 20% of the polymer system. In some embodiments, the quantum efficiency is between about 20% and about 40%.

In some embodiments, the polymer precursor solution is rapidly curable. In some embodiments, the polymer precursor solution cures in less than about 60, about 40, about 30, about 20, about 15, about 10, or about 5 seconds upon exposure to UV light.

In some embodiments, the resultant polymer is a composite of one or more of the following repeat units:

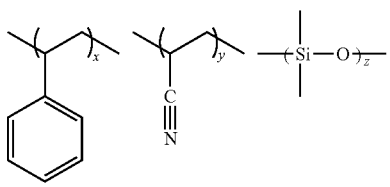

Any methods of manufacturing the oxygen conduit, enzymatic region, and oxygen sensing region can include a variety of different steps discussed above. For purposes of summarizing the disclosure, certain aspects, advantages and features of the inventions have been described herein. It is to be understood that not necessarily any or all such advantages are achieved in accordance with any particular embodiment of the inventions disclosed herein. No aspects of this disclosure are essential or indispensable.

Each reference cited in the discussion above is hereby incorporated by reference in its entirety.

Optical Enzymatic Sensor

Disclosed herein are example embodiments of optical glucose sensors. At least one advantageous feature of the disclosed optical glucose sensors is that they are configured to reduce mechanical tolerance requirements in manufacture and operation. The disclosed sensors include a plurality of waveguides configured to direct light to and from a target material, such as an oxygen sensing polymer. Excitation waveguides can receive light from an excitation source in a transmitter that is housed separately from the sensor. Similarly, emission waveguides can deliver light from the sensor to a detector on the transmitter. Proper alignment of such a sensor with the transmitter can determine whether excitation light enters the sensor and reaches the target material as well as whether light emitted from the target material reaches a detector. Accordingly, the sensors disclosed herein are configured to increase the tolerances for achieving proper alignment through the use of total internal reflections at boundaries of materials. The orientation of these boundaries is such that the transmitter with the light sources and detectors can be attached to the sensor without being precisely aligned while still maintaining optical connection with the sensor. This can reduce costs and complexity associated with manufacture of such sensors.

Also disclosed herein are example systems that include a disposable sensor and a separately housed transmitter with an emitter array and an emission detector. An optical interconnect couples the optics of the disposable sensor to the optics of the transmitter. The transmitter is configured to couple to a portion of the sensor that extends out of a patient when in use. Alignment pins on the transmitter can facilitate correct alignment with the optics of the sensor. The sensor and optical interconnect are configured so that the transmitter can be aligned with relatively large variations in position while still achieving suitable optical alignment. Accordingly, optical connections conveying excitation and emission signals between the transmitter and the sensor can be readily made without precise alignment of the optical pathways.

The disclosed optical glucose sensors are advantageously configured to operate using luminescent lifetime measurements. Luminescent lifetime measurements provide advantages relative to other optical sensors such as intensity- or amplitude-based measurements. For example, lifetime measurements can be relatively immune to background fluorescence or luminescence. As another example, lifetime measurements can be relatively immune to intensity or amplitude variations associated with changes in optical coupling or photobleaching of a target sensing molecule. Lifetime measurements may be challenging, however, due at least in part to nanosecond lifetimes making it difficult to perform such measurements with small, inexpensive instrumentation. However, the disclosed optical glucose sensors utilize target materials that have lifetimes on the order of microseconds rather than nanoseconds, making reliable measurements possible using relatively small and inexpensive materials, such as optical sources and detectors. Furthermore, lifetime measurements of oxygen also make possible factory calibration and potentially calibration-free optical sensors for oxygen sensing due at least in part to the lifetime of the relevant materials being based on fixed, quantum chemistry properties of the material (e.g., an oxygen sensing polymer).

Other advantages of the disclosed optical glucose sensors include a relatively high sensitivity to low glucose concentrations. The signal to noise ratio of the lifetime measurement does not generally diminish with decreasing glucose concentrations. The disclosed oxygen sensing polymer, for example, can enable oxygen levels to be measured with relatively high sensitivity from ambient oxygen tissue concentrations to relatively small oxygen concentrations. This is due at least in part to the optical glucose sensor being a differential oxygen sensing device. For example, for low glucose levels, a difference between reference and working oxygen concentrations is small, but the optical lifetime measurements from the oxygen sensing polymer for the set of oxygen measurements is not generally diminished due to lower glucose concentration.

Other advantages of the disclosed optical glucose sensors include an ability to perform self-assessment tests prior to measurements. For example, the optical glucose sensors can include a relatively low power light source and a high power light source. The low power light source can be used to interrogate the sensor to determine whether a proper optical connection exists. If no proper optical connection exists, the transmitter can be configured to not emit light from the high power light source. This can increase the safety of a user by reducing or preventing the high power light source from potentially shining in the eye of a person when the transmitter is disconnected from the sensor. The optical glucose sensor can also advantageously be configured to provide an optical signal from the low power light source with a known lifetime decay to calibrate the transmitter and optical system before glucose measurements are made. The lower power light source can be configured so that the light from the light source is reflected by the target material instead of inducing a luminescent signal.

Optical Glucose Sensor Overview

The optical glucose sensors described herein are a part of a continuous glucose monitoring system. The monitoring system is generally an opto-enzymatic, percutaneous sensing system that utilizes a disposable sensor. The system includes an implantable optical sensor, a transmitter optically coupled to the sensor, an analysis engine, and a computing device. The disposable sensor contains a small percutaneous sensing element that is inserted/implanted into the tissue. The sensor is an optical-enzymatic sensor that provides interstitial fluid measurements of analytes, glucose for example, when optically interrogated with visible light. The sensor provides a measurement of the interstitial glucose based on the difference between an interstitial reference oxygen measurement and measurements of the oxygen remaining after a two-stage enzymatic reaction of glucose and oxygen. When implanted in the patient, the optical sensor can be in optical communication with the transmitter.

The optical sensor can include a sensor subassembly that is a polymer laminate structure connected to an optical interconnect component that interfaces with the transmitter. The top layer of the polymer laminate structure contains an oxygen conduit (e.g., a hemoglobin polymer matrix embedded within siloxane) to transport oxygen. The middle layer contains an enzymatic hydrogel to transduce glucose into changes in oxygen partial pressure, an oxygen sensing polymer (e.g., platinum-porphyrin immobilized in a hydrophobic oxygen permeable polymer) to transduce oxygen partial pressure into luminescent lifetime signals, and an optical circuit to direct light to interrogate the oxygen sensing polymer to obtain the luminescent signals. The optical circuit includes a miniaturized, structured waveguide with a plurality of optical channels connected to a plurality of contiguous oxygen sensing polymer volumes adjacent to the enzymatic hydrogel and at least one spatially-distinct oxygen sensing polymer volume adjacent to the oxygen conduit. The bottom layer of the sensor subassembly is a structural polymer (e.g., a robust biocompliant polymer film) for mechanical integrity.

The monitoring system generally works by determining lifetimes (e.g., decay rates) of luminescent emissions from the oxygen sensing polymer. For example, when the oxygen sensing polymer is excited with a suitable frequency of light, the porphyrin dye in the polymer matrix produces a strong luminescent emission. The lifetimes of the optical emissions are quantitatively correlated with the partial pressure of oxygen in the oxygen sensing polymer. The net oxygen consumed by the diffusion-limited reaction of glucose and oxygen is quantitatively correlated with the interstitial glucose concentration. The net oxygen consumed by the reaction is calculated as the difference in the oxygen concentration remaining after the reaction (in the presence of glucose) and a reference oxygen concentration (in the absence of glucose) ($O_{2\ reference} - O_{2\ remaining}$).

In use, the transmitter can be affixed to a patient's skin so that it is in optical communication with the sensor. The transmitter can provide one or more of the functions of: (1) optically interrogating the sensor, (2) processing the received optical sensor signals, (3) having the capabilities to control, power, and communicate, and (4) being configured to form a mechanical optical interconnect with the sensor. The transmitter of the monitoring system contains instrumentation to optically interrogate the optical sensor, a microprocessor to convert the raw optical signals into measurements, and a wireless transceiver to transmit the measurements to an external receiver. In some embodiments, the transmitter enables real-time data communication with other electronic devices such as smartphones. The transmitter includes optical excitation sources such as single stage laser diodes that emit 405 nm light corresponding to the peak absorption wavelength of a luminescent dye in the target material. The detector on the transmitter can be a multi-pixel, miniaturized silicon photomultiplier chip. The transmitter is configured to form a mechanical optical interconnect with the optical sensor. The transmitter is also configured to optically interrogate the sensor and to receive emitted light from the sensor to determine analyte concentrations. The transmitter can be configured to take measurements at any time interval, for example, every 30 seconds, or each minute and can therefore, provide real-time monitoring. The transmitter can be configured to transmit bursts of glucose readings to an analysis engine or other computing device. For example, the transmitter may transmit bursts of glucose readings every five minutes to an analysis engine. The analysis engine receives bursts of glucose readings from which it determines results, including time series glucose levels, trends, patterns, and alerts.

A portable computing device, such as a cell phone, wearable computing device, tablet, personal digital assistant, or other computing device may include an application that enables viewing of results from the analysis engine as well as sending queries. Alerts may be viewed on the portable computing device as well as system alarms (such as low battery).

Example Optics of Glucose Sensor

Figure 43A:
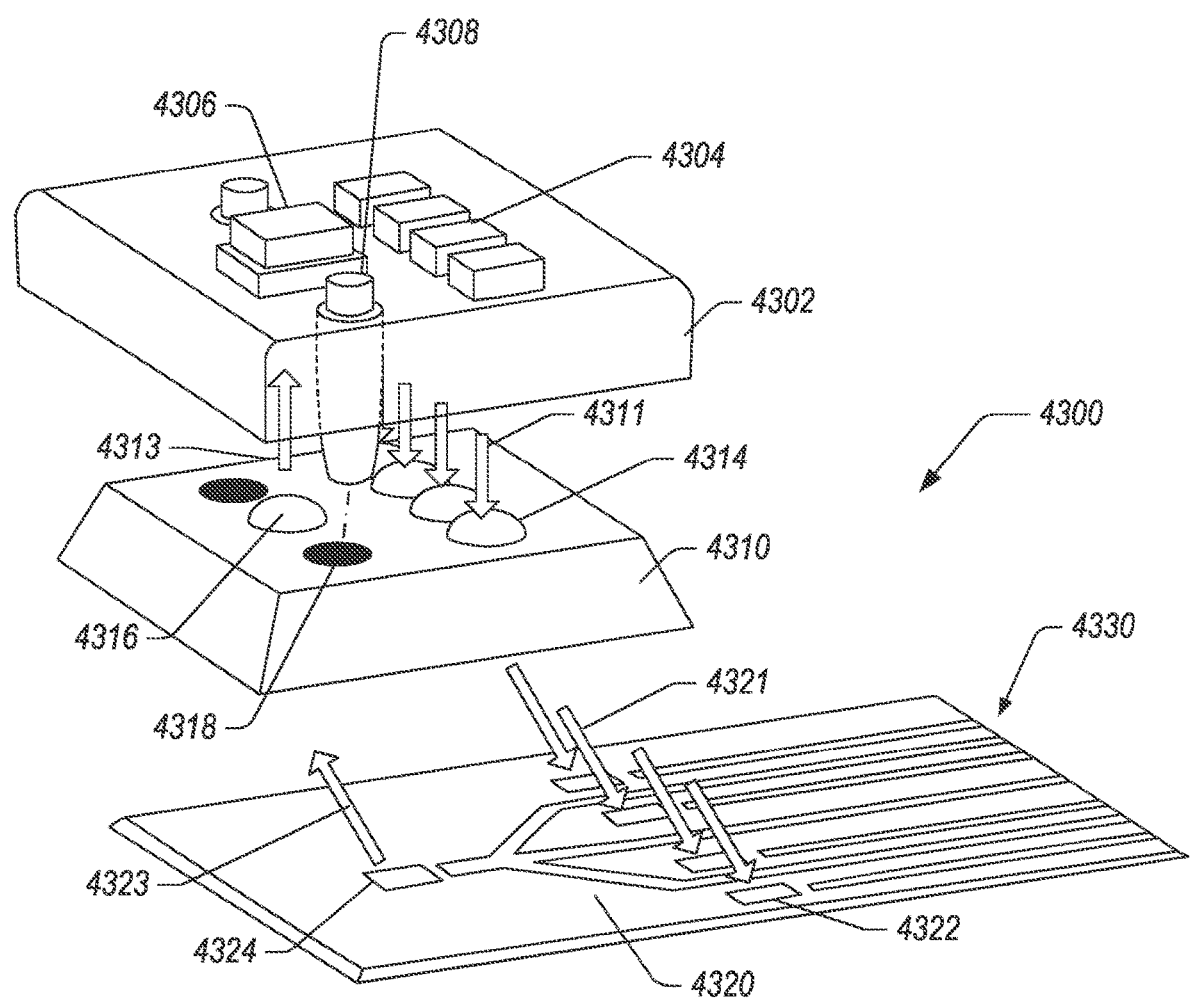
FIG. 43A illustrates an example optical glucose sensor configured to couple to an optical interconnect and configured to deliver light to and from a target material for glucose measurements, according to an embodiment of the present invention.

FIG. 43A illustrates an example optical glucose sensor 4300 configured to couple to an optical interconnect 4302 (e.g., housed in a transmitter) and configured to deliver light to and from a target material for glucose measurements. The optical glucose sensor 4300 mechanically and optically couples to the transmitter (not shown) by coupling to the optical interconnect 4302 using a sensor optical interface 4310 attached to a sensor body 4320. In some embodiments, the sensor optical interface 4310 is a chip bonded to the sensor body 4320.

The transmitter mechanically couples to the sensor 4300 through alignment pins 4308 on the optical interconnect 4302 that are configured to mate with alignment receptacles 4318 on the sensor optical interface 4310. The sensor optical interface 4310 can include features 4314 and 4316 configured to mate with or be complementary with optical features (such as lenses) on the optical interconnect 4302. In some embodiments, these features can assist in aligning the optical interconnect 4302 relative to the sensor optical interface 4310 as well. In some embodiments, the sensor optical interface 4310 includes optical elements (e.g., lenses) instead of or in addition to the excitation sources and optics 4304 and/or detector and optics 4306. The transmitter optically couples to the sensor 4300 through excitation sources and optics 4304 on the optical interconnect 4302 that are configured to transmit excitation light to waveguides 4330 on the sensor body 4320. The transmitter also optically couples to the sensor 4300 through a detector and optics 4306 on the optical interconnect 4302 that is configured to detect emission light from the waveguides 4330 on the sensor body 4320.

When interrogating the sensor 4300, the transmitter can produce excitation light 4311 and deliver that light to the sensor using the excitation sources and optics 4304. The excitation light 4311 is received at the sensor optical interface 4310 where it undergoes total internal reflection at an internal boundary between materials in the sensor optical interface 4310, as described in greater detail herein with reference to FIGS. 45A and 45B. The reflected excitation light 4321 arrives at the waveguide 4330 at an excitation light receiving element 4322, where it again undergoes total internal reflection to enter the waveguide 4330. In response to the interrogation, the transmitter can receive emitted light that can be analyzed to determine glucose levels. The emitted light 4323 exits the waveguide 4330 at an emission transmission element 4324 where it undergoes total internal reflection from the waveguide to the sensor optical interface 4310. Within the sensor optical interface 4310, the emitted light 4323 undergoes internal total reflection once again where the redirected emitted light 4313 is incident on the optics and detector 4306 on the optical interconnect 4302. As illustrated, the excitation optical path and the emission optical path are separate entering and leaving the sensor body 4320 through the sensor optical interface 4310. The optical paths are combined and separated in the sensor 4300 using the waveguides 4330. The waveguides 4330 can be made to be flexible so that when the sensor body 4320 bends (e.g., during and after insertion into a patient), the optical signals (e.g., excitation and emission light) are not substantially diminished.

As described in greater detail elsewhere herein, the sensor 4300 can be configured to have a low-mechanical tolerance optical interface between the sensor optical interconnect 4302 and the sensor body 4320 through the sensor optical interface 4310. Asymmetric geometries can be used at the optical interfaces between elements (e.g., the optical interconnect 4302, the sensor optical interface 4310, and the sensor body 4320) to decrease the sensitivity of the optical transmission efficiency on mechanical positioning of the optical interconnect 4302 with respect to the sensor elements (e.g., the excitation receiving elements 4322 and/or emission receiving elements 4324).

To decrease the effects of misalignment between the optical interconnect 4302 and the sensor body 4320, the sensor optical interface 4310, the excitation receiving elements 4322, and the emission receiving elements 4324 can be configured to have an increasing physical dimension orthogonal to the direction of light travel in at least one axis. This can decrease mechanical sensitivity in the axis of the change in the physical dimension. For example, to decrease sensitivity in the direction parallel to the optical axis in the waveguides 4330, the excitation receiving elements 4322 can be configured to have a wide collection aperture in the sensor body 4320 compared to the aperture of the light transmitted from the sensor optical interface 4310. Similarly, the sensor emission path can be configured to have a narrow emission aperture in the sensor body 4320 compared to the emission path receiving the light in the sensor optical interface 4310.

In some embodiments, the light path from the sensor optical interconnect 4310 into the sensor body 4320 is relatively shallow to decrease the sensitivity of positioning in at least one axis parallel to the direction of light travel in the waveguides 4330. For example, the angle of total internal reflection in the sensor body 4320 at the emission receiving element 4324 can be less than or equal to about 10 degrees, less than or equal to about 20 degrees, or less than or equal to about 30 degrees. The angle of total internal reflection in the sensor optical interface 4310 can be configured to be complementary to the total internal reflection in the emission receiving element 4324 to induce a targeted total angle change through sensor body 4320 and the sensor optical interface 4310. In some embodiments, the total change in direction of the optical path from the sensor body 4320 (e.g., from the waveguides 4330) to the optical interconnect 4302 can be about 90 degrees. A similar configuration can be implemented for the excitation pathways as well so that the total change in optical path direction is about 90 degrees while also achieving a relatively shallow angle of incidence entering the sensor body 4320 through the excitation receiving element 4322. In some embodiments, misalignment in the direction perpendicular to the optical path in the waveguides 4330 can be achieved using lenslets in the optical interconnect 4302 and/or on the sensor optical interface 4310. For example, these lenslets (e.g., the lenses that are part of the excitation sources and optics 4304 and/or the detector and optics 4306) can focus or collimate the light to and from the sensor body 4320. By reducing the sensitivity to mechanical misalignment, manufacturing costs and complexity can be reduced.

In some embodiments, the excitation receiving elements 4322 and/or the emission receiving elements 4324 can be wider than the waveguide 4330. For example, the receiving elements 4322, 4324 can be about 5 mm wide. In certain implementations, the receiving elements 4322, 4324 can be larger than the waveguides (e.g., wider and/or deeper), thereby having a relatively large volume making them easier to manufacture. In some implementations, the receiving elements 4322, 4324 can have an index of refraction that is the same or substantially the same as the waveguide 4330. In some embodiments, the optical interconnect 4302 has a relatively small exit aperture for excitation light 4311 that is delivered to the sensor optical interface 4310. In certain implementations, the excitation light 4311 is configured to enter the sensor optical interface 4310 collimated. In some embodiments, the optical interconnect 4302 has a relatively large exit aperture for emission light 4323 that leaves the sensor optical interface 4310. In certain implementations, the emission light 4311 is configured to enter the sensor optical interface 4310 collimated.

Figure 43B:
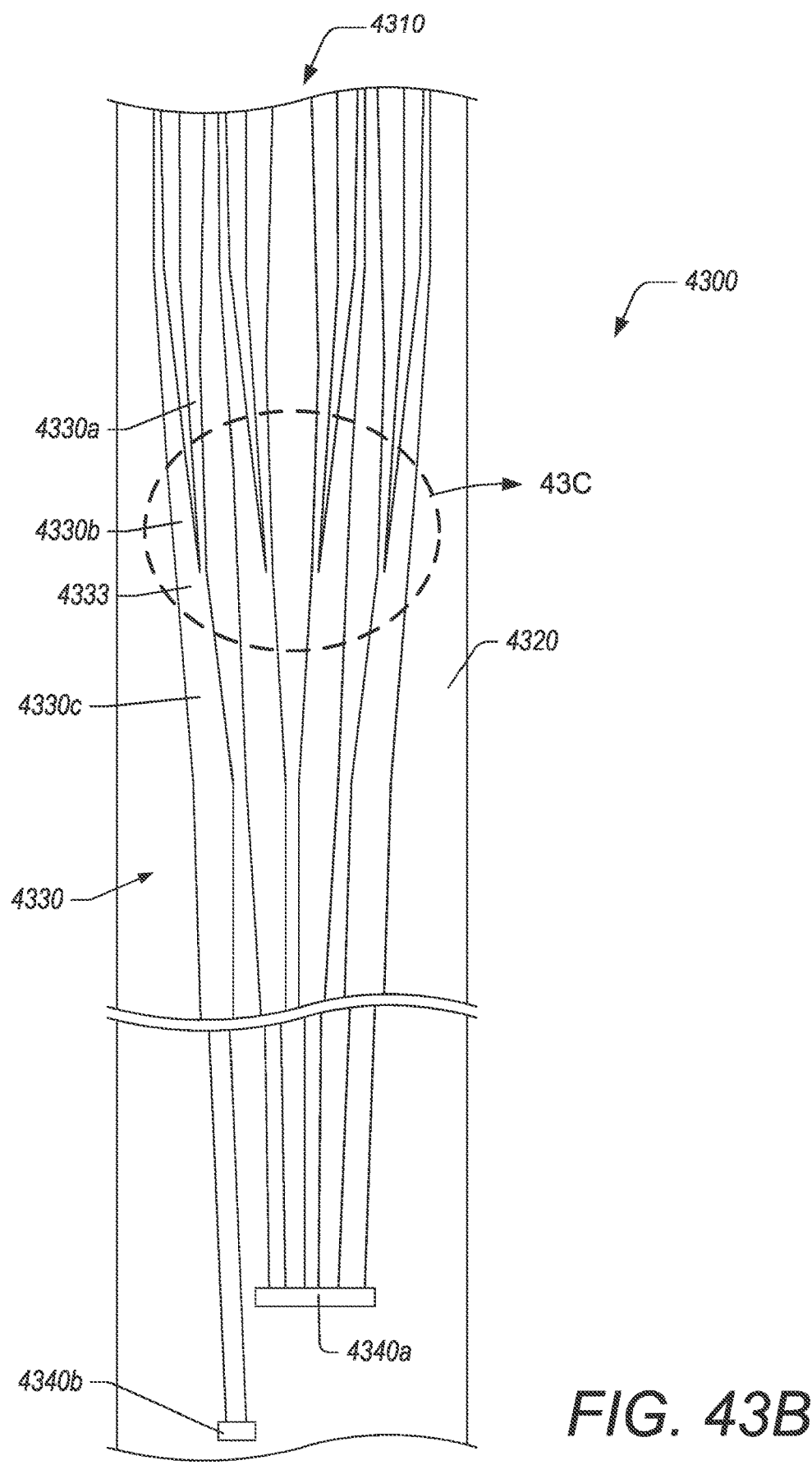
FIG. 43B illustrates the sensory body and waveguides of the example optical glucose sensor illustrated in FIG. 43A, according to an embodiment of the present invention.

FIG. 43B illustrates the sensory body 4320 and waveguides 4330 of the example optical glucose sensor 4300 illustrated in FIG. 43A. For the illustrated sensor 4300, excitation light travels from the top of the page in the waveguides 4330 towards the target materials 4340a, 4340b, which in some embodiments is an oxygen sensing polymer in the reaction region (4340a) and the reference region (4340b). Emitted light travels from the target materials 4340a, 4340b in the waveguides towards the top of the page. The waveguides 4330 each include an excitation path 4330a, an emission path 4330b, and a transmission path 4330c that all meet at a branching point 4333. An advantageous feature of the waveguides 4330 is that, at the branching point 4333, the cross-sectional area of the emission path 4330b is greater than the cross-sectional area of the excitation path 4330c so that a majority of the emitted light enters the emission path 4330b from the transmission path 4330c. In addition, the cross-sectional area of the emission path 4330*b* decreases while the cross-sectional area of the excitation path 4330*a* increases from the branching point 4333 towards the sensor optical interface 4310 (towards the top of the page). This allows for a larger target for excitation light entering the waveguides 4330, making it easier to sufficiently mechanically align the sensor optical interface 4310 and the optical interconnect 4302.

In use, the sensor 4300 and the optical interconnect 4302 operate to excite a target material 4340*a*, 4340*b* with excitation light. The target material can be, for example, a reaction chamber 4340*a* comprising an oxygen sensing polymer, a glucose inlet, and an enzymatic hydrogel with oxygen conduit; or a reference chamber 4340*b* comprising an oxygen sensing polymer with an oxygen conduit), as described in greater detail elsewhere herein with reference to FIGS. 38 and 40, for example. The excitation light/signal travels within the excitation path 4330*a* and the transmission path 4330*c* to an optrode or other optical sensing device to excite the target materials 4340*a*, 4340*b* (e.g., an oxygen sensing polymer). The target material 4340*a*, 4340*b* produce an emission or luminescent light signal that travels from the optrode to the emission path 4330*b* via the transmission path 4330*c*, some of which is described in greater detail herein with reference to FIGS. 20 and 40.

The reaction chamber 4340*a* includes an enzymatic hydrogel with three contiguous glucose reaction volumes (as previously described in detail herein with reference to FIG. 2B, for example), where an inlet regulates glucose entering into the first reaction volume. The three contiguous glucose reaction volumes inside the enzymatic hydrogel each have a dimension of approximately 0.1 mm×0.1 mm×0.1 mm, respectively. All three glucose reaction volumes contain the same enzymatic hydrogel material. In some embodiments, glucose diffuses through the inlet into the first reaction volume and undergoes a reaction with the glucose oxidase enzyme in the hydrogel. The unreacted glucose diffuses into the second reaction volume and undergoes another reaction with the glucose oxidase enzyme in the hydrogel, and the remaining unreacted glucose diffuses into the third glucose reaction volume where it is reacted. The rate of diffusion of glucose in each volume is determined by the permeability of the hydrogel. The oxygen conduit supplies the same oxygen flux to each progressive volume from a homogeneous oxygen concentration within the oxygen conduit that is transported through an oxygen permeable, hydrophobic membrane. The glucose oxidase and catalase enzymatic reactions consume oxygen in proportion to the amount of glucose in each reaction volume. The total oxygen remaining in the entire enzymatic hydrogel depends on the interstitial oxygen concentration that is supplied by the oxygen conduit and the diffusion limited oxygen consumption that is dependent on the interstitial glucose concentration.

To measure the oxygen concentration remaining in the enzymatic hydrogel, all three reaction volumes of the enzymatic hydrogel are in physical contact with an adjacent oxygen sensing polymer layer operating as a reference volume for oxygen measurements. The oxygen conduit is also in physical contact with an adjacent oxygen sensing polymer layer. The three glucose reaction portions of the target material 4340*a* reaction volume and the reference material 4340*b* reaction volume are interrogated optically through separate optrodes to excite the luminescent dye in each volume and to obtain oxygen measurements for the illuminated region of each one. For each optrode, there is a dedicated waveguide and optical source that generates and delivers the excitation pulse of light to each optical sensing polymer in in each volume in target material 4340*a* reference material 4340*b*. Each of these waveguides returns the luminescent emission signal from the oxygen sensing polymer in each volume, i.e., each of the three reaction volumes in the target material 4340*a* reference material 4340*b*, to a single common detector. The four oxygen sensing polymer volumes are each interrogated with a short 100 microsecond light pulse temporally-multiplexed with 400 microsecond luminescent emission observation periods after each pulse.

Figure 43C:
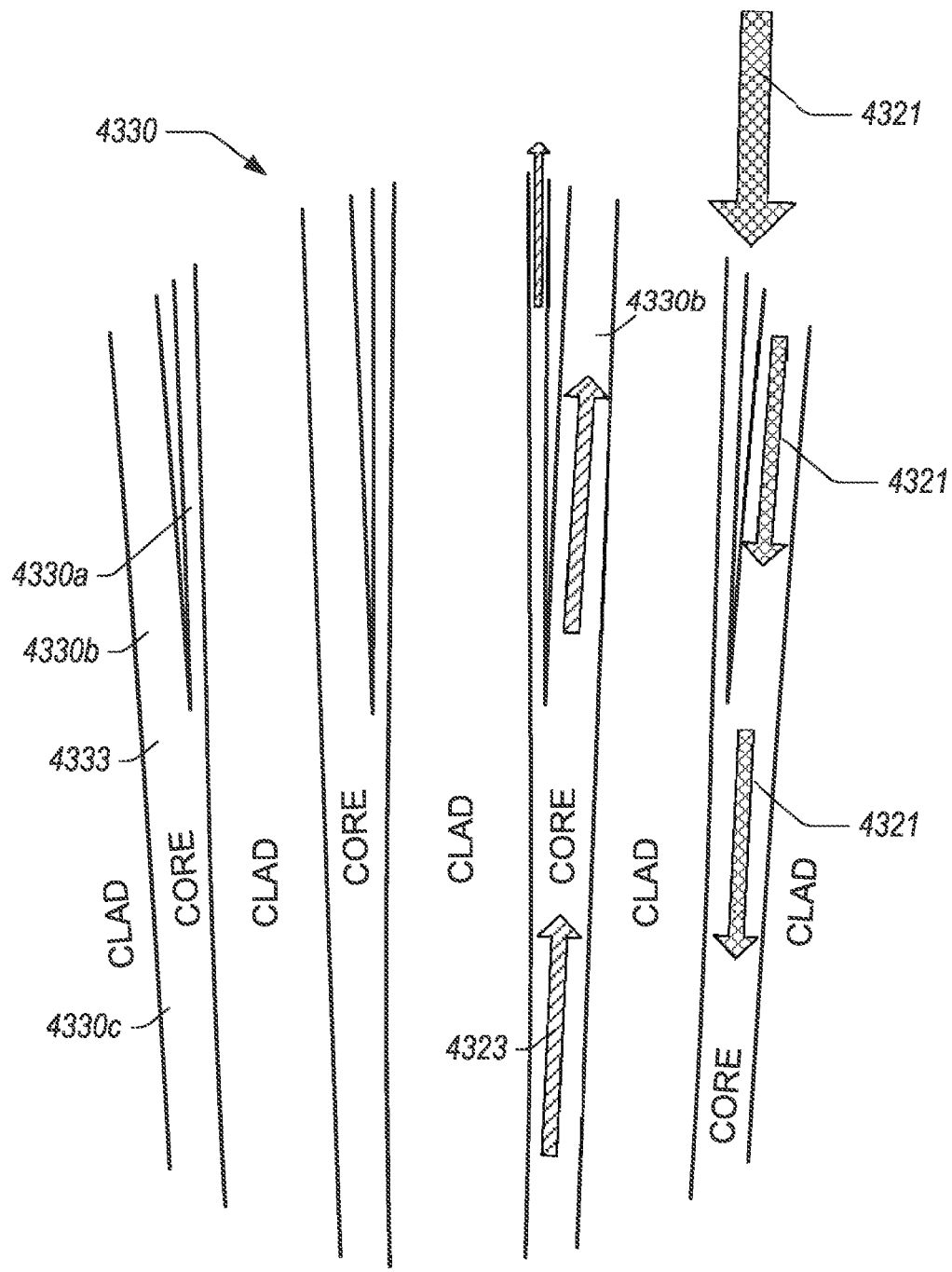
FIG. 43C illustrates a portion of the waveguides of the example optical glucose sensor of FIG. 43A where excitation and emission paths merge, according to an embodiment of the present invention.

FIG. 43C illustrates a portion of the waveguides 4330 of the example optical glucose sensor 4300 embodiment of FIG. 43A where excitation paths 4330*a* and emission paths 4330*b* merge. The branching point 4333 in each of the waveguides 4330 can act as an efficient beam splitter/combiner system. The excitation path 4330*a* and the emission path 4330*b* are separate entering and leaving the sensor body 4320 with respect to the sensor optical interface 4310. The excitation path 4330*a* is tapered, having its widest cross-sectional area at the sensor optical interface 4310 and its narrowest cross-sectional area moving towards the target materials 4340*a* and 4340*b*, in order to inject into a transmission path 4330*c* in the sensor body 4320 optical circuit. The waveguides 4330 can be configured to maintain the multimode light characteristics in the transition between transmission paths 4330*c* and excitation paths 4330*a* or between transmission paths 4330*c* and emission paths 4330*b*. The transmission path 4330*c* splits into two paths at the branching point 4333, the excitation path 4330*a* and the emission path 4330*b* where the width of the emission path 4330*b* is greater than the width of the excitation branch 4330*a* at the branching point 4333 in order to bias a majority of the emitted light 4323 into entering the emission path 4330*b*. In some embodiments, the ratio of the widths is approximately 4 to 1. In certain implementations, this beam splitter arrangement can result in about 81% efficiency in dividing light into appropriate paths, compared to about 50% efficiency for dichroic mirrors.

As can be seen in FIG. 43C, the geometry of the excitation path 4330*a* and emission path 4330*b* directs a majority of the excitation light 4321 into the excitation path 4330*a* and a majority of the emission light 4323 into the emission path 4330*b*.

Figure 44A:
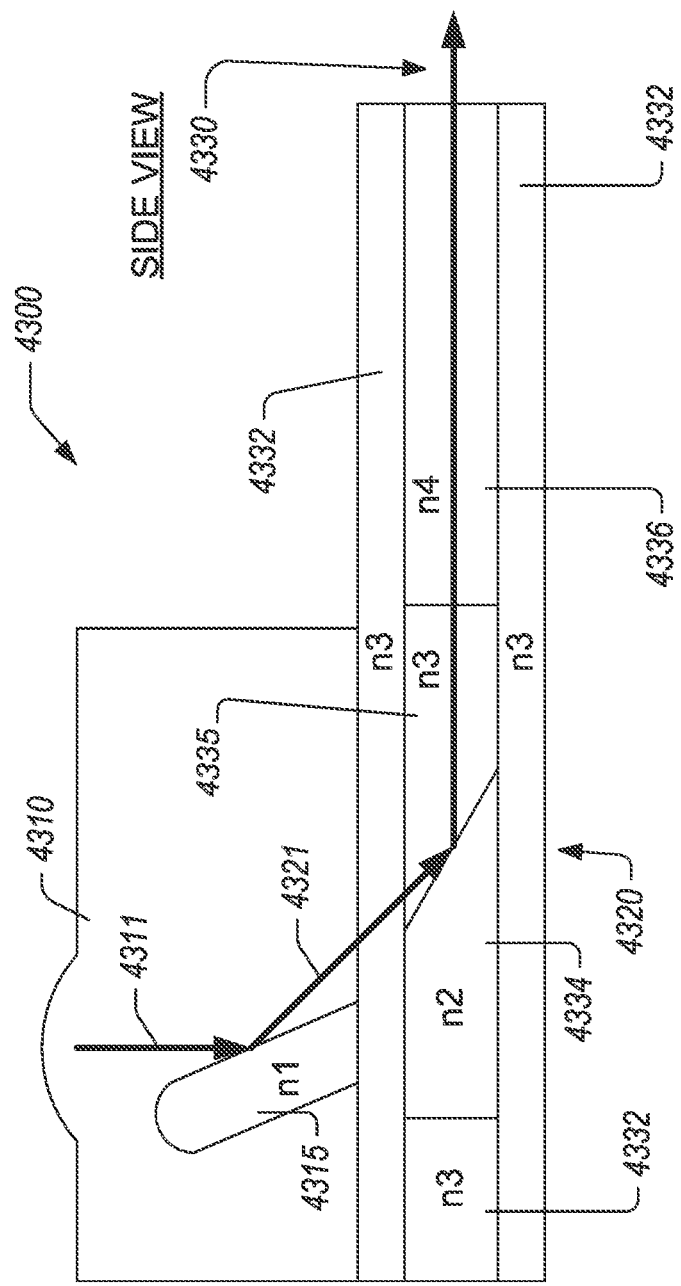
FIGS. 44A and 44B respectively illustrate a cut-away side view and a top view of an example sensor with relatively large misalignment tolerance parallel to an optical path in a waveguide, according to an embodiment of the present invention.
Figure 44B:
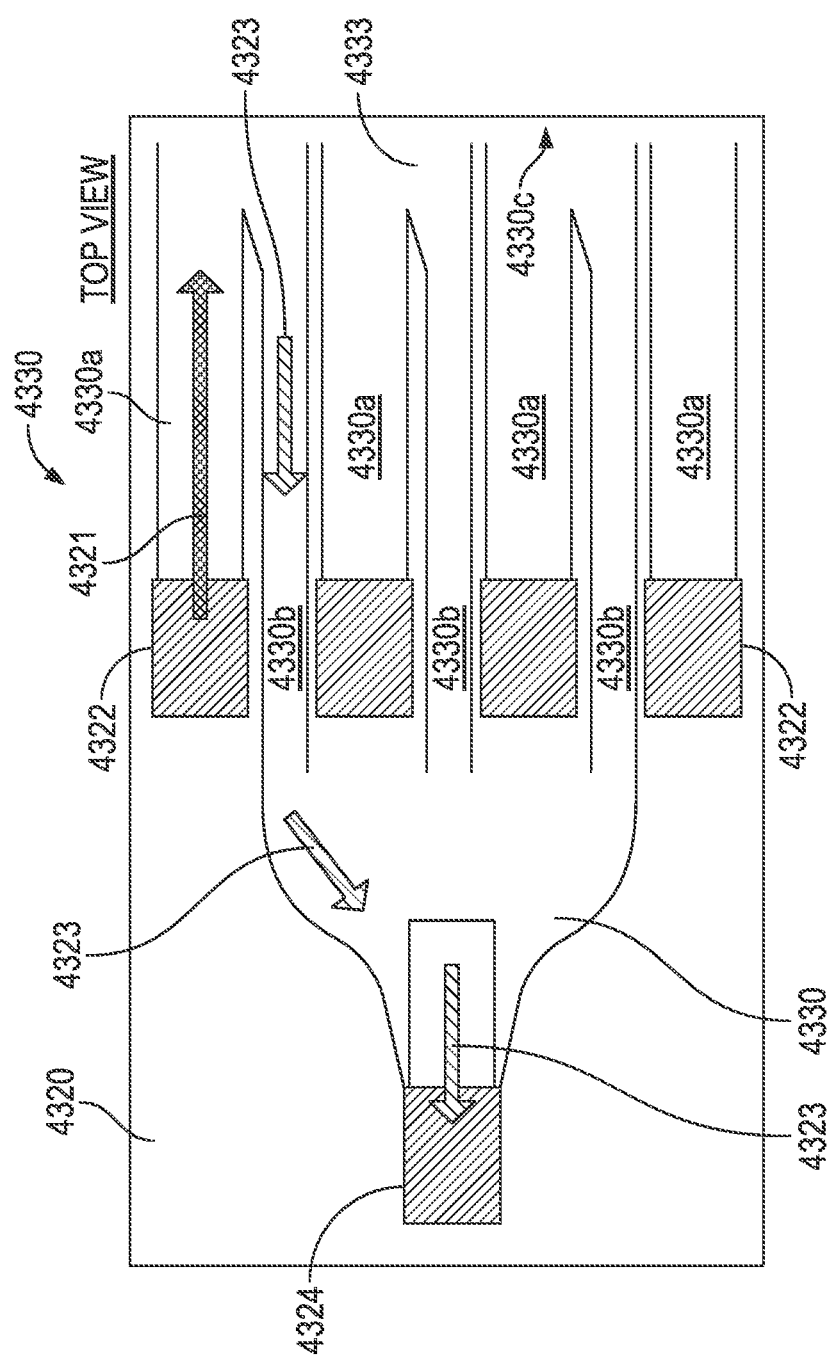

FIGS. 44A and 44B respectively illustrate a cut-away side view and a top view of an example sensor 4300 with a sensor optical interface 4310. The sensor 4300 can include a sensor waveguide system 4330 that is part of the sensor body 4320, the sensor waveguide system 4330 having a plurality of measurement waveguides. As illustrated in the cut-away side view of FIG. 44A, materials can be arranged and selected to direct excitation light 4311 (or emission light) through a sensor optical interface 4310 through two or more total internal reflections at boundaries between materials. For example, the sensor optical interface 4310 can include a first redirecting element 4315 comprising a first material with a first index of refraction n1, the first material adjacent to another material with a larger index of refraction. In certain implementations, the first index of refraction can be about 1 and the material of the first redirection element 4315 can be air. The index of refraction of the adjacent material can be configured to be approximately the same as for cladding 4332 to reduce reflections (and signal loss) at the boundary between the sensor body 4320 and the sensor optical interface 4310. The boundary between the first redirecting element 4315 and the adjacent material in the sensor optical interface 4310 can be configured so that incident light from the optical interconnect of the transmitter undergoes total internal reflection at the boundary.

The reflected or redirected excitation light 4321 can then enter the sensor body 4320. Within the sensor body 4320, materials can be arranged so that boundaries between materials are configured such that the redirected excitation light 4321 undergoes another total internal reflection to be redirected into the excitation path 4330*a* of the waveguide 4330. For example, a second material 4334 with a second index of refraction, n2, can be arranged with an included planar surface that is adjacent to a third material 4335 with a third index of refraction, n3, where n3>n2. Due to the combination of the difference in indices of refraction and the inclination of the surfaces, the redirected excitation light 4321 undergoes total internal reflection to be redirected into the core 4336 of the waveguide 4330, the core 4336 being surrounded by cladding 4332. The core 4336 can have a fourth index of refraction, n4, that is close to but greater than the index of refraction of the cladding 4332 (e.g., n3<n4) so that light is maintained within and directed along the waveguide by undergoing total internal reflection at the boundary between the cladding 4332 and the core 4336. Another advantage of the inclination of the boundary between the second material 4334 and the third material 4335 is that it relaxes mechanical alignment requirements by providing a larger acceptable range of positions for the optical interconnect 4302 along a direction parallel to the optical path down the waveguide 4330.

By way of example, the first material 4315 can be air with an index of refraction of 1 (n1=1.0). The adjacent material (cladding 4332 in this example) in the sensor optical interconnect can have an index of refraction of 1.53. The second material 4334 in the sensor body 4320 can be a UV-cured material (e.g., an adhesive) with an index of refraction of about 1.32 (e.g., an acrylate). The third material can be cladding 4332, such as an acrylate, with an index of refraction of about 1.53. The core 4336 can also be an acrylate with an index of refraction of about 1.56.

As described above, the sensor 4300 can include a plurality of measurement waveguides in a sensor waveguide system 4330. An individual measurement waveguide can include a transmission path 4330c having a transmission aperture at a first end of the measurement waveguide (e.g., at the target material 4340a, 4340b) and a branching point 4333.

As depicted in FIG. 44B, the individual measurement waveguide can include an excitation path 4330a having an excitation aperture 4322 at a second end of the measurement waveguide opposite the first end, the excitation path 4330a extending from the branching point 4333 to the excitation aperture 4322. The excitation aperture 4322 can be a boundary between different materials where excitation light 4321 undergoes total internal reflection to be redirected into the excitation path 4330a of the waveguide. For example, the excitation aperture 4322 can be where the second material 4334 and third material 4332 meet.

The individual measurement waveguide can include an emission path 4330b having an emission aperture 4324 at the second end of the measurement waveguide, the emission path 4330b extending from the branching point 4333 to the emission aperture 4324. The emission aperture 4324 can be constructed in a fashion similar to the excitation aperture 4322, where two materials form a boundary; the indices of refraction of the materials and the inclination of the boundary configured to redirect the emitted light 4323 by way of total internal reflection into the sensor optical interconnect 4310. In some embodiments, individual emission paths 4330b join together at a combined emission aperture 4324 such that emitted light 4323 from a plurality of emission paths is redirected at the emission aperture 4324 into the sensor optical interconnect 4310.

The individual measurement waveguides can include a core 4336 comprising a core material having a core index of refraction n4 and cladding material 4332 having a cladding index of refraction n3 less than the core index of refraction (n3<n4), the cladding material 4332 surrounding the core material 4336 to form the excitation path 4330a, the emission path 4330b, and the transmission path 4330c. In some embodiments, a boundary between the cladding 4332 and the core 4336 is configured to be inclined in such a way as to form the emission aperture 4324 and/or the excitation apertures 4322, as described in greater detail herein with reference to FIGS. 45A and 45B.

As depicted in FIG. 44B, individual measurement waveguides 4330 are configured to receive excitation light 4321 at the excitation aperture 4322, guide the excitation light 4321 along the excitation path 4330a from the excitation aperture 4322 to the branching point 4333, and guide the excitation light 4321 along the transmission path 4330c from the branching point 4333 to the transmission aperture (in the direction towards the right side of FIG. 44B) for excitation of a target material 4340a, 4340b. The individual waveguides 4330 are further configured to receive emitted light 4323 from the target material 4340a, 4340b (coming from the right side in FIG. 44B) at the transmission aperture, guide the emitted light 4323 into and along the transmission path 4330c from the transmission aperture to the branching point 4333, and guide a majority of the emitted light 4323 into and along the emission path 4330b (because of its widest cross-sectional area at the branching point 4333) from the branching point 4333 to the emission aperture 4324. The individual waveguides can be configured to direct emitted light 4323 from a plurality of emission paths 4330b to a combined emission aperture 4324 of the sensor waveguide system 4330.

The excitation and emission apertures 4322, 4324 can be configured such that the excitation aperture 4322 has a first interface material with a first index of refraction and the emission aperture 4324 has a second interface material with a second index of refraction lower than the first optical interface index of refraction, the apertures having an interface between the first interface material and the second interface material. The optical path of excitation light 4321 through the sensor optical interface to a measurement waveguide begins in a first direction, experiences total internal reflection within the sensor optical interface and then again at the interface between the first optical interface material and the second optical interface material, thereby experiencing total internal reflection to end in a second direction substantially perpendicular to the first direction. Similarly, the optical path of emitted light from a measurement waveguide through the sensor optical interface begins in the second direction, experiences total internal reflection at the interface between the first optical interface material and the second optical interface material, enters the sensor optical interface 4310 and is totally internally reflected again to be redirected to the optical interconnect 4302, for a total redirection of about 90 degrees.

Figure 45A:
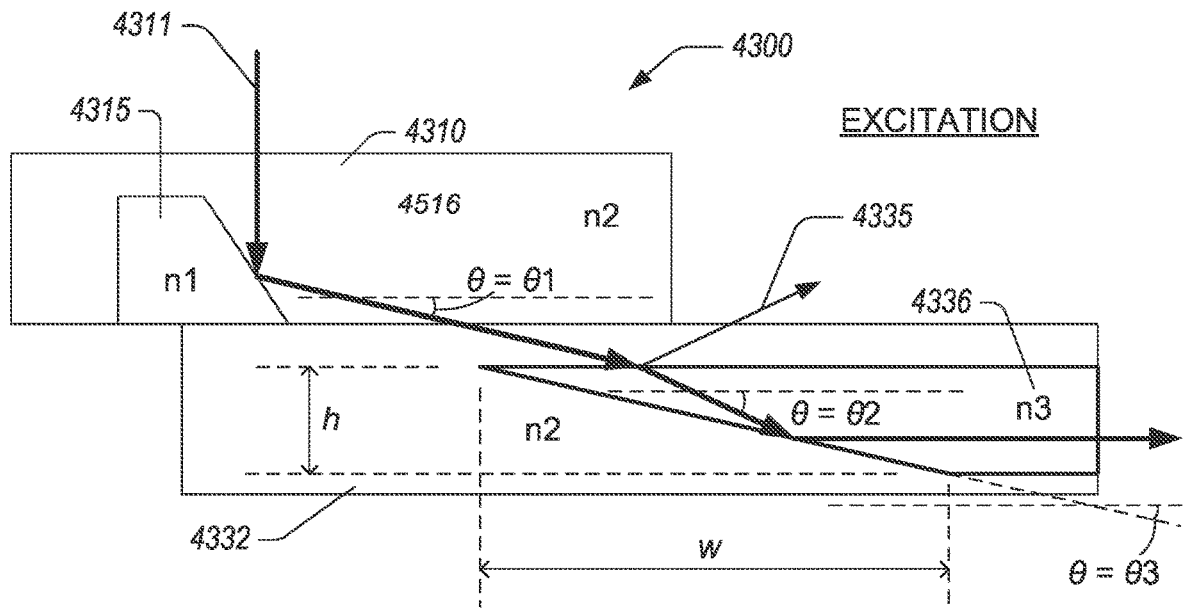
FIGS. 45A and 45B illustrate other example embodiments of sensors with sensor optical interfaces configured to relay excitation and emission light from a waveguide.
Figure 45B:
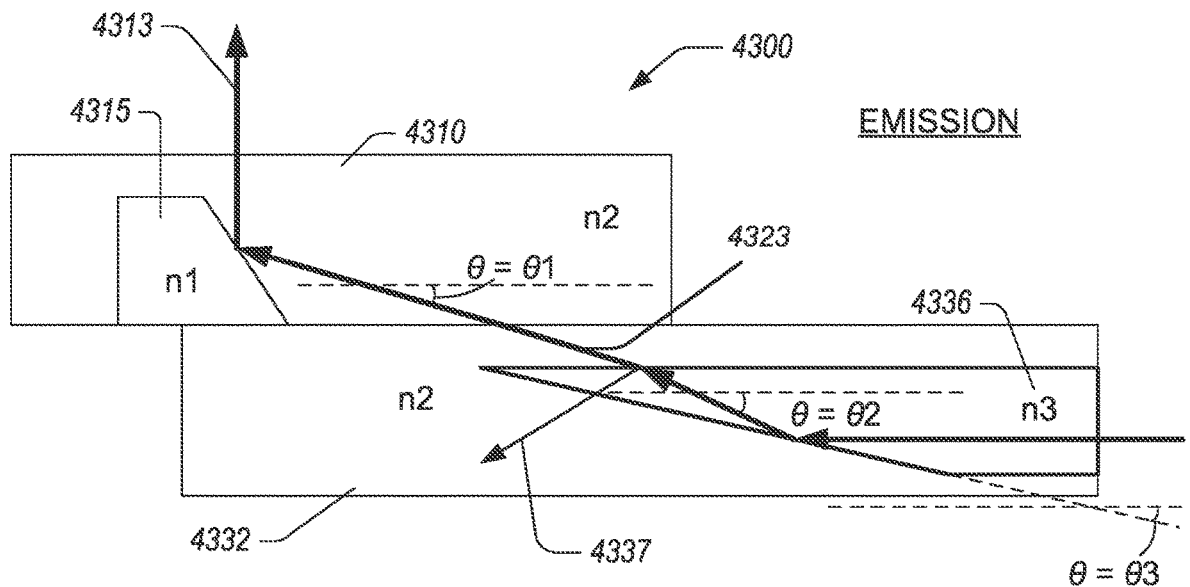

FIGS. 45A and 45B illustrate additional embodiments of sensors 4300 with sensor optical interfaces 4310 configured to relay excitation light 4321 and emission light 4323 from a waveguide 4330. The excitation and emission apertures illustrated respectively in FIGS. 45A and 45B represent apertures having fewer materials and being simpler to manufacture than the aperture configuration illustrated in FIG. 44A.

In the illustrated exemplary embodiment, the core 4336 and cladding 4332 are cut to form an inclined boundary to reflect light with little or no light lost in the reflection. For example, excitation light 4311 enters the sensor optical interface 4310 and encounters a boundary between a first material 4315 (e.g., air, n1=1) and a second material 4316 (e.g., acrylate, n2=1.53). Due at least in part to the shallow angle of incidence of the light relative to the angle of the boundary, the excitation light 4311 is reflected at the boundary and enters the sensor body 4320. After reflection at the boundary in the sensor optical interface 4310, the optical path of the light forms an angle, θ1 of about 15°, relative to the optical axis of the waveguide. The reflected excitation light 4321 then crosses a boundary between cladding 4332 and the core 4336. At this boundary, a small fraction (e.g., less than or equal to about 5%, less than or equal to about 3%, or less than or equal to about 2%) of light 4335 is reflected out of the waveguide 4330 and the light is refracted so that its angle, θ2, relative to the optical axis of the waveguide 4330 increases to about 20 degrees. The light encounters a boundary between the core 4336 and the cladding 4332, and because of the shallow angle of incidence of the light relative to the angle of the boundary (e.g., θ3 is about 10 degrees, but θ3 can be less than or equal to about 30 degrees, less than or equal to about 20 degrees, less than or equal to about 10 degrees, or less than or equal to about 5 degrees relative to a planar surface of the sensor body 4320 or optical axis of the waveguide 4330) and because the difference in indices of refraction (e.g., n3>n2), the reflected light 4321 undergoes total internal reflection so that its optical path is redirected to be substantially parallel with the optical/longitudinal axis of the waveguide 4330. As depicted in FIG. 45B, the emission light path is similarly configured. The angle θ1 that the emitted light entering the sensor optical interface 4310 makes with the optical axis of the waveguide 4330 can be about 19 degrees, whereas for the excitation light leaving the sensor optical interface 4310, the angle θ1 was about 15 degrees. The differences in angles are due at least in part to the geometries of the system. For example, at the boundary between the core 4336 (n=n3) and the cladding 4332 (n=n2), a small fraction (e.g., less than or equal to about 3%, less than or equal to about 2%, or less than or equal to about 1%) of light 4337 is reflected out of the waveguide 4330 and the remaining light is refracted so that its angle, θ1, relative to the optical axis of the waveguide 4330 is about 19 degrees.

The core 4336 can be shaped to have a relatively shallow inclination relative to a plane of the waveguide. Generally, a redirection optical element is positioned at about 45 degrees to redirect an optical path about 90 degrees. However, the size of the target for the incident light is about the same distance as the height of the core 4336, which can be a relatively small target. The problems in these cases is that a relatively small misalignment in light source may result in a complete loss of optical signal in the waveguide 4330. The sensors disclosed herein solve this problem by using a combination of redirection elements to achieve a total redirection of the optical path of about 90 degrees. In particular, redirection within the sensor body 4320, e.g., at the boundary between the cladding 4332 and the core 4336, can be accomplished using a planar surface that is shallower or more acute than a 45 degree optical redirection element. This can increase the effective size of the target for the light. As illustrated in FIG. 45A, the size, w, of the target for the reflected excitation light 4321 is about 280 μm with a waveguide thickness, h, of about 50 μm (e.g., a thickness of the core 4336). In general, the target size, w, of the redirection element increases with decreasing angle (e.g., w=h*cot(θ3)). By making the target size, w, larger, greater allowances for misalignment can be made without significant or complete signal loss relative to systems that use a 45 degree redirection element, for example.

Figure 46A:
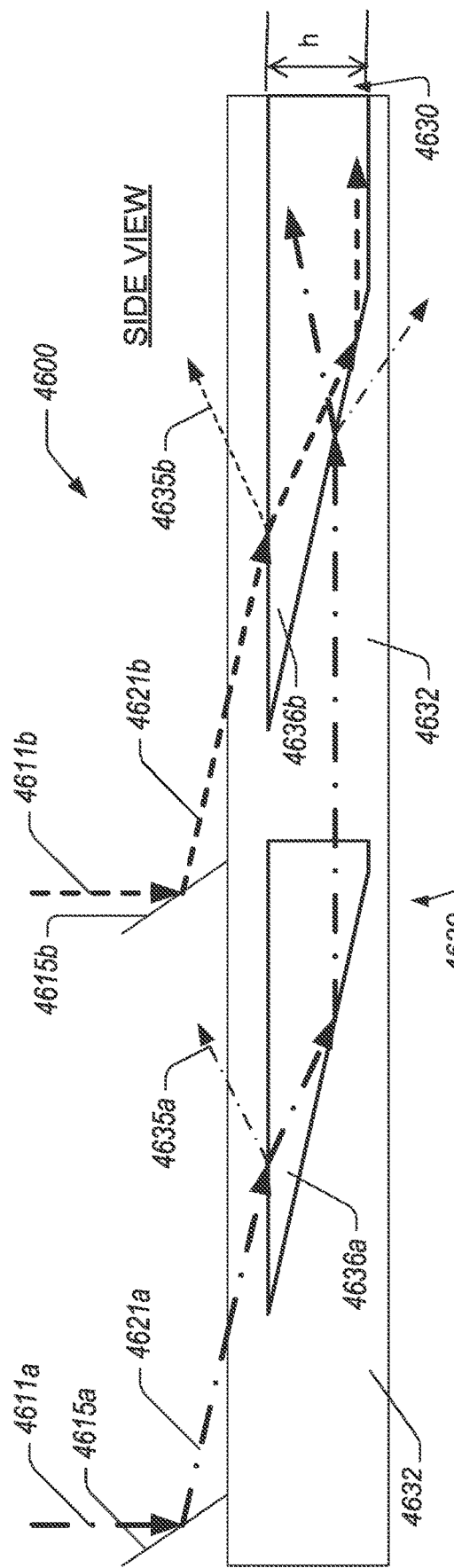
FIGS. 46A and 46B illustrate an optical glucose sensor with two excitation sources per waveguide, according to an embodiment of the present invention.
Figure 46B:
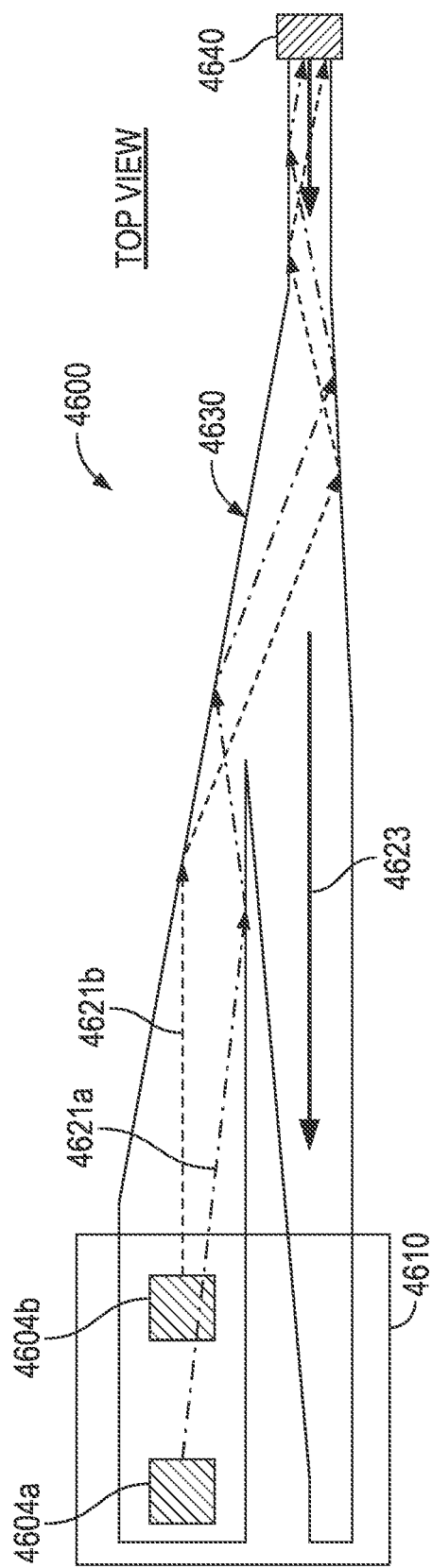

FIGS. 46A and 46B illustrate an example embodiment of an optical glucose sensor 4600 with two excitation sources 4604a, 4604b per waveguide 4630. The waveguide 4630 employs a similar configuration to the waveguide 4330 described herein with reference to FIGS. 45A and 45B. For example, the waveguide 4630 includes a tapered planar bevel design to decrease positional sensitivity along the optical axis of the waveguide 4630 for coupling into the planar waveguide structure. As described herein, this exemplary design provides a positional window of about 283.5 μm along the optical axis of the waveguide 4630 corresponding to a thickness of about 50 μm for the core 4636a, 4636b of the waveguide 4630. For comparison, for a 50 μm waveguide thickness, a 45 degree redirection element would have a positional window of about 50 μm along the optical axis of the waveguide 4630.

The sensor 4600 can include two light sources per waveguide to provide integrated fault detection of the sensor optical circuit and/or to calibrate the sensor 4600. A first light source 4604a can be configured to provide red excitation light 4611a that is redirected at boundary 4615a and redirected at a boundary between core 4636a and cladding 4632, with a small portion of light 4635a being reflected out of the sensor body 4620. The first light source 4604a can be configured to be relatively low-powered for safety concerns. The first light source 4604a can be configured to provide light having a color or wavelength spectrum tailored to not excite the target material (e.g., so as to not induce fluorescence in the target material, which in some embodiments is an oxygen sensing polymer).

A second light source 4604b can be configured to provide blue excitation light 4611b that is redirected at boundary 4615b and redirected at a boundary between core 4636b and the cladding 4632, with a small portion of light 4635b being reflected out of the sensor body 4620. The second light source 4604b can be configured to be relatively high-powered for performing glucose measurements. The second light source 4604b can be configured to provide light having a color or wavelength spectrum tailored to excite the target material (e.g., so as to induce fluorescence in the target material).

The sensor 4600 can be configured to include integrated fault detection of the sensor optical circuit (e.g., to verify the connection between the optical interconnect 4302, the sensor optical interface 4310, and the sensor body 4620). To do so, the sensor 4600 transmits an optical signal(s) having a known temporal decay (e.g., lifetime) with a tailored wavelength configured to not cause fluorescence in the oxygen sensing polymer of the target 4640. Accordingly, the light is substantially reflected by the target material 4640 (e.g., the oxygen sensing polymer). By detecting the signal sufficiently corresponding to the known excitation signal, the sensor 4600 can determine: (1) whether a proper optical connection exists, (2) that the operation of the detection system is proper, (3) that operation of the optics of the sensor 4600 through the sensor optical interface 4310 is proper, (4) verify temporal stability of lifetime measurements, and/or (5) determine noise of measurements.

The sensor 4600 can be configured to include integrated calibration of lifetime measurements from a luminescent source. For example, the sensor 4600 can use the first light source 4604a to transmit a signal(s) of a known temporal decay (lifetime) with a proper wavelength to not excite the oxygen sensing polymer in the target material 4640. Accordingly, the excitation signal is substantially reflected by the target material 4640, e.g., oxygen sensing polymer. By measuring the lifetime of the return optical signal, and because the light is reflected from the target material 4640 rather than exciting it, the measured lifetime can be calibrated so as to correspond to the known lifetime of the excitation signal. For example, this data can be acquired for a number of data points and a map of the measured lifetime as a function of known lifetime can be generated. Similarly, a map of the known lifetime as a function of measured lifetime can be generated. These maps can be used to determine transfer functions of lifetime measurements to account for potential biases in the detection system. These signals can also be used to determine dark noise interference and/or system non-linearity.

In some embodiments, the first light source 4604a is used to verify satisfactory connection conditions and to provide calibration information prior to using the second light source 4604b. For example, for each waveguide, the first light source 4604a can provide excitation light having a wavelength that does not excite the target material. If a suitable or acceptable signal is seen in return, then the sensor 4600 can fire the second light source 4604b to excite the target material (oxygen sensing polymer in some embodiments) and detect fluorescence decay lifetime to determine glucose concentrations. Thus, the second light source 4604b can be configured to be fired in a particular waveguide after the first light source 4604a if the measured signal from the excitation provided by the first light source 4604a indicates that proper operating conditions are present. In addition, the first and second light sources 4604a, 4604b can be fired multiple times per waveguide per measurement to improve a signal to noise ratio of the response.

Figure 47A:
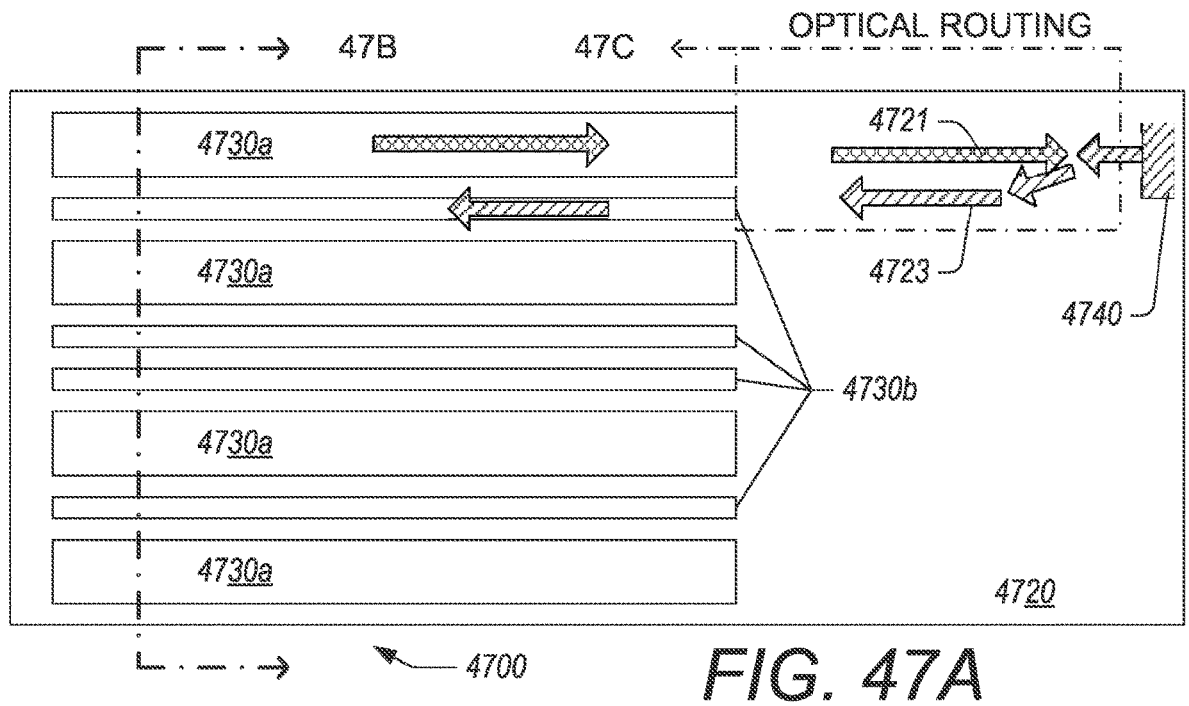
FIGS. 47A-47C illustrate an example of optical routing of different optical signals in an example optical glucose sensor, according to an embodiment of the present invention.
Figure 47B:
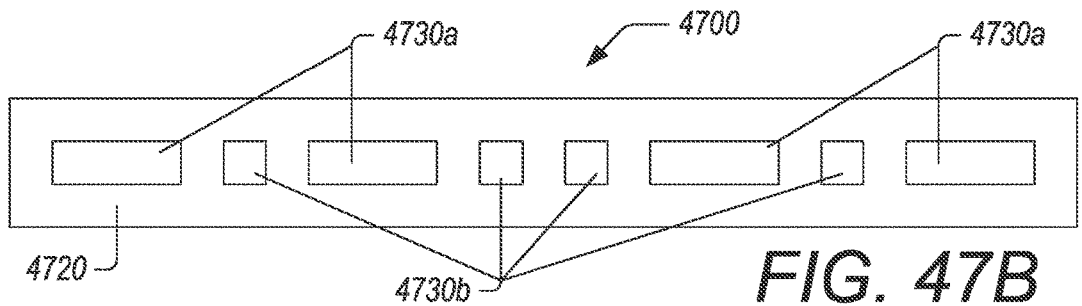
Figure 47C:
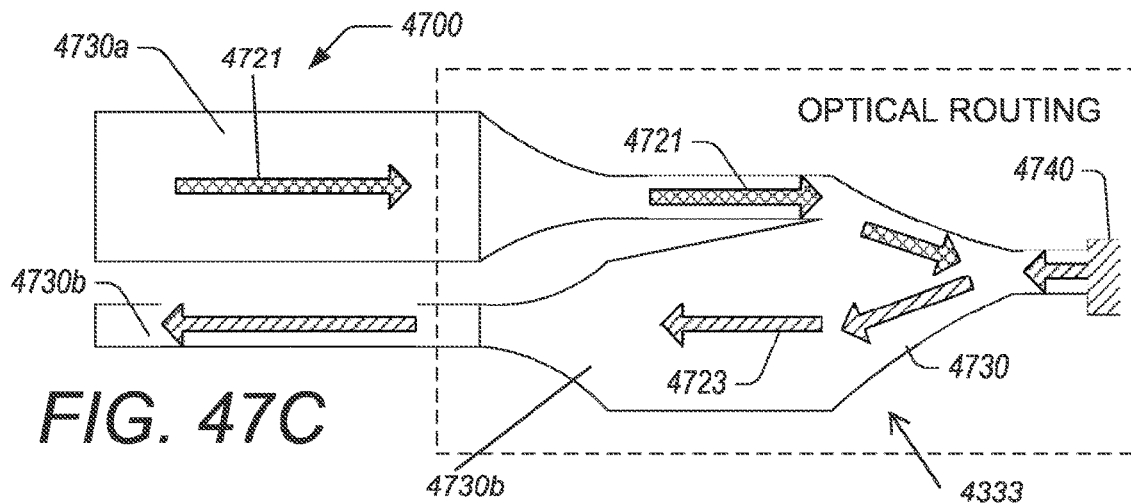

FIGS. 47A-47C illustrate an example of optical routing of different optical signals in an example optical glucose sensor 4700. The optical routing of sensor 4700 with sensor body 4720 includes directing light using excitation paths 4730a, emission paths 4730b, and transmission paths to deliver excitation light 4721 to a target 4740 and to deliver emission light 4723 from the target 4740. As described elsewhere herein, excitation light 4721 can be delivered to the target material 4740 using a combination of an excitation path 4730a and a transmission path of a waveguide 4730. Similarly, emission light 4723 can be delivered from the target material 4740 to the sensor optical interface for measurements. As depicted in FIG. 47C, the sizes of the excitation path 4730a and emission path 4730b in the waveguide 4730 can be configured to change along the optical axis of the waveguide 4730 so that a majority of emission light 4723 enters the emission path 4730b and/or to provide a relatively large target for excitation light 4321 from the sensor optical interface to enter the excitation path 4730a. At a point where the transmission path 4730 branches into the excitation path 4730a and emission path 4730b (branching point 4333), the width of the emission path 4730b can be greater than the width of the excitation path such that a majority of the emission light 4723 enters the emission path 4730b. Similarly, at a point at an end of the emission path 4730b and at a beginning of the excitation path 4730a, the width of the excitation path can be greater than the width of the excitation path such that a majority of the excitation light 4721 enters the excitement path 4730a.

Example Signals in an Optical Glucose Sensor

Figure 48A:
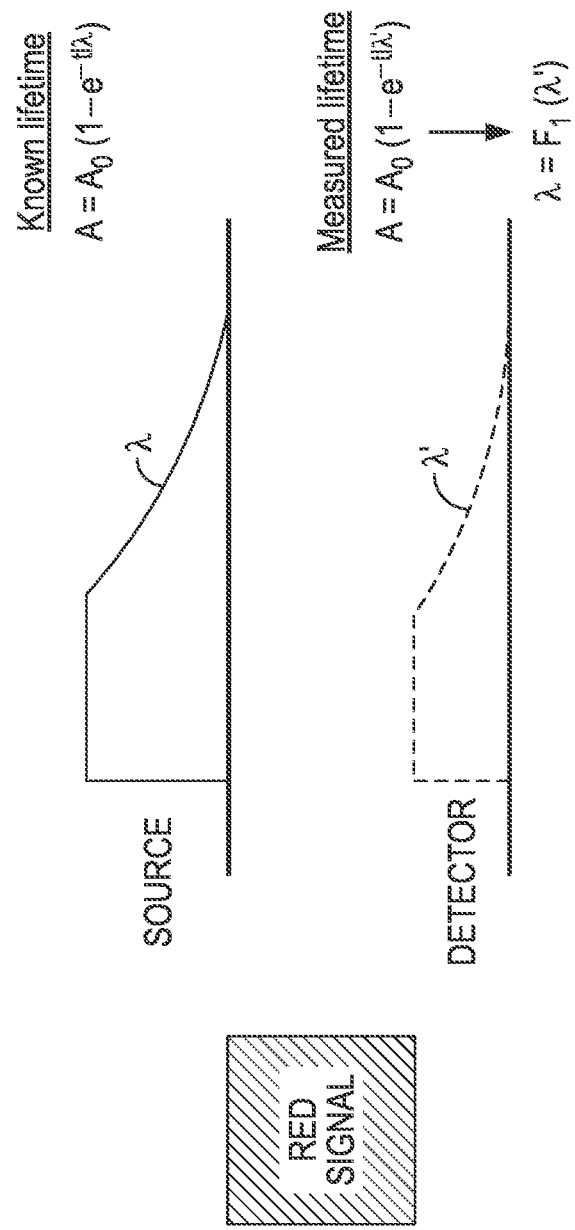
FIGS. 48A and 48B illustrate examples of signals in an optical glucose sensor, the signals used to calibrate the sensor and to measure glucose concentrations, according to an embodiment of the present invention.
Figure 48B:
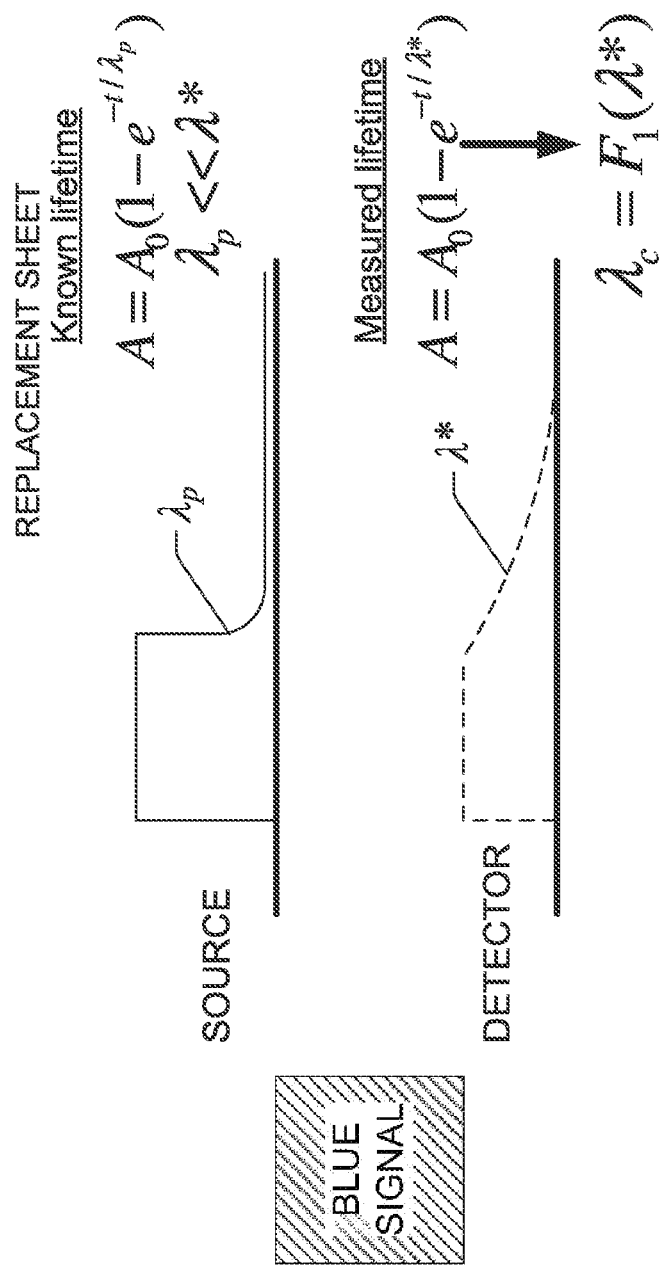

FIGS. 48A and 48B illustrate examples of signals in an optical glucose sensor, the signals used to verify proper optical connections, to calibrate the sensor, and to measure glucose concentrations. The lifetime (temporal decay) obtained from the emission of the oxygen sensing polymer is quantitatively correlated with the oxygen partial pressure in the oxygen sensing polymer. For example, the relationship of lifetime to oxygen concentration in the oxygen sensing polymer follows the Stern Volmer equation.

The oxygen measurement is based on the luminescence lifetime of an oxygen-sensitive luminescent dye in the oxygen sensing polymer or target material. The lifetime expresses the amount of time the luminescent dye (or luminophore) remains in an excited state following excitation by light of a suitable frequency. To measure the lifetime, a time-domain approach is used in which the target material is excited with a pulse of light and then the time-dependent intensity is measured. The lifetime is calculated from the slope of the log of intensity versus time. The target material is first illuminated with an optical signal at a wavelength that does not excite the luminescent dye but with a known lifetime decay to calibrate the transmitter and optical system before each glucose measurement is made. The light is reflected by the dye instead of inducing a luminescent signal. Accordingly, a transfer function, $F_1(\lambda)$, can be determined that maps a measured lifetime, $\lambda'$, to a known lifetime, $\lambda$. In addition, the pre-interrogation pulse ensures that proper optical connections have been maintained before each measurement. Once this transfer function is known, the target material can be interrogated with an optical signal that excites the luminescent dye and the fluorescence signal can be measured as a function of time. Using this measured signal, a lifetime can be determined, $\lambda^*$, and mapped to a fluorescence lifetime, $\lambda_c$, of the target material using the transfer function, $F_1(\lambda)$, determined using the first light source.

As previously discussed, the red signal light source can be a low-intensity light source of a red wavelength. The blue signal light source can be a higher intensity class 3 source of a blue wavelength. The excitation light is guided to a red luminescent dye, in some implementations. The red dye can be configured to have a high quantum efficiency for converting the blue excitation into a red emission with a lifetime decay signal. The red luminescent dye does not have a high quantum efficiency for converting the red excitation source into an emission with a lifetime decay signal, but reflects some of the red excitation light as a return emission.

In some embodiments, the red signal is provided for a tailored period and modulated (with a desired amplitude signal characteristic), while the blue source will be pulsed. The return signal can be detected by the same emitter as a higher power blue light source. When the low power red light source is detected with appropriate signal characteristics, this indicates that it is safe to energize the higher intensity light source.

The return signal from the red source can be detected by the same emitter as for a higher power blue source. The red source signal can be modulated with a known lifetime decay. When the low power red light source is detected it will have a measured lifetime decay. This known versus measured signal will allow the sensor to be calibrated for lifetime decay when appropriate. This method allows individual channels to be assessed for quality, operation, and calibrated for lifetime decay, when the channel is excited by the dual source approach.

In certain implementations, the blue signal can be a modulated light that is similar to a digital signal that is turned on and off intermittently. In various implementations, the blue signal can be a sinusoidal signal used in a phase-based method to determine lifetime. To create the red light decay signal for calibration purposes, a digital method may be used to decrease the amplitude of the source signal at specified times from a digital source.

As described herein, the sensor can be configured to have a dual source configuration for each waveguide to provide fault or integrity checks for each channel of the sensor. The sampling of the excitation with the emission response may be repeated multiple times for each channel to improve the signal to noise of the response. After the one or more series of measurements are made, the sensor system can be configured to pause until a subsequent measurement cycle begins (e.g., 30 sec later, 1 min later, 5 min later, etc.).

The foregoing disclosure provides for embodiments of optical analyte sensors with innovative features. These optical analyte sensors are generally described in the context of glucose measurements. However, it should be understood that features of the disclosed sensors can be applicable to other analyte measurements. Moreover, while several components, techniques and aspects have been described with a certain degree of particularity, it is manifest that many changes can be made in the specific designs, constructions and methodology herein above described without departing from the spirit and scope of this disclosure.

It is to be understood that the embodiments of the invention described herein are not limited to particular variations set forth herein as various changes or modifications may be made to the embodiments of the invention described and equivalents may be substituted without departing from the spirit and scope of the embodiments of the invention. As will be apparent to those of skill in the art upon reading this disclosure, each of the individual embodiments described and illustrated herein has discrete components and features that may be readily separated from or combined with the features of any of the other several embodiments without departing from the scope or spirit of the embodiments of the present invention. In addition, many modifications may be made to adapt a particular situation, material, composition of matter, process, process act(s) or step(s) to the objective(s), spirit or scope of the embodiments of the present invention. All such modifications are intended to be within the scope of the claims made herein.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. Additionally, numeric ranges are inclusive of the numbers defining the range, and any individual value provided herein can serve as an endpoint for a range that includes other individual values provided herein. For example, a set of values such as 1, 2, 3, 8, 9, and 10 is also a disclosure of a range of numbers from 1-10, from 1-8, from 3-9, and so forth.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A continuous health monitoring system comprising:
   a sensor configured to be implanted in a patient, the sensor comprising multiple waveguides; and
   a controller configured to be adhered to skin of the patient and in optical communication with the sensor, the controller comprising:
      an optical assembly with a plurality of emitters corresponding to each of a reference region and a plurality of working regions in the sensor, each of the plurality of emitters for the plurality of working regions configured to emit a plurality of optical interrogation signals at a same wavelength via respective waveguides in the sensor;
      a single common detector configured to separately receive and measure each of a plurality of optical emissions from the sensor, the plurality of optical emissions indicative of an interstitial analyte concentration of an analyte in the patient;
      a processor in communication with the plurality of emitters of the optical assembly and the single common detector, the processor configured to determine a measure of analyte concentration based on decay rates of the plurality of optical emissions;
      a memory in communication with the processor configured to store the measure of analyte concentration; and
      a transmitter in communication with the processor configured to transmit the measure of analyte concentration.

2. The system of claim 1, wherein the analyte is glucose.

3. The system of claim 1, wherein the analyte is lactate.

4. The system of claim 1, wherein the processor is further configured to determine a frequency, a timing, and/or a duration for emitting the plurality of optical interrogation signals.

5. The system of claim 4, further comprising:
   a receiver in communication with the processor, the receiver configured to receive a protocol for determining the frequency, the timing, and/or the duration for emitting the plurality of optical interrogation signals;

wherein the memory is configured to store a plurality of determined measures of analyte concentrations determined during a time interval; and wherein the transmitter is further configured to transmit the plurality of determined measures of analyte concentrations determined during the time interval in a burst transmission.

6. The system of claim 1, wherein the plurality of emitters of the optical assembly are selected from the group consisting of a laser or LED.

7. The system of claim 1, wherein the plurality of optical emissions are luminescent emissions.

8. A method for continuous health monitoring using an analyte monitoring system comprising a sensor implanted in a patient and a controller adhered to skin of the patient, the method comprising:

emitting, by a plurality of emitters in the controller corresponding to each of a plurality of working regions and a reference region in the sensor, a plurality of optical interrogation signals at a same wavelength via respective waveguides in the sensor implanted in the patient;

separately measuring, by a single common detector in the controller, each of a plurality of optical emissions from the plurality of working regions and the reference region in the sensor, the plurality of optical emissions indicative of an interstitial analyte concentration of an analyte in the patient; and determining, by a processor, a measure of analyte concentration based on decay rates of the plurality of optical emissions.

9. The method of claim 8, further comprising:

storing, by a memory, the measure of analyte concentration; and transmitting, by a transmitter, the measure of analyte concentration.

10. The method of claim 8, wherein the analyte is glucose.

11. The method of claim 8, further comprising determining, by the processor, a frequency, a timing, and/or a duration for emitting the plurality of optical interrogation signals.

12. The method of claim 11, further comprising:

receiving, by a receiver, a protocol for determining the frequency, the timing, and/or the duration for emitting the plurality of optical interrogation signals;

storing, by a memory, a plurality of determined measures of analyte concentrations determined during a time interval; and transmitting, by a transmitter, the plurality of determined measures of analyte concentrations determined during the time interval in a burst transmission.

13. The method of claim 8, wherein the plurality of emitters are selected from the group consisting of a laser or LED.

14. The method of claim 8, wherein the plurality of optical emissions are luminescent emissions.

15. The method of claim 8, wherein the analyte is lactate.

16. The method of claim 8, further comprising determining, by the processor, oxygen consumption for each of a reference region and the plurality of working regions based on the decay rates of the plurality of optical emissions.

17. The method of claim 16, wherein determining the measure of analyte concentration comprises determining a sum of net oxygen consumption differences between each of the plurality of working regions and the reference region.

18. A non-transitory computer-readable medium storing instructions for continuous health monitoring using an analyte monitoring system comprising a sensor implanted in a patient and a controller adhered to skin of the patient, the instructions that when executed, perform a method comprising:

emitting, by a plurality of emitters in the controller corresponding to each of a plurality of working regions and a reference region in the sensor, a plurality of optical interrogation signals at a same wavelength via respective waveguides in the sensor implanted in the patient;

separately measuring, by a single common detector in the controller, each of a plurality of optical emissions from the plurality of working regions and the reference region the sensor, the plurality of optical emissions indicative of an interstitial analyte concentration of an analyte in the patient;

determining, by a processor, a measure of analyte concentration based on decay rates of the plurality of optical emissions;

storing, by a memory, the measure of analyte concentration; and transmitting, by a transmitter, the measure of analyte concentration.

19. The non-transitory computer-readable medium storing instructions for continuous health monitoring of claim 18, wherein the plurality of emitters are selected from the group comprising a laser or LED.

20. The non-transitory computer-readable medium storing instructions for continuous health monitoring of claim 18, wherein the plurality of optical emissions are luminescent emissions.

21. The non-transitory computer-readable medium storing instructions for continuous health monitoring of claim 18, wherein the analyte is selected from the group consisting of glucose and lactate.

22. A controller for continuous health monitoring comprising:

an optical assembly with a plurality of emitters corresponding to each of a reference region and a plurality of working regions in a sensor configured to be implanted in a subject, each of the plurality of emitters for the plurality of working regions configured to emit a plurality of optical interrogation signals at a same wavelength via respective optical pathways to the sensor;

a detector configured to separately receive and measure each of a plurality of optical emissions from the sensor, the plurality of optical emissions indicative of an interstitial analyte concentration of an analyte in the subject; and a processor in communication with the plurality of emitters of the optical assembly and the detector, the processor configured to determine oxygen consumption for each of the reference region and the plurality of working regions based on decay rates of the plurality of optical emissions, the processor configured to determine a measure of analyte concentration based on a sum of net oxygen consumption differences between each of the plurality of working regions and the reference region.

23. The controller of claim 22, further comprising a temperature sensor for measuring a temperature, wherein the processor is in communication with the temperature sensor, and wherein determining the measure of analyte concentration comprises the processor calibrating the plurality of optical emissions based on the measured temperature.

* * * * *